US010294450B2

(12) United States Patent
Kamen et al.

(10) Patent No.: US 10,294,450 B2
(45) Date of Patent: May 21, 2019

(54) FLUID PUMPING AND BIOREACTOR SYSTEM

(71) Applicant: DEKA Products Limited Partnership, Manchester, NH (US)

(72) Inventors: Dean Kamen, Bedford, NH (US); Jason A. Demers, Manchester, NH (US); Frederick Morgan, Canton, MA (US); Timothy D. Moreau, Manchester, NH (US); Brian D. Tracey, Litchfield, NH (US); Matthew Ware, Merrimack, NH (US); Dirk A. van der Merwe, Canterbury, NH (US); Richard J. Lanigan, Concord, NH (US); Michael A. Baker, Manchester, NH (US); David Blumberg, Jr., Deerfield, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 29 days.

(21) Appl. No.: 15/288,900

(22) Filed: Oct. 7, 2016

(65) Prior Publication Data

US 2017/0101618 A1 Apr. 13, 2017

Related U.S. Application Data

(60) Provisional application No. 62/246,191, filed on Oct. 26, 2015, provisional application No. 62/239,793, (Continued)

(51) Int. Cl.
*C12M 1/36* (2006.01)
*C12M 1/00* (2006.01)
(Continued)

(52) U.S. Cl.
CPC ......... *C12M 41/48* (2013.01); *A61L 27/3683* (2013.01); *A61L 27/38* (2013.01); (Continued)

(58) Field of Classification Search
CPC ........ A61K 35/42; A61K 35/30; A61K 35/12; A61K 49/0054; A61K 49/0073; A61K 2300/00; A61K 35/28; A61K 31/4545; A61K 35/50; A61K 45/06; A61K 9/0019; A61K 2035/124; A61K 31/10; A61K 35/00; A61K 35/19; A61K 35/32; A61K 35/34; A61K 35/35; A61K 9/0085; C12N 2533/90; C12N 5/0688; C12N 2501/11; C12N 2501/115; C12N 2501/117; C12N 2501/119; C12N 2501/16; C12N 2501/415; C12N 2506/45; C12N 2533/30; C12N 2533/50; C12N 2533/52; C12N 2533/54; C12N 2533/70; C12N 5/0068; C12N 5/0602; C12N 5/0667; C12N 5/0668; C12N 1/08; C12N 5/0605; C12N 2799/022; C12N 2502/025; C12N 2502/1142; C12N 2502/30; C12N 2513/00; C12N 2533/74; C12N 2533/80; C12N 5/0062; C12N 5/0644; C12N 5/066; C12N 5/0663; C12N 5/0686; C12N 5/069; A61F 2210/0076; A61F 2/142; A61F 2/2415; A61F 2/06; A61F 2002/30962; A61F 2240/002; A61F 2/042; A61F 2/30942; A61L 2430/16; A61L 27/16; A61L 27/18; A61L 27/3633; A61L 27/3683; A61L 27/38; A61L 27/3804; A61L 27/3839; A61L 27/54; A61L 27/58; A61L 27/3808; A61L 27/3826; A61L 27/507; A61L 27/383; A61L 15/32; A61L 2430/36; A61L 27/227; A61L 27/3834; A61L 31/047; A61L 2300/414; A61L 2300/64; A61L 2430/10; (Continued)

(56) References Cited

U.S. PATENT DOCUMENTS 1,133,254 A 3/1915 Backus
1,664,576 A 4/1928 Staples
(Continued)

FOREIGN PATENT DOCUMENTS

DE 3605640 8/1987
DE 3627231 2/1988
(Continued)

OTHER PUBLICATIONS

Capulli, A. K. et al., *JetValve: Rapid Manufacturing of biohydrid scaffolds for biomimetic heart valve replacement*, Biomaterials 133, 2017, pp. 229-241.
Invitation to pay additional fees, PCT/US2017/060389, Intl. filing date Nov. 7, 2017.
Stuart, M.P., et al., *Successful Low-Cost Scaffold-Free Cartilage Tissue Engineering Using Human Cartilage Progenitor Cell Spheroids Formed by Micromolded Nonadhesive Hydrogel*, Hindawi, Stem Cells International, vol. 2017, 11p.
(Continued)

*Primary Examiner* — Deborah K Ware
(74) *Attorney, Agent, or Firm* — Kathleen Chapman

(57) ABSTRACT

A fluid pumping and bioreactor system including at least two cassettes, at least one storage reservoir, at least one bioreactor, at least one manifold including valve modules, and tubing to connect the cassettes to the storage reservoir and the bioreactor. The cassettes can include pumps, valves, and fluid conduits and can be communicatively connected to the at least one manifold. The bioreactor can include an adapter and fluid conduits extending through the adapter from the exterior of the bioreactor to the interior of the bioreactor. System and method for generating a tissue for transplant by decellularizing and recellularizing a supplied tissue.

11 Claims, 89 Drawing Sheets

Related U.S. Application Data filed on Oct. 9, 2015, provisional application No. 62/266,548, filed on Dec. 11, 2015.

(51) Int. Cl.

| | |
|---|---|
| *C12M 3/00* | (2006.01) |
| *C12N 5/071* | (2010.01) |
| *A61L 27/36* | (2006.01) |
| *A61L 27/38* | (2006.01) |
| *C12M 1/12* | (2006.01) |

(52) U.S. Cl.
CPC ............ *C12M 21/08* (2013.01); *C12M 23/40* (2013.01); *C12M 23/42* (2013.01); *C12M 25/14* (2013.01); *C12M 29/00* (2013.01); *C12N 5/0602* (2013.01)

(58) Field of Classification Search
CPC ............ A61L 2430/20; A61L 2430/22; A61L 2430/26; A61L 27/24; A61L 27/26; A61L 27/3604; A61L 27/3625; A61L 27/3886; A61L 27/3895; A61L 27/52; A61L 57/54; A61L 27/60; C12M 21/08; C12M 23/40; C12M 23/42; C12M 25/14; C12M 29/00; C12M 41/48; C12M 45/05; C12M 45/06; C12M 45/09; C12M 47/04; A61B 2562/0233; A61B 2576/023; A61B 5/0044; A61B 5/0068; A61B 5/0071; A61B 5/0084; A61B 5/02028; A61B 5/4887; A61B 5/007; G01N 2021/6423; G01N 2021/6439; G01N 2021/6463; G01N 2021/6484; G01N 21/6456; C07K 14/52; A61M 1/0088; A61M 1/3472; A61M 1/3482; A61M 1/3489; A61M 1/367; B01D 63/026; B29C 64/106; B29L 2031/7532; B33Y 70/00; B33Y 80/00
See application file for complete search history.

(56) References Cited

U.S. PATENT DOCUMENTS

| | | |
|---|---|---|
| 1,792,906 A | 2/1931 | Heilos |
| 2,313,551 A | 3/1943 | Hurlbut |
| 2,525,251 A | 10/1950 | Willard |
| 2,526,017 A | 10/1950 | Figg |
| 2,703,055 A | 3/1955 | Veth |
| 2,776,854 A | 1/1957 | Billstrom |
| 2,834,504 A | 5/1958 | Anniq |
| 2,902,253 A | 9/1959 | Page |
| 2,917,465 A | 12/1959 | Begley |
| 3,002,804 A | 10/1961 | Kilian |
| 3,048,121 A | 8/1962 | Sheesley |
| 3,339,956 A | 9/1967 | Bencene |
| 3,449,864 A | 6/1969 | Prost-Dame |
| 3,481,076 A | 12/1969 | Bedard |
| 3,540,694 A | 11/1970 | Cornelius |
| 3,570,486 A | 3/1971 | Engelsher |
| 3,722,858 A | 3/1973 | Sugimoto |
| 3,727,882 A | 4/1973 | Burris |
| 3,814,548 A | 6/1974 | Rupp |
| 3,856,338 A | 12/1974 | Johnsson |
| 4,049,352 A | 9/1977 | Lardon et al. |
| 4,056,224 A | 11/1977 | Lolachi |
| 4,072,934 A | 2/1978 | Hiller |
| 4,073,521 A | 2/1978 | Mena |
| 4,093,176 A | 6/1978 | Contastin |
| 4,161,264 A | 7/1979 | Johnson et al. |
| 4,212,589 A | 7/1980 | Bosio |
| 4,230,300 A | 10/1980 | Wiltse |
| 4,247,018 A | 1/1981 | Credle |
| 4,272,824 A | 6/1981 | Lewinger et al. |
| 4,427,415 A | 1/1984 | Cleveland |
| 4,431,425 A | 2/1984 | Thompson |
| 4,468,219 A | 8/1984 | George |
| 4,479,760 A | 10/1984 | Bilstad et al. |
| 4,479,761 A | 10/1984 | Bilstad |
| 4,479,762 A | 10/1984 | Bilstad |
| 4,573,994 A | 3/1986 | Fischell |
| 4,576,211 A | 3/1986 | Valentini |
| 4,583,971 A | 4/1986 | Bocquet |
| 4,606,734 A | 8/1986 | Larkin |
| 4,634,430 A | 1/1987 | Polaschegg |
| 4,648,868 A | 3/1987 | Hardwick |
| 4,650,339 A | 3/1987 | Chetcuti et al. |
| 4,662,540 A | 5/1987 | Schroter |
| 4,662,829 A | 5/1987 | Nehring |
| 4,667,927 A | 5/1987 | Oscarsson |
| 4,696,671 A | 9/1987 | Epstein |
| 4,698,160 A | 10/1987 | Haraguchi |
| 4,718,447 A | 1/1988 | Marshall |
| 4,721,138 A | 1/1988 | Simonazzi |
| 4,778,451 A | 10/1988 | Kamen |
| 4,798,580 A | 1/1989 | DeMeo et al. |
| 4,804,366 A | 2/1989 | Zdeb |
| 4,807,660 A | 2/1989 | Aslanian |
| 4,808,161 A | 2/1989 | Kamen |
| 4,818,186 A | 4/1989 | Pastrone |
| 4,825,444 A | 4/1989 | Johna |
| 4,826,482 A | 5/1989 | Kamen |
| 4,828,543 A | 5/1989 | Weiss |
| 4,833,922 A | 5/1989 | Frick |
| 4,850,978 A | 7/1989 | Dudar |
| 4,855,714 A | 8/1989 | Clarkson |
| 4,925,444 A | 5/1990 | Orkin |
| 4,927,198 A | 5/1990 | Fennell |
| 4,976,162 A | 12/1990 | Kamen |
| 5,004,351 A | 4/1991 | Salaba |
| 5,005,604 A | 4/1991 | Aslanian |
| 5,006,050 A | 4/1991 | Cooke |
| 5,045,068 A | 9/1991 | Kawai |
| 5,051,922 A | 9/1991 | Toral |
| 5,062,774 A | 11/1991 | Kramer et al. |
| 5,069,792 A | 12/1991 | Prince |
| 5,088,515 A | 2/1992 | Kamen |
| 5,098,262 A | 3/1992 | Wecker |
| 5,098,371 A | 3/1992 | Juji et al. |
| 5,106,366 A | 4/1992 | Steppe |
| 5,113,904 A | 5/1992 | Aslanian |
| 5,116,316 A | 5/1992 | Sertic et al. |
| 5,122,116 A | 6/1992 | Kriesel |
| 5,146,414 A | 9/1992 | McKown |
| 5,150,796 A | 9/1992 | Pierson |
| 5,156,186 A | 10/1992 | Manska |
| 5,167,837 A | 12/1992 | Snodgrass |
| 5,178,182 A | 1/1993 | Kamen |
| 5,186,333 A | 2/1993 | Pierson |
| 5,197,787 A | 3/1993 | Matsuda |
| 5,255,072 A | 10/1993 | Mikasa |
| 5,266,272 A | 11/1993 | Griner et al. |
| 5,267,956 A | 12/1993 | Beuchat |
| 5,272,646 A | 12/1993 | Farmer |
| 5,279,504 A | 1/1994 | Williams |
| 5,290,076 A | 3/1994 | Smith |
| 5,292,306 A | 3/1994 | Wynkoop |
| 5,294,157 A | 3/1994 | Smith |
| 5,302,093 A | 4/1994 | Owens |
| 5,324,422 A | 6/1994 | Colleran et al. |
| 5,325,884 A | 7/1994 | Mirel |
| 5,330,426 A | 7/1994 | Kriesel |
| 5,336,053 A | 8/1994 | Wynkoop |
| 5,342,422 A | 8/1994 | Wimboeck |
| D350,823 S | 9/1994 | Lanigan |
| 5,350,357 A | 9/1994 | Kamen et al. |
| 5,351,686 A | 10/1994 | Steuer |
| 5,355,890 A | 10/1994 | Aguirre |
| 5,378,126 A | 1/1995 | Abrahamson |
| 5,384,714 A | 1/1995 | Kidd |
| 5,385,540 A | 1/1995 | Abbott |
| 5,401,059 A | 3/1995 | Ferrario |
| 5,408,420 A | 4/1995 | Slocum |
| 5,411,472 A | 5/1995 | Steg, Jr. |

(56) References Cited

U.S. PATENT DOCUMENTS

| | | |
|---|---|---|
| 5,421,823 A | 6/1995 | Kamen et al. |
| 5,423,738 A | 6/1995 | Robinson |
| 5,428,527 A | 6/1995 | Niemi |
| 5,429,485 A | 7/1995 | Dodge |
| 5,431,626 A | 7/1995 | Bryant |
| 5,438,510 A | 8/1995 | Bryant |
| 5,439,355 A | 8/1995 | Jimison |
| 5,463,228 A | 10/1995 | Krause |
| 5,466,220 A | 11/1995 | Brenneman |
| 5,474,683 A | 12/1995 | Bryant |
| 5,478,337 A | 12/1995 | Okamoto |
| 5,482,440 A | 1/1996 | Dennehey et al. |
| 5,496,273 A | 3/1996 | Pastrone et al. |
| 5,507,412 A | 4/1996 | Ebert et al. |
| 5,558,255 A | 9/1996 | Sancoff |
| 5,569,181 A | 10/1996 | Heilman et al. |
| 5,575,310 A | 11/1996 | Kamen |
| 5,578,012 A | 11/1996 | Kamen |
| 5,579,244 A | 11/1996 | Brown |
| 5,584,671 A | 12/1996 | Schweitzer, Jr. |
| 5,588,816 A | 12/1996 | Abbott |
| 5,593,290 A | 1/1997 | Greisch |
| 5,628,908 A | 5/1997 | Kamen et al. |
| 5,634,896 A | 6/1997 | Bryant |
| 5,638,737 A | 6/1997 | Mattson |
| 5,645,531 A | 7/1997 | Thompson et al. |
| 5,647,391 A | 7/1997 | Chan et al. |
| 5,649,810 A | 7/1997 | Schweitzer, Jr. |
| 5,651,775 A | 7/1997 | Walker |
| 5,653,533 A | 8/1997 | Green |
| 5,681,285 A | 10/1997 | Ford |
| 5,713,865 A | 2/1998 | Manning |
| 5,716,343 A | 2/1998 | Kriesel |
| 5,755,683 A | 5/1998 | Houle |
| 5,758,095 A | 5/1998 | Albaum |
| 5,776,103 A | 7/1998 | Kriesel |
| 5,795,328 A | 8/1998 | Barnitz |
| 5,808,181 A | 9/1998 | Wamsiedler |
| 5,816,779 A | 10/1998 | Lawless |
| 5,823,026 A | 10/1998 | Finke |
| 5,837,905 A | 11/1998 | Strauss et al. |
| 5,868,162 A | 2/1999 | Dickerson, Jr. |
| 5,879,328 A | 3/1999 | Holmberg |
| 5,883,299 A | 3/1999 | Green |
| 5,935,105 A | 8/1999 | Manning |
| 5,935,332 A | 8/1999 | Caucal |
| 5,938,634 A | 8/1999 | Packard |
| 5,965,821 A | 10/1999 | Grudzien |
| 5,989,423 A | 11/1999 | Kamen |
| 6,022,483 A | 2/2000 | Aral |
| 6,041,801 A | 3/2000 | Gray et al. |
| 6,065,941 A | 5/2000 | Gray et al. |
| 6,070,761 A | 6/2000 | Bloom et al. |
| 6,109,881 A | 8/2000 | Snodgrass et al. |
| 6,136,586 A | 10/2000 | Budowsky |
| 6,149,627 A | 11/2000 | Uber, III |
| 6,165,154 A | 12/2000 | Gray et al. |
| 6,210,361 B1 | 4/2001 | Kamen et al. |
| 6,214,231 B1 | 4/2001 | Cote et al. |
| 6,217,847 B1 | 4/2001 | Contag et al. |
| 6,218,182 B1 | 4/2001 | Naughton et al. |
| 6,223,130 B1 | 4/2001 | Gray et al. |
| 6,234,997 B1 | 5/2001 | Kamen et al. |
| 6,245,570 B1 | 6/2001 | Grimm et al. |
| 6,264,458 B1 | 7/2001 | Marcuz et al. |
| 6,302,653 B1 | 10/2001 | Bryant et al. |
| 6,321,597 B1 | 11/2001 | Demers et al. |
| 6,343,614 B1 | 2/2002 | Gray et al. |
| 6,364,857 B1 | 4/2002 | Gray et al. |
| 6,382,923 B1 | 5/2002 | Gray |
| 6,416,293 B1 | 7/2002 | Bouchard et al. |
| 6,464,667 B1 | 10/2002 | Kamen et al. |
| 6,485,263 B1 | 11/2002 | Bryant et al. |
| 6,503,062 B1 | 1/2003 | Gray et al. |
| 6,520,747 B2 | 2/2003 | Gray et al. |
| 6,527,758 B2 | 3/2003 | Ko |
| 6,547,026 B2 | 4/2003 | Kamen et al. |
| 6,604,908 B1 | 8/2003 | Bryant |
| 6,605,223 B2 | 8/2003 | Jorgensen et al. |
| 6,610,040 B1 | 8/2003 | Fowles et al. |
| 6,642,019 B1 | 11/2003 | Anderson et al. |
| 6,663,359 B2 | 12/2003 | Gray |
| 6,726,656 B2 | 4/2004 | Kamen et al. |
| 6,749,403 B2 | 6/2004 | Bryant et al. |
| 6,796,702 B2 | 9/2004 | Wire et al. |
| 6,808,369 B2 | 10/2004 | Gray et al. |
| 6,814,547 B2 | 11/2004 | Childers et al. |
| 6,877,713 B1 | 4/2005 | Gray et al. |
| 6,910,797 B2 | 6/2005 | Falcon |
| 6,929,751 B2 | 8/2005 | Bowman et al. |
| 6,949,079 B1 | 9/2005 | Westberg et al. |
| 6,952,963 B2 | 10/2005 | Delmevo |
| 7,011,742 B2 | 3/2006 | Rosiello |
| 7,083,719 B2 | 8/2006 | Bowman et al. |
| 7,114,384 B1 | 10/2006 | Bates et al. |
| 7,214,210 B2 | 5/2007 | Kamen et al. |
| 7,278,776 B2 | 10/2007 | Helbing et al. |
| 7,354,190 B2 | 4/2008 | Demers et al. |
| 7,422,868 B2 | 9/2008 | Fan et al. |
| 7,461,968 B2 | 12/2008 | Demers et al. |
| 7,544,179 B2 | 6/2009 | Distler et al. |
| 7,560,245 B2 | 7/2009 | Hattori et al. |
| 7,604,987 B2 | 10/2009 | Hutmacher et al. |
| 7,632,078 B2 | 12/2009 | Demers et al. |
| 7,632,080 B2 | 12/2009 | Tracey et al. |
| 7,662,139 B2 | 2/2010 | Demers et al. |
| 7,726,362 B2 | 6/2010 | Demers et al. |
| 7,794,141 B2 | 9/2010 | Perry et al. |
| 7,798,997 B2 | 9/2010 | Kamen et al. |
| 7,874,718 B2 | 1/2011 | Demers et al. |
| 7,959,196 B2 | 6/2011 | Dale et al. |
| 7,967,138 B2 | 6/2011 | Ryan et al. |
| 7,993,050 B2 | 8/2011 | Demers et al. |
| 8,158,102 B2 | 4/2012 | Demers et al. |
| 8,197,439 B2 | 6/2012 | Wang et al. |
| 8,236,515 B2 | 8/2012 | Charm et al. |
| 8,241,905 B2 | 8/2012 | Forgacs et al. |
| 8,292,594 B2 | 10/2012 | Tracey et al. |
| 8,470,520 B2 | 6/2013 | Ott et al. |
| 8,485,800 B2 | 7/2013 | Lanigan et al. |
| 8,492,140 B2 | 7/2013 | Smith et al. |
| 8,585,377 B2 | 11/2013 | Kamen et al. |
| 8,691,974 B2 | 4/2014 | Gatenholm et al. |
| 8,708,950 B2 | 4/2014 | Scarpaci et al. |
| 8,709,793 B2 | 4/2014 | Taboas et al. |
| 8,840,581 B2 | 9/2014 | McGill et al. |
| 8,870,549 B2 | 10/2014 | Tracey et al. |
| 8,968,232 B2 | 3/2015 | Kamen et al. |
| 9,005,885 B2 | 4/2015 | Ott |
| 9,022,969 B2 | 5/2015 | Helmore et al. |
| 9,078,971 B2 | 7/2015 | Scarpaci et al. |
| 9,121,403 B2 | 9/2015 | Lanigan et al. |
| 9,242,027 B2 | 1/2016 | Bellan et al. |
| 9,248,225 B2 | 2/2016 | Demers et al. |
| 9,248,233 B2 | 2/2016 | Kamen et al. |
| 9,315,043 B2 | 4/2016 | Murphy et al. |
| 9,358,332 B2 | 6/2016 | McGill et al. |
| 9,526,426 B1 | 12/2016 | Lim |
| 9,604,858 B2 | 3/2017 | Kamen et al. |
| 9,719,964 B2 | 8/2017 | Blumberg et al. |
| 9,724,458 B2 | 8/2017 | Grant et al. |
| 9,765,916 B2 | 9/2017 | Kang et al. |
| 9,957,960 B2 | 5/2018 | Lanigan et al. |
| 9,999,717 B2 | 6/2018 | van der Merwe et al. |
| 2003/0052065 A1 | 3/2003 | Rosiello |
| 2003/0215945 A1 | 11/2003 | Atala |
| 2003/0229302 A1 | 12/2003 | Robinson et al. |
| 2005/0094485 A1 | 5/2005 | Demers et al. |
| 2005/0095141 A1 | 5/2005 | Lanigan et al. |
| 2005/0095152 A1 | 5/2005 | Dale et al. |
| 2005/0095576 A1 | 5/2005 | Demers et al. |
| 2006/0195064 A1 | 8/2006 | Plahey et al. |
| 2006/0199260 A1 | 9/2006 | Zhang et al. |
| 2007/0275363 A1 | 11/2007 | Bertram et al. |

(56) References Cited

U.S. PATENT DOCUMENTS

| | | |
|---|---|---|
| 2008/0058697 A1 | 3/2008 | Kamen et al. |
| 2008/0073610 A1 | 3/2008 | Manning et al. |
| 2008/0108968 A1 | 5/2008 | Demers et al. |
| 2008/0113331 A1 | 5/2008 | Demers et al. |
| 2008/0138223 A1 | 6/2008 | Lanigan et al. |
| 2008/0175719 A1 | 7/2008 | Tracey et al. |
| 2009/0035845 A1 | 2/2009 | Galiher et al. |
| 2009/0035856 A1 | 2/2009 | Galliher et al. |
| 2009/0185920 A1 | 7/2009 | Lanigan |
| 2009/0208577 A1 | 8/2009 | Xu et al. |
| 2009/0215109 A1 | 8/2009 | Hennecke |
| 2011/0136225 A1 | 6/2011 | Vunjak-Novakovic et al. |
| 2011/0165676 A1* | 7/2011 | Hopkins ............... C12N 1/08 435/378 |
| 2011/0306931 A1 | 12/2011 | Kamen et al. |
| 2012/0064050 A1* | 3/2012 | Calle ................ A61K 35/42 424/93.21 |
| 2012/0089238 A1 | 4/2012 | Kang et al. |
| 2012/0209195 A1 | 8/2012 | Kamen et al. |
| 2012/0221025 A1 | 8/2012 | Simpson et al. |
| 2012/0250024 A1 | 10/2012 | Noda et al. |
| 2013/0143323 A1 | 6/2013 | Frost et al. |
| 2013/0144374 A1* | 6/2013 | Zilla .................. A61F 2/06 623/1.15 |
| 2013/0156744 A1 | 6/2013 | Taylor et al. |
| 2013/0344490 A1 | 12/2013 | Kim |
| 2014/0074029 A1 | 3/2014 | Kamen et al. |
| 2014/0377864 A1 | 12/2014 | Sumitran-Holgersson et al. |
| 2015/0014558 A1 | 1/2015 | Lanigan et al. |
| 2015/0050166 A1 | 2/2015 | Tracey et al. |
| 2015/0119994 A1 | 4/2015 | Kang et al. |
| 2015/0182560 A1 | 6/2015 | Calle et al. |
| 2015/0238656 A1 | 8/2015 | Orlando et al. |
| 2015/0375453 A1 | 12/2015 | Yost et al. |
| 2016/0022903 A1 | 1/2016 | Kamen et al. |
| 2016/0025544 A1 | 1/2016 | Kamen et al. |
| 2016/0030658 A1 | 2/2016 | van der Merwe et al. |
| 2016/0101227 A1 | 4/2016 | Norris et al. |
| 2016/0144114 A1 | 5/2016 | Kamen et al. |
| 2016/0239025 A1 | 8/2016 | ven der Merwe et al. |
| 2016/0245277 A1 | 8/2016 | Lanigan et al. |
| 2018/0127705 A1 | 5/2018 | Langenfeld et al. |

FOREIGN PATENT DOCUMENTS

| | | |
|---|---|---|
| EP | 0154191 | 9/1985 |
| EP | 0335378 | 10/1989 |
| FR | 2560049 | 8/1985 |
| FR | 2717919 | 3/1994 |
| WO | WO8706119 | 10/1987 |
| WO | WO9312825 | 7/1993 |
| WO | WO9408549 | 4/1994 |
| WO | WO9412235 | 6/1994 |
| WO | WO9422566 | 10/1994 |
| WO | WO9529455 | 11/1995 |
| WO | WO9613790 | 5/1996 |
| WO | WO9640328 | 12/1996 |
| WO | WO9704712 | 2/1997 |
| WO | WO9910028 | 3/1999 |
| WO | WO0118396 | 3/2001 |
| WO | WO0386509 | 10/2003 |
| WO | WO05042139 | 10/2004 |
| WO | WO05044337 | 10/2004 |
| WO | WO05044435 | 10/2004 |
| WO | WO 2005/042139 | 5/2005 |
| WO | WO 2005/044337 | 5/2005 |
| WO | WO 2005/044435 | 8/2005 |
| WO | 2007/009036 A2 | 1/2007 |
| WO | WO 2009/094179 | 7/2009 |
| WO | WO 2009/094182 | 7/2009 |
| WO | WO 2009/094183 | 7/2009 |
| WO | WO 2009/094184 | 7/2009 |
| WO | WO 2009/094185 | 7/2009 |
| WO | WO 2009/094186 | 7/2009 |
| WO | WO 2012/162515 | 11/2012 |
| WO | WO1306399 | 1/2013 |
| WO | WO 2014/110590 | 7/2014 |
| WO | WO14110590 | 7/2014 |
| WO | WO 2015/054577 | 4/2015 |
| WO | WO1554577 | 4/2015 |
| WO | WO 2015/066705 | 5/2015 |
| WO | WO1566705 | 5/2015 |
| WO | 2015/138999 A1 | 9/2015 |
| WO | WO 2015/138999 | 9/2015 |
| WO | WO 2015/183976 | 12/2015 |
| WO | WO1885832 | 5/2018 |

OTHER PUBLICATIONS

Urbano, J.J. et al., *Lung Scaffolds for Bioengineered Organ*, XXIV Congresso Brasileiro de Engenharia Biomedica—CBEB 2014, pp. 2014-2016.
Written Opinion of the International Searching Authority, PCT/US2016/056138, Int. filing date Oct. 7, 2016.
Invitation to Pay Additional Fees and, Where Applicable, Protest Fee, dated Jan. 16, 2017, received in International patent application No. PCT/US2016/056138, 7 pgs.
U.S. Appl. No. 11/787,112, filed Apr. 13, 2007, U.S. Pat. No. 7,794,141.
PCT/US2008/055000, Feb. 26, 2008, WO2008/106440.
U.S. Appl. No. 11/871,712, filed Oct. 12, 2007, U.S. Pat. No. 8,317,492.
U.S. Appl. No. 11/871,787, filed Oct. 12, 2007, 2008-0253911.
U.S. Appl. No. 11/871,793, filed Oct. 12, 2007, U.S. Pat. No. 8,888,470.
U.S. Appl. No. 11/871,803, filed Oct. 12, 2007, U.S. Pat. No. 7,967,022.
U.S. Appl. No. 11/871,821, filed Oct. 12, 2007, 2008-0240929.
U.S. Appl. No. 29/342,647, filed Aug. 28, 2009, U.S. Pat. No. D650,896.
U.S. Appl. No. 12/038,648, filed Feb. 27, 2008, U.S. Pat. No. 8,042,563.
U.S. Appl. No. 12/038,474, filed Feb. 27, 2008, U.S. Pat. No. 8,491,184.
U.S. Appl. No. 12/072,908, filed Feb. 27, 2008, U.S. Pat. No. 8,246,826.
U.S. Appl. No. 12/199,452, filed Aug. 27, 2008, U.S. Pat. No. 8,357,298.
U.S. Appl. No. 29/323,597, filed Aug. 27, 2008, U.S. Pat. No. D639,930.
U.S. Appl. No. 29/323,523, filed Aug. 27, 2008, U.S. Pat. No. D606,197.
U.S. Appl. No. 29/323,527, filed Aug. 27, 2008, U.S. Pat. No. D633,619.
U.S. Appl. No. 29/323,528, filed Aug. 27, 2008, U.S. Pat. No. D606,198.
U.S. Appl. No. 29/323,529, filed Aug. 27, 2008, U.S. Pat. No. D624,180.
U.S. Appl. No. 29/323,610, filed Aug. 27, 2008, U.S. Pat. No. D612,336.
U.S. Appl. No. 29/323,556, filed Aug. 27, 2008, U.S. Par. No. D598,109.
U.S. Appl. No. 29/323,615, filed Aug. 27, 2008, U.S. Pat. No. D636,077.
U.S. Appl. No. 12/199,055, filed Aug. 27, 2008, U.S. Pat. No. 8,393,690.
PCT/US08/011663, Oct. 10, 2008, WO2009/051669.
U.S. Appl. No. 12/199,062, filed Aug. 27, 2008, U.S. Pat. No. 8,771,508.
U.S. Appl. No. 12/199,068, filed Aug. 27, 2008, U.S. Pat. No. 8,562,834.
U.S. Appl. No. 12/199,077, filed Aug. 27, 2008, U.S. Pat. No. 9,028,691.
U.S. Appl. No. 10/751,166, filed Jan. 3, 2004, U.S. Pat. No. 7,507,169.
U.S. Appl. No. 12/199,166, filed Aug. 27, 2008, 2009-0107335.
U.S. Appl. No. 12/199,176, filed Aug. 27, 2008, 2010-0056975.

(56) References Cited

OTHER PUBLICATIONS

U.S. Appl. No. 12/198,947, filed Aug. 27, 2008, U.S. Pat. No. 8,863,772.
U.S. Appl. No. 12/199,196, filed Aug. 27, 2008, U.S. Pat. No. 8,425,471.
U.S. Appl. No. 12/864,357, filed Jul. 23, 2010, U.S. Pat. No. 9,248,225.
PCT/US2009/000440, Jan. 23, 2009, WO2009/094185.
PCT/US2009/000436, Jan. 23, 2009, WO2009/094182.
PCT/US2009/000439, Jan. 23, 2009, WO2009/094184.
PCT/US2009/000437, Jan. 23, 2009, WO2009/094183.
U.S. Appl. No. 12/864,293, filed Jul. 23, 2010, U.S. Pat. No. 9,028,400.
U.S. Appl. No. 12/864,322, filed Jul. 23, 2010, U.S. Pat. No. 8,840,581.
U.S. Appl. No. 29/340,041, filed Jul. 13, 2009, U.S. Pat. No. D613,411.
U.S. Appl. No. 12/549,285, filed Aug. 27, 2009, U.S. Pat. No. 8,409,441.
U.S. Appl. No. 29/355,297, filed Feb. 4, 2010, U.S. Pat. No. D658,130.
U.S. Appl. No. 12/730,197, filed Mar. 23, 2010, U.S. Pat. No. 8,366,316.
U.S. Appl. No. 29/375,255, filed Sep. 20, 2010, U.S. Pat. No. D640,372.
U.S. Appl. No. 12/916,021, filed Oct. 29, 2010, 2011-0105877.
U.S. Appl. No. 13/018,054, filed Jan. 31, 2011, U.S. Pat. No. 8,968,232.
U.S. Appl. No. 29/384,953, filed Feb. 7, 2011, U.S. Pat. No. D646,392.
U.S. Appl. No. 13/178,191, filed Jul. 7, 2011, U.S. Pat. No. 8,708,950.
PCT/US11/43196, Jul. 7, 2011, WO/2012/006425.
U.S. Appl. No. 13/156,282, filed Jun. 8, 2011, U.S. Pat. No. 8,459,292.
U.S. Appl. No. 13/280,274, filed Oct. 24, 2011, U.S. Pat. No. 8,499,780.
U.S. Appl. No. 13/352,250, filed Jan. 17, 2012, U.S. Pat. No. 9,649,418.
U.S. Appl. No. 14/122,166, filed Nov. 25, 2013, U.S. Pat. No. 9,724,458.
PCT/US12/39369, May 24, 2012, WO2012/162515.
U.S. Appl. No. 13/480,444, filed May 24, 2012, U.S. Pat. No. 9,717,834.
U.S. Appl. No. 13/480,454, filed May 24, 2012, U.S. Pat. No. 9,517,295.
U.S. Appl. No. 13/480,236, filed May 24, 2012, U.S. Pat. No. 9,364,655.
U.S. Appl. No. 13/569,793, filed Aug. 8, 2012, U.S. Pat. No. 8,545,698.
U.S. Appl. No. 13/569,623, filed Aug. 8, 2012, U.S. Pat. No. 8,721,884.
U.S. Appl. No. 13/619,266, filed Sep. 14, 2012, U.S. Pat. No. 8,992,075.
U.S. Appl. No. 13/619,343, filed Sep. 14, 2012, U.S. Pat. No. 8,992,189.
U.S. Appl. No. 13/624,460, filed Sep. 21, 2012, U.S. Pat. No. 9,272,082.
U.S. Appl. No. 13/657,628, filed Oct. 22, 2012, U.S. Pat. No. 8,870,549.
U.S. Appl. No. 13/667,679, filed Nov. 2, 2012, U.S. Pat. No. 9,861,732.
PCT/US12/63336, Nov. 2, 2012, WO2013/067359.
U.S. Appl. No. 13/684,995, filed Nov. 26, 2012, U.S. Pat. No. 8,926,294.
U.S. Appl. No. 13/745,730, filed Jan. 18, 2013, U.S. Pat. No. 8,721,879.
U.S. Appl. No. 13/790,974, filed Mar. 8, 2013, U.S. Pat. No. 9,539,379.
U.S. Appl. No. 13/855,620, filed Apr. 2, 2013, 2013-0304020.
U.S. Appl. No. 13/914,138, filed Jun. 10, 2013, U.S. Pat. No. 8,985,133.
U.S. Appl. No. 13/969,947, filed Aug. 19, 2013, U.S. Pat. No. 9,302,037.
U.S. Appl. No. 14/059,806, filed Oct. 22, 2013, 2014-0102958.
U.S. Appl. No. 14/213,702, filed Mar. 14, 2014, 2014-0299544.
PCT/US2014/029509, Mar. 14, 2014, WO2014/144909.
U.S. Appl. No. 14/132,838, filed Dec. 18, 2013, U.S. Pat. No. 9,597,442.
U.S. Appl. No. 14/213,578, filed Mar. 14, 2014, 2014-0199193.
U.S. Appl. No. 14/262,178, filed Apr. 25, 2014, U.S. Pat. No. 9,115,708.
U.S. Appl. No. 14/262,101, filed Apr. 25, 2014, U.S. Pat. No. 9,555,179.
U.S. Appl. No. 14/262,275, filed Apr. 25, 2014, U.S. Pat. No. 9,366,781.
U.S. Appl. No. 15/399,895, filed Jan. 6, 2017, U.S. Pat. No. 9,795,728.
U.S. Appl. No. 14/313,809, filed Jun. 24, 2014, U.S. Pat. No. 9,603,985.
U.S. Appl. No. 14/466,437, filed Aug. 22, 2014, U.S. Pat. No. 9,839,775.
U.S. Appl. No. 14/522,761, filed Oct. 24, 2014, U.S. Pat. No. 9,839,776.
U.S. Appl. No. 14/521,654, filed Oct. 23, 2014, 2015-0042366.
U.S. Appl. No. 14/525,071, filed Oct. 27, 2014, 2015-0050166.
U.S. Appl. No. 14/589,829, filed Jan. 5, 2015, U.S. Pat. No. 9,700,660.
U.S. Appl. No. 14/666,059, filed Mar. 23, 2015, U.S. Pat. No. 9,951,768.
U.S. Appl. No. 14/672,764, filed Mar. 30, 2015, U.S. Pat. No. 9,535,021.
U.S. Appl. No. 14/673,822, filed Mar. 30, 2015, U.S. Pat. No. 9,677,554.
U.S. Appl. No. 14/692,801, filed Apr. 22, 2015, U.S. Pat. No. 9,987,407.
PCT/US15/32702, May 27, 2015, WO2015/183976.
U.S. Appl. No. 14/703,674, filed May 4, 2015, U.S. Pat. No. 9,987,410.
U.S. Appl. No. 14/732,571, filed Jun. 5, 2015, U.S. Pat. No. 10,058,694.
PCT/US15/34570, Jun. 5, 2015, WO2015/188154.
U.S. Appl. No. 14/723,237, filed May 27, 2015, 2016-0058933.
PCT/US15/32711, May 27, 2015, WO2015/183981.
U.S. Appl. No. 14/798,401, filed Jul. 13, 2015, 2016-0082173.
U.S. Appl. No. 14/834,073, filed Aug. 24, 2015, 2016-0175506.
U.S. Appl. No. 15/837,182, filed Dec. 11, 2017, 2018-0104466.
U.S. Appl. No. 15/012,764, filed Feb. 1, 2016, 2016-0144093.
U.S. Appl. No. 15/056,701, filed Feb. 29, 2016, U.S. Pat. No. 9,550,018.
U.S. Appl. No. 15/181,248, filed Jun. 13, 2016, U.S. Pat. No. 10,098,996.
U.S. Appl. No. 14/620,284, filed Jun. 13, 2016, U.S. Pat. No. 9,700,711.
U.S. Appl. No. 14/626,606, filed Jun. 6, 2016, 2017-0128652.
U.S. Appl. No. 14/626,646, filed Jun. 30, 2016, 2017-0000938.
U.S. Appl. No. 14/621,587, filed Mar. 17, 2017, 2017-0268495.
U.S. Appl. No. 14/621,671, filed Dec. 21, 2016, 2017-0100533.
U.S. Appl. No. 14/942,209, filed Dec. 29, 2016, U.S. Pat. No. 10,060,867.
U.S. Appl. No. 62/298,721, filed Jan. 23, 2017, 2017-0130705.
U.S. Appl. No. 62/322,622, filed Feb. 3, 2017, 2017-0143886.
U.S. Appl. No. 15/150,723, filed Feb. 14, 2017, U.S. Pat. No. 9,981,079.
U.S. Appl. No. 62/339,723, filed Feb. 28, 2017, 2017-0326282.
PCT/US05/36797, Mar. 20, 2017, WO2006/042301.
U.S. Appl. No. 62/403,030, filed Mar. 24, 2017, 2017-0319765.
U.S. Appl. No. 15/262,535, filed Jun. 12, 2017, 2017-0342972.
U.S. Appl. No. 29/579,660, filed Jun. 29, 2017, 2017-0296803.
U.S. Appl. No. 29/579,662, filed Jun. 28, 2017, U.S. Pat. No. 10,077,766.
U.S. Appl. No. 29/579,664, filed Aug. 7, 2017, 2017-0368252.
U.S. Appl. No. 29/579,669, filed Oct. 20, 2017, 2018-0055984.

(56) References Cited

OTHER PUBLICATIONS

U.S. Appl. No. 29/579,667, filed May 8, 2018, 2018-0256803.
U.S. Appl. No. 29/579,671, filed Jun. 18, 2018, 2018-0296746.
Badrossamay et al., "Engineering hybrid polymer-protein super-aligned nanofibers via rotary jet spinning", Biomaterials 35, pp. 3188-3197, 2014.
Badrossamay et al., "Nanofiber Assembly by Rotary Jet-Spinning", Nano Lett. 10(6), pp. 2257-2261, Jun. 9, 2010.
Bajaj et al., "3D Biofabrication Strategies for Tissue Engineering and Regenerative Medicine", Annu Rev Biomed Eng. 16, pp. 247-276, Jul. 11, 2014.
Bhattacharjee et al., "Writing in the granular gel medium", Sci. Adv., pp. 1-6, Sep. 25, 2015.
Boland et al., "Tailoring Tissue Engineering Scaffolds Using Electrostatic Processing Techniques: A study of Poly(Glycolic Acid) Electrospinning", J. Macromol. Sci.—Pure Appl. Chem., A38(12), pp. 1231-1243, 2001.
Bose et al., "Bone tissue engineering using 3D printing", Materials Today, vol. 16:12, pp. 496-504, Dec. 2013.
Capulli et al., "JetValve: Rapid manufacturing of biohybrid scaffolds for biomimetic heart valve replacement", Biomaterials 133, pp. 229-241, 2017.
Cole, D.B., "An Integrated Heterodyne Interferometer with On-chip Detectors and Modulators", Dissertation, Submitted to Department of Electrical Engineering and Computer Science, MIT, 206 pp. 2015.
Deravi et al., "Design and Fabrication of Fibrous Nanomaterials Using Pull Spinning", Macrol. Mater. Eng. 1600404, pp. 1-14, 2017.
Derby, B., "Printing and Prototyping of Tissues and Scaffolds", Science 338, pp. 921, 2012.
Dunn, et al., "Gemini Interfaces in Aqueous Lubrication with Hydrogels", Tribol Lett 54, pp. 59-66, 2014.
Edmond et al., "Prevention of Mis-Prescribing in the Elderly: A Potential Use for Micro-Computers," Proceedings of the 8th Annual Symposium on Computer Applications in Medical Care, Washington, DC, USA, Nov. 4-7, pp. 357-360, 1984.
Hohman et al., "Electrospinning and electrically forced jets. Ii. Applications", Physics of Fluids, vol. 13:8, Aug. 2001.
Kunstar et al., "Label-free Raman monitoring of extracellular matrix formation in three-dimensional polymeric scaffolds", J.R. Soc. Interface, Jul. 3, 2013.
Li et al., "Recent advances in bioprinting techniques: approaches, applications and future projects", Journal of Translational Medicine 14:271, 15 pp, 2016.
Liu et al., "Rapid injection of fluorescent sensor into a cell by local mechanical stimulus using optical tweezers", Department of Micro-Nano systems Engineering, Nagoya University, 1 pp, Japan, 2014.
Manandhar et al., "Evaluation of dialysis adequacy in patients under hemodialysis and effectiveness of dialysers reuses", Nepal Med Coll J 11(2), pp. 107-112, 2009.
Marx, V., "Organs from the Lab", Nature, vol. 522, pp. 373-377, Jun. 18, 2015.
Mather et al., "Meeting the Needs of Monitoring in Tissue Engineering", Regenerative Medicine, vol. 2:2, pp. 145-160, Apr. 2007.
McCullen et al., "Nanofibrous composites for tissue engineering applications", WIREs Nanomedicine and Nanobiotechnology, vol. 1, pp. 369-390, Jul./Aug. 2009.
Meyer, U., "The History of Tissue Engineering and Regenerative Medicine in Perspective", *Fundamentals of Tissue Engineering and Regenerative Medicine*, Meyer et al., eds., Springer, ISBN: 978-3-540-77754-0, pp. 5-12, 2009.
Moliver et al., "Decision Support for Medical Treatment: A TPM Prescription System on a Central Hospital computer", Proceedings of the 11th Annual Symposium on Computer Applications in Medical Care, Washington, DC, USA, Nov. 1-4, pp. 246-254, 1987.
Murphy, S., "3D Bioprinting of Tissues and Organs", Nature Biotechnology, vol. 32:8, pp. 773-785, Aug. 2014.
Nam et al., "Imaging Strategies for Tissue Engineering Applications", Tissue Engineering: Part B, vol. 21:1, pp. 88-102, 2015.
Ntziachristos, V., "Fluorescence Molecular Imaging", Annu. Rev. Biomed. Eng. Aug. 2006, pp. 1-33, 2006.
Ogura et al., "Online Support Functions of Prescription Order System and Prescription Audit in an Integrated Hospital Information System", Med. Inform., vol. 13:3, pp. 161-169, 1988.
Ogura et al., One-line Prescription Order and Prescription Support in an Integrated Hospital Information System, Med. Inform, vol. 104, pp. 287-299, 1985.
Peeters et al., "Bioluminescence-mediated longitudinal monitoring of adipose-derived stem cells in a large mammal ex vivo organ culture", Scientific Reports, 5:13960, pp. 1-12, Sep. 9, 2015.
Persidis, A., "Tissue Engineering", Nature Biotechnology 17, pp. 508-510, 1999.
Price et al., "Automated Decellularization of Intact, Human-Sized Lungs for Tissue Engineering", Tissue Engineering: Part C, vol. 21:1, 2015.
Price et al., "Development of a Decellularizied Lung Bioreactor System for Bioengineering the Lung: The Matrix Reloaded", Tissue Engineering: Part A, vol. 16:8, 2010.
So, P. TC., "Two-photon Fluorescence Light Microscopy", Encyclopedia of Life Sciences, pp. 1-5, 2002.
Tokarev et al., "Touch- and Brush-Spinning of Nanofibers", Adv. Mater., pp. 1-7, 2015.
Twardowski, Z.J., "Dialyzer Reuse—Part II: Advantages and Disadvantages", Seminars in Dialysis, pp. 217-226, 2006.
Urbano et al., "Decellularized Lung Scaffolds for Bioengineered Organs", Med Sci tech 55:66-70, 2014.
Weymann et al., "Perfusion-Decellularization of Porcine Lung and Trachea for Respiratory Bioengineering", Artificial Organs 39(12):1024-32, Dec. 2015.
Written Opinion PCT/US2004/035952, dated Apr. 30, 2006, 11 pages.
Written Opinion PCT/US2004/035970, dated Nov. 23, 2007, 10 pages.
Written Opinion PCT/US2004/036144, dated Apr. 30, 2006, 6 pages.
Written Opinion, PCT/US2017/060389, dated May 11, 2018, 9 pages.
Xu et al., "Monitoring Tissue Engineering Using Magnetic Resonance Imaging", Journal of Bioscience and Bioengineering 106:6, pp. 515-527, 2008.
Yeo et al., "Nanosensors for Regenerative Medicine", Journal of Biomedical Nanotechnology, vol. 10, pp. 2722-2746, 2014.
U.S. Appl. No. 08/027,328, filed Mar. 3, 1993, U.S. Pat. No. 5,350,357.
U.S. Appl. No. 09/784,529, filed Feb. 2, 2001, U.S. Pat. No. 6,547,026.
U.S. Appl. No. 10/266,997, filed Oct. 8, 2002, U.S. Pat. No. 6,726,656.
U.S. Appl. No. 10/696,969, filed Oct. 30, 2003, U.S. Pat. No. 8,158,102.
PCT/US04/35970, Oct. 29, 2004, WO2005/044337.
U.S. Appl. No. 10/696,893, filed Oct. 30, 2003, U.S. Pat. No. 7,461,968.
PCT/US04/35952, Oct. 29, 2004, WO2005/044435.
U.S. Appl. No. 10/696,818, filed Oct. 30, 2003, U.S. Pat. No. 7,354,190.
PCT/US04/36144, Oct. 29, 2004, WO2005/042139.
U.S. Appl. No. 10/697,176, filed Oct. 30, 2003, US 2005-0095141.
U.S. Appl. No. 10/696,984, filed Oct. 30, 2003, US 2005-0095152.
U.S. Appl. No. 10/697,450, filed Oct. 30, 2003, U.S. Pat. No. 7,632,080.
U.S. Appl. No. 10/697,862, filed Oct. 30, 2003, U.S. Pat. No. 7,662,139.
U.S. Appl. No. 10/696,990, filed Oct. 30, 2003, U.S. Pat. No. 7,632,078.
U.S. Appl. No. 11/787,213, filed Apr. 13, 2007, US 2008-0058697.
U.S. Appl. No. 11/787,212, filed Apr. 13, 2007, U.S. Pat. No. 8,292,594.
U.S. Appl. No. 11/927,081, filed Oct. 29, 2007, US 2008-0113331.
U.S. Appl. No. 11/927,101, filed Oct. 29, 2007, U.S. Pat. No. 7,726,362.

(56) References Cited

OTHER PUBLICATIONS

U.S. Appl. No. 11/926,992, filed Oct. 29, 2007, U.S. Pat. No. 7,874,718.
U.S. Appl. No. 11/926,891, filed Oct. 29, 2007, U.S. Pat. No. 7,993,050.
U.S. Appl. No. 11/926,777, filed Oct. 29, 2007, US 2008-0138223.
U.S. Appl. No. 11/926,646, filed Oct. 29, 2007, US 2008-0108968.
U.S. Appl. No. 12/258,823, filed Oct. 27, 2008, U.S. Pat. No. 7,959,196.
U.S. Appl. No. 12/389,646, filed Feb. 20, 2009, US 2009-0185920.
U.S. Appl. No. 13/021,532, filed Feb. 4, 2011, U.S. Pat. No. 8,485,800.
U.S. Appl. No. 13/667,696, filed Nov. 2, 2012, U.S. Pat. No. 9,078,971.
U.S. Appl. No. 13/942,282, filed Jul. 15, 2013, U.S. Pat. No. 9,121,403.
U.S. Appl. No. 13/952,263, filed Jul. 26, 2013, U.S. Pat. No. 9,604,858.
U.S. Appl. No. 15/805,790, filed Nov. 7, 2017, US 2018-0127705.
PCT/US17/60389, Nov. 7, 2017, WO/2018/085832.
U.S. Appl. No. 14/341,207, filed Jul. 25, 2014, U.S. Pat. No. 9,719,964.
U.S. Appl. No. 14/967,093, filed Dec. 11, 2015, US 2016-0239025.
U.S. Appl. No. 14/723,221, filed May 27, 2015, U.S. Pat. No. 9,999,717.
U.S. Appl. No. 14/732,564, filed Jun. 5, 2015, US 2016-0101227.
U.S. Appl. No. 14/840,591, filed Aug. 31, 2015, U.S. Pat. No. 9,957,960.

* cited by examiner

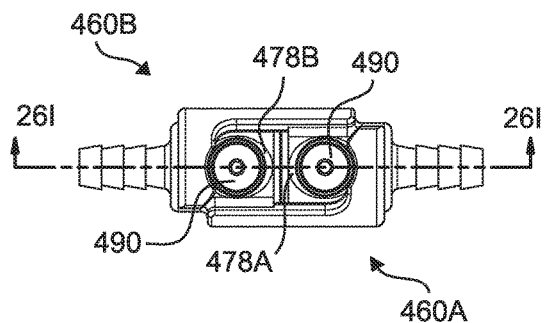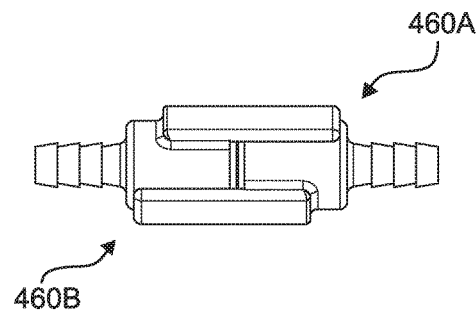
FIG. 49A    FIG. 49B
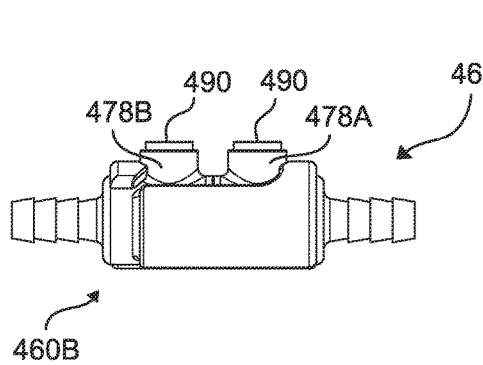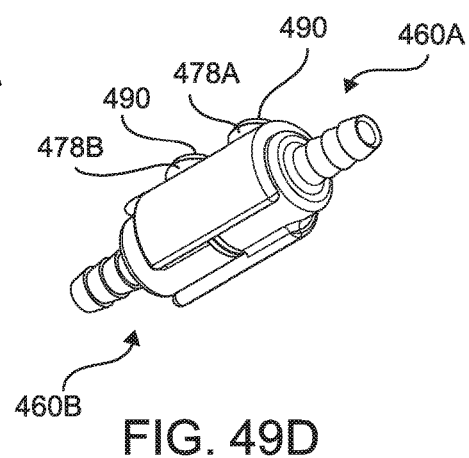
FIG. 49C    FIG. 49D
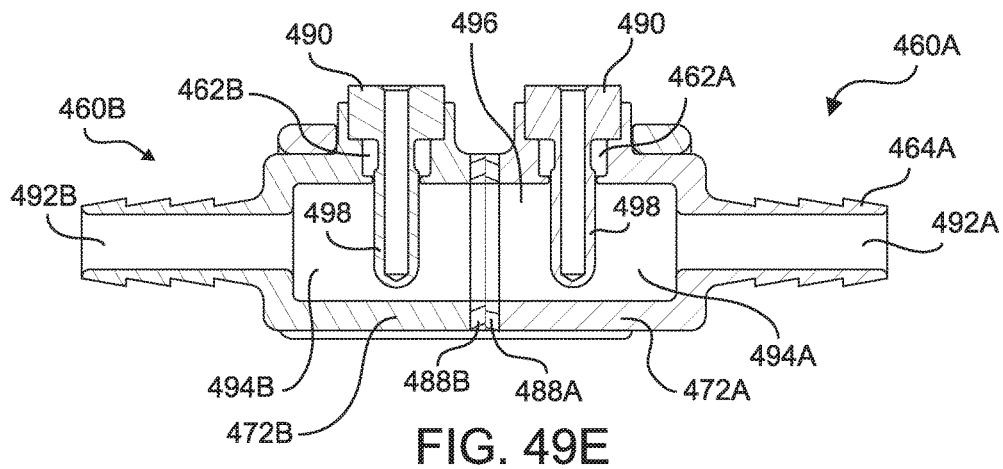
FIG. 49E

FLUID PUMPING AND BIOREACTOR SYSTEM

CROSS REFERENCE TO RELATED APPLICATIONS

This application claims the benefit of U.S. Provisional Application Ser. No. 62/246,191 filed Oct. 26, 2015, entitled Fluid Pumping and Bioreactor Set, U.S. Provisional Application Ser. No. 62/239,793 filed Oct. 9, 2015, entitled Tissue Engineering System and Method, and U.S. Provisional Application Ser. No. 62/266,548 filed Dec. 11, 2015, entitled Fluid Pumping and Bioreactor System, which are incorporated herein by reference in their entirety.

BACKGROUND

The present teachings relate to a set of components that enable fluid delivery, and specifically to selectively pumping fluid through a variety of fluid flow pathways to achieve, for example, but not limited to, specimen engineering.

According to the United States Department of Health and Human Services, there were approximately 125,000 individuals in the U.S. alone awaiting organ transplant as of early July 2015. Wait times vary by organ, but substantial percentages (and in some cases the majority) of individuals must wait for years before a needed organ may become available. As of July 2015, it was projected that about 15% of these individuals should expect to wait for a period of five years or longer. Over this waiting period, among other concerns, individuals may be subjected to reduced quality of life, disruptive and demanding medical treatments, and increased mortality rate.

Even after an individual receives a transplant, risks and burdens for the individual still exist. Transplantation may be coupled with the possibility of rejection. To help prevent this, medications are required to suppress the immune system for the rest of the individual's lifetime. Rejection may still occur and suppression of the immune system comes with its own suite of concerns.

The sciences of specimen engineering and regenerative medicine present possible solutions which may alleviate such waitlists and problems. One promising technology is the process of decellularization and subsequent recellularization of a specimen or group of specimens to create compatible specimens for transplant. A biological specimen may be a grouping of cells and the associated extra cellular matrix including, but not limited to a tissue, group of tissues, organ, organ system, or group of organs. With this technology the potential exists, e.g., for an organ which is compatible with a patient's immune system to be processed on demand into a transplant for the patient.

In general, a specimen or group of specimens such as an organ may be decellularized, ex vivo, with a number of fluids, enzymes, and chemicals. These may include biological grade detergents which can lyse cells. Cellular remains may then be carried away. Left behind is an extracellular matrix which may serve as a scaffold that may be recellularized with new cells that may be compatible with the target patient. The recellularized extracellular matrix scaffold may be a viable specimen or organ which can then be transplanted into a patient. The term, ex vivo, is defined herein to refer to activities that occur outside of a body and is inclusive of the term in vitro.

This technology is still, however, maturing and many needs which would allow the benefits of the technology to be realized have yet to be met. Currently, a need exists for a system and process which allow decellularization/recellularization procedures to be performed on a large scale with speed, efficiency, precision, repeatability, versatility, and flexibility. Additionally, a need exists for a system which is simple to set up and configure and requires little to no maintenance/cleaning. These needs may be at least partially met by a potentially disposable or durable system including a sealable enclosure or container for the target specimen or group of specimens.

SUMMARY

The needs set forth herein as well as further needs and advantages are addressed by the present examples, which illustrate solutions and advantages described below.

A fluid pumping system can include, but is not limited to including, a fluid handling set including a cassette having a body and a sheet covering a pumping chamber and a plurality of fluid valves associated with the cassette, a controller, and a manifold including a plurality of modules. Each of the plurality of modules can include, but is not limited to including, a pneumatic block including a plurality of pressure supply lines and a plurality of module valves. The plurality of module valves can be in communication with the plurality of pressure supply lines and a plurality of fluid outlets. The plurality of pressure supply lines and the plurality of fluid outlets can be associated with each of the plurality of module valves. At least one of the plurality of fluid outlets can be in communication with the sheet. Each of the plurality of modules can also include a plurality of module control boards. At least one of the plurality of module control boards can receive a first command from the main controller. At least one of the plurality of module control boards can generate, based on the first command, at least one module command addressed to at least one recipient module of the plurality of modules. The at least one recipient module control board can be associated with the at least one recipient module that can receive the at least one module command. The at least one recipient module control board can generate, based on the at least one module command, a plurality of valve commands enabling flow to the plurality of fluid valves of the at least one recipient module. The plurality of valve commands can toggle positions of the plurality of fluid valves. The plurality of valve commands can selectively apply pressure to the flexible sheet via the fluid outlets.

The valves can optionally include bi-stable valves. Each of the plurality of modules can optionally be coupled to at least one other module of the plurality of modules. The pressure supply lines of each of the plurality of modules can optionally be in fluid communication with the pressure supply lines of other of the plurality of modules. The control board of each module can optionally generate feedback data on a predetermined schedule.

A fluid pumping system for a tissue engineering system can include, but is not limited to including, a fluid handling set including a plurality of pneumatically-controlled fluid-pumping cassettes, a main controller, and a manifold including a plurality of pneumatic valve modules. The plurality of pneumatic valve modules can share a plurality of pressure buses. Each of the plurality of pneumatic valve modules can include a plurality of valves. Each of the plurality of valves can have an outlet in pneumatic communication with an associated cassette of the plurality of pneumatically-controlled fluid-pumping cassettes. Each of the plurality of valves can have at least one inlet in communication with a pressure bus of the plurality of pressure buses. Each of the pneumatic valve modules can include a control board configured to command actuation of the plurality of valves to selectively supply pressure to the associated cassette. The pressure can pump fluid through the fluid handling set. The control board can receive a main controller command from the main controller.

Each of the modules can optionally include a portion of each of the plurality of pressures buses. The plurality of pressure buses can be formed when at least one of the plurality pneumatic valve modules is coupled to at least another of the plurality of pneumatic valve modules. The fluid handling set can optionally include three pumping cassettes. A first cassette of the plurality of pneumatically-controlled fluid-pumping cassettes can optionally include a plurality of source ports, a plurality of outlet ports in communication with at least one storage reservoir, a second cassette of the plurality of pneumatically-controlled fluid-pumping cassettes including a plurality of inlet ports in communication with the at least one storage reservoir and a plurality of outlet ports in communication with a bioreactor, and a third cassette of the plurality of pneumatically-controlled fluid-pumping cassettes including a plurality of inlet ports in communication with the at least one storage reservoir and a plurality of outlet ports in communication with a bioreactor. The fluid pumping system can optionally include a communications bus enabling communications among the plurality of pneumatic valve modules formed as at least one of the plurality of pneumatic valve modules is coupled to at least another of the plurality of pneumatic valve modules.

A fluid pumping system can include, but is not limited to including, a pneumatically driven first pumping cassette and at least one pneumatically driven second cassette. The fluid pumping system can also include a storage reservoir, the storage reservoir being connected to the first pumping cassette by at least a first fluid line. The storage reservoir can be connected to the at least one second cassette by at least a second fluid line. The fluid pumping system can still further include a bioreactor configured to house a biological specimen. The bioreactor can be in fluid communication with each of the at least one second cassette. The fluid pumping system can also include a manifold. The manifold can include, but is not limited to including, a plurality of valve modules. The plurality of valve modules can be coupled together to form a plurality of pressure supply buses, a communication bus, and a power bus. Each of the valve modules can include a plurality of valves. Each of the valve modules can include a control board. The fluid pumping system can still further include a main controller configured to generate a main controller command directed to the manifold. At least one of the control boards can be configured to receive the main controller command. At least one of the control boards can be configured to send module commands over the communications bus to recipient modules of the valve modules. The recipient modules can actuate, based on the module commands, the plurality of valves associated with the recipient module. The actuating can effect pumping of fluid by the first pumping cassette and the at least one second cassette.

The communications bus can optionally include a CAN-bus. The main controller can optionally be configured to generate and send a role command for each of the plurality of valve modules. Each of the role commands can optionally be sent to one of the recipient modules over the communications bus. The role command can optionally specify a valve configuration for each of the plurality of valves of the one of the recipient modules. The control board of the one of the recipient modules can optionally be configured to alter a valve setting for each of the plurality of valves associated with the one of the recipient modules based on the role command. The valve setting for each of the recipient module valves can optionally be a default setting. The default setting can optionally be modifiable by the role command. Each of the control boards can optionally be configured to generate valve state data. The control boards can optionally send the valve state data over the communications bus. The valve state data can optionally be generated each time a valve is actuated. Each of the control boards can optionally be configured to generate feedback data on a predetermined schedule. The control boards can optionally send the feedback data over the communications bus. The predetermined schedule can optionally be periodic, for example, but not limited to, every 100 ms. The feedback data can optionally include a pressure data signal generated by a pressure sensor. The pressure sensor can optionally be associated with the control board.

A system for engineering a tissue can include, but is not limited to including, at least one cassette having a flexible sheet covering at least one pumping chamber, the flexible sheet covering at least one cassette fluid valve. The system can also include a bioreactor housing the tissue. The bioreactor can be in fluid communication with the at least one cassette. The system can further include a controller and at least one module. Each at least one module can have at least one pressure bus and at least one valve, where the valve is in communication with the pressure bus. Each at least one module can have an outlet port associated with each or the valves. The outlet port can be in communication with the flexible sheet. The at least one module can include a first module having a first module processor. The first module processor can receive at least one controller command from the controller and can generate, based on the controller command, at least one second module command addressed to at least one second module. The at least one second module can have a second module processor that can receive the at least one second module command and can generate, based on the at least second module command, at least one valve command. The at least one valve command can govern fluid flow through the at least one valve of the at least one second module. The at least one valve can control pressure applied to the flexible sheet via the outlet ports. The tissue and the bioreactor can receive the fluid flow metered based on the at least one controller command. The tissue can be decellularized based on the fluid flow.

A fluid pumping system for engineering a tissue can include, but is not limited to including, a plurality of fluid pumping cassettes. The fluid pumping cassettes can be pneumatically controlled. The fluid pumping system can also include a bioreactor housing the tissue. The bioreactor can be in fluid communication with at least one of the plurality of fluid pumping cassettes. The fluid pumping system can still further include a controller and a plurality of pneumatic valve modules sharing a plurality of pressure buses. Each of the plurality of pneumatic valve modules can include a plurality of valves. Each of the plurality of valves can have a valve outlet port. The valve outlet port can be in pneumatic communication with at least one of the plurality of fluid pumping cassettes. The valve outlet port can be in selective pneumatic communication with at least valve one inlet. The at least one valve inlet can be in communication with at least one of the plurality of pressure buses. Each of the plurality of pneumatic valve modules can include a control board that can receive at least one controller command from the controller. The control board can command, according to the at least one controller command, actuation of the valves of each of the plurality of pneumatic valve modules. The actuation can selectively supply pressure to the associated cassette. The pressure can establish a fluid pathway within the associated cassette.

A fluid pumping system can include, but is not limited to including, a pneumatically driven first cassette and at least one pneumatically driven second cassette. The fluid pumping system can also include a storage reservoir in fluid communication with the first cassette and the at least one second cassette and a controller generating at least one command. The fluid pumping system can still further include a bioreactor housing a biological specimen. The bioreactor can be in fluid communication with the at least one second cassette. The fluid pumping system can also include a manifold. The manifold can include, but is not limited to including, a plurality of valve modules. Each of the valve modules can include, but is not limited to including, a plurality of valves, a control board, a communication bus enabling data communication among the plurality of valve modules, and a plurality of pressure buses distributing a plurality of pressures to the plurality of valve modules. The at least one valve module of the plurality of valve modules can receive the at least one command. The control board of the at least one valve module can send module commands over the communications bus to at least one recipient module of the plurality of valve modules. The plurality of valves of the recipient module can be actuated based on the module commands. The actuation can enable pumping of fluid by the first cassette and the second cassette. The fluid can be a tissue engineering agent.

The manifold can optionally include a power bus providing power to the plurality of valve modules. The pumping of the fluid by the second cassette can optionally deliver at least one decellularization agent to the biological specimen. The pumping can optionally be in accordance with a predetermined schedule. The pumping of the fluid can optionally deliver at least one recellularization agent to the biological specimen. The pumping can optionally be in accordance with the predetermined schedule.

A method for engineering a tissue can include, but is not limited to including, covering at least one pumping chamber and at least one fluid valve of at least one cassette with a flexible sheet, housing the tissue in a bioreactor, the bioreactor being in fluid communication with the at least one cassette, receiving, by at least one module processor, at least one controller command from a controller, generating, by the at least one module processor, at least one module command based on the controller command, the at least one module command being addressed to at least one recipient module, receiving, by the at least one recipient module, the at least one module command, and generating, by the at least one recipient module, a plurality of valve commands based on the at least one module command. The plurality of valve commands can govern fluid flow through the plurality of valves of the at least one recipient module. The at least one valve controlling pressure applied to the flexible sheet via the outlet ports. The method can further include decellularizing the tissue using the fluid flow metered based on the at least one controller command.

A system for mixing solutions for engineering a tissue and providing mixed solutions to the tissue can include, but is not limited to including, a fluid handling set. The fluid handling set can include, but is not limited to including, a plurality of pumping cassettes and at least one storage reservoir. The pumping cassettes can pump the fluid. The system can also include at least one mixing cassette. The at least one mixing cassette can mix the solutions. The at least one mixing cassette can be in fluid communication with at least one storage reservoir and can supply the solutions to at least one storage reservoir. The plurality of pumping cassettes can be in communication with the at least one storage reservoir. The system can still further include a bioreactor housing the tissue. The bioreactor can be in fluid communication with at least one of the plurality of pumping cassettes. The system can also include a controller and a plurality of pneumatic valve modules sharing a plurality of pressure buses. Each of the plurality of pneumatic valve modules can include, but is not limited to including, a plurality of valves. Each of the plurality of valves can include, but is not limited to including, an outlet port. The outlet port can be in pneumatic communication with at least one of the at least one mixing cassette and the plurality of pumping cassettes. Each of the plurality of valves can also include at least one inlet that can be in communication with at least one of the plurality of pressure buses. The at least one inlet can be in selective pneumatic communication with the outlet port. Each of the plurality of pneumatic valve modules can include, but is not limited to including, a control board receiving at least one controller command from the controller. The control board can command, according to the at least one controller command, actuation of at least one of the plurality of pneumatic valve modules. The actuation can selectively supply pressure to at least one of the at least one mixing cassette and the plurality of pumping cassettes. The pressure can establish a fluid pathway in the at least one of the at least one mixing cassette and the plurality of pumping cassettes.

The plurality of pumping cassettes can optionally include pneumatically controlled cassettes. At least one of the mixing cassette and the plurality of pumping cassettes can optionally be a disposable cassette.

An automated system for mixing solutions to engineer a tissue can include, but is not limited to including, a plurality of solutions and at least one mixing cassette. The at least one mixing cassette can mix selected of the plurality of solutions. The at least one mixing cassette can be in fluid communication with the plurality of solutions. The automated system can also include a bioreactor housing the tissue. The bioreactor can be in fluid communication with at least one of a plurality of bioreactor cassettes. The automated system can still further include a controller and a plurality of pneumatic valve modules sharing a plurality of pressure buses. Each of the plurality of pneumatic valve modules can include, but is not limited to including, a plurality of valves. Each of the plurality of valves can include, but is not limited to including, an outlet port. The outlet port can be in pneumatic communication with at least one of the at least one mixing cassette and the plurality of bioreactor cassettes. Each of the plurality of valves can also include at least one inlet being in communication with at least one of the plurality of pressure buses. The at least one inlet can be in selective pneumatic communication with the outlet port. Each of the plurality of pneumatic valve modules can include, but is not limited to including, a control board receiving at least one controller command from the controller. The control board can command, according to the at least one controller command, actuation of the valves of the one of the pneumatic valve modules. The actuation can selectively supply pressure to at least one of the at least one mixing cassette and the plurality of pumping cassettes. The pressure can establish a fluid pathway in the at least one of the at least one mixing cassette and the plurality of pumping cassettes.

An automated system for recellularizing decellularized tissue can include, but is not limited to including, at least one cassette having a flexible sheet covering at least one pumping chamber. The flexible sheet can cover at least one fluid valve. The automated system can also include a bioreactor housing the tissue. The bioreactor can be in fluid communication with the at least one cassette. The automated system can still further include a controller, at least one first module, and at least one second module. Each of the at least one first and second modules can include, but is not limited to including, at least one pressure bus and at least one valve. The at least one valve can be in communication with the at least one pressure bus. Each of the at least one first and second modules can include, but is not limited to including, an outlet port associated with each of the at least one valves. The outlet port can be in communication with the flexible sheeting. The automated system can still further include a processor. The first module can include a first module processor receiving at least one controller command from the controller. The first module processor can generate, based on the controller command, at least one module command addressed to the at least second module. The at least second module can include a second module processor that can receive the at least one second module command and can generate, based on the at least one second module command, a plurality of valve commands. The plurality of valve commands can govern fluid flow through the at least plurality of valves of the at least one second module. The at least one valve can control pressure applied to the flexible sheet via the outlet ports. The tissue can receive the fluid flow metered based on the at least one controller command. The tissue can be recellularized based on the fluid flow.

In some configurations of the present disclosure, a method for generating a tissue for transplant may include, but is not limited to including, iteratively decellularizing and recellularizing a supplied tissue. In some configurations, the method may include preparing the supplied tissue by decellularizing the supplied tissue a plurality of times. In some configurations, the method may include refining the tissue for transplant by decellularizing the iteratively decellularized and recellularized supplied tissue a plurality of times. In some configurations, the method may include introducing at least one agent to the supplied tissue, removing an undesired component of the supplied tissue with the at least one agent, and rinsing the supplied tissue. In some configurations, rinsing the supplied tissue may include rinsing the supplied tissue with an isotonic solution. In some configurations, rinsing the supplied tissue may include rinsing the supplied tissue with phosphate buffered solution. In some configurations, the at least one agent can include, but is not limited to including, a detergent, a Triton series detergent, sodium dodecyl sulfate, peracetic acid, ethanol, an enzyme solution, a nuclease, DNase, RNase, protease inhibitors, water, purified water, deionized water, and distilled water. In some configurations, the method may include freezing the supplied tissue. In some configurations, the method may include alternately freezing and thawing the supplied tissue. In some configurations, the method may include introducing endothelial cells, epithelial cells, clara cells, goblet cells, alveolar type I cells, alveolar type II cells to the decellularized supplied tissue. In some configurations, the method may include introducing a cell culture to the decellularized supplied tissue. In some configurations, the method may include introducing stem cells or cells of at least one tissue specific phenotype to the decellularized supplied tissue.

In accordance with another configuration of the present disclosure, a method for creating a transplantable lung from a donor lung may include, but is not limited to including, decellularizing the donor lung. The method may further include recellularizing the decellularized donor lung. The method may further include decellularizing the recellularized donor lung. The method may further include creating the transplantable lung by recellularizing the decellularized recellularized donor lung. In some configurations, the donor lung may include a lung that is from a different species than the intended recipient. In some configurations, recellularizing the donor lung may include recellularizing the donor lung with cells from the intended recipient.

In accordance with another configuration of the present disclosure, a method for creating a transplantable tissue from a donor tissue may include, but is not limited to including, decellularizing the donor tissue. The method may further include recellularizing the donor tissue. The method may further include repeating decellularization and recellularization of the donor tissue until a predefined number of iterations have been completed.

In accordance with another configuration of the present disclosure, a method for iteratively decellularizing and recellularizing a donor tissue to generate a transplantable tissue may include decellularizing the donor tissue a first predefined number of times. The first predefined number of times may be set or predetermined for each iteration of a predefined number of iterations. The method may further include recellularizing the donor tissue a second predefined number of times. The second predefined number of times may be set or predetermined for each iteration of the predefined number of iterations. The method may further include repeating decellularization and recellularization until the predefined number of iterations have been completed.

In accordance with another configuration of the present disclosure, a method for creating a transplantable tissue from a donor tissue may include, but is not limited to including, decellularizing the donor tissue with a first decellularization protocol. The method may further include recellularizing the donor tissue with a first recellularization protocol. The method may further include decellularizing the donor tissue with a second decellularization protocol. The method may further include recellularizing the donor tissue with a second recellularization protocol. In some configurations, the method may include decellularizing the donor tissue with a first decellularization protocol, recellularizing the donor tissue with a first recellularization protocol, decellularizing the donor tissue with a second decellularization protocol, recellularizing the donor tissue with a second recellularization protocol, and repeating for a predefined number of iterations.

In accordance with another configuration of the present disclosure, a method for creating a transplantable tissue form a donor tissue may include, but is not limited to including, repetitively decellularizing the donor tissue until a predefined number of decellularization cycles are complete. The method may further include repetitively recellularizing the donor tissue until a predefined number of recellularization cycles are complete. The method may further include repeating repetitively decellularizing and repetitively recellularizing until a predefined number of method iterations have been completed. In some configurations, each cycle of the predefined number of decellularization cycles may include using a different decellularization protocol. In some configurations, each cycle of the predefined number of recellularization cycles may include using a different recellularization protocol. In some configurations, the donor tissue may include, but is not limited to including, at least one lung. In some configurations the donor tissue may be a lung. In some configurations, the donor tissue may include at least a part of a pulmonary circuit. In some configurations, the donor tissue may include at least a part of an excretory system. In some configurations, the donor tissue may include at least a part of a circulatory system. In some configurations, the donor tissue may include a kidney, bladder, ureter, urethrea, heart, ear, liver, trachea, or circulatory vessel.

In accordance with another configuration of the present disclosure, a method for creating a transplantable tissue from a donor tissue may include, but is not limited to including, decellularizing the donor tissue. The method may further include determining if a predefined number of decellularization cycles have been completed and repeating decellularizing the donor tissue if the number of decellularization cycles performed is below the predefined number of decellularization cycles. The method may further include recellularizing the donor tissue. The method may further include determining if a predefined number of recellularization cycles have been completed and repeating recellularizing the donor tissue if the number of recellularization cycles performed is below the predefined number of decellularization cycles.

In accordance with another configuration of the present disclosure, a method for creating a transplantable tissue from a donor tissue may include, but is not limited to including, iteratively decellularizing and recellularizing a supplied tissue for a number of iterations. Each iteration of the number of iterations may include decellularizing the donor tissue. Each iteration of the number of iterations may include determining if a predefined number of decellularization cycles have been completed and repeating decellularizing the donor tissue if the number of decellularization cycles performed is below the predefined number of decellularization cycles. Each iteration of the number of iterations may include, but is not limited to including, recellularizing the donor tissue. Each iteration of the number of iterations may include, but is not limited to including, determining if a predefined number of recellularization cycles have been completed and repeating recellularizing the donor tissue if the number of recellularization cycles performed is below the predefined number of decellularization cycles. In some configurations, a different decellularization protocol may be used in each iteration. In some configurations, at least one different decellularization protocol may be used in each iteration. In some configurations, a different recellularization protocol may be used in each iteration. In some configurations, at least one different recellularization protocol may be used in each iteration. In some configurations, the decellularization protocol may remain constant in each iteration. In some configurations, the recellularization protocol may remain constant in each iteration. In some configurations, the decellularization protocol may remain constant in each iteration while the recellularization protocol differs in at least one iteration. In some configurations, the decellularization protocol may remain constant in each iteration while a different recellularization protocol is used in each iteration. In some configurations, the recellularization protocol may remain constant in each iteration and the decellularization protocol while the decellularization protocol differs in at least one iteration. In some configurations, the recellularization protocol may remain constant in each iteration while the decellularization protocol differs in each iteration. In some configurations, the method may further include recellularizing with a first recellularization protocol and a second recellularization protocol in alternating fashion. In some configurations, the method may further include decellularizing with a first decellularization protocol and a second decellularization protocol in alternating fashion. In some configurations, the predefined number of decellularization cycles in at least one cycle can be greater than one. In some configurations, the predefined number of recellularization cycles in at least one cycle can be greater than one. In some configurations, the method may further include decellularizing with at least a first decellularization protocol at least once in the number of iterations and a second decellularization protocol at least once in the number of iterations. In some configurations, the first decellularization protocol and second decellularization protocol may include using at least one different agent. In some configurations, the first decellularization protocol and second decellularization protocol may differ in at least one temporal parameter. In some configurations, the method may further include recellularizing with at least a first recellularization protocol at least once in the number of iterations and a second recellularization protocol at least once in the number of iterations. In some configurations, the first recellularization protocol and second recellularization protocol may use at least one different agent. In some configurations, the first recellularization protocol and second recellularization protocol may differ in at least one temporal parameter. In some configurations, the method may further include decellularizing with a plurality of different decellularization protocols and recellularizing with a plurality of different recellularization protocols. Each of the plurality of different decellularization protocols and plurality of recellularization protocols may be scheduled for use in an iteration of the number of iterations. In some configurations, the method may further include decellularizing with a plurality of different decellularization protocols and recellularizing with a plurality of different recellularization protocols. The decellularization protocol may be altered at a first rate and the recellularization protocol may be altered at a second rate. In some configurations, the first rate can be greater than the second rate. In some configurations, the first rate can be less than the second rate.

The system of the present teachings for generating a tissue for transplant can include, but is not limited to including, at least one pump chamber, at least one pressure supplier and power supplier, at least one fluid supply, at least one fluid pathway opened and closed by at least one valve, at least one tissue enclosure housing the tissue, and at least one sensor sensing at least the characteristics of the fluid supplies. The at least one sensor can sense at least pressure and power from the pressure power supplies. The system can further include a user interface receiving fluid control data, and at least one computer controller. The computer controller can manage the at least one pressure and power supplier to actuate the at least one the pump chamber to pump the at least one fluid supply into and out of the at least one pump chamber based on a first schedule. The computer controller can also manage the sensor data from the at least one sensor, and manage the fluid control data. The computer controller can also manage opening and closing the at least one valve to enable or disable fluid flow through the at least one fluid pathway based on a second schedule, the sensor data, and the fluid control data. The computer controller can also manage iteratively alternating decellularization and recellularization of the tissue with the at least one fluid supply based on the first schedule, the second schedule, the fluid control data, and the sensor data.

The computer controller can optionally manage decellularizing the tissue a plurality of consecutive times, and decellularizing the iteratively decellularized and recellularized tissue a plurality of times. The computer controller can manage decellularizing by introducing at least one agent to the supplied tissue, removing an undesired component of the supplied tissue with the at least one agent, and rinsing the supplied tissue with at least one rinsing agent. The at least one rinsing agent can optionally be, for example, but not limited to, an isotonic solution and a phosphate buffered solution. The at least one agent can optionally be, but is not limited to being, any of a detergent, a Triton series detergent, sodium dodecyl sulfate, peracetic acid, ethanol detergent, Triton series detergent, sodium dodecyl sulfate, peracetic acid, ethanol, an enzyme solution, a nuclease, DNase, RNase, protease inhibitors, water, purified water, deionized water, and distilled water. The computer controller can optionally manage the decellularizing by managing freezing the supplied tissue and manage the decellularizing by managing alternately freezing and thawing the supplied tissue. The at least one computer controller can optionally manage recellularizing by managing introducing a cell culture to the decellularized supplied tissue. The computer controller can optionally manage the recellularizing by managing introducing endothelial cells, epithelial cells, ciliated cells, clara cells, goblet cells, alveolar type I, and/or alveolar type II cells to the decellularized supplied tissue. The computer controller can optionally manage the recellularizing by managing introducing stem cells or cells of at least one tissue specific phenotype to the decellularized supplied tissue. The second schedule may be dynamically determined based on the first schedule.

In accordance with another configuration of the present disclosure, a system for engineering a tissue can include, but is not limited to including, at least one cassette having a flexible sheet covering at least one pumping chamber, the flexible sheet covering at least one cassette fluid valve, a bioreactor housing the tissue, the bioreactor being in fluid communication with the at least one cassette, a controller generating at least one controller command, and at least one valve module, each of the at least one valve modules, having at least one pressure bus, each of the at least one valve modules having at least one valve operably communicating with the pressure bus, each of the at least one valve modules having an outlet port, the outlet port being associated with each of the at least one valves, the outlet port operably communicating with the flexible sheet, the at least one valve module including a first module having a first module processor, the first module processor receiving the at least one controller command, the first module processor generating, based on the controller command, at least one second module command addressed to at least one second module, the at least one second module having a second module processor receiving the at least one second module command and generating, based on the at least second module command, at least one valve command governing fluid flow through the at least one valve of the at least one second module, the at least one valve controlling pressure applied to the flexible sheet via the outlet ports, the at least one controller command metering the fluid flow to the tissue and the bioreactor, the tissue being decellularized based on the fluid flow.

In accordance with another configuration of the present disclosure, an automated system for recellularizing decellularized tissue can include, but is not limited to including, at least one cassette having a flexible sheet covering at least one pumping chamber, the flexible sheet covering at least one fluid valve, a bioreactor housing the tissue, the bioreactor being in fluid communication with the at least one cassette, a controller generating at least one controller command, and at least one first valve module and at least one second valve module, each of the at least one first and second valve modules having at least one pressure bus and at least one valve, the at least one valve operably communicating with the pressure bus, each of the at least one valves being associated with an outlet port, the outlet port operably communicating with the flexible sheeting, the first valve module having a first module processor, the first module processor receiving the at least one controller command, the first module processor generating, based on the controller command, at least one module command addressed to the at least second module, the at least second module having a second module processor receiving the at least one second module command and generating, based on the at least one second module command, a plurality of valve commands, the plurality of valve commands governing fluid flow through the at least one valve of the at least one second valve module, the at least one valve controlling pressure applied to the flexible sheet via the outlet ports, the at least one controller command metering the fluid flow to the tissue, the tissue being recellularized based on the fluid flow.

In accordance with another configuration of the present disclosure, a system for engineering a transplantable tissue from a donor tissue can include, but is not limited to including, a recipe including recipe steps, a graphical user interface (GUI) receiving GUI input, and a controller accessing the recipe steps, the GUI input, and at least one default value, the controller forming directions based on arbitrating the at least one default value, the recipe steps, and the GUI input, the controller executing the directions to engineer the transplantable tissue from the donor tissue. The controller can optionally include updating the GUI and updating the recipe.

In accordance with another configuration of the present disclosure, a method for decellularizing tissue can include, but is not limited to including, configuring at least one valve in a fluid path according to a recipe, continually adjusting the fluid path by manipulating the at least one valve based on the recipe, pumping water through the continually-adjusted fluid path past at least one of the at least one valve to a mix cassette, the amount of the water being based on the recipe, pumping at least one solution through the continually-adjusted fluid path past at least one of the at least one valve to the mix cassette, the amount of the at least one solution being based on the recipe, mixing the water and the at least one solution in the mix cassette to form a medium, the amount of the mixing being based on the recipe, pumping the medium through the continually-adjusted fluid path to a reservoir based on the recipe, pumping the medium through the continually-adjusted fluid path from the reservoir to a bioreactor based on the recipe, the medium becoming a used medium in the bioreactor, and pumping the used medium through the continually-adjusted fluid path from the bioreactor to a drain based on the recipe. The water can optionally include deionized water. The method can optionally include filtering the water, deaerating the water, and if the amount of the water exceeds a pre-selected threshold, storing at least part of the water. The at least one solution can optionally include concentrated solution.

In accordance with another configuration of the present disclosure, a set for decellularizing tissue can include, but is not limited to including, at least one reservoir including a plurality of ports, the plurality of ports including at least one mix port and at least one pump port, at least one bioreactor including at least one bioreactor port, at least one pump cassette, the pump cassette including at least one pump, at least one reservoir port fluidically connecting the at least one pump cassette to the at least one reservoir at the at least one pump port, the at least one pump cassette including at least one bioreactor interface port fluidically connecting the at least one pump cassette to the at least one bioreactor at the at least one bioreactor port, the at least one pump cassette including at least one first fluid bus and at least one pump cassette valve, the at least one pump cassette valve managing the routing of a first fluid from the at least one reservoir through the at least one pump to the at least one bioreactor interface port, at least one mix cassette including at least one dilution port, the at least one dilution port fluidically coupling the at least one mix cassette with a medium, the at least one mix cassette include at least one reservoir port fluidically coupling the at least one mix cassette with the at least one reservoir, the at least one mix cassette including at least one solution port fluidically coupling the at least one mix cassette with at least one second fluid, the at least one mix cassette including at least one mix pump, the at least one mix cassette including at least one second fluid bus, the at least one mix cassette including at least one mix cassette valve managing the routing of the at least one second fluid from the at least one solution port through the at least one mix pump to the at least one reservoir port, and tubing enabling the fluidic connections at least among the at least one first fluid bus and the at least one second fluid bus. The at least one reservoir can optionally include at least one vent port, at least one overflow port, and at least one level sensor. The at least one pump cassette can optionally include at least one waste port fluidically coupling the at least one pump cassette to at least one waste receptacle. The at least one pump cassette can optionally include at least one loop line port enabling heating of a fluid circulating in the at least one pump cassette. The at least one first fluid bus and the at least one pump cassette valve can optionally manage flow from the at least one reservoir through the at least one loop line port. The at least one bioreactor can optionally include an adapter including a first face and an second face opposing the first face, an enclosure including a first section and a second section, the first section including a first side and a second side, the enclosure including a liquid-tight seal between the first section and the first face, the enclosure including at least one enclosure pass-through, the enclosure including a liquid-tight seal between at least a portion of the second section and at least a portion of the first section, a first fluid line operably coupled to the adapter, the first fluid line coupling the at least one enclosure pass-through and the adapter, and a second fluid line disposed on the second face, the second fluid line fluidically coupled with the first fluid line, the first fluid line coupled with the second fluid line forming a closed fluid path.

In accordance with another configuration of the present disclosure, a method for engineering a tissue can include, but is not limited to including, covering at least one pumping chamber and at least one fluid valve of at least one cassette with a flexible sheet, housing the tissue in a bioreactor, the bioreactor being in fluid communication with the at least one cassette, receiving, by at least one module processor, at least one controller command from a controller, generating, by the at least one module processor, at least one module command based on the controller command, the at least one module command being addressed to at least one module, receiving, by the at least one module, the at least one module command, generating, by the at least one module, a plurality of valve commands based on the at least one module command, the plurality of valve commands governing fluid flow through a plurality of valves of the at least one module, the at least one fluid valve controlling pressure applied to the flexible sheet via the outlet ports, and decellularizing the tissue using the fluid flow metered based on the at least one controller command. The plurality of pumping cassettes can optionally include pneumatically controlled cassettes. The at least one of mixing cassette and the plurality of pumping cassettes can optionally include disposable cassettes.

In accordance with another configuration of the present disclosure, a method for generating a tissue for transplant can include, but is not limited to including, iteratively decellularizing and recellularizing a biological specimen until the tissue is generated.

These aspects of the present teachings are not meant to be exclusive and other features, aspects, and advantages of the present teachings will be readily apparent to those of ordinary skill in the art when read in conjunction with the appended claims and accompanying drawings.

BRIEF DESCRIPTION OF THE SEVERAL VIEWS OF THE DRAWING

These and other features and advantages of the present teachings will be better understood by reading the following detailed description, taken together with the drawings wherein:

FIG. 42 is a perspective pictorial illustration of an example of a first side of a second cassette of the present teachings including cassette sheeting exploded away from the second cassette;

FIG. 43 is a pictorial view a first side of the second cassette of FIG. 42;

FIG. 49A is a perspective diagram of an example of a first side of fittings of the present teachings mated together;

FIG. 49B is a perspective diagram of an example of a second side of fittings of the present teachings mated together;

FIG. 49C is a perspective diagram of an example of a third side of fittings of the present teachings mated together;

FIG. 49D is a perspective diagram of an example of a fourth side of fittings of the present teachings mated together;

FIG. 49E a pictorial cross sectional illustration taken at line 26I-26I of FIG. 49A of an example of fittings of the present teachings mated together;

DETAILED DESCRIPTION

Figure 1:
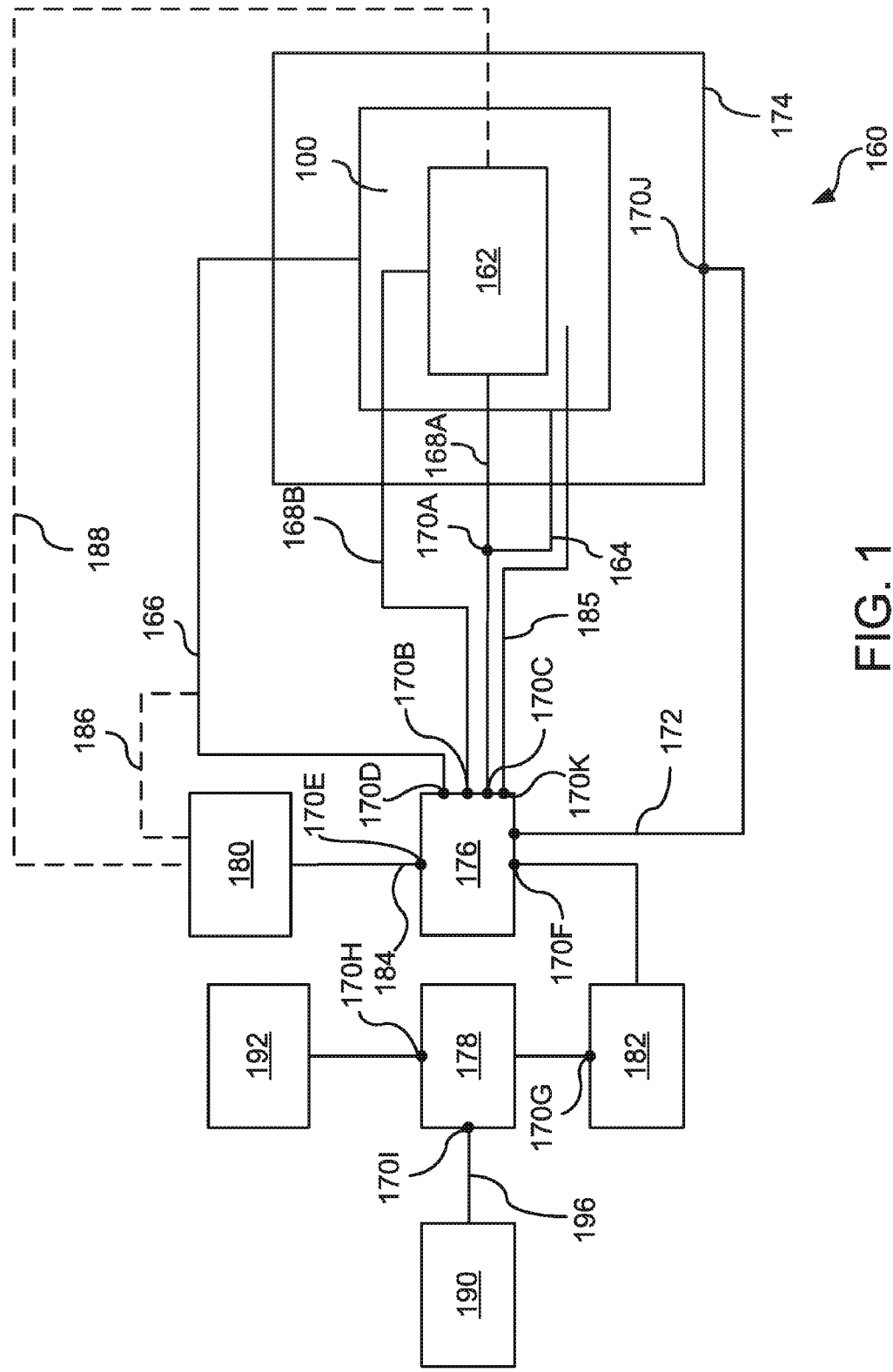
FIG. 1 is a schematic block diagram of an example of the fluid system of the present teachings.

Referring now to FIG. 1, fluid circuit 160 can include, but is not limited to including, enclosure 100, which can be, but is not limited to being, a bioreactor in fluid circuit 160. Enclosure 100 may contain biological specimen 162, which may be, but is not limited to being, a tissue, group of tissues, organ, organ system, or group of organs. In some configurations, biological specimen 162 may be a lung or pair of lungs. In some configurations, a plurality of enclosures 100, for example, but not limited to, connected enclosures 100L (FIG. 12) may be included in fluid circuit 160 and each may contain biological specimen 162. Fluid circuit 160 can also include any number of fluid paths 196, 186, 188, 184, 172, 164, 166, 168A, 168B, 185 in various configurations. At least some fluid paths may enter enclosure 100 in a variety of locations. Fluid may selectively be transferred through such fluid pathways by actuating valves 170A-K of fluid circuit 160 cooperatively to make and break fluid communication pathways in fluid circuit 160. The number and location of valves in various configurations may differ from that shown in FIG. 1.

Still referring to FIG. 1, fluid may be transferred into and out of enclosure 100 via inlet fluid path 164, through, for example, but not limited to, supply line 319 (FIG. 27) and outlet/drain fluid path 166 through, for example, but not limited to, drain line 311 (FIG. 27) respectively Other fluid pathways, for example, but not limited to, fluid pathway 185 may also be used for transferring fluid to and from enclosure 100. In another configuration, a single fluid pathway may be used to transfer fluid both into and out of enclosure 100. Thus, fluid may be introduced to and removed from enclosure 100 such that biological specimen 162 can be bathed in fluid. Additionally, fluid may be recirculated through enclosure 100. Fluid may also be delivered and drawn from or circulated through biological specimen 162 through one or more specimen fluid paths 168A, 168B. The quantity, entry points, size, etc. of specimen fluid paths 168A, 168B may depend on biological specimen 162. In various configurations, specimen fluid paths 168A, 168B may be placed in fluid communication with pre-existing anatomical pathways of biological specimen 162 such that fluid may be perfused through biological specimen 162. For example, specimen fluid paths 168A, 168B may connect to any or a combination of the following: circulatory system pathways (e.g. vasculature, lymphatic vessels), respiratory pathways, ducts (e.g. bile duct), excretory system fluid pathways, digestive system passageways, anatomical cavities, anatomical canals (e.g. alimentary canal), portions of such canals (e.g. stomach), or other anatomical pathways. Fluid flow through specimen fluid paths 168A, 168B may be controlled such that the same specimen fluid path 168A, 168B may be used to both deliver fluid to or draw fluid from a biological specimen 162. Thus, with multiple specimen fluid paths 168A, 168B both antegrade and retrograde perfusion of biological specimen 162 may be performed, in some configurations, without reconfiguration of the fluid circuit 160. In some configurations fluid circuit 160 can be reconfigured either automatically or manually to control fluid flow.

Continuing to refer to FIG. 1, enclosure 100 may be placed in container 174. Container 174 may be filled with fluid such that enclosure 100 can be bathed in and/or suspended in the fluid. In some configurations, fluid circuit 160 may include container fluid pathway 172 for transferring fluid into and out of container 174. Alternatively, enclosure 100 may create a sterile barrier between the interior of enclosure 100 and the surrounding environment, and container 174 may be filled using any fluid supply, for example, but not limited to, tap water, which may or may not be included in or transferred by fluid circuit 160. To transfer fluid through fluid circuit 160, one or more first and second pumps 176, 178 may be included. First and second pumps 176, 178 may be any of or a combination of a variety of different pump types. Any suitable fluid pump, for example, but not limited to, a peristaltic pump, may be used. In some configurations, membrane-based fluid pumps as described, for example, but not limited to, in relation to U.S. Pat. No. 5,350,357, filed Mar. 3, 1993, and entitled PERITONEAL DIALYSIS SYSTEMS EMPLOYING A LIQUID DISTRIBUTION AND PUMPING CASSETTE THAT EMULATES GRAVITY FLOW, which is hereby incorporated by reference herein in its entirety, may be used.

Continuing to still further refer to FIG. 1, in fluid circuit 160, second pump 176 and first pump 178 can be included. In some configurations, there may be a plurality of second pumps 176 and/or first pumps 178. Second pump 176 may be used to pump fluid to and from or circulate fluid through enclosure 100, biological specimen 162, container 174, waste reservoir 180, and/or storage reservoir 182. Fluid in enclosure 100 or biological specimen 162 may be pumped to waste reservoir 180, for example, but not limited to, when the fluid is spent or to maintain a desired fluid level within enclosure 100. In fluid circuit 160, second pump 176 may draw fluid from enclosure 100 via drain fluid path 166 or from biological specimen 162 via specimen fluid paths 168A, 168B. Fluid may then be transferred though waste fluid path 184 to waste reservoir 180. In some configurations, fluid may passively drain to waste reservoir 180 via drain paths 186 and 188. Second pump 176 may use storage reservoir or reservoirs 182 as a fluid supply. First pump 178 may pump fluid to storage reservoir 182 such that second pump 176 can have a sufficient supply of fluid to deliver to enclosure 100, biological specimen 162, and/or container 174. In some configurations, first pump 178 may also be capable of pumping directly to enclosure 100, biological specimen 162, and/or container 174. Additionally, first pump 178 may supply different varieties of fluid to storage reservoir or reservoirs 182 such that second pump 176 may deliver fluid to enclosure 100 and/or biological specimen 162 based on a predefined recipe or list of steps. First pump 178 may also provide fluid mixtures to storage reservoir or reservoirs 182. For example, first pump 178 may pump a plurality of different fluids to create fluid admixtures and/or dilute one or more solutions to desired concentrations. One or a number of sources 190 may be included in fluid circuit 160 and first pump 178 may draw from or deliver to these sources 190 via source fluid pathway or pathways 196. Sources 190 may be various reservoirs such as, for example, but not limited to, vials, compliant reservoirs, bags, and drums. Sources 190 may contain a variety of different solutions, mediums, fluids, biological agents, cells, etc. A non-limiting list of potential contents of sources 190 in Table I is as follows:

TABLE I

| | | |
|---|---|---|
| Purified Water (Distilled, Reverse Osmosis, DeIonized etc.) | Medical Grade Water | Cell Lysing Agent |
| Detergent (Research Grade, Proteomic Grade, 2D Grade, etc.) | Non-ionic Detergent | Ionic Detergent |
| Zwitterionic Detergent | Polyoxyethylene Ether | Triton X-100 |
| Other Triton Series Detergents | Octylphenoethylene Oxide | Polyoxyethylene Sorbitans |
| Polyethylene Glycol (PEG) | Sodium Dodecyl Sulfate (SDS) | Vasodilators |
| Sodium Nitroprusside | Anti-coagulant | Heparin |
| Sodium Deoxycholate (SDC) | Biocompatible/Osmotically Isotonic Solution | Osmotically Incompatible Solution (Hypertonic/Hypotonic) |
| Hypertonic salt solution (e.g. NaCl solution) | Hank's Balanced Salt Solution | Phosphate Buffered Solution (PBS) |
| Saline Solution | Buffering Solutions | pH Buffers |
| Good's Buffer | HEPES Buffer | Catalysts (Chemical or Biologic) |
| Enzyme Solution | Proteolytic Enzyme Solution | Trypsin Solution |
| Chymotypsin Solution | Elastase | Collagenase |
| Dispase | Ficin | Papain |
| Pepsin | Alkaline Protease | Protease Inhibitors |
| Collagenase Inhibitors | Ethylenediaminetetraacetic acid | Sulfylhydryl protease inhibitors |
| Serine protease inhibitors | Anti-Pathogen Solution | Anti-biotics (Penicillin, Streptomycin, etc.) |
| Anti-fungals | Bacteriostatic Agents | Peracetic Acid |
| Chelating Agents | Cytostatic Agents | Cytolytic Agents |
| Cytocidal Agents | Ammonium Solutions | Ammonium Hydroxide |
| Nucleases | DNase | RNase |
| Nuclease Inhibitors | Dyes (e.g. Evan's Blue Dye) | Other Markers (Radioactive Markers, Fluorescent Markers, etc.) |
| Cell Size Particles (e.g. 5 μm nanospheres) | Nano Bead Particles (unmarked or chemically marked e.g. for fluorescence) | Heparinized Blood |
| Hydrolytic Enzyme Solutions | Hyaluronidase | Glucuronidase |
| Neuraminidase | Bacterial Species (e.g. species that secrete one or more desired enzyme) | Alcohols |

TABLE I-continued

| | | |
|---|---|---|
| Fixation Agents | Formalin | Neutral Buffered Formalin |
| Aldehyde Fixation Agents | Alcoholic Fixation Agents | Bouin Solution |
| Anti-oxidant Solution | Glutathione Ethyl Ester | Cell Culture Media |
| Broths | Fisher/Iscove/McCoy/Dulbecco's etc. Medium | Nutrient Solutions |
| Minimal Essential Medium | MEM Amino Acid Solution | Basal Medium Supplements |
| Insulin-Transferrin-Selenium | Growth Factor Solutions | Serums |
| Serum Xenologous to Inteneded Recipient | Fetal Bovine Serum (FBS) | Horse Serum |
| Human Serum | Serum From Intended Recipient | Serum with Low pH and/or Mg Ions |
| Heat Inactivated Serum | Cell Cultures | Cells Non-immunogenic to Intended Recipient |
| Patient Specific Stem Cells | Fibroblasts | Endothelial Cells |
| Epithelial Cells | Stem Cells | Pluri-potent Cells and/or Induced Pluri-potent Cells |
| Progenitor Cells | Fetal Associated Cells | Embryonic Stem Cells |
| Adult Stem Cells | Anti-Apoptotic Agents | Whole Blood |
| Hydrocortisone | Albumin (of any origin) | Differentiation Medium |
| Vitamins | Fixed Carbon Source | Glucose |
| Aerated Solution or Solution with High Level of Dissolved Oxygen | Mitogens | Angiogenesis Inducing Compounds |

Continuing to refer to FIG. 1, contents of sources 190 may be provided in any concentration. Additionally, contents of sources 190 may be provided in various different forms. Contents may be in a liquid form or aqueous solution. Alternatively, contents of sources 190 may be in a form which could require reconstitution or rehydration. For example, contents for some sources 190 may be in a dried, powdered, or lyophilized form. If the contents of source 190 require reconstitution, a pump such as first pump 178 in fluid circuit 160 may pump a reconstituting agent to source 190 to reconstitute the contents of that source 190. Water source 192 may be, for example, but not limited to, a purified water source. Water for water source 192 may be provided via a variety of suitable purification means such as a reverse osmosis system or distillation system. In some configurations, water source 192 may be supplied by a distillation system such as that described in U.S. Patent Publication No. 2014/0183025, filed Jul. 26, 2013, and entitled WATER VAPOR DISTILLATION APPARATUS, METHOD, AND SYSTEM, which is incorporated by reference herein in its entirety. Water from water source 192 may be used for a variety of applications. For example, first pump 178 may be used to draw from water source 192 to reconstitute contents of one or more source 190, or may draw from water source 192 to dilute the contents of source 190. Dilution may occur in source 190, first pump 178 or storage reservoir or reservoirs 182. To provide a desired supply fluid for second pump 176, first pump 178 may pump fluid to storage reservoir or reservoirs 182 from water source 192 and one or more source 190 in specified ratios. In some configurations, water source 192 may be replaced with another diluent source or a cell culture source.

Figure 2:
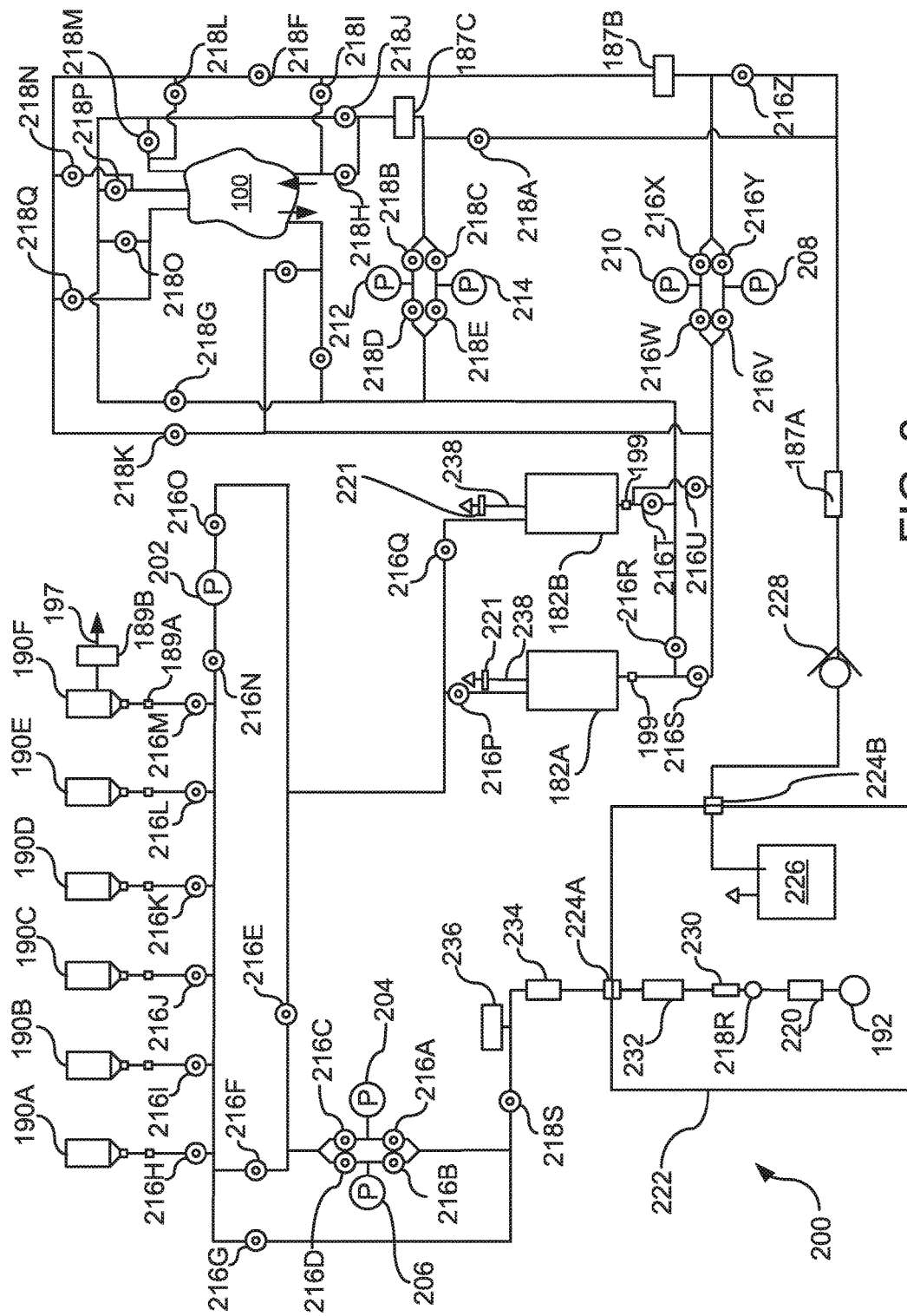
FIG. 2 is a schematic diagram of a fluid circuit of another example of the present teachings.

Referring now to FIG. 2, fluid circuit 200 can include, but is not limited to including, enclosure 100, fluid pumps 202, 204, 206, 208, 210, 212, 214, and valves 216A-Z and 218A-218S. By operating fluid pumps 202, 204, 206, 208, 210, 212, 214 and valves 216A-Z and 218A-218S cooperatively, fluid may be pumped throughout fluid circuit 200. In some configurations, fluid may be drawn into fluid circuit 200 via pumps 204 and 206. Pumps 204 and 206 may draw fluid from any of source 190A-F and/or from water source 192. Though six sources 190A-F are shown, any number of sources 190A-F may be in communication with fluid circuit 200. In some configurations, one or more of sources 190A-F may be vented by, for example, vent 197, to the atmosphere. A filter 189B between the atmosphere and at least one of the one or more sources 190A-F may be included. In some configurations, one or more source 190A-F may be associated with filter 189A between the one or more source 190A-F and a valve 216H-216M. Both filters 189A and 189B may be included in some configurations. Filters 189A, B may be any suitable variety of filters in some configurations, for example, but not limited to, a 0.2 micron filter. In some configurations, one or more sources 190A-F may be compliant. Fluid circuit 200 can include partitioned portion 222 which may be disconnected from the rest of fluid circuit 200 via connectors 224A, 224B. Partitioned portion 222 may be a reusable section or a section which may require infrequent cleaning. Fluid circuit 200, outside of partitioned portion 222, may be disposable and may be replaced after each use, or may be replaced after a defined number of uses. Alternatively, fluid circuit 200, outside of partitioned portion 222, may require cleaning or sterilization after each use or after a predefined period of time/number of uses. Components in partitioned portion 222 can include drain reservoir 226 to accommodate waste fluid from fluid circuit 200. One or more one way valve or check valve 228 can be included to help discourage or stop waste fluid from back flowing into fluid circuit 200. Water source 192 for fluid circuit 200 can be included in partitioned portion 222.

Continuing to refer to FIG. 2, a number of components may be included between water source 192 and the rest of fluid circuit 200. At least one filter may be included to isolate non-sterile portions of fluid circuit 200 from sterile portions. For example, in some configurations, first filter 220 can filter water entering fluid circuit 200 from water source 192. Filter 220 may help to prevent potential contaminants in water from water source 192 from entering the rest of fluid circuit 200, and may help to prevent backwards contamination. First filter 220 may be any suitable filter, and in some configurations may be a 0.2 micron filter. Inlet valve 218R can be included in partitioned portion 222 sharing a pathway with first filter 220. Valve 218R may be a solenoid valve and may be operated to control the flow of water into fluid circuit 200. Regulator 232 may be included to regulate the pressure of water entering fluid circuit 200. In some configurations, the pressure value which regulator 232 regulates to may be between 5-18 psi (e.g. 7 psi), though the pressure value may differ in other configurations. Deaerator 230 may also be included in partitioned portion 222 to remove air from the incoming water. Second filter 234 which may be substantially the same as or identical to the first filter 220 and may be included and may provide a redundant aid to protect against any potential contaminants. Second filter 234 may also help to prevent backwards contamination. First filter 220 and second filter 234 may isolate valve 218R and deaerator 230 from the rest of fluid circuit 200 allowing valve 218R and deaerator 230 to be in a non-sterile portion of fluid circuit 200. Depending on pump types, expected flow rates, and desired throughput, accumulator 236 may be included to help ensure a sufficient supply of fluid at a desired pressure is available.

Still referring to FIG. 2, pumps 202, 204, and 206 may mix fluid to create various admixtures or may deliver fluid directly from a source 190A-F or a water source 192 to storage reservoirs 182A, 182B. Admixtures may include fluid or solution diluted to a desired concentration and/or various "cocktails" consisting of a variety of different components. Pumps 202, 204, and 206 may draw fluid from any source 190A-F and/or water source 192 in a predefined ratio and deliver this fluid to storage reservoirs 182A, 182B. The predefined ratio may be chosen to create the desired fluid admixture. Storage reservoirs 182A, 182B may include vents 238 which prevent pressure build up within the storage reservoirs 182A, 182B. In some configurations vent filter 221 such as a 0.2 micron filter may be included in vent 238 between the interior of storage reservoirs 182A, 182B and a vent reservoir, for example, but not limited to, the atmosphere.

Figure 8:
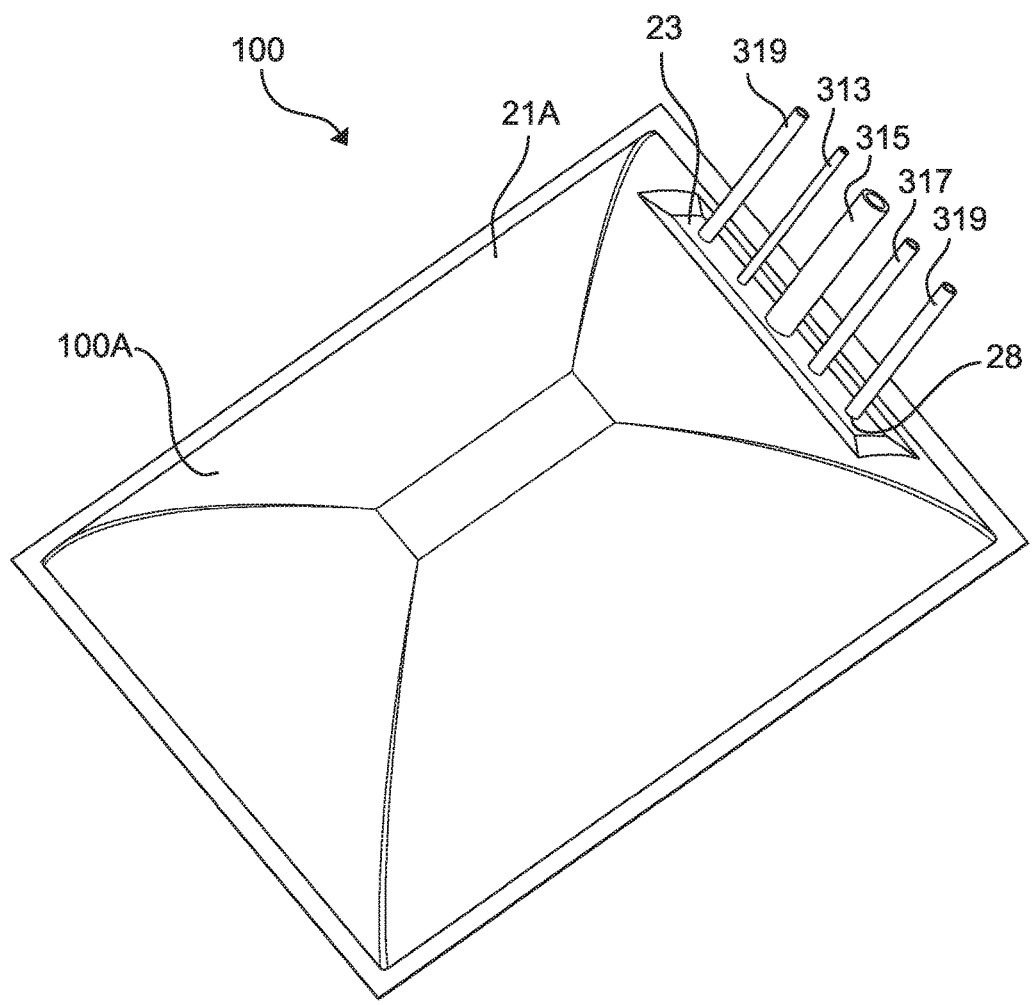
FIG. 8 is a perspective diagram of the exterior of an example of an enclosure of the present teachings having external fluid lines.

Continuing to refer primarily to FIG. 2, when storage reservoirs 182A, 182B contain a desired admixture or fluid, the fluid may be pumped to/from enclosure 100 or, for example, biological specimen 162 (FIG. 1) within enclosure 100. In some configurations, filters 199 may be included. In some configurations, fluid circuit 200 can include pumps 208, 210, 212, and 214 which may be used to control the transfer of fluid to/from enclosure 100 and to/from biological specimen 162 (FIG. 1). Pumps 208, 210, 212, and 214 may be used to pump fluid to waste reservoir 226 when, for example, the fluid is considered used or spent. Pumps 202, 204, 206, 208, 210, 212, 214 may be any of a variety of pumps. In some configurations, pumps 204, 206, 208, 210, 212, 214 may be, but are not limited to being, any of or a combination of the following: centrifugal pumps, positive displacement pumps, peristaltic pumps, diaphragm pumps, vane pumps, and metering pumps. Valves 216A-Z and 218A-218S may be any of or a combination of a variety of valve types including but not limited to the following: solenoid valves, variable valves, and rotary valves, ball valves, pinch valves, bi-stable valves and membrane valves. In some configurations, each or at least one of valves 216A-Z and 218A-218S may include a combination of valves which may be of different types. For example, each or at least one of valves 216A-Z and 218A-218S may include a pneumatic valve which controls a fluid valve. In some configurations, the pneumatic valve may be a bi-stable pressure control valve which supplies pressure to a membrane type "volcano valve" to open/close the "volcano valve". In some configurations at least some valves, fluid pathways, and pumps may be incorporated into a fluid handling cassette or set including a plurality of fluid handling cassettes Referring now primarily to FIG. 3, enclosure 100 may be a rigid structure which can be of a substantially constant volume. In other configurations, enclosure 100 may be a flaccid structure which may change in volume as fluid/material is introduced and removed from enclosure 100. In some configurations, enclosure 100 may be a bag whose interior volume is sealed from the exterior environment. The seal separating enclosure 100 from the surrounding environment may be a fluid-tight and/or liquid tight seal. The seal may allow the interior of enclosure 100 to remain sterile while the exterior of enclosure 100 is in a non-sterile environment. Enclosure 100 may include adapter 23. Adapter 23 may serve as a tubing interface which can include a variety of enclosure pass-throughs 1002 which can extend from first side 23A of adapter 23 to opposing second side 23B of adapter 23. Pass-throughs 1002 may be orifices such as orifices 28 (FIG. 8). First side 23A of adapter 23 may face or be associated with the exterior of enclosure 100 while second side 23B of adapter 23 may face the interior of enclosure 100. Pass-throughs 1002 in adapter 23 may provide ports for a number of fluid lines or tubes 1000A, 1000B, 1000C, 1000D. Fluid lines 1000A, 1000B, 1000C, 1000D may be fed through or penetrate through pass-throughs 1002 from either of first side 23A (see fluid line 1000B) or second side 23B (see fluid line 1000C) of adapter 23 to provide a fluid communication path between the interior and exterior of enclosure 100 (fluid line 1000A is in a position to provide the fluid communication path).

Figure 3:
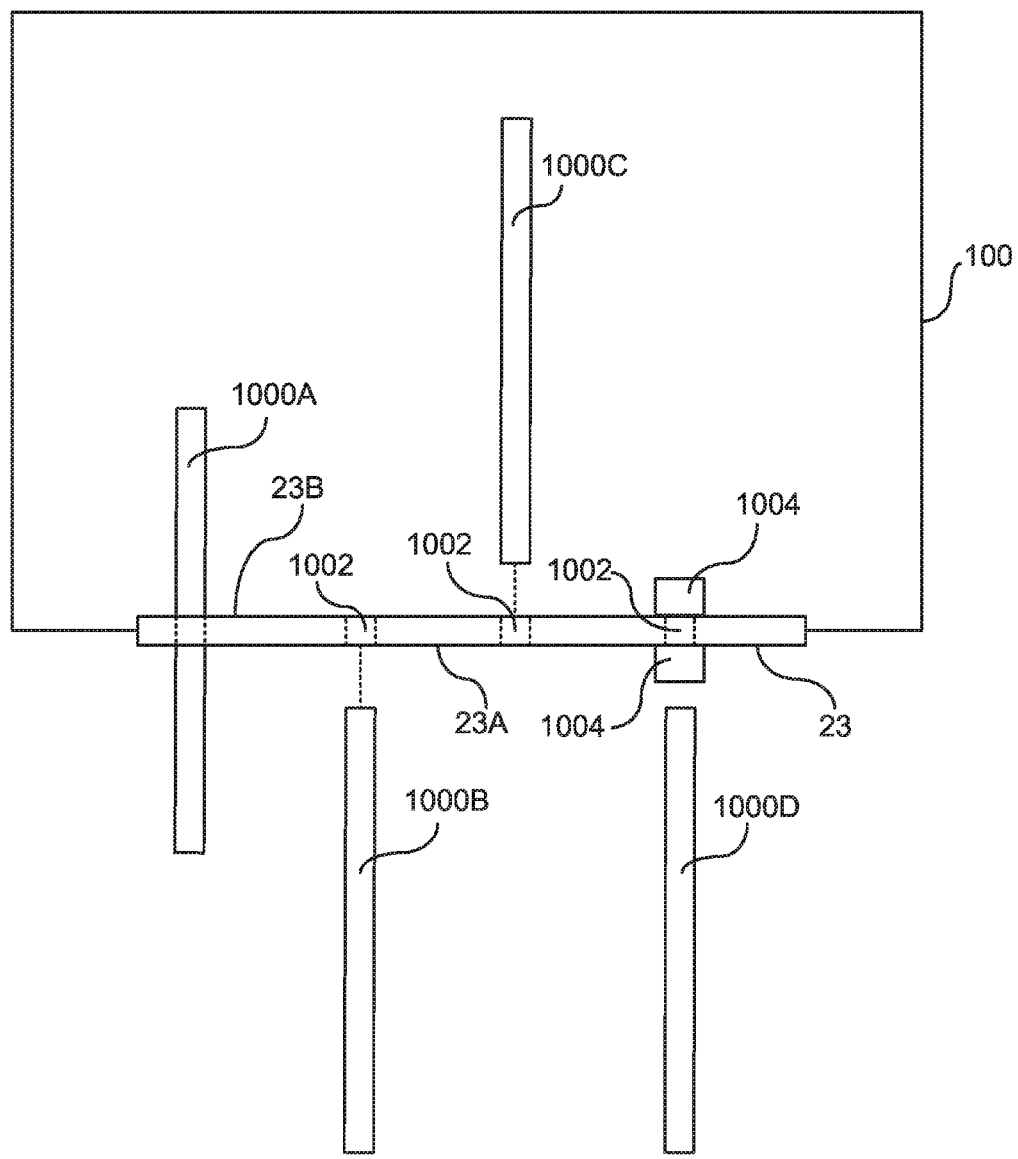
FIG. 3 is a representational block diagram of an example of an enclosure, a number of fluid lines, and an adapter of the present teachings.

Continuing to refer to FIG. 3, alternatively, one or more pass-through(s) 1002 may be associated with line fitting 1004 located on one or both of first side 23A and/or second side 23B of adapter 23. Fitting 1004 may be any of a variety of fittings such as a barb fitting, luer lock fitting, quick connect fitting, etc. One or more fluid line 1000A, 1000B, 1000C, 1000D may be attached to fittings 1004 on adapter 23 to provide a fluid pathway through pass-through 1002 to the exterior and/or interior of enclosure 100. Fluid lines 1000A, 1000B, 1000C, 1000D may each have a dedicated purpose or may be generic and utilized as a specific scenario requires. In configurations where enclosure 100 is used in decellularization processes and other specimen engineering related applications, one or more of the fluid lines may be a supply line through which fluid may be supplied to the interior of enclosure 100. One or more of fluid lines 1000A, 1000B, 1000C, 1000D may be a drain line via which fluid may be drained or removed from the interior of enclosure 100. One or more of fluid lines 1000A, 1000B, 1000C, 1000D may also be used for both supplying and draining fluid. One or more of fluid lines 1000A, 1000B, 1000C, 1000D may be a specimen line through which fluid may be pumped to or from one or more biological specimen 162 (FIG. 1) such as a tissue. Specimen(s) 162 (FIG. 1) may be any suitable group of cells and their surrounding extracellular matrix. Specimen(s) 162 (FIG. 1) may also be a tissue, group, or groups of tissues such as an organ or organ system, e.g. a lung or lungs. Various configurations may include differing numbers of lines. For example, different configurations may include a different number of fluid lines 1000A, 1000B, 1000C, 1000D depending on the type of specimen 162 (FIG. 1) to be placed in enclosure 100. Using the example of an organ such as a lung, there may be three specimen lines (e.g. one for the pulmonary artery, one for the pulmonary vein, and one for the trachea) in addition to a supply line and a drain line. The size of the fluid conduit in fluid lines 1000A, 1000B, 1000C, 1000D may depend, for example, but not limited to, on one or more of the following: specimen(s) 162 (FIG. 1), type/specimen, desired fluid flow rate, desired flow impedance through the line, enclosure 100 size, adapter 23 size, fitting 1004 size, and pass-through 1002 size.

Continuing to still further refer to FIG. 3, enclosure 100 can provide a sterile closed environment for the specimen. Enclosure 100 can be suspended in a suspension fluid, without sterilizing the suspension fluid which may speed a decellularization process and may help augment efficiency. Suspending enclosure 100 in a suspension fluid may improve perfusion of fluid throughout the specimen(s) 162 (FIG. 1). The temperature of the suspension fluid may be controlled which could aid in optimization of the decellularization process.

Figure 4:
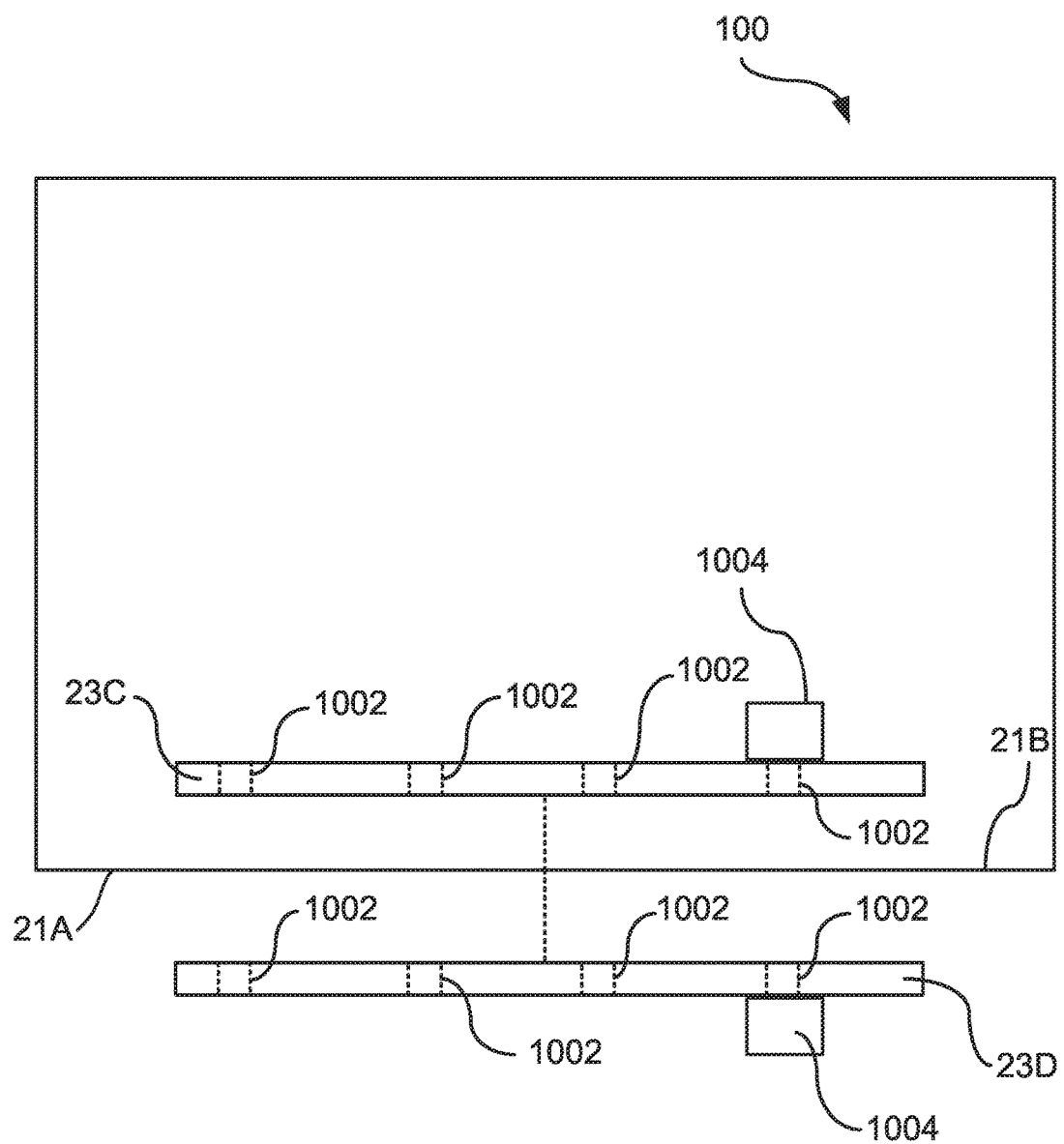
FIG. 4 is a representational block diagram of another example of the enclosure of the present teachings having multiple adapter parts.

Referring now to FIG. 4, first adapter part 23C and second adapter part 23D may be included. First adapter part 23C may be attached to interior surface 21B of enclosure 100, second adapter part 23D may be attached to exterior surface 21A of enclosure 100. Each of first and second adapter parts 23C, D may include pass-throughs 1002 which may be aligned with one another when adapter parts 23C, D are coupled to enclosure 100. In some configurations, each of adapter parts 23C, D may include at least one fitting 1004. At least one fitting 1004 may only be included on a single side of each of adapter parts 23C, D. Fittings 1004 may be placed on faces of adapter parts 23C, D which may be non-adjacent when adapter parts 23C, D are attached to enclosure 100.

Figure 5:
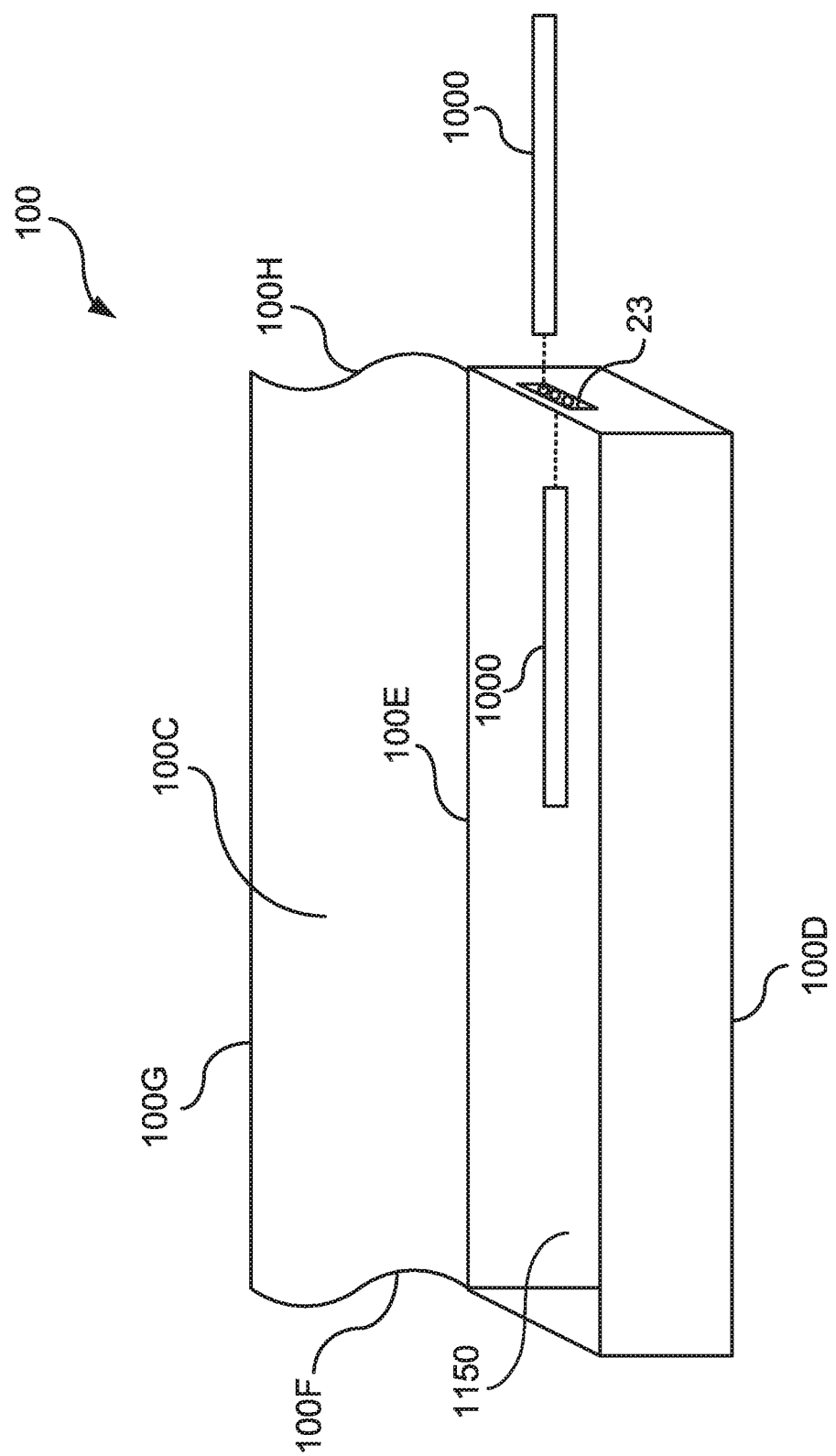
FIG. 5 is a representational block diagram of a partially assembled enclosure and a number of fluid lines of the present teachings.

Referring now to FIG. 5, enclosure 100 may be provided in a partially assembled or constructed manner. For example, enclosure 100 may be provided in multiple pieces (e.g. a first and second part) or may be provided as a clamshell. Enclosure 100 may be a clamshell which includes first part 100C which may be joined to second part 100D. In some configurations, first part 100C may be continuous with second part 100D. Alternatively, first part 100C may be attached to second part 100D along first edge 100E, for example, but not limited to, by heat bonding, laser welding, ultrasonic welding, solvent bonding, or any other suitable attachment process. In some configurations first edge 100E and one or more of second edge 100F, third edge 100G, or fourth edge 100H of first part 100C may be attached to second part 100D of enclosure 100. Alternatively, for example in configurations in which enclosure 100 is round or not polygonal, between 20-80% of first part 100C of enclosure 100 may be provided already joined to second part 100D of enclosure 100.

Continuing to refer to FIG. 5, in some configurations, enclosure 100 may be provided as a clamshell with first part 100C being continuous with second part 100D. Additionally, an edge or portion of first part 100C may be joined to second part 100D. At least one edge or portion of first part 100C may be open or not joined to second part 100D. While first part 100C is not completely joined or sealed to second part 100D of enclosure 100, fluid lines 1000 may be fed through or attached to adapter 23. Adapter 23 may be located in any of the plurality of parts of enclosure 100. For example, adapter 23 may be located on second part 100D of the enclosure 100.

Figure 6:
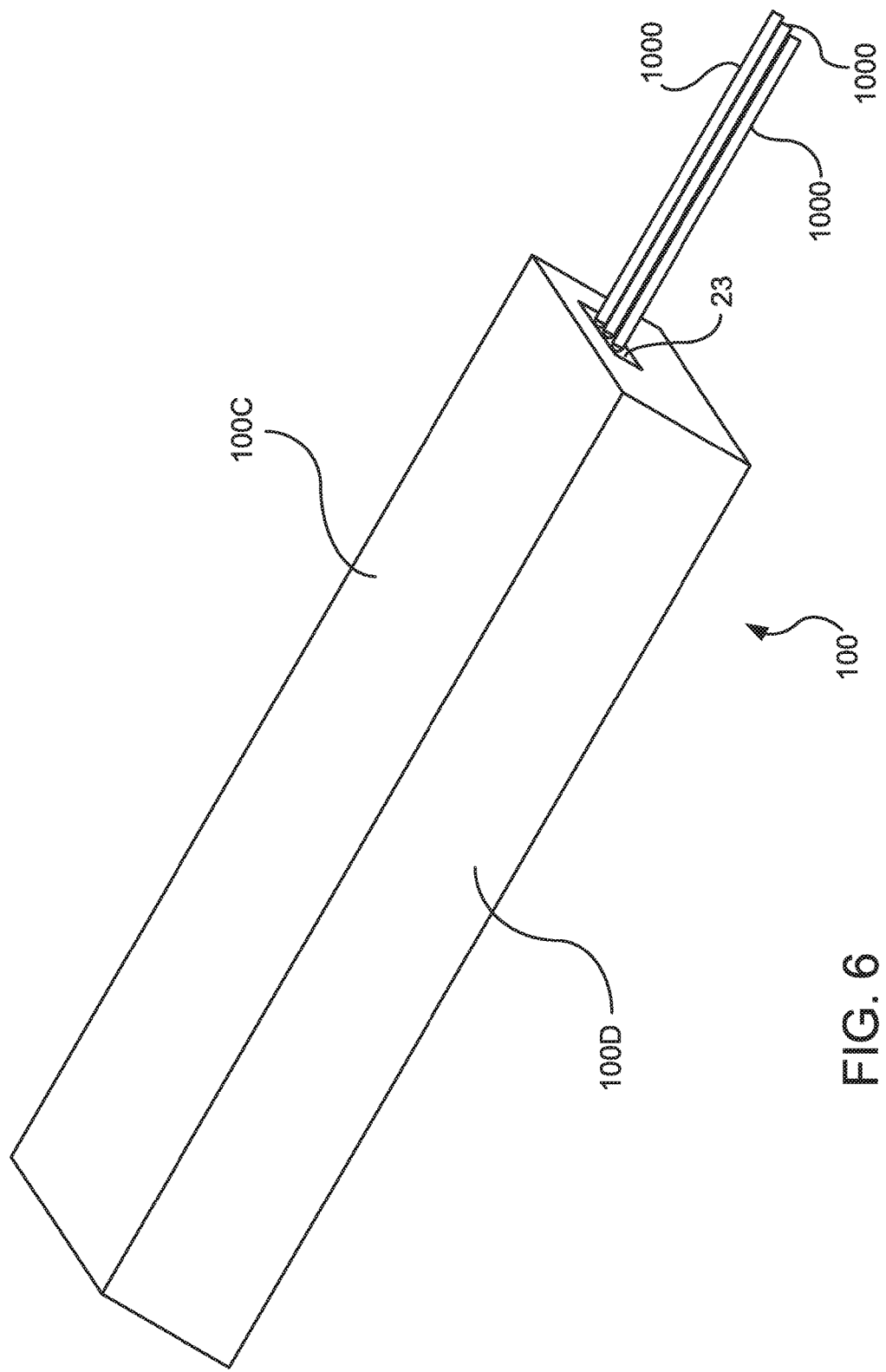
FIG. 6 is a representational block diagram of an assembled enclosure and a number of fluid lines of the present teachings.

Referring now to FIG. 6, once any fluid lines 1000 have been attached or fed through adapter 23 to provide fluid communication between an interior cavity 1150 (FIG. 5) in enclosure 100 and fluid sources and reservoirs exterior to enclosure 100, first part 100C and second part 100D of enclosure 100 may be joined creating a seal between interior cavity 1150 (FIG. 5) and the surrounding environment. Any parts of enclosure 100 may be joined together using any suitable process. In some configurations, enclosure 100 may be heat sealed or bonded together.

Figure 7:
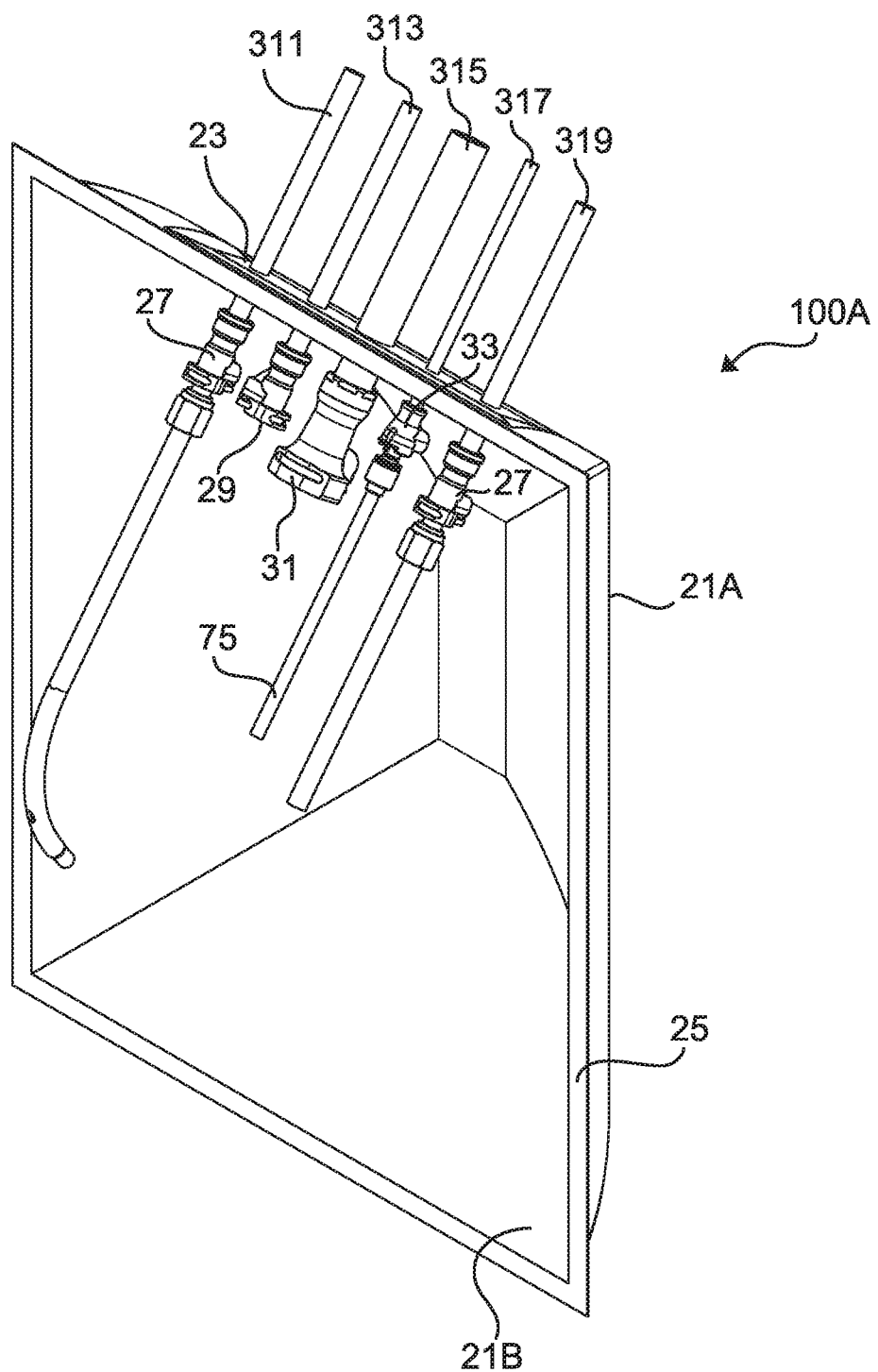
FIG. 7 is a perspective diagram of the interior of an example of an enclosure of the present teachings having optional interior tubing connectors.

Referring now to FIG. 7, enclosure first section 100A can include adapter 23 and any number of fluid lines (e.g. fluid lines 311, 313, 315, 317, and 319). Enclosure first section 100A can further include exterior surface 21A, sealing surface 25, and interior surface 21B. Supply/drain lines 311 and 319 can penetrate adapter 23 and can terminate at tubing connector 27. Supply line 319 and drain line 311 may supply fluid to enclosure 100 (FIG. 3) and drain fluid from enclosure 100 (FIG. 3). Supply line 319 and drain line 311 may supply fluid and drain fluid simultaneously. In some configurations, a separate pass-through adapter or number of pass-through adapters (not shown) may be included for one or more line 311, 313, 315, 317, 319. Supply line 319, and drain line 311 for example can have a separate pass-through adapter or each have a separate pass-through adapter. Pass-through adapters may be placed, for example, but not limited to, on a portion of enclosure 100 opposite adapter 23. Specimen line 313 can penetrate adapter 23 and can terminate at tubing connector 29 supplying fluid to specimen 162 (FIG. 1). Specimen line 315 can penetrate adapter 23 and can terminate at tubing connector 31 supplying fluid to specimen 162 (FIG. 1). Specimen line 317 can penetrate adapter 23 and can terminate at tubing connector 33, supplying fluid to other parts of specimen 162 (FIG. 1). Specimen lines 313, 315, 317 can also be used to drain fluid from specimen 162 (FIG. 1). Tubing connectors 27, 29, 31, 33 may be any number of or a combination of tubing connectors such as quick connects, luer locks, or other line fittings. Fluid lines 319, 317, 315, 313, and 311 may, in some configurations, have an outer diameters in the range of, for example, but not limited to, 0.125-0.5 inch or smaller or larger. Fluid lines 311, 313, 315, 317, 319 may be silicone lines which may be interference fit into pass-throughs 1002 (FIG. 3) in adapter 23. Fluid lines 311, 313, 315, 317, 319 may have outer diameters slightly larger (e.g. ⅛ inch larger) than pass-through 1002 (FIG. 3) dimensions such that a radial seal may be created when fluid lines 311, 313, 315, 317, 319 are in place in pass-through 1002 (FIG. 3). In some configurations, the inner diameters of fluid lines 311, 313, 315, 317, 319 may be sized to be substantially equal the size of their respective pass throughs 1002 (FIG. 3) in adapter 23.

Still referring primarily to FIG. 7, enclosure first section 100A can be partially sealed to enclosure second section 100B (FIG. 10) at sealing surface 25. Specimen(s) 162 (FIG. 1) (e.g. target tissue or group of tissues, for example an organ) can be inserted into partially sealed enclosure 100 (FIG. 5). Specimen lines 313, 315, 317 may then be placed into communication with specimen(s) 162 (FIG. 1). For example, tubing connectors 29, 31, and 33 may be attached to specimen connecting lines, such as, for example, specimen line 75. Partially sealed enclosure 100 (FIG. 3) can be completely sealed at sealing surface 25. After enclosure 100 (FIG. 3) is completely sealed, specimen(s) 162 (FIG. 1), for example, but not limited to, a lung, can proceed through a decellurization process, for example.

After completion of the decellularization process, specimen(s) 162 (FIG. 1) can remain within enclosure 100 (FIG. 3) for preservation, subsequent processing, and until use. For example, enclosure 100 may serve as a start to finish receptacle for a biological specimen 162 (FIG. 1) as it goes through a complete tissue or specimen engineering process. After preparation, the biological specimen 162 (FIG. 1) may remain in enclosure 100 until it is ready to be used for transplant. A biological specimen 162 may be put through a multi-step tissue or specimen engineering process including, for example, decellularized, recellularized, and storage until use all within the same enclosure 100.

Referring now primarily to FIG. 8, adapter 23 can be, for example, laser welded into enclosure first section 100A, however any form of fluid/liquid-tight coupling arrangement could be used, for example, ultrasonic welding, other welding techniques, heat sealing or bonding, and gluing. In configurations in which adapter 23 is laser welded to enclosure 100, adapter 23 may be made, but is not limited to being made, of a material which is dark, black, or absorbs light at the desired welding wavelength. A seal between adapter 23 and enclosure 100 can also be pressure tight. Adapter 23 can be any thickness and size. For example, adapter 23 can measure 7.5" high×1.25" wide×0.25" thick, though in some configurations, adapter 23 need not be rectilinear and may take any shape. Adapter 23 can be scalable relative to the size of the target tissue(s) or specimen(s) 162 (FIG. 1), the size of enclosure 100, and the size of any fluid lines 311, 313, 315, 317, and 319, for example. Adapter 23 can be surrounded or embedded between layers of the enclosure 100 material, for example, but not limited to, layers of enclosure first section 100A, or can be sealed to exterior surface 21A or interior surface 21B (FIG. 6) of enclosure 100. Further, adapter 23 could include multiple layers, and the layers could be sealed to exterior surface 21A or interior surface 21B (FIG. 6) of enclosure 100. Adapter 23 may, in some configurations, include a first portion and a second portion with the first portion attached to interior surface 21B (FIG. 6) of enclosure 100 and the second portion attached to exterior surface 21A of enclosure 100 (see FIG. 7). Still further, adapter 23 could be molded into or over molded onto enclosure 100. Adapter 23 could be formed of high density polyethylene (HDPE), and may be made of a gamma sterilization compatible material. In other configurations, adapter 23 may be made of a material which may be heat sterilized for example, but not limited to, autoclaved or gas sterilized for example, but not limited to, with ethylene oxide without being degraded or compromised. In some configurations, adapter 23 is not required to be sterilized, which can increase the types of materials suitable for constructing adapter 23.

Figure 9:
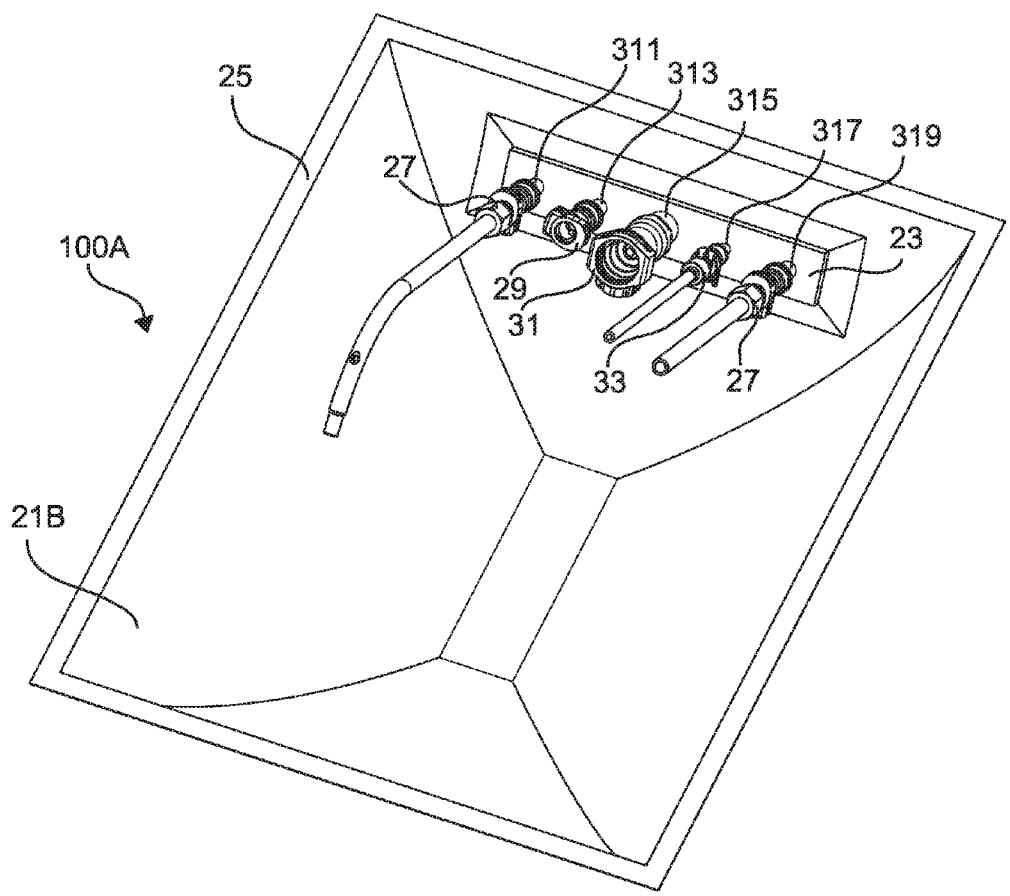
FIG. 9 is a perspective diagram of the interior of an example of an enclosure of the present teachings having optional tubing connectors.

Referring now to FIG. 9, adapter 23 can accommodate a suite of fluid lines 311, 313, 315, 317, 319 including tubing connectors 27, 29, 31, 33 such as quick connects. Adapter 23 may, for example, but not limited to, accommodate a supply (tubing connector 27), drain (tubing connector 27), and three specimen interfaces (tubing connectors 29, 31, and 33). Any number of tubing connectors and specimen interfaces can be accommodated, depending on the application and the specimen 162 (FIG. 1) size or type, for example.

Figure 10:
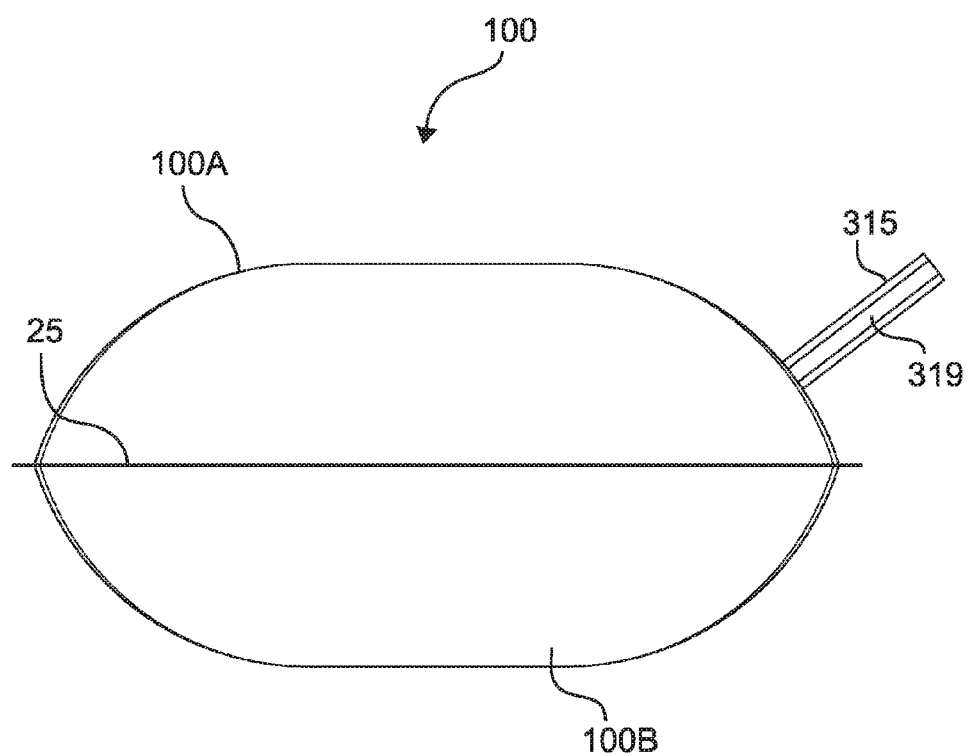
FIG. 10 is a side view diagram of the exterior of an example of a sealed enclosure of the present teachings.

Referring now to FIG. 10, a side view of an example of enclosure 100 is shown. Enclosure 100 may be sealed at sealing surface 25 and may include enclosure first section 100A, enclosure second section 100B, and fluid lines 319, 315. There can be more than two sections of enclosure 100, depending on the application. Enclosure 100 can be, but is not limited to being, constructed of a mixture of nylon and linear low density polyethylene (LLDPE). The materials for enclosure 100 may be chosen depending on the desired durability, puncture resistance, pliability, bonding/welding compatibilities, permeability, chemical compatibility, etc. of the material. In some configurations, enclosure 100 may be constructed of a multilayer material in which each strata of the multi-layered material can be chosen for a particular characteristic. Materials that are suitable for undergoing autoclaving, gamma sterilization, or other sterilization procedure can also be selected for manufacturing enclosure 100. Puncture-resistant materials can also be chosen, for example, the percentage of nylon in a multilayer material including both nylon and LLDPE can be increased. The material used to construct enclosure 100 can be based on the chemicals that enclosure 100 could hold for the application. For example, materials that are non-reacting with the chemicals could be chosen, or materials that have known reactions that are desirable for the applications could be chosen. Enclosure 100 could be coated on the inside or outside to affect permeability, for example enclosure 100 could include a metalizing layer. Multi-layer construction of enclosure 100 could incorporate multiple types of materials to accommodate certain applications. In some configurations, adapter 23 (FIG. 9) and enclosure 100 may be constructed of compatible materials to enable coupling (e.g. ultrasonic or laser welding) of adapter 23 (FIG. 9) to or within enclosure 100. For example, enclosure 100 could include an outer polymer layer and an inner polymer layer, where the layers could surround a nylon layer and potentially one or more other layers.

Figure 11:
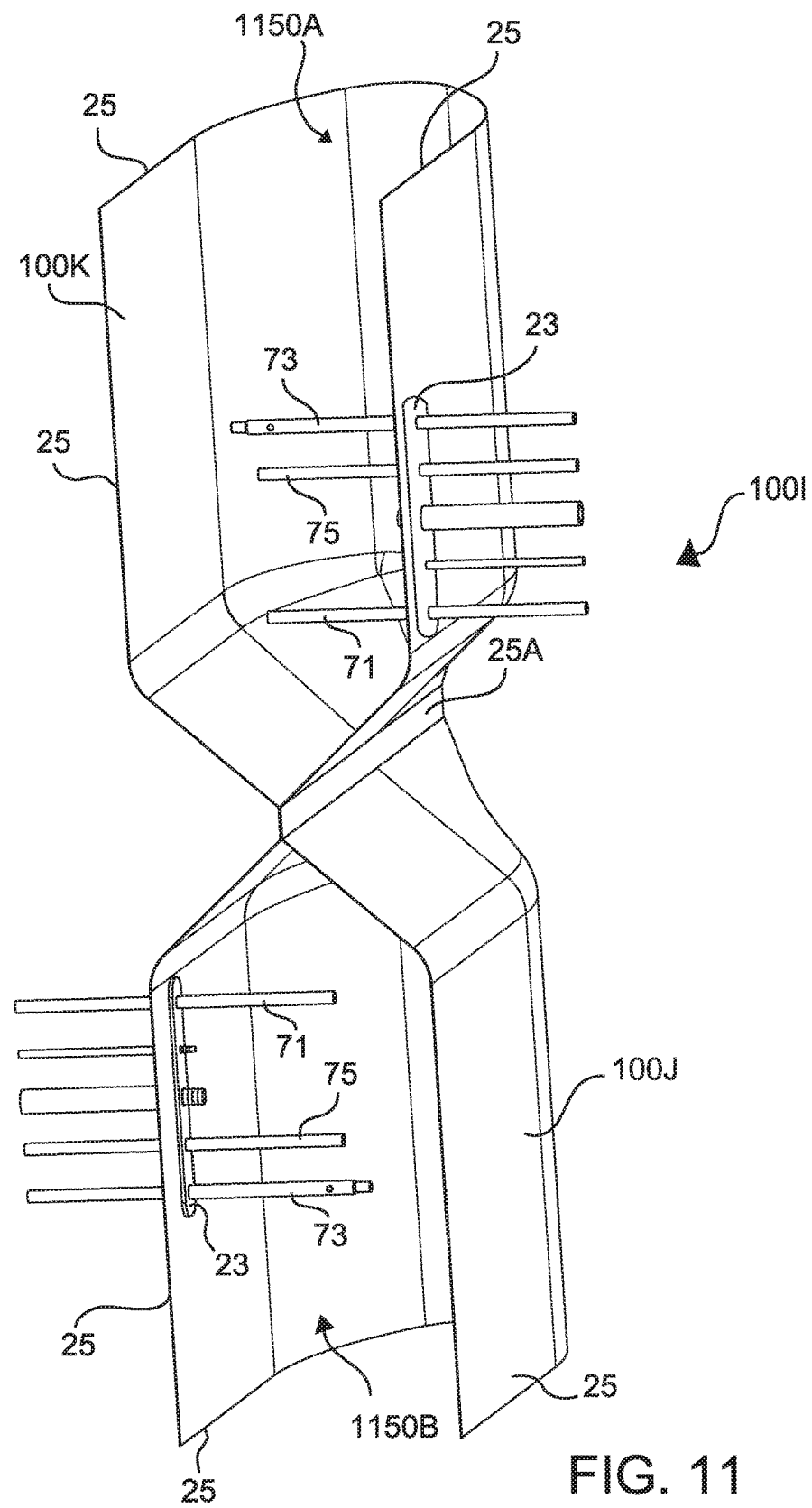
FIG. 11 is a perspective diagram of an example of an enclosure of the present teachings having multiple interior cavities.

Referring now to FIG. 11, enclosure 100I can include, but is not limited to including, multiple interior cavities 1150A, B. Enclosure 100, in a partially sealed state, can include first enclosure portion 100J and second enclosure portion 100K. First enclosure portion 100J and second enclosure portion 100K may be sealed to one another at sealing surface 25 and/or dividing sealing region 25A. Dividing sealing region 25A may be created to isolate interior cavities 1150A, B to prevent fluid and/or liquid communication between interior cavities 1150A, B. Each of interior cavities 1150A, B may be associated with adapter 23 which can allow fluid tubes, e.g. fluid lines 311, 313, 315, 317, 319, 71, 73, 75 that can be exterior and/or interior to cavities 1150A, B to be coupled to adapter 23.

Figure 12:
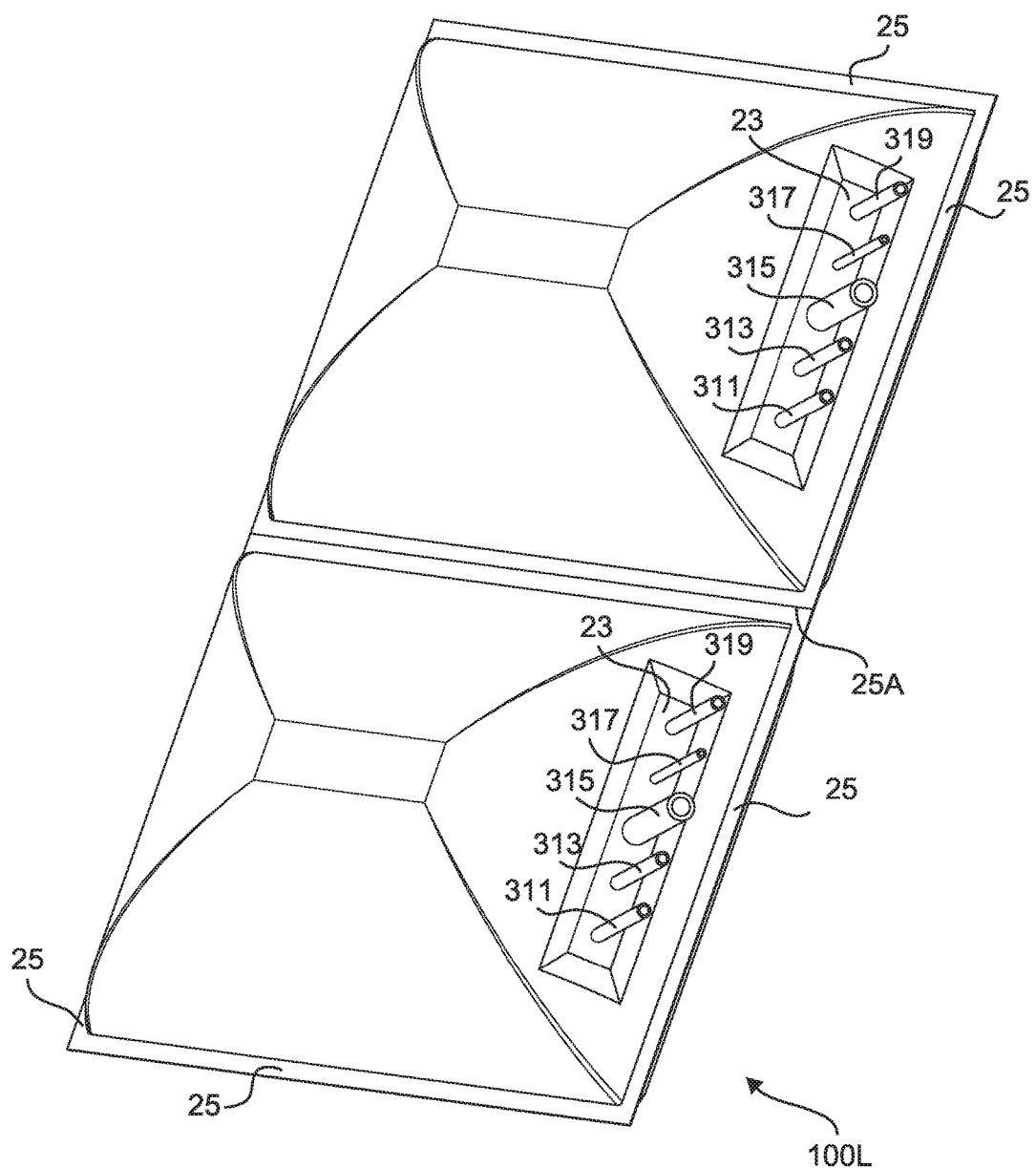
FIG. 12 is a perspective diagram of an example of an enclosure of FIG. 11.

Referring now primarily to FIG. 12, enclosure 100I (FIG. 11) is depicted in a sealed state. First enclosure portion 100J and second enclosure portion 100K can be continuous with one another and form clamshell connected enclosure 100L. First enclosure portion 100J may be folded into contact with second enclosure portion 100K. A seal may then be formed between first enclosure portion 100J and second enclosure portion 100K. In some configurations, a seal is formed between two enclosure portions 100J, 100K at dividing sealing region 25A as shown in FIG. 11. After any specimen(s) 162 (FIG. 1) have been inserted and after any manipulation of fluid tubes, e.g. fluid lines 71, 73, 75 on interior of cavities 1150A (FIG. 11), 1150B (FIG. 11), interior cavities 1150A (FIG. 11), 1150B (FIG. 11) may be completely sealed from the surrounding environment at various of sealing surfaces 25.

Figure 13A:
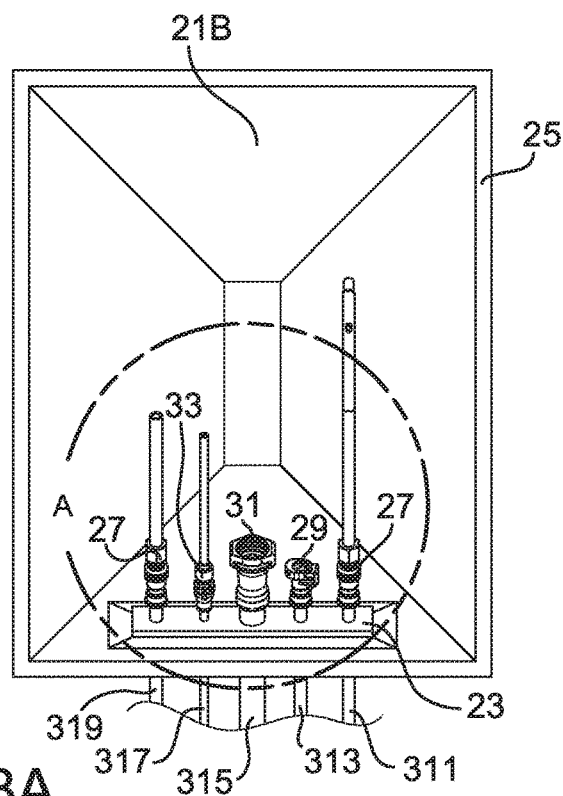
FIG. 13A is a perspective diagram of the interior of an example of an enclosure of the present teachings having optional interior tubing connectors.
Figure 13B:
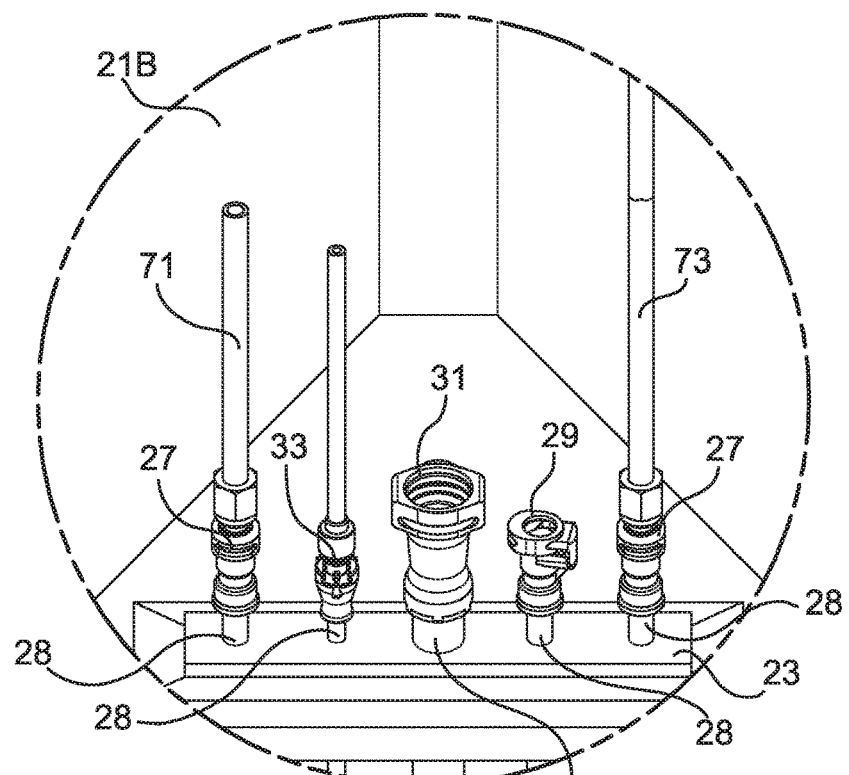
FIG. 13B is a perspective diagram of a detailed view of the indicated region of FIG. 13A.

Referring now primarily to FIG. 13A and FIG. 13B (which shows a detailed view of region A of FIG. 13A), interior surface 21B can include adapter 23. Various types of tubing connectors 27, 29, 31, and 33 may be introduced to the interior of enclosure 100 (FIG. 10) via adapter 23. Tubing connectors 27 can be used, for example, for inlet and drain fluid lines 71, 73 to deliver fluid to and extract fluid from enclosure 100 (FIG. 10). Fluid lines 311, 313, 315, 317, 319 associated with tubing connectors 27, 29, 31, 33 can be inserted into adapter 23 through orifices 28 in adapter 23. Orifices 28, for example, can be milled into adapter 23 for specific-sized lines or may be formed during molding of adapter 23. Alternatively, adapter 23 may be formed as a solid structure which can be welded to enclosure 100 (FIG. 10). Orifices 28 may be added afterword. For example orifices 28 may be milled (e.g. drilled) or punched through enclosure 100 (FIG. 10) and adapter 23 after welding the two together. In other configurations, enclosure interior 21B can include, for example, but not limited to, pre-cut line holes which may align with orifices 28 milled, punched, formed, etc. in adapter 23.

Figure 14:
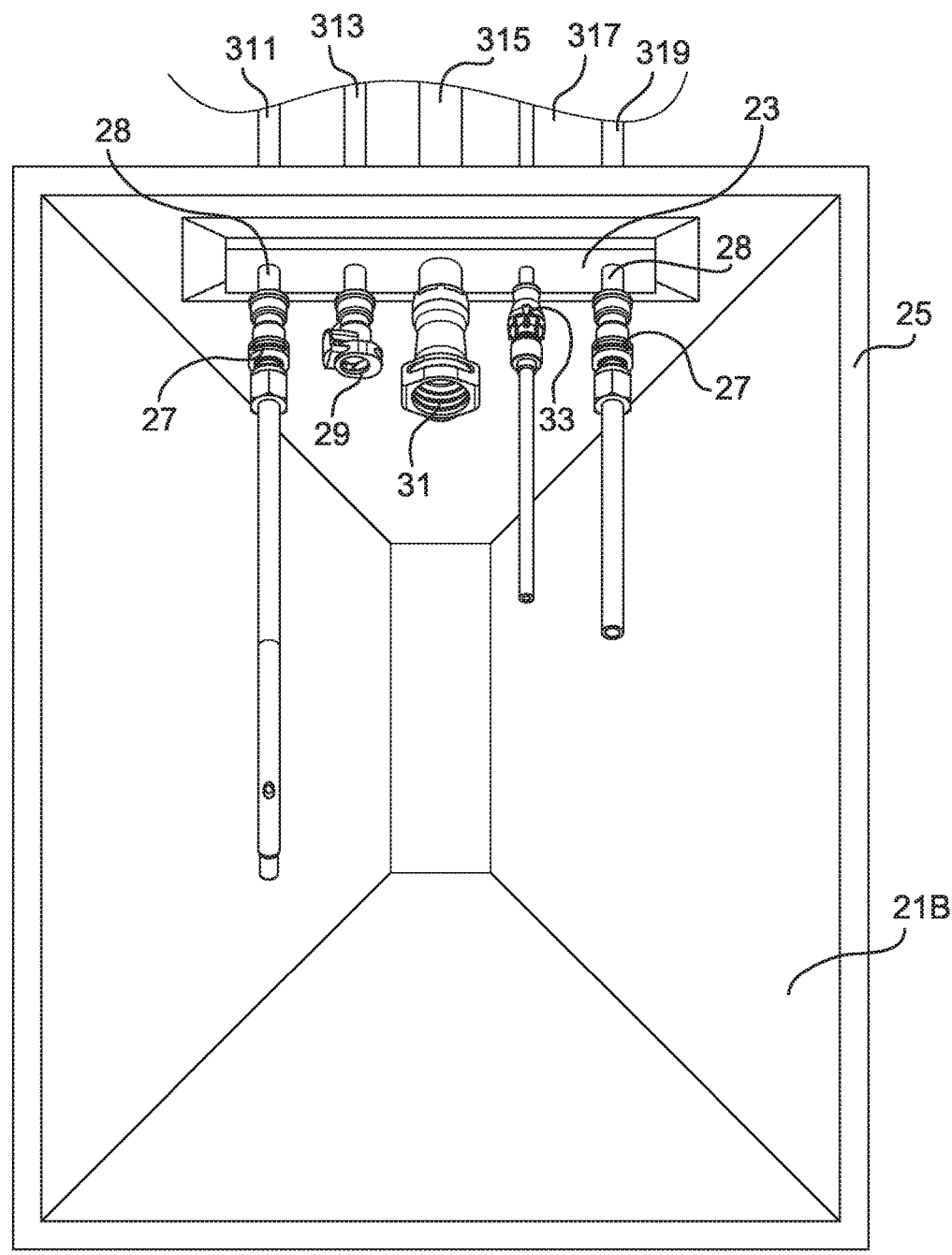
FIG. 14 is a perspective diagram of an example of an enclosure of the present teachings having interior and exterior tubing and an interior adapter.

Referring now primarily to FIG. 14, tubing connectors 27, 29, 31, and 33 can be provided at the terminal ends of fluid lines 311, 313, 315, 317, 319 respectively. Fluid lines 311, 313, 315, 317, 319 can pass through adapter 23 at orifices 28. Depending on the fluid line, or the configuration, fluid line 311, 313, 315, 317, 319 may be passed from the outside of enclosure 100 (FIG. 10) to the interior of enclosure 100 (FIG. 10) or vice versa.

Figure 15:
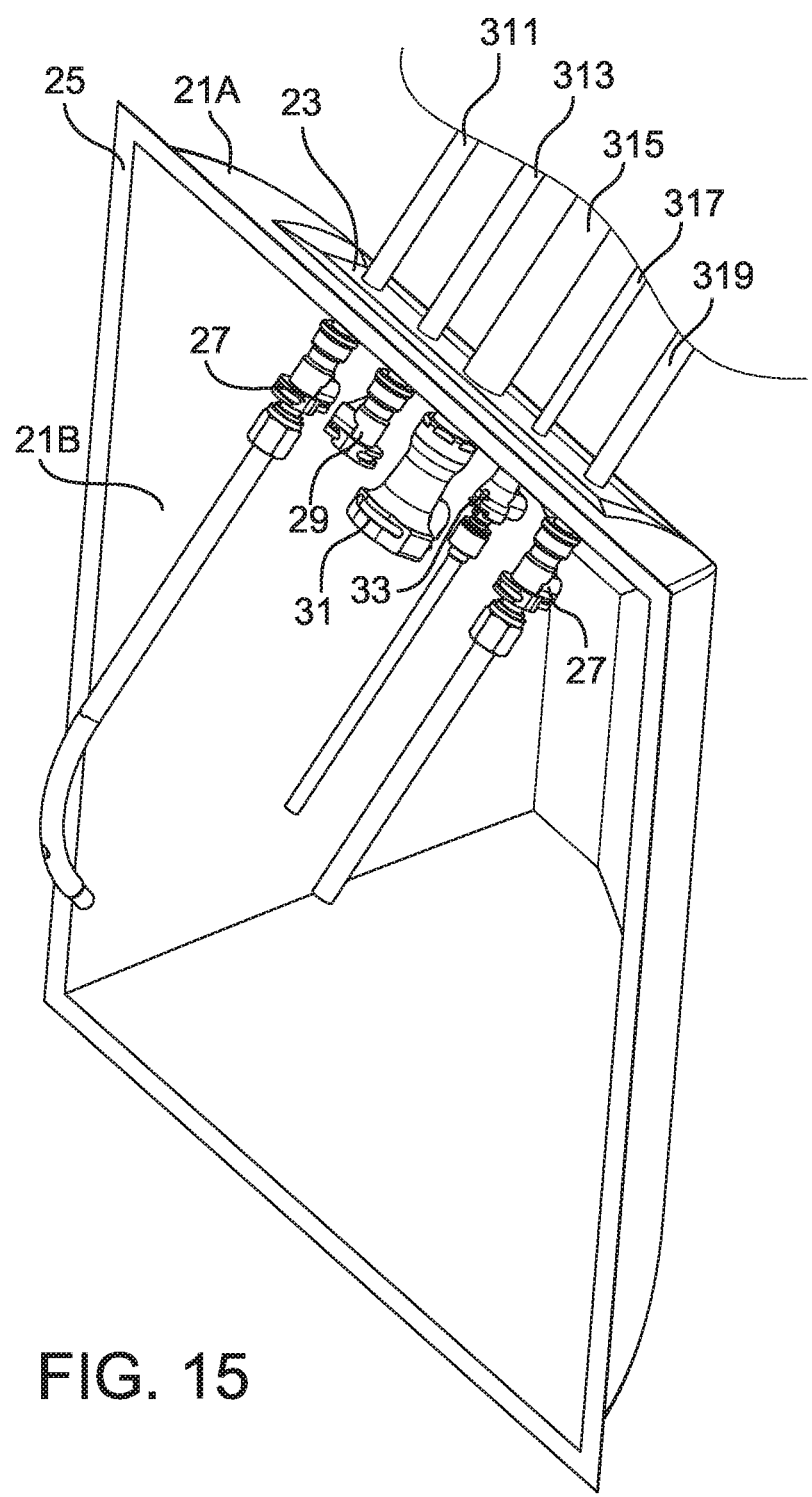
FIG. 15 is a perspective diagram of an example of an enclosure of the present teachings having interior and exterior tubing and an exterior adapter.

Referring now primarily to FIG. 15, adapter 23 can provide a pass-through extending from exterior surface 21A to interior surface 21B of enclosure 100 (FIG. 10). Fluid lines 311, 313, 315, 317, 319 may extend through the pass-through to adapter 23.

Figure 16A:
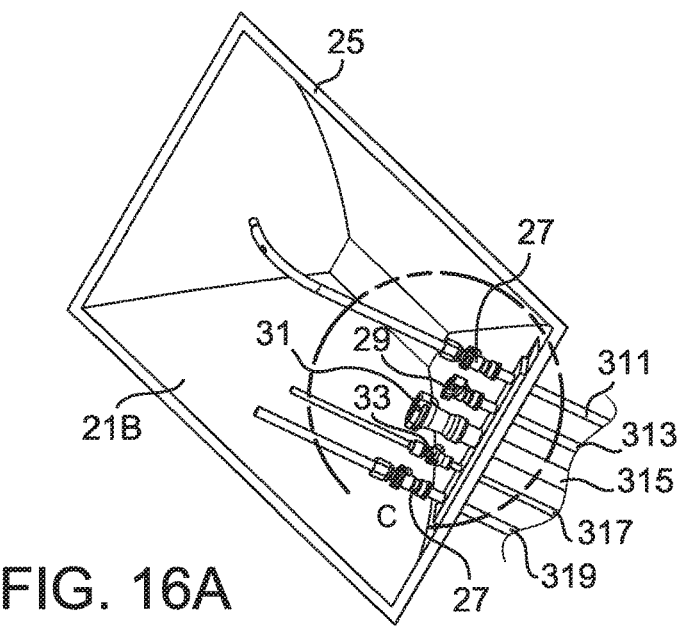
FIG. 16A is a perspective diagram of an example of an enclosure of the present teachings having optional interior tubing connectors.
Figure 16B:
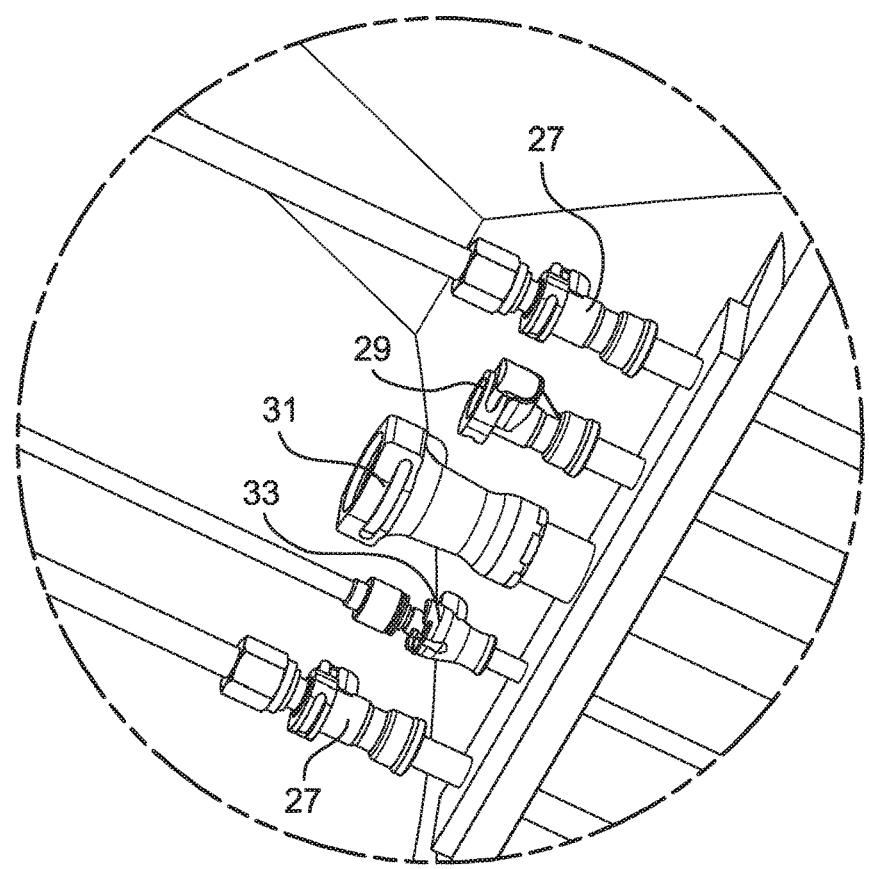
FIG. 16B is a perspective diagram of a detailed view of the indicated region of FIG. 16A.

Referring now to FIG. 16A and FIG. 16B (which shows a detailed view of region C of FIG. 11), optional interior tubing connectors 27, 29, 31, and 33 can be of various types, depending on the application. For example, tubing connector 31 attached to fluid line 315 can be large enough to accommodate an attachable fluid conduit having an outer diameter of, for example, but not limited to, about 0.5 inch. Further, tubing connector 29 can be sized to accommodate a fluid conduit having an outer diameter of, for example, but not limited to, about 0.25 inch. Tubing connector 33 can be sized to accommodate a fluid conduit having an outer diameter of, for example, but not limited to, about 0.125 inch. After enclosure 100 (FIG. 10) has been sealed at sealing surface 25, fluid lines 311, 319 attached to tubing connectors 27 can deliver and extract fluid from enclosure 100 (FIG. 10) after the target specimen(s) 162 (FIG. 2), for example a lung, has been placed in fluid communication with, for example, but not limited to, fluid lines 313, 315, 317 via tubing connectors 29, 31, and 33.

Figure 17:
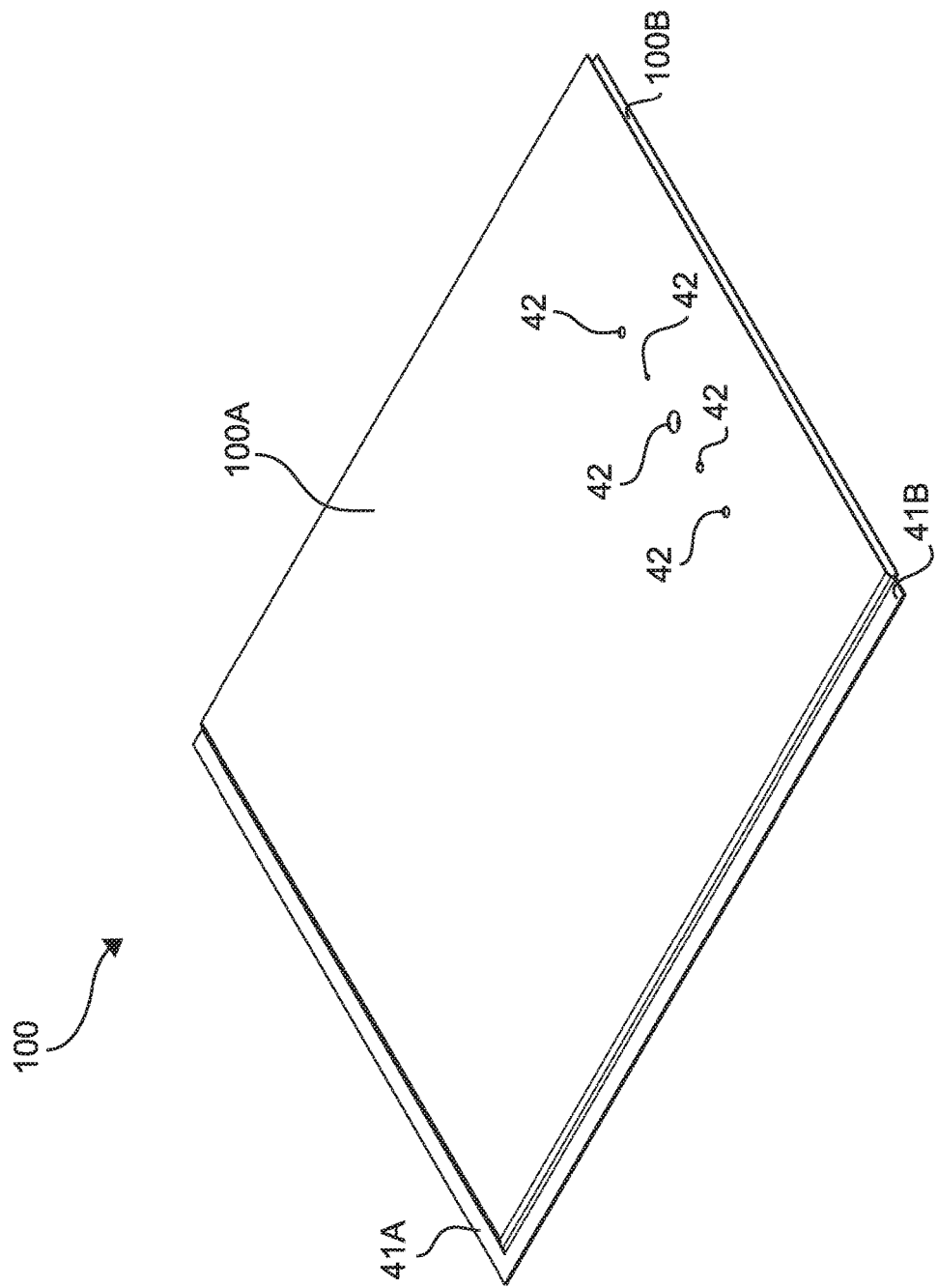
FIG. 17 is a perspective diagram of an example of an enclosure of the present teachings having pre-cut line inlets.

Referring now to FIG. 17, enclosure 100 can be provided in a flattened state where enclosure 100 has a small interior volume. Enclosure 100 may be later filled with fluid, specimen(s) 162 (FIG. 1), and other materials when used. Additionally, enclosure 100 may be provided partially sealed to facilitate connection of tubing to and placement of specimen(s) 162 (FIG. 1) into enclosure 100. Enclosure 100 may be later completely sealed to isolate the interior volume of enclosure 100 from the exterior environment. Enclosure 100 may be manufactured with pre-formed tubing holes 42. Enclosure first section 100A can be sealed during manufacture to enclosure second section 100B at, for example, first edge 41A and possibly second edge 41B, or vice versa.

Figure 18:
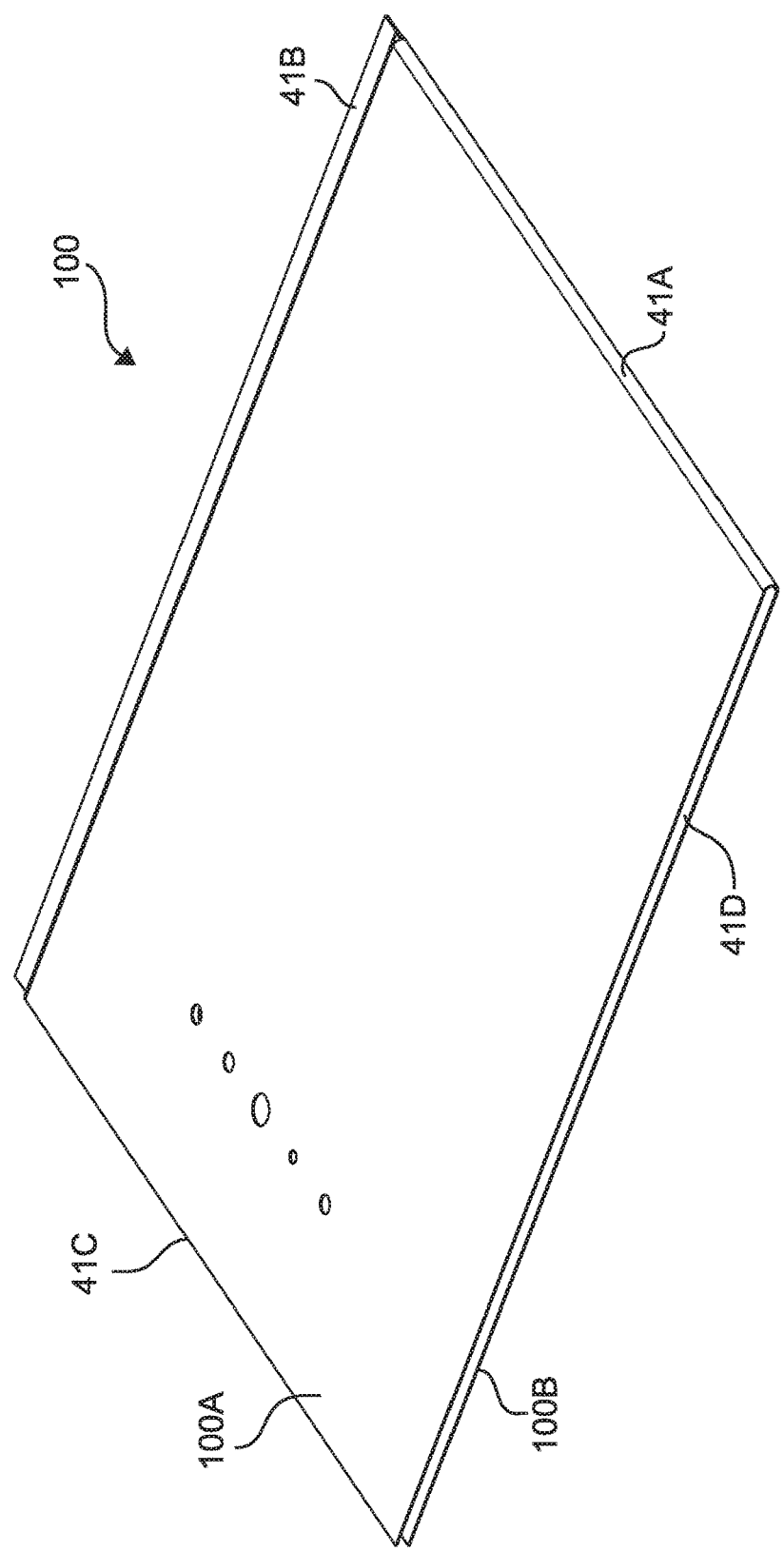
FIG. 18 is a perspective diagram of an example of an enclosure of the present teachings having pre-cut line inlets.

Alternatively, and referring now to FIG. 18, in another configuration, enclosure 100 may be provided as a clamshell with enclosure first section 100A which is continuous with enclosure second section 100B along first edge 41A. Additionally, an edge or portion of enclosure first section 100A may be joined to enclosure second section 100B. For example, enclosure first section 100A and enclosure second section 100B may be joined along second edge 41B. At least one edge (e.g. edges 41C, 41D) or portion of enclosure first section 100A may be open or not joined to enclosure second section 100B.

Figure 19:
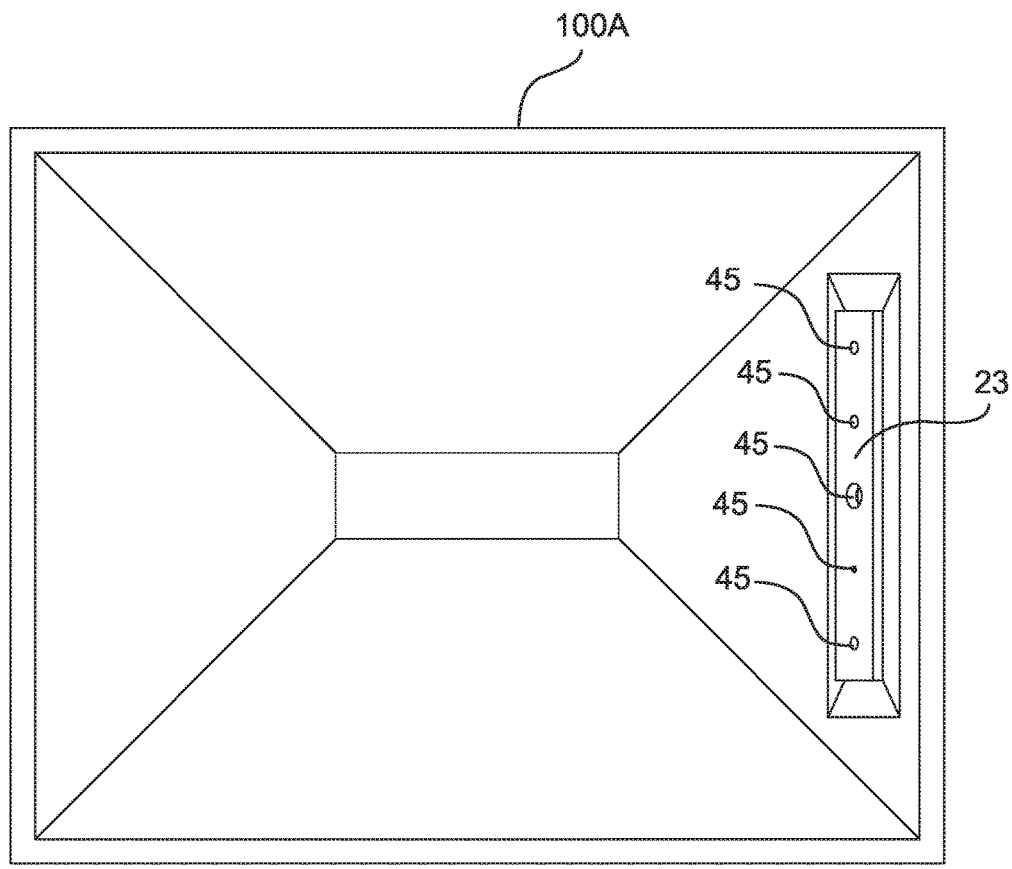
FIG. 19 is a perspective diagram of an example of the interior of an enclosure of the present teachings having an adapter.
Figure 20:
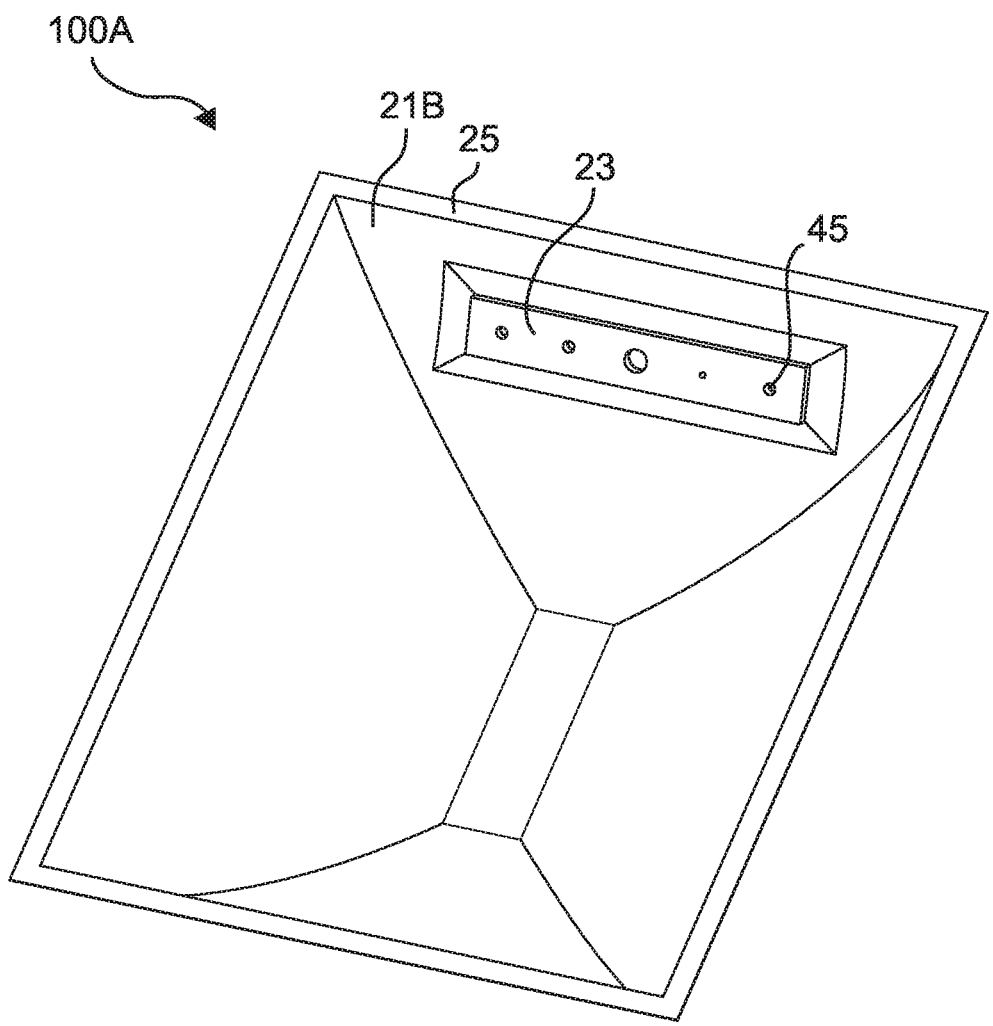
FIG. 20 is a perspective diagram of an example of an enclosure of the present teachings having an adapter with pre-set line inlets.

Referring now to FIGS. 19 and 20, adapter 23 having tubing ports 45 can be attached to enclosure first section 100A. Enclosure first section 100A can be perforated, for example, but not limited to, after adapter 23 becomes attached to enclosure first section 100A. There can be any number and size of tubing ports 45, depending on the application.

Figure 21:
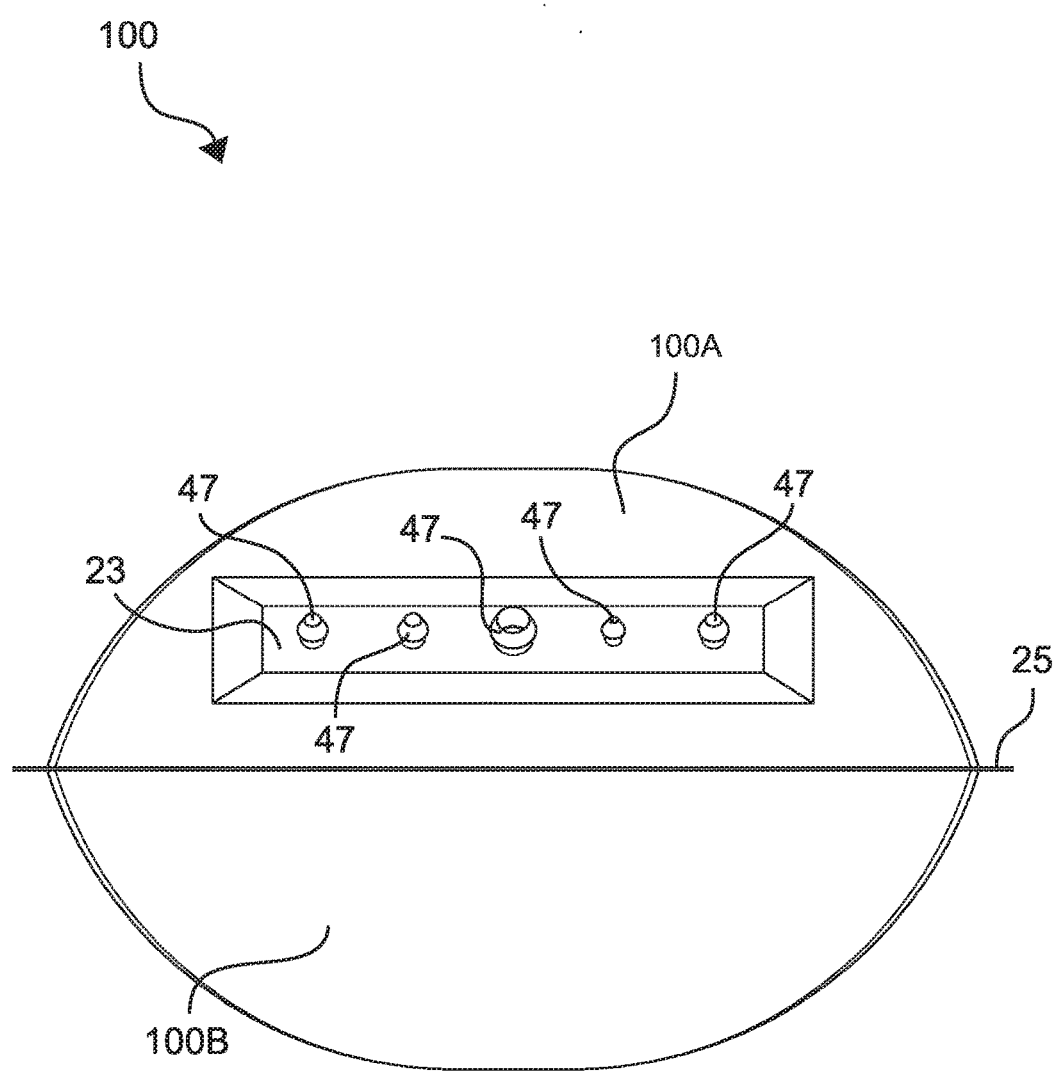
FIG. 21 is a side view diagram of an example of a sealed enclosure of the present teachings having external barbed fittings.
Figure 22:
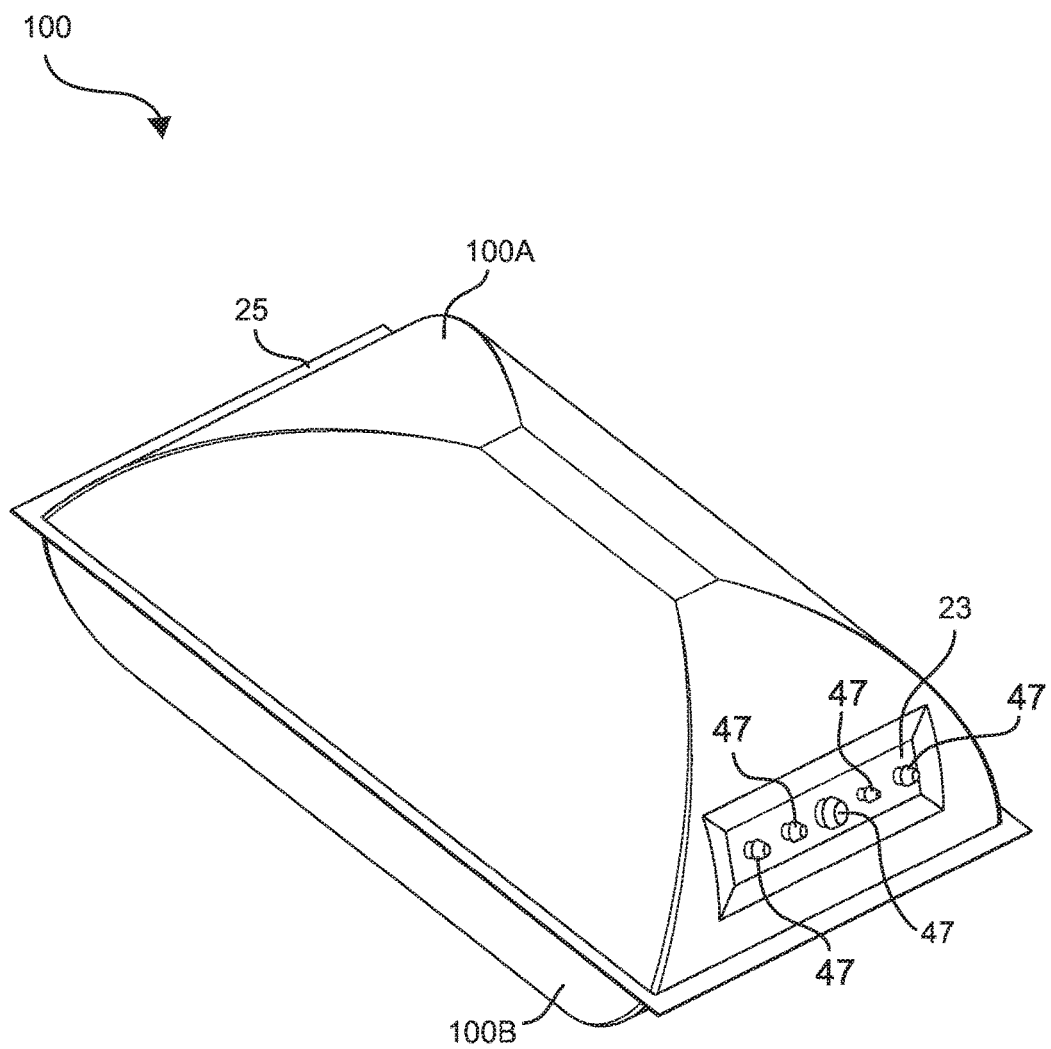
FIG. 22 is a perspective diagram of an example of a sealed enclosure of the present teachings having exterior barbed fittings.

Referring now primarily to FIGS. 21 and 22, enclosure 100, sealed at sealing surface 25, can include adapter 23 accommodating one or more barbed fitting 47 for retaining, for example, but not limited to, a line such as any or a combination of fluid lines 311, 313, 315, 317, 319 (FIG. 15). Barbed fittings 47 can be various shapes and styles, and can extend from a number of faces of adapter 23. For example, adapter 23 may include one or more barbed fitting 47 for each fluid line 311, 313, 315, 317, 319 (FIG. 15) with which it may be associated. Adapter 23 may, for example, include barbed fittings 47 extending from adapter 23 to the exterior of enclosure 100.

Figure 23:
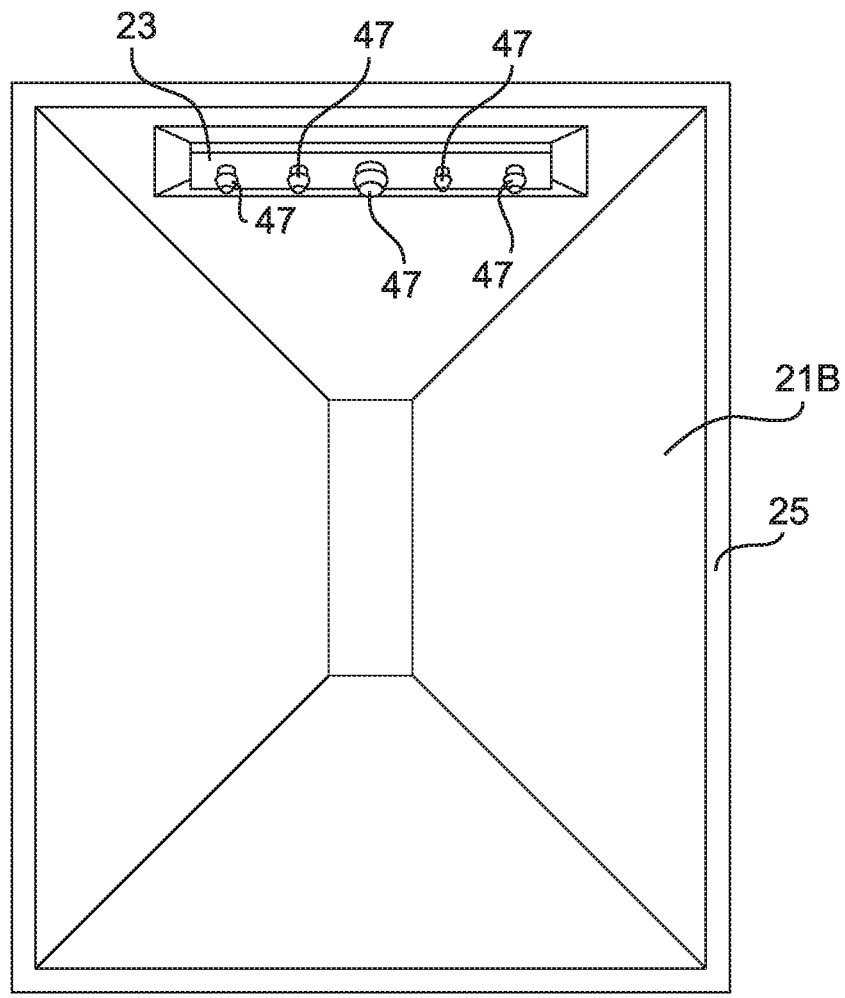
FIG. 23 is a perspective diagram of an example of an enclosure of the present teachings having interior barbed fittings on the adapter.
Figure 27:
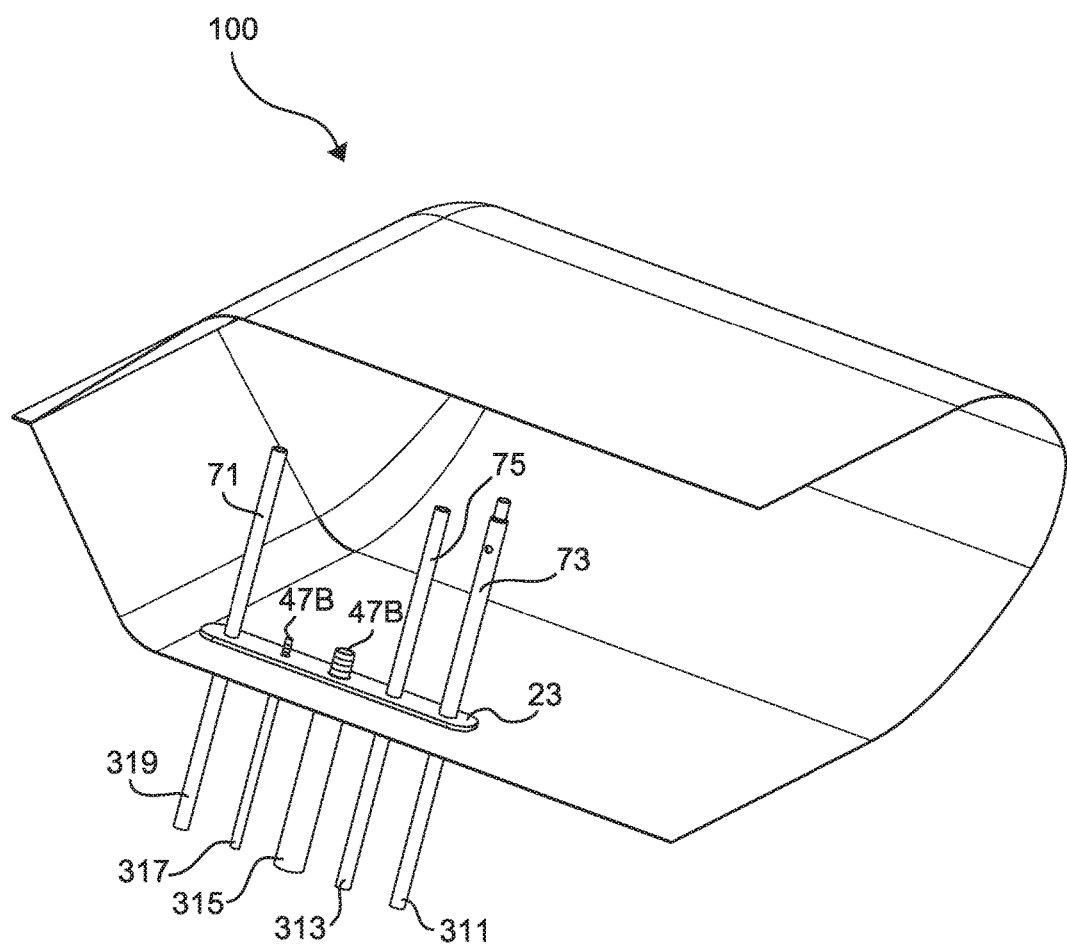
FIG. 27 is a perspective diagram of an example of an enclosure of the present teachings having barbed fittings on multiple faces of the adapter.

Referring now primarily to FIG. 23, adapter 23 may instead or additionally include one or more barbed fitting(s) 47 for retaining, for example, but not limited to, lines such as fluid lines 71, 73, and 75 (FIG. 27) disposed within the interior of the enclosure 100 (FIG. 27). As above, such fittings can be various shapes and styles and may extend from adapter 23 into the interior volume of enclosure 100 (FIG. 27).

Figure 24:
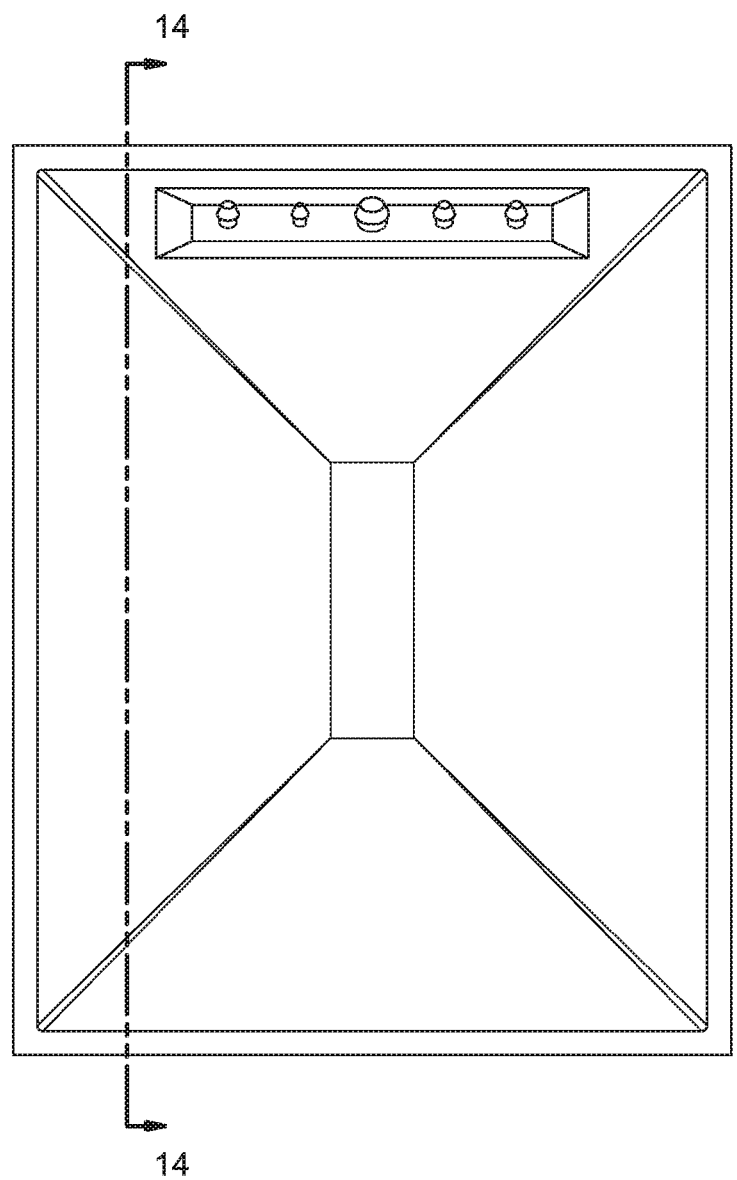
FIG. 24 is a perspective diagram of an example of the interior of an enclosure of the present teachings.
Figure 25A:
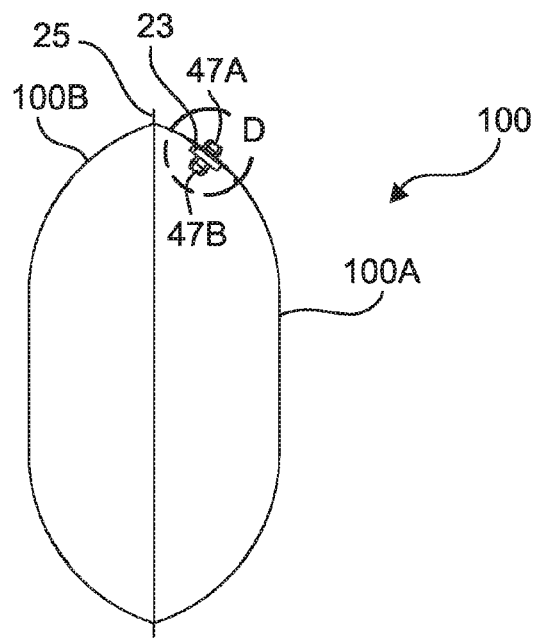
FIG. 25A is a cross sectional view of an example of an enclosure of the present teachings taken at line 14-14 of FIG. 24.

Referring now to FIGS. 24 and 25A, a cross section of enclosure 100 taken at line 14-14 (FIG. 24) is shown. Enclosure first section 100A, may be sealed at sealing surface 25 to enclosure second section 100B. Adapter 23 may be attached to enclosure 100. Adapter 23 may include one or more exterior barbed fitting 47A and one or more interior barbed fittings 47B. Barbed fittings 47A, 47B may each include a lumen which may be in fluidic communication with each other via a pathway in adapter 23. Tubing may be attached to each of exterior barbed fittings 47A and interior barbed fittings 47B to allow for fluid to be transferred into and out of enclosure 100.

Figure 25B:
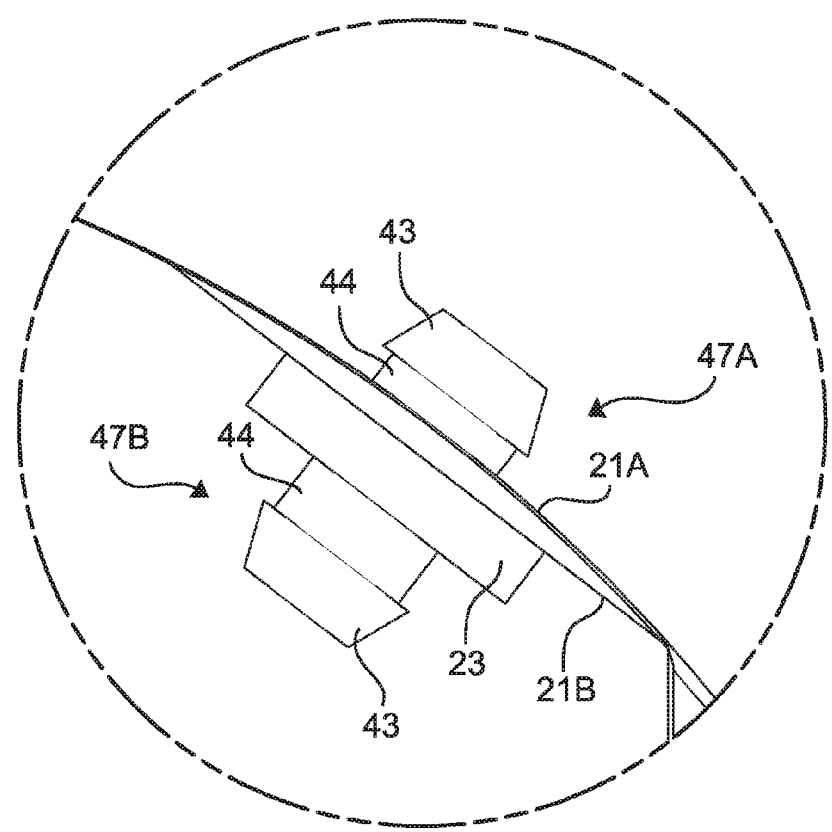
FIG. 25B is a detailed view of region D of FIG. 25A.

Referring now primarily to FIG. 25B, a detailed view of region D of FIG. 25A is shown. Adapter 23 may be attached to one of interior surface 21B or exterior surface 21A of enclosure 100 (FIG. 25A). In some configurations, barbed fittings 47A, 47B can include stem 44 and barb 43. At least a portion of barb 43 may have a larger diameter than stem 44. In some configurations, barb 43 may be a formed as a conical frustum or series of stacked conical frustums. Stem 44 of each of barbed fittings 47A, 47B may be inserted and retained within orifice 28 in adapter 23. Stem 44 of barbed fitting 47A, 47B may also extend through enclosure 100 to either the interior or exterior of enclosure 100 depending on exterior/interior surfaces 21A, 21B adapter 23 is coupled to. Alternatively, barbed fittings 47A, 47B may be formed integrally with adapter 23 during manufacture of adapter 23. One or more exterior barded fitting 47A or one or more interior barbed fitting 47B can be omitted, depending on the application.

Figure 26:
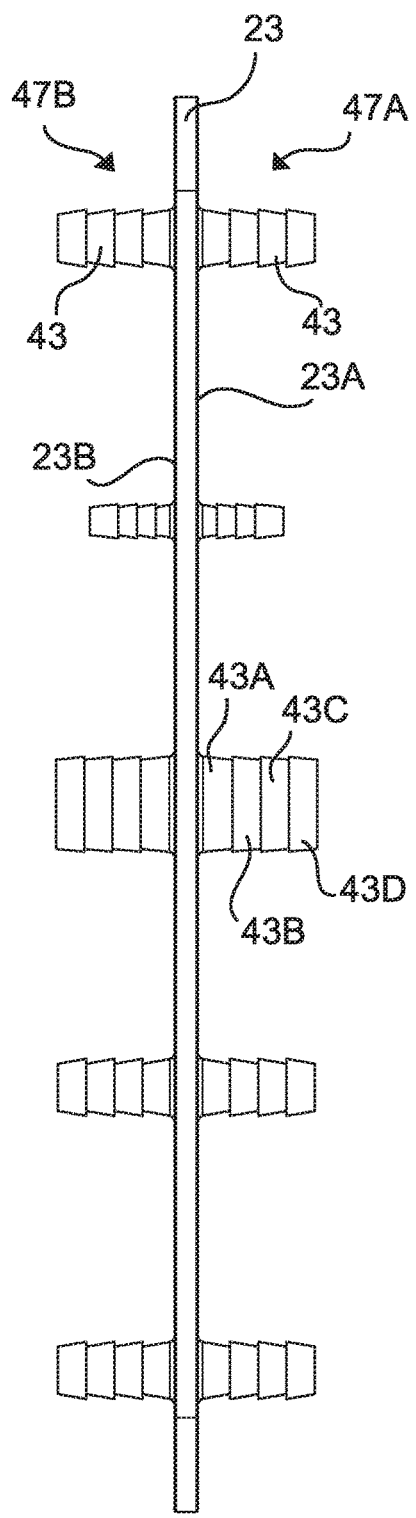
FIG. 26 is a side view diagram of an example of an adapter of the present teachings.

Referring now to FIG. 26, adapter 23 may include barbed fittings 47A, 47B on first side or face 23A and second side or face 23B. Barbed fittings 47A, 47B may, for example, be projections including a stacked series of conical frustums 43A, 43B, 43C, 43D. Barbed fittings 47A, 47B may be sized to fit a variety of different tubing sizes.

Referring now also to FIG. 27, fluid lines 311, 313, 315, 317, 319, 71, 73, 75 may be connected to barbed fittings 47A (FIG. 26), 47B to establish fluid communication pathways between the interior and the exterior of enclosure 100. Including barbed fittings 47A (FIG. 26), 47B on the multiple faces of adapter 23 may allow at least some tubing connectors such as tubing connectors 27, 29, 31, 33 (FIG. 13B) to be omitted. Instead, fluid lines such as fluid lines 311, 313, 315, 317, 319, 71, 73, 75 may directly couple to adapter 23 via barbed fittings 47A (FIG. 26), 47B.

Figure 28A:
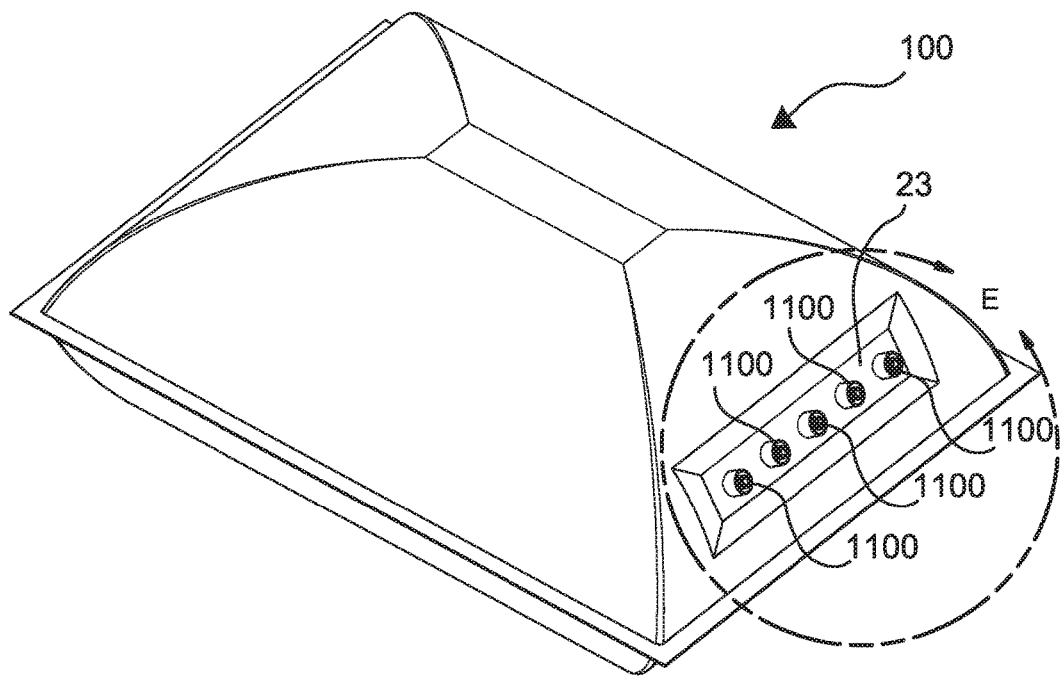
FIG. 28A is a perspective diagram of an example of an adapter of the present teachings having tubing connectors.
Figure 28B:
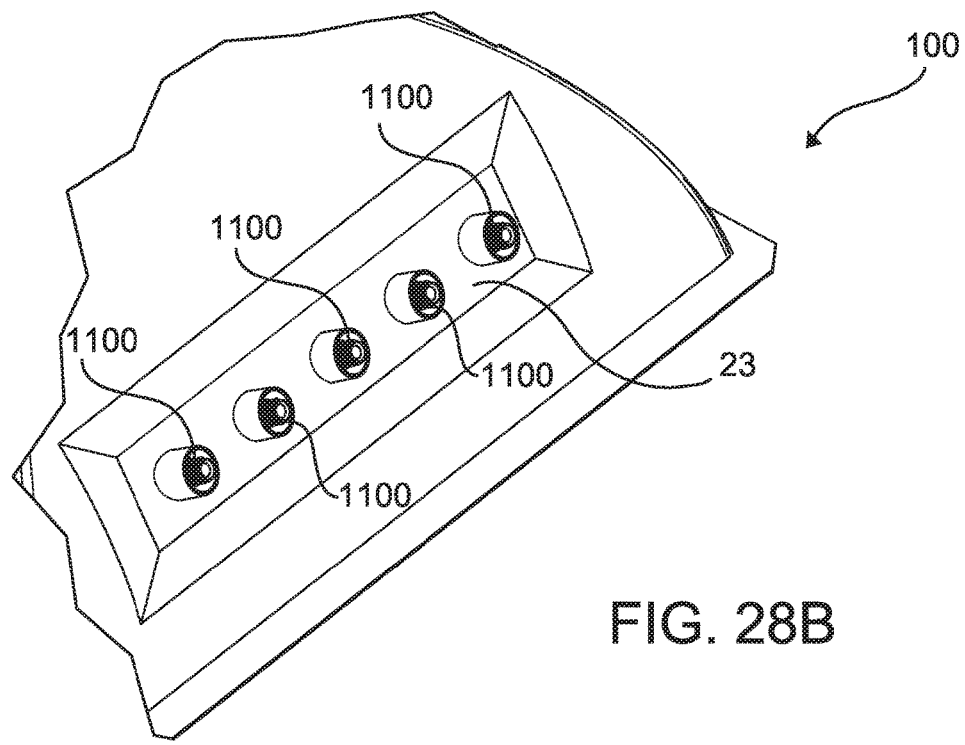
FIG. 28B is a detailed view of region E of FIG. 28A.

Referring now to FIG. 28A and FIG. 28B (which depicts a detailed view of region E of FIG. 28A), enclosure 100 may include adapter 23 having a number of tubing connectors 1100. Tubing connectors 1100 may be any of a variety of tubing connectors such as luer type connectors. Tubing connectors 1100 may be attached to adapter 23 via any suitable process and in some configurations may be welded, solvent bonded, attached with a fixative, etc. Similarly to barbed fittings 47A (FIG. 26), 47B (FIG. 25B), tubing connectors 1100 may be disposed on more than one side of the adapter 23. At least one tubing connector 1100 may be accessible to tubing located external to enclosure 100 and at least one tubing connector 1100 may be accessible to tubing disposed inside enclosure 100. Each of the fluid lines which may be attached to the adapter 23 may include a cooperating mating structure which may mate with tubing connectors 1100 on the adapter 23.

Figure 29:
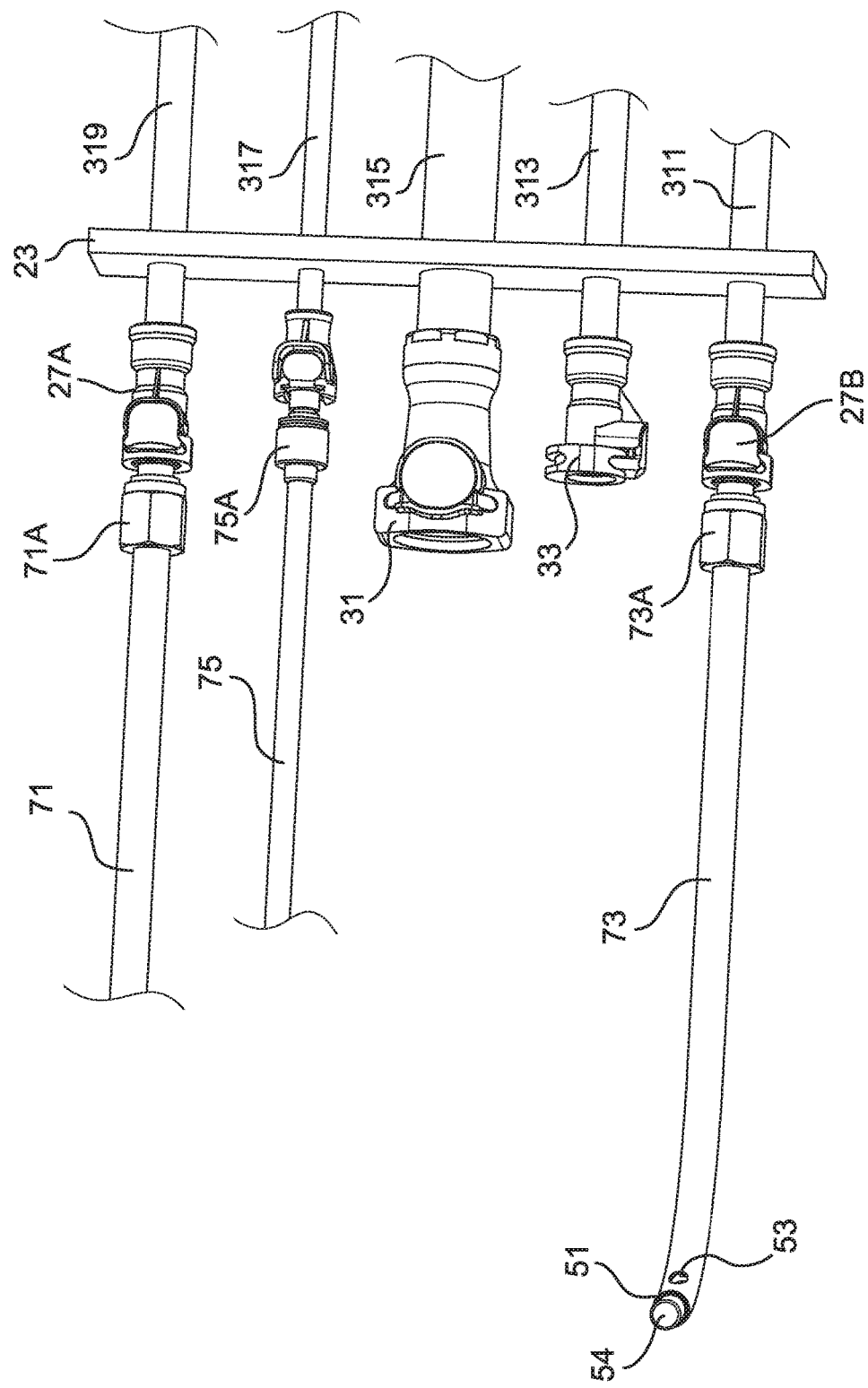
FIG. 29 is a detailed perspective diagram of an example of an enclosure of the present teachings having interior and exterior tubing.
Figure 30:
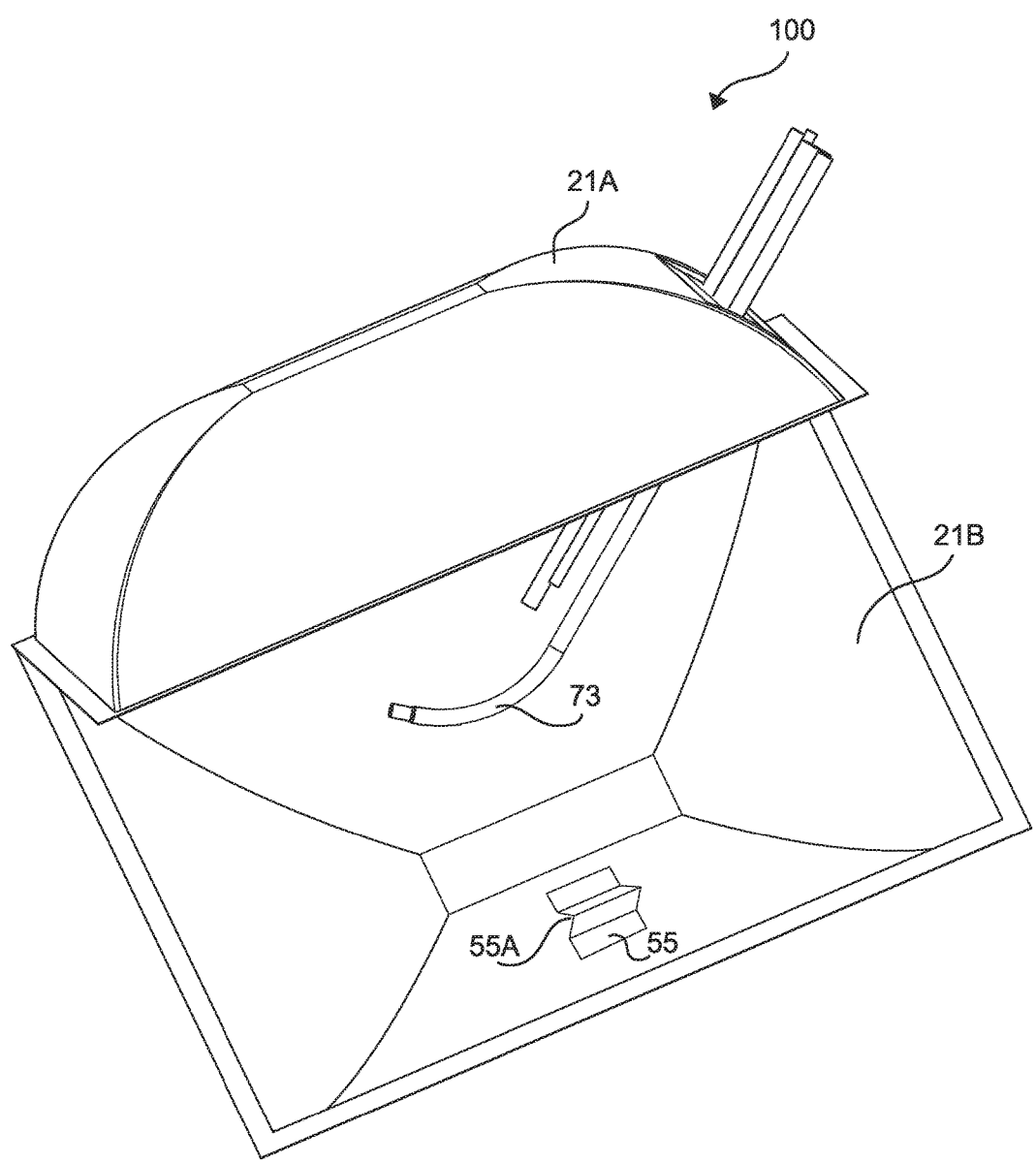
FIG. 30 is a perspective diagram of an example of an enclosure of the present teachings having a tether.

Referring now primarily to FIG. 29, tubing connector 27A (which may be a quick connect) can attach to fluid line 71. Fluid line 71 may include mating body 71A which may mate into tubing connector 27A. Fluid may be delivered from reservoir 182 (FIG. 1) to the interior of enclosure 100 (FIG. 30) via supply line 311 and fluid line 71. Specimen line 75 may include a mating body 75A which may mate into tubing connector 29. Fluid may be delivered from reservoir 182 (FIG. 1) to specimen 162 (FIG. 1) in enclosure 100 (FIG. 30) via line 313 and specimen line 75. Tubing connector 27B (which may be a quick connect) can attach to drain line 73 which can include at least one drain hole 53. Drain line 73 may include mating body 73A which may mate into tubing connector 27B. Drain line 73 may also include drain line end 51 which may include, for example, but not limited to, one or more positioner 54. Positioner 54 may in some configurations be a magnetic element and/or at least one weight. Magnetic elements may include magnets or materials which react to the presence of a magnetic field such as certain rare earth metals, transition metals, or various alloys. If positioner 54 is a magnetic element, a magnet external to enclosure 100 (FIG. 30) may be used to affirmatively position drain line end 51. If positioner 54 is a weight, positioner 54 may be used to passively position drain line 73 at the bottom of enclosure 100 (FIG. 30). If enclosure 100 (FIG. 30) is repositioned (e.g. flipped over), positioner 54 may passively bring drain line 73 to a new position within enclosure 100 (FIG. 30). Positioners 54 may also be included at other locations on drain line 73 or may be included on other fluid lines (e.g. fluid and specimen lines 71, 75). Positioners 54 may be attached to a fluid line in any suitable manner. In some configurations, positioner 54 is interference fit into drain line end 51. Alternatively, a weight, or metallic/magnetic element positioned 54 may be embedded in drain line end 51 (or at other locations) in drain line 73 (or other line) via, an overmolding process for example.

Referring now to FIG. 30, enclosure 100 which has been partially exploded is shown. In some configurations, interior surface 21B of enclosure 100 may include one or a number of straps or tethers 55. Tether(s) 55 may be used to tether or strap one or more lines (e.g. drain line 73) in place during usage. Before enclosure 100 is sealed, the desired line or lines may be attached to or otherwise associated with tether 55 which in turn may be attached to interior surface 21B of enclosure 100. The desired line or lines may, for example be placed into channel 55A between tether 55 and interior surface 21B of enclosure 100. Flanking each side of channel 55A, tether 55 may be coupled to enclosure 100. Tether 55 may be attached to the bag using any method, for example, but not limited to, heat sealed.

Figure 31:
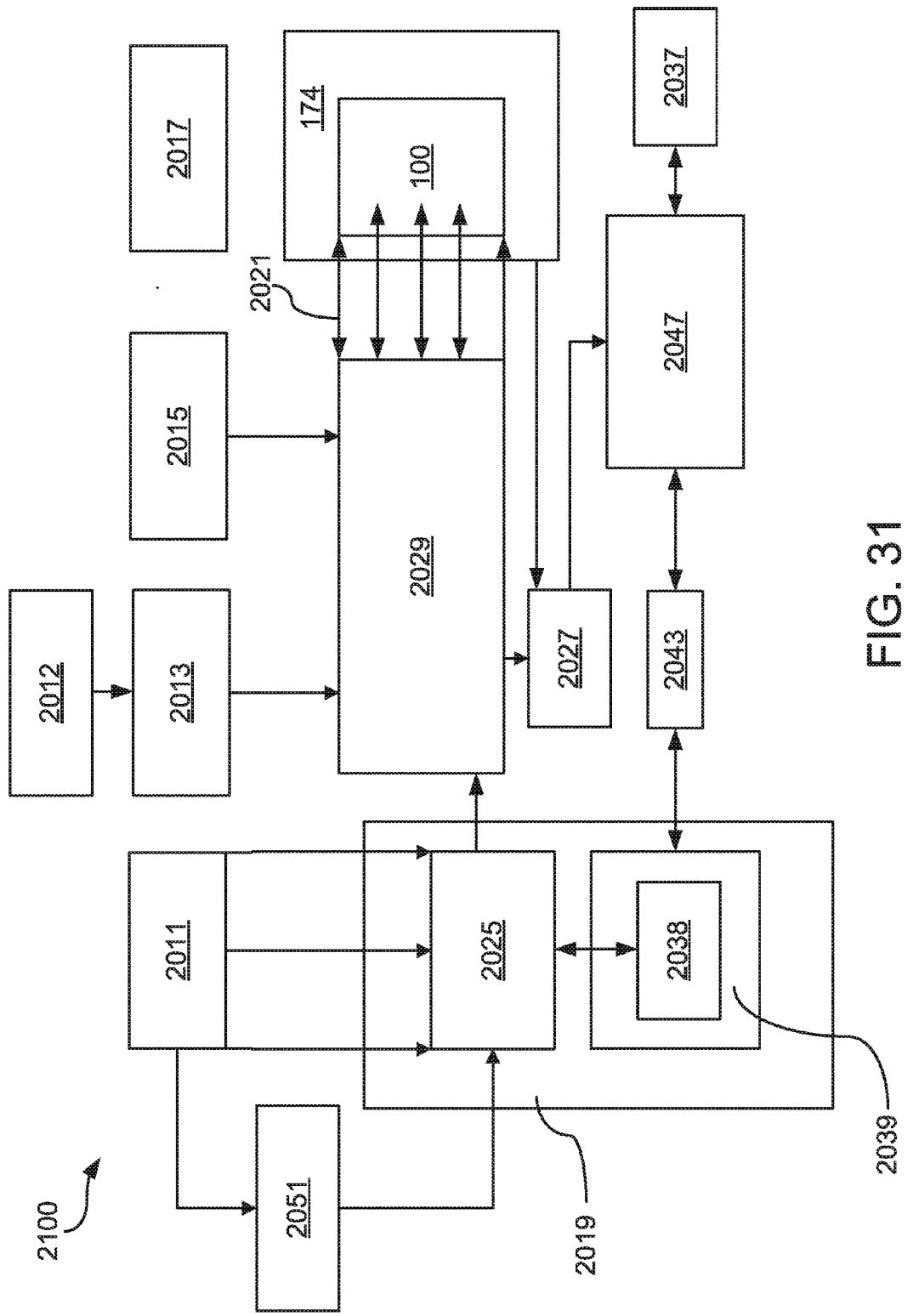
FIG. 31 is a schematic block diagram of components of a system of the present teachings and fluid and signal pathways of the system.

Referring to FIG. 31, system 2100 for use in specimen engineering can include, but is not limited to including, one or more valve module 2019. Valve module 2019 can include pneumatic distribution assemblies 2025 which can be in fluid communication with parts of fluid circuit 2029 via fluid conduits, a manifold or combination thereof for example. Pneumatic distribution assemblies 2025 may include one or more valves which may be actuated to selectively place parts of fluid circuit 2029 in communication with pressure supplied from pressure source 2011. Each pneumatic distribution assembly 2025 can include, for example, but is not limited to including, four or fewer valves. Pneumatic distribution assemblies 2025 may also include manifolds which may connect valves of pneumatic distribution assembly 2025 to a common bus or buses. Pressure source 2011 may provide fluid at one or more positive pressure and one or more negative pressure. Pressure regulator 2051 may be included to help regulate pressure from pressure source 2011. Pressure source 2011 may provide pressure at positive and negative pressure rail (e.g. −500 mmHg and 900 mmHg) which may be individually stepped up or down by regulator 2051 to other pressures. The pressures may instead or additionally be stepped up or down by modulating the opening of valves of pneumatic distribution assemblies 2025 such that the pressure supplied at a part of fluid circuit 2029 is maintained at a desired value. Pneumatic distribution assemblies 2025 may include one or more pressure sensor.

Referring again to FIG. 31, controller 2047 may control the flow of fluid through fluid circuit 2029, for example, to/from enclosure 100. Controller 2047 can provide commands to valve module 2019 control circuitry 2039 which can pump fluid through system 2100. Controller 2047 can communicate commands to valve module 2019 through PCAN (CANbus interface) 2043, and can receive information about fluid pathway 2029 and the fluid therein from sensors 2027. Sensors 2027 can include, but are not limited to including, temperature, pressure, conductivity, leak detection, air-in-line, flow rate, level sensors, and weight sensors. Controller 2047 can calibrate pressure sensors through CANbus 2043, update pressure readings, and display flow diagram valve pressures. Though the example configuration uses CANbus interface 2043, any other communication interface may be used.

Continuing to refer to FIG. 31, controller 2047 may be initialized by setting default values 3059 (FIG. 31B) for parameters used during, for example, but not limited to, the decellularization process. In some configurations, default values 3059 (FIG. 31B) can be provided for the usage of enclosure 100 and filtered levels of reservoirs 182 (FIG. 1). Default values 3059 (FIG. 31B) can also be provided for volumes such as, for example, but not limited to, pump volumes and pump volumes to/from enclosure 100. Default values 3059 (FIG. 31B) can be further provided for times such as, for example, but not limited to, delayed operation start time, delayed operation current time, pump start time, last reservoir swap time, and last run time. Default values 3059 (FIG. 31B) can also be provided for toggles such as, for example, but not limited to, resume in progress, stop in progress, was paused, bolus required, and overrides. Toggles 3057 (FIG. 31B) can be initialized to, for example, but not limited to, false, off, true, and on. Default values 3059 (FIG. 31B) can be provided for states such as, for example, but not limited to, mixing state, solution pump operating state, and bolus state, and modes such as pressure mode, flow mode, time control mode, volume control mode, and bolus control mode. Default values 3059 (FIG. 31B) for certain parameters can be initially set such as, for example, but not limited to, fill pressure (for example, −225 mmHg), delivery pressure (for example, 600 mmHg), minimum flow (for example, an alarm level such as 25 ml/min), maximum flow, flow rate (for example, as fast as possible such as 975 ml/min), minimum pressure (for example, an operational limit such as −200 mmHg), maximum pressure (for example, an operational limit such as 550 mmHg), fill pressure in flow mode (for example, −100 mmHg), delivery pressure in flow mode (for example, 100 mmHg), minimum flow in flow mode (for example an alarm level such as 25 ml/min), maximum flow in flow mode (for example an alarm level such as 500 ml/min), flow rate in pressure mode (for example a limit such as 100 ml/min), minimum pressure in pressure mode (for example a limit such as −100 mmHg), and maximum pressure in pressure mode (for example a limit such as 100 mmHg).

Continuing to refer to FIG. 31, valve module 2019 may also include control circuitry 2039 providing, for example, but not limited to, control signals and power to pneumatic distribution assemblies 2025. Control circuitry 2039 may include one or more processor 2038 which may provide commands to pneumatic distribution assemblies 2025. In some configurations, separate control circuitry 2039 for each pneumatic distribution assembly 2025 may be included. Valve module 2019 may include one or more valve module of the type disclosed in U.S. Provisional Patent Application Ser. No. 62/091,351, filed Dec. 12, 2014, and entitled Modular Valve Apparatus and System, which is hereby incorporated by reference herein in its entirety.

Referring again primarily to FIG. 31, controller 2047 can connect to processor 2038 through CANbus interface 2043, and can locate devices in valve module 2019, in particular at least one pneumatic distribution assembly 2025 that can be connected through CANbus interface 2043 to controller 2047. Controller 2047 can locate at least one pneumatic distribution assembly 2025 by sending CANbus messages and awaiting replies, repeating the message send and waiting cycle up to, for example, five times. The response time can be, for example, but not limited to, 0.005-0.01 seconds. Controller 2047 can count the number of pneumatic distribution assemblies 2025 that are located by tracking the number of pneumatic distribution assemblies 2025 that respond to the CANbus message. After devices are found, controller 2047 can execute a step-by-step decellularization according to, for example, but not limited to, recipe 2047A (FIG. 31A), and in addition, controller 2047 can accept override commands from, for example, but not limited to, GUI 2037 (FIG. 31A).

Figure 31A:
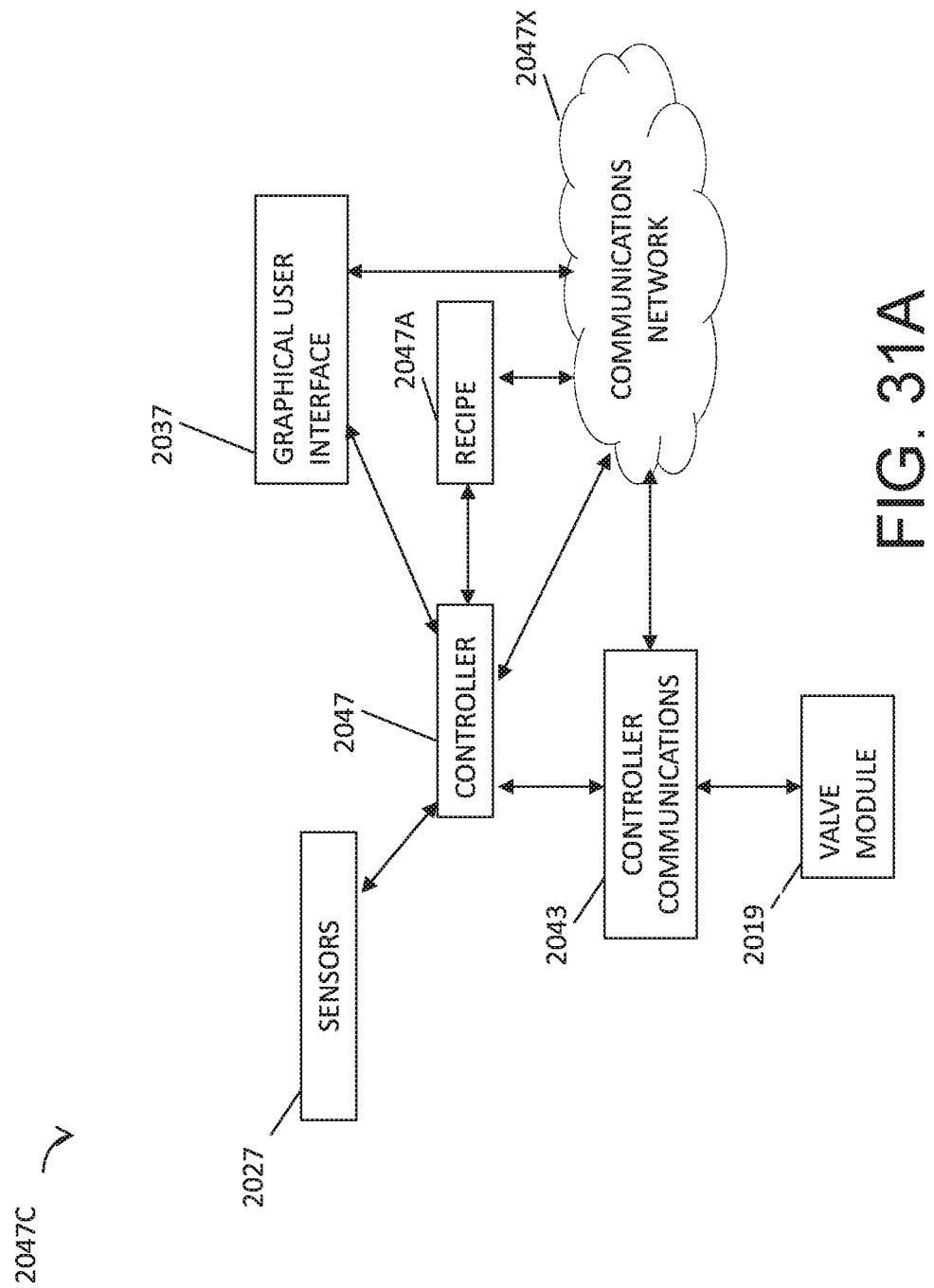
FIG. 31A is a schematic block diagram of components of the control system of the present teachings.

Referring now to FIG. 31A, controller 2047 can communicate with, for example, but not limited to, sensors 2027, GUI 2037, controller communications 2043, and recipe 2047A either directly or through communications network 2047X. Some configurations can include 2-way communications between recipe 2047A and controller 2047, as well as 2-way communications between GUI 2037 and controller 2047. In some configurations, controller 2047 can read and modify recipe 2037 either statically or dynamically. Further, controller 2047 can receive information from GUI 2037, such as, for example, recipe override information, and can supply information to GUI 2037 as the system proceeds through decellularization and/or recellularization processes. Some configurations can include 2-way communications between GUI 2037 and recipe 2047A. In some configurations, GUI 2037 can read and modify recipe 2047A when, for example, a step, precondition, pressure, port, flow rate, mode, and/or duration is entered into GUI 2037 that differs from recipe 2047A. Some configurations can include 1-way communications between recipe 2047A and controller 2047 in which controller 2047 can read, but not modify, recipe 2047A. Some configurations can include 2-way communications among all of recipe 2047A, GUI 2037, and controller 2047. In some configurations, controller 2047 can direct fluid flow based on both recipe 2047A and GUI 2037 by receiving information from recipe 2047A and/or GUI 2037, reconciling conflicting commands dynamically, opening/closing valves, and starting/stopping pumps based on the reconciled commands. In some configurations, controller 2047 can dynamically update GUI 2037 while receiving commands from GUI 2037. In some configurations recipe 2047A can be isolated from changes attempted through GUI 2037, and can be isolated from modifications attempted by controller 2047.

Referring again to FIG. 31A, controller 2047 can manage valve activity, for example, opening and closing valves, based on recipe 2047A, GUI 2037, and the automatic processing of controller 2047. The states of valves 216A-Z, 218A-R (FIG. 2) can include, but are not limited to including, open, closed, and disabled. In some configurations, there can be, for example, but not limited to, five types of valves 216A-Z, 218A-R (FIG. 2): positive 2-way chamber valves, negative 2-way chamber valves, 3-way fluid valves, pressure sensor valves, and unused valves. Some valve functions that can be performed and the automatic processing that can be performed with respect to the functions are set out in TABLE II.

TABLE II

| Valve function | Automatic processing |
| --- | --- |
| Update mixing valves | (1) update mixing count<br>(2) if mixing count is greater than 6, reset mixing count, set mixing active to false and inlet valve open to false, also close all open mixing valves<br>(3) insure solution pump is not bypassed<br>(4) block a pause state<br>(5) warn if reservoir has failed to fill in the expected number of strokes |
| Close all open valves (except atmospheric pressure and reservoir pressures) | (1) update valve states<br>(2) close fluid valves<br>(3) close mixing valves reported as open (all valves on reservoir input side except atmosphere and reservoirs-in)<br>(4) handle water solenoid valve specially<br>(5) disable internal mixing valve control logic<br>(6) close all non-mixing valves reported open (all valves on the reservoir out to/from pumps bag or drain) |

TABLE II-continued

| Valve function | Automatic processing |
| --- | --- |
| Set static valves and start pumps for operations | (1) close any open valves<br>(2) open the valves used for this step<br>(3) set up for special bolus operations<br>(4) close reservoir-outs that may be open<br>(5) determine the solution to be used for this step<br>(6) open valves for this step<br>(7) configure and start the perfuse and exchange pumps for this step, for example, set mode, set fill pressure, set delivery pressure, set minimum flow rate, set maximum flow rate, set target flow rate, set minimum pressure, set maximum pressure, set number of strokes<br>(8) allow for zero values in recipe 2047A for unused mode parameters<br>(9) set mirror mode off<br>(10) get pump run status<br>(11) update display for any pump in non-idle state including frozen, mirror mode off<br>(12) start perfuse/exchange pumps only if pump configuration is not mode off and if exchange/perfuse pump configuration is mode off<br>(13) when both pumps are active and if system 2048B is in mirror mode then set the mode to exchange mirrors<br>(14) compute a modified flow rate = target flow rate * pre-selected scale factor/100<br>(15) set the modified rate to a flow rate limit if the modified rate > flow rate limit<br>(16) start both perfuse and exchange pumps, both pumps can be running and neither as mirror - start both by configuring both with type, fill pressure, delivery pressure, and target flow rate<br>(17) recompute bag direction for both pumps<br>(18) update display of pump override parameters |

Referring again primarily to FIG. 31A, controller 2047 can log data, for example pressure data. To maintain the size of the log, controller 2047 can trim excessive old first elements off the log while adding new data to the end of the log. Controller 2047 can decide dynamically or statically which elements to trim. Controller 2047 can also adjust the logging sample rate, for example, based on the amount of memory available. Errors, email information, valve status, pump configuration, pump status, control status, reservoir status, preconditions, recipe step status, priming status, starting and stopping decellularization/recellularization, GUI selections, logging status, solution status, override status, bolus status, enclosure status, recipe load status, hardware status, and system state can be logged. Logged data can be accessed by selected logging tab 3211B (FIG. 31D).

Figure 31B:
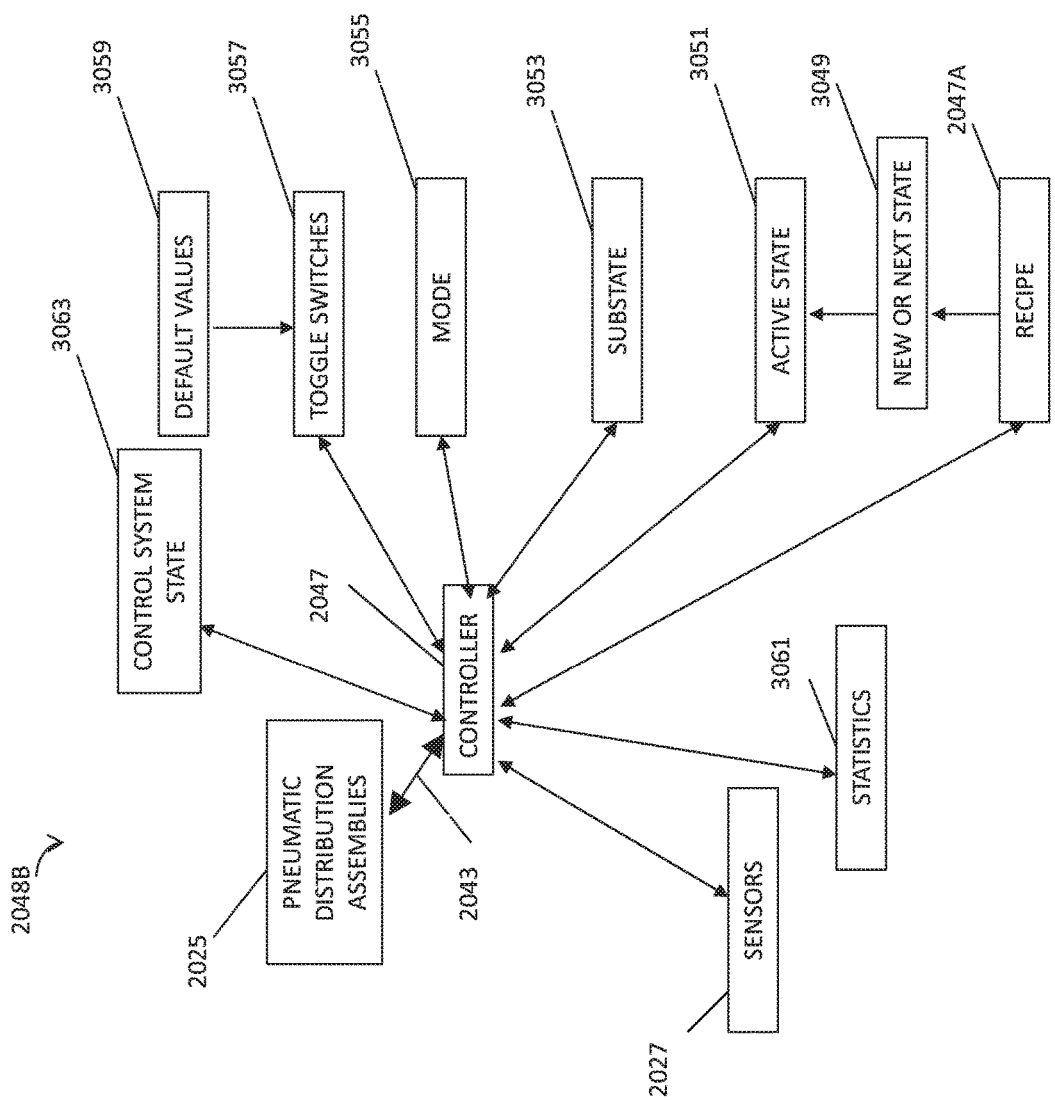
FIG. 31B is a schematic block diagram of the controller and items managed by the controller of the present teachings.

Referring primarily to FIG. 31B, controller 2047 can recognize internal processing modes 3055 or states 3051/3049 that can guide execution of recipe 2047A (FIG. 31A). System 2048B can enter active states 3051 such as are listed in Table III. In Table III, some of the many active states 3051 to which system 2048B can enter are listed along with the status of GUI buttons/boxes (B) and intra/inter process communication flags (F). When state 3051 is associated with processes (P) or other states (S), a required status of the process and/or state to enable active state 3051 to be properly entered is shown.

TABLE III

| State | Precondition | B/F/S/P | Status |
| --- | --- | --- | --- |
| Not connected, i.e. not connected state | Disconnect hw push button enabled | B | False |
| | Connect to hw push button enabled | B | True |
| | Start push button enabled | B | False |
| | Stop push button enabled | B | False |
| | Pause push button enabled | B | False |
| | Skip step push button enabled | B | False |
| | Jump to step push button enabled | B | False |
| | Add note push button enabled | B | False |
| | Restart step push button enabled | B | False |
| | Process running | F | False |
| | Process pause | S | False |
| | Process ready to proceed | F | True |
| | Select file push button enabled | B | False |
| | Restore state push button enabled | B | False |
| | Save file push button enabled | B | False |
| | Toggle sequence edit push button enabled | B | False |
| | Report pump state push button enabled | B | False |
| Connected but no recipe 2047A (FIG. 31A) has | Disconnect hw push button enabled | B | True |
| | Connect to hw push button enabled | B | False |
| | Set up chambers | P | |
| | Stop all pumps | P | Ready To Run[1] |

TABLE III-continued

| State | Precondition | B/F/S/P | Status |
|---|---|---|---|
| been loaded, i.e. connected state | Logging enable check box enabled | B | True |
| | Logging rate hertz double spin box enabled | B | True |
| | Organ connector check boxes enabled | B | True |
| | Bag check box enabled | B | True |
| | Pump check boxes enabled | B | False |
| | Start push button enabled | B | False |
| | Stop push button enabled | B | False |
| | Pause push button enabled | B | False |
| | Skip step push button enabled | B | False |
| | Jump to step push button enabled | B | False |
| | Add note push button enabled | B | True |
| | Restart step push button enabled | F | False |
| | Process running | S | False |
| | Process pause | F | False |
| | Non mixing valve overridden | F | True |
| | Process ready to proceed | B | True |
| | Select file push button enabled | B | True/False[2] |
| | Restore state push button enabled | B | True |
| | Report pump states push button enabled | | |
| Prime lines and enclosure 100 (FIG. 31F), i.e. prime operations state | Disconnect hw push button enabled | B | True |
| | Connect to hw push button enabled | B | False |
| | Start push button enabled | B | False |
| | Stop push button enabled | B | True |
| | Pause push button enabled | B | True |
| | Skip step push button enabled | B | False |
| | Jump to step push button enabled | B | False |
| | Add note push button enabled | B | True |
| | Restart step push button enabled | B | False |
| | Process running | F | False |
| | Process pause | S | False |
| | Process ready to proceed | F | False |
| | Select file push button enabled | B | False |
| | Report pump states push button enabled | B | True |
| | Restore state push button enabled | B | False |
| Connected and ready to run, i.e. ready to run state | Disconnect hw push button enabled | B | True |
| | Connect to hw push button enabled | B | False |
| | Solution level configure | P | |
| | Insure that all open valves are closed | P | |
| | Reset pump control settings | P | Ready To Run[3] |
| | Start push button enabled | B | True |
| | Stop push button enabled | B | False |
| | Pause push button enabled | B | False |
| | Skip step push button enabled | B | True |
| | Jump to step push button enabled | B | True |
| | Add note push button enabled | B | True |
| | Restart step push button enabled | B | False |
| | Process running | F | False |
| | Process pause | F | False |
| | Non-mixing valve overridden | F | False |
| | Process ready to proceed | F | True |
| | Select file push button enabled | B | True |
| | Report pump states push button enabled | B | True |
| | Restore state push button enabled | B | True/False[4] |
| | Toggle sequence edit push button enabled | B | True |
| | Set exchange/perfuse/inlet/solution pump control configuration | P | Set Various Parameters[5] |
| Running, i.e. process running state Bolus required and bolus delivery not complete state | Pump valve override | P | Reset Pump[6] |
| | Disconnect hw push button enabled | B | True |
| | Connect to hw push button enabled | B | False |
| | Enable override active reservoir selection | B | False[7] |
| | Start push button enabled | B | False |
| | Stop push button enabled | B | True |
| | Pause push button enabled | B | True |
| | Skip step push button enabled | B | False |
| | Jump to step push button enabled | B | False |
| | Add note push button enabled | B | True |
| | Restart step push button enabled | B | True |
| | Process running | F | True |
| | Process pause | S | False |
| | Select file push button enabled | B | False |
| | Save file push button enabled | B | False |
| | Restore state push button enabled | B | False |
| | Toggle sequence edit push button enabled | B | False |
| Pause i.e. process pause state | Disconnect hw push button enabled | B | True |
| | Connect to hw push button enabled | B | False |
| | Start push button enabled | B | True |
| | Stop push button enabled | B | True |

TABLE III-continued

| State | Precondition | B/F/S/P | Status |
|---|---|---|---|
| | Pause push button enabled | B | False |
| | Skip step push button enabled | B | True |
| | Jump to step push button enabled | B | True |
| | Add note push button enabled | B | True |
| | Restart step push button enabled | B | True |
| | Process running | F | False |
| | Process pause | S | True |
| Process complete, i.e. process complete state | Disconnect hw push button enabled | B | True |
| | Connect to hw push button enabled | B | False |
| | Stop all pumps | P | Process complete[8] |
| | Execute stop sequence | P | Stop all pumps[9] |
| | Insure that all open valves are closed | P | Process complete[10] |
| | Start push button enabled | B | False |
| | Stop push button enabled | B | False |
| | Pause push button enabled | B | False |
| | Skip step push button enabled | B | False |
| | Jump to step push button enabled | B | False |
| | Add note push button enabled | B | True |
| | Restart step push button enabled | B | False |
| | Process running | F | False |
| | Process pause | S | False |
| | Non mixing valve overridden | F | False |
| | Ready to proceed | F | True |
| | Process control file loaded | F | False[11] |
| | Select file push button enabled | B | True |
| | Save file push button enabled | B | |
| | Restore state push button enabled | B | |
| | Toggle sequence edit push button enabled | B | |
| Perform precondition 3203 (FIG. 31F) (empty reservoir, fill reservoir, connecting to hardware) i.e. preconditions for transient state | Disconnect hw push button enabled | B | True |
| | Connect to hw push button enabled | B | False |
| | Stop all pumps | P | Process complete[12] |
| | Execute stop sequence | P | Stop all pumps[13] |
| | Insure that all open valves are closed | P | Process complete[14] |
| | Start push button enabled | B | False |
| | Stop push button enabled | B | True |
| | Pause push button enabled | B | True |
| | Skip step push button enabled | B | False |
| | Jump to step push button enabled | B | False |
| | Add note push button enabled | B | True |
| | Restart step push button enabled | B | False |
| | Process running | F | False |
| | Process pause | S | True |
| | Non mixing valve overridden | F | False |
| | Ready to proceed | F | True |
| | Process control file loaded | F | False[15] |
| | Select file push button enabled | B | True |
| | Save file push button enabled | B | False |
| | Restore state push button enabled | B | False |
| | Toggle sequence edit push button enabled | B | False |
| | Set reservoirs to dual or single depending on parameter settings | B | |
| | Get the solution for the active step | P | |
| | Display status | P | |

[1] No pumps should be active, this should take a second or two to complete
[2] True if there is a saved state file
[3] Set the state of all valves in the valve reported states list to close valve, then close all valves
[4] True if there is a saved state file
[5] Parameters are type, fill pressure, deliver pressure, minimum pressure, maximum pressure
[6] Reset pump diagnostics when a recipe is started
[7] Block manual override of active reservoirs when running
[8] No pumps should be running, this can take a second or two to complete
[9] And valve actions
[10] Close all valves in the valve reported states
[11] Force a reload of the file for the next session
[12] No pumps should be running, this can take a second or two to complete
[13] And valve actions
[14] Close all valves in the valve reported states
[15] Force a reload of the file for the next session Referring again primarily to FIG. 31B, controller 2047 can connect to hardware using, for example, a process that can include, but is not limited to including, if CANbus 2043 (FIG. 31A) is disconnected, controller 2047 can connect CANbus 2043 (FIG. 31A), start control of system 2048B, and read the hardware configuration before a search for devices is initiated. Controller 2047 can wait, for example, for twenty seconds for system 2048B to respond. Controller 2047 can also update hardware status by getting the status of any of pumps 202, 204, 206, 208, 210, 212, 214 (FIG. 2), getting the level of reservoirs 182A/B (FIG. 31F), and showing the status of any of pumps 202, 204, 206, 208, 210, 212, 214 (FIG. 2) to be frozen/idle. Controller 2047 can also reset hardware through hardware tab 3211A (FIG. 31D). if CANbus 2043 (FIG. 31A) is connected, controller 2047 can reset resettable items in system 2048B, reset state 3051 to CANbus disconnected, update CANbus display and status display, and update the state of GIU 2037 (FIG. 31A).

Continuing to refer to FIG. 31B, other states 3051/3049 and substates 3053 can be entered, such as, for example, but not limited to, process running state, process paused state, process complete state, control system ready, control system configuring pumps, control system executing command, and unexpected state. Controller 2047 can process conditions such as waiting for completion of, for example, reservoirs filling or other system events to occur. Controller 2047 can indicate certain ongoing events such as reservoir filling and/or emptying and bolus delivery, and an indication of the status of a specific reservoir. There can be a transient state, a preconditions state, that can be induced while controller 2047 awaits precondition 3203 (FIG. 31D) such as, for example, but not limited to, priming or filling reservoir 182A/B (FIG. 31F) in preparation for a next of steps 3201 (FIG. 31D) of recipe 2047A (FIG. 31A). Controller 2047 can require certain conditions to be true, and certain conditions to be met before new or next state 3049 can transition to active state 3051. Modes 3055 and substates 3053 can be subject to similar criteria. In addition to states 3051/3049, controller 2047 can associate processing steps with substates 3053 such as, for example, but not limited to, idle, emptying reservoirs 182A/B (FIG. 31F), waiting on hardware, filling a single reservoir 182A/B (FIG. 31F), filling dual reservoirs 182A/B (FIG. 31F), and running using reservoir x while filling reservoir y.

Continuing to refer to FIG. 31B, controller 2047 can execute steps associated with modes such as time control mode, volume control mode, and bolus control mode. If recipe 2047A (FIG. 31A) dictates that the system is in volume control mode, controller 2047 (FIG. 31A) can access a flow rate of liquid traveling through the system, for example, by user input, and compute an approximate time that step 3201 (FIG. 31D) will require such as, for example, but not limited to, time=V*60/FR, where V=volume 3215 and FR=flow rate. In some configurations, the approximate time can be padded, by for example 5%, to avoid underestimating the volume. If recipe 2047A (FIG. 31A) dictates that the system is in time control mode or bolus mode, controller 2047 (FIG. 31A) can access, from recipe 2047A (FIG. 31A), duration 3213 (FIG. 31D) required for step 3201 (FIG. 31D). Controller 2047 (FIG. 31A) can set an approximate time for a bolus to complete. In some configurations, the bolus time can be approximately sixty seconds.

Referring now to FIG. 31B, system 2048B can enter the process running state when it begins executing the steps of recipe 2047A (FIG. 31A). Controller 2047 can initialize state and total pause times to, for example, zero, and start time of recipe 2047A (FIG. 31A) to, for example, local time. The steps of recipe 2047A (FIG. 31A) can each include a duration. Starting and ending times of each step can be determined based on the start time of recipe 2047A (FIG. 31A). Each step 3201 (FIG. 31D) could also have preconditions 3203 (FIG. 31D), which can be checked and fulfilled before step 3201 (FIG. 31D) is executed. If recipe 2047A (FIG. 31A) is restarted, or if another recipe 2047A (FIG. 31A) is loaded, controller 2047 can perform housekeeping such as, for example, setting an appropriate active state 3051. To pause and resume recipe 2047A (FIG. 31A), except in certain circumstances such as, for example, when the pausing or resuming is from step 3201 (FIG. 31D) in which priming is occurring, preconditions 3203 (FIG. 31D) can be checked for next step 3201 (FIG. 31D). Automatic changes of state 3049/3051 and other processing of states 3049/3051 can be blocked while in a paused state. Controller 2047 can stop any of pumps 3225-3228 (FIG. 31F), for example, but not limited to, before proceeding to next step 3201 (FIG. 31D) in recipe 2047A (FIG. 31A), as a part of recipe 2047A (FIG. 31A), as a part of an error condition, and as part of a manual override. For example, a stop button may be pressed during preconditions 3203 (FIG. 31D) for step 3201 (FIG. 31D) of recipe 2047A (FIG. 31A). Several toggle switches 3057 such as, for example, but not limited to, mixing valve overridden, wait for reservoirs to be full and empty, and empty both reservoirs, can be used to provide information about the activity of pumps 3225-3228 (FIG. 31F). After toggling the information switches, controller 2047 can stop some of pumps 3225-3228 (FIG. 31F), and can insure that some of valves 216A-Z, 218A-R (FIG. 2), depending on the requirements of recipe 2047A (FIG. 31A), are closed. Pumps 3225-3228 (FIG. 31D) can take, for example, a few seconds, to complete closing.

Referring still to FIG. 31B, controller 2047 can set an intended next processing state 3049. In some configurations, controller 2047 can move system 2048B from expected next state 3049 to active state 3051 as shown in Table IV.

TABLE IV

| Active state | New state | Other contingency | Result |
| --- | --- | --- | --- |
|  | Not connected |  | Allow change[16] |
|  | Process complete state |  | Allow change, Process abort or stop |
| Not connected | Connected | Process control file (recipe) not loaded | Allow change, Process not ready to proceed |
| Not connected | Connected | Process control file (recipe) loaded | Set ready to run state, Allow change |
| Not connected | Ready to run | Hardware connected | Allow change |
| Connected | Ready to run |  | Allow change |
| Process complete | Ready to run | Process control file (recipe) loaded | Allow change |
| Ready to run | Process running |  | Init state/total pause time, recipe start/end time, Check preconditions, Allow change |
| Process running | Process pause |  | Set state before pause, Allow change |

TABLE IV-continued

| Active state | New state | Other contingency | Result |
|---|---|---|---|
| Process pause | Preconditions | | Allow change |
| Process running | Process abort or stop | | Allow change, Don't wait for reservoir empty/full, Don't empty both reservoirs, Stop all pumps, Insure that all open valves are closed |

[16]Set this flag to communicate to other processes that the system is prepared to allow a change of state Referring still primarily to FIG. 31B, controller 2047 can update active state 3051, i.e. manage changes of state 3049/3051, for example, multiple times/second. When in volume mode, controller 2047 can also adjust the projected end time of a step of recipe 2047A (FIG. 31A) after, for example, twenty strokes based on, for example, the time the last ten strokes took. Controller 2047 can set chamber volumes for each of pumps 202, 204, 206, 208, 210, 212, 214 (FIG. 2) through CANbus interface 2043. Controller 2047 may not be able to update active state 3051 if system 2948B is not ready to proceed, and this can happen when prerequisite conditions such as emptying and filling reservoirs 182 (FIG. 1) are being performed. A bolus may be handled differently. If recipe 2047A (FIG. 31A) has been completed (i.e. if system 2048B is in process complete state), then controller 2047 may not need to test preconditions, and controller 2047 can set substate 3053 to idle. Otherwise, if system 2048B is not in process complete state, and if system 2048B is not ready to proceed, controller 2047 can check for state change preconditions being met, and, if system 2048B is ready to proceed and active state 3051 is not the same as next state 3049, then controller 2047 can set active state 3051 to next state 3049 and then update GUI 2037 (FIG. 31A).

Continuing to refer primarily to FIG. 31B, controller 2047 can update the progress of each step of recipe 2047A (FIG. 31A). In some configurations, controller 2047 may not update the progress when system 2048B is in prime operations state, or when system 2048B is in pause state if state 3051/3049 before pause state was prime operations state. Controller 2047 can compute the time that the step requires to run if the mode is time control mode and if system 2048B is running, and can set state 3051/3049 to process complete if the step is 100% complete, active state 3051 is running, and the number of steps has reached its maximum on the current of active steps 3051. Otherwise, controller 2047 can reset control settings of any of pumps 202, 204, 206, 208, 210, 212, 214 (FIG. 2), send e-mail if necessary, and change to the next step of recipe 2047A (FIG. 31A) (all of pumps 202, 204, 206, 208, 210, 212, 214 (FIG. 2) may be stopped at this time). Controller 2047 can insure that there are several seconds of accumulation before setting the actual volume to prevent stale data from affecting volume steps if in volume control mode, and can update volumes when needed for volume control mode steps. Controller 2047 can move system 2048B to process complete state when, for example, the step is 100% volume complete and active state 3051 is process running, and recipe 2047A (FIG. 31A) has come to a last of active steps 3051. Otherwise if the process is not complete, controller 2047 can reset control settings of any of pumps 202, 204, 206, 208, 210, 212, 214 (FIG. 2), send e-mail if necessary, and go to next active step in recipe 2047A (FIG. 31A). If an error is detected, controller 2047 can issue an error alert. Controller 2047 can increment the state and the total pause times, reset the times on change of step or start of process, and update progress bars on GUI 2037 (FIG. 31A) if system 2048B has moved to process complete state.

Figure 31C:
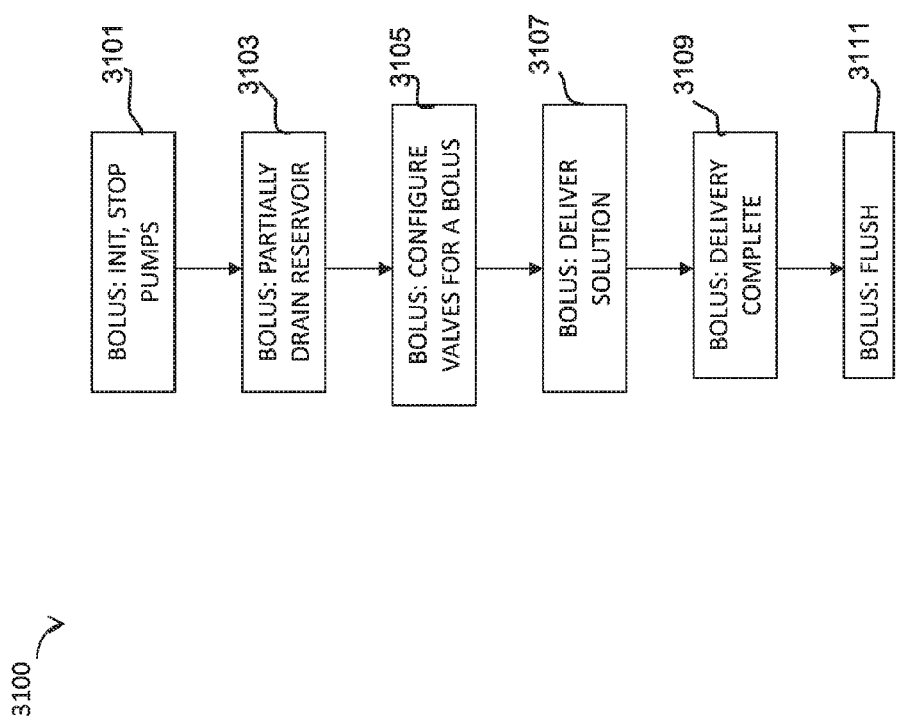
FIG. 31C is a schematic block diagram of the process for managing bolus delivery in the system of the present teachings.
Figure 31D:
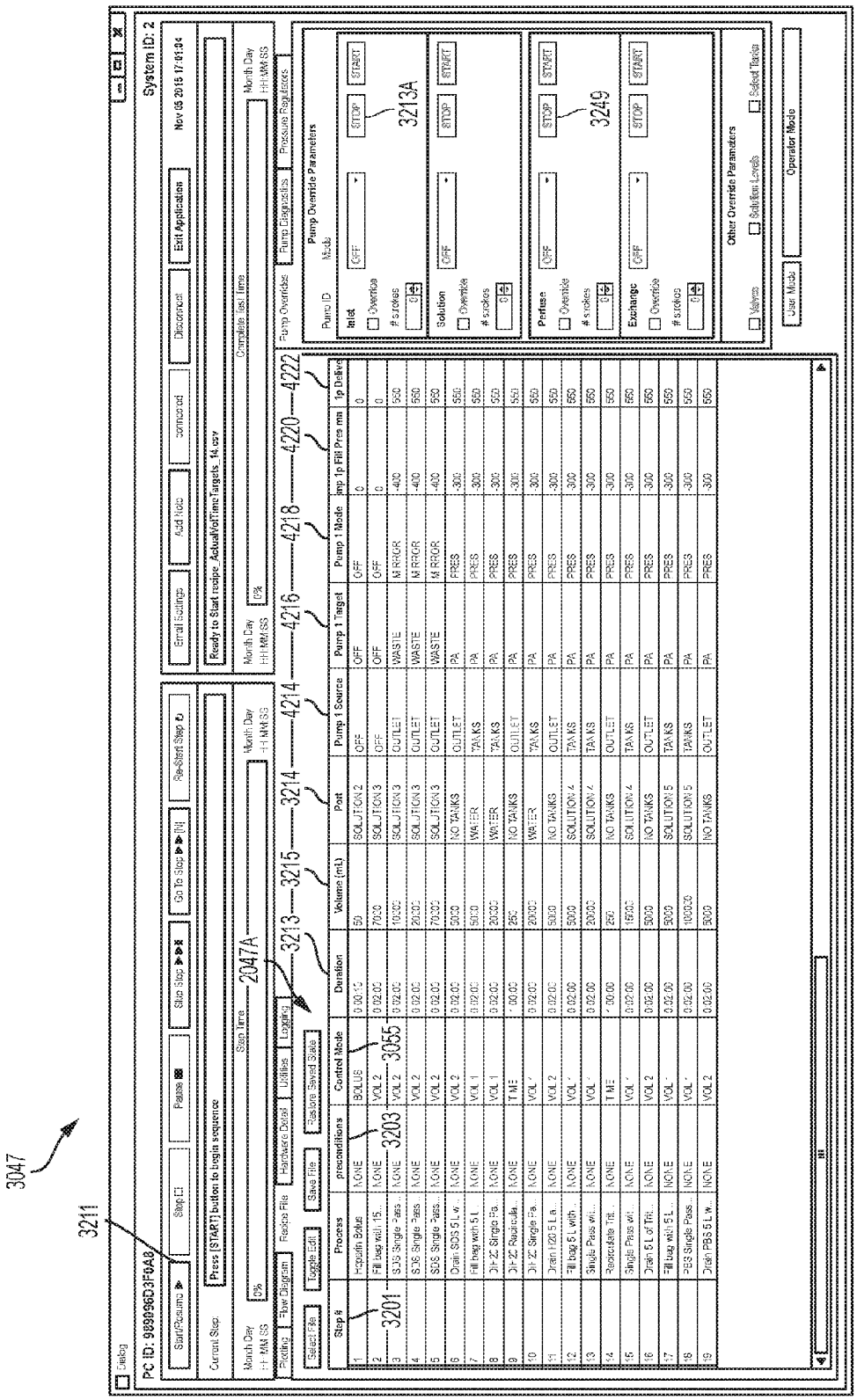
FIG. 31D is a graphical user interface of a recipe display of the present teachings.
Figure 31E:
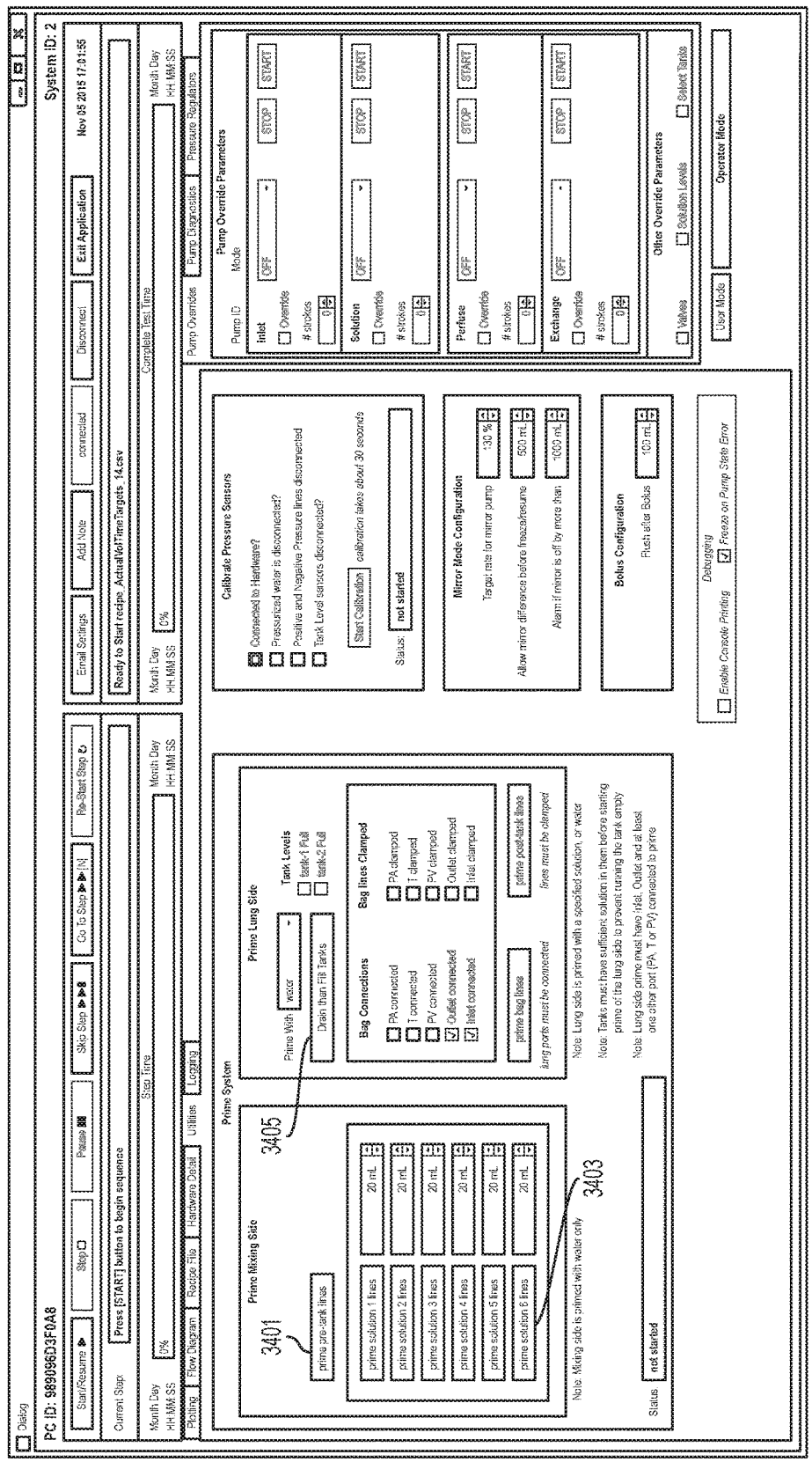
FIG. 31E is a graphical user interface of a priming display of the present teachings.
Figure 31F:
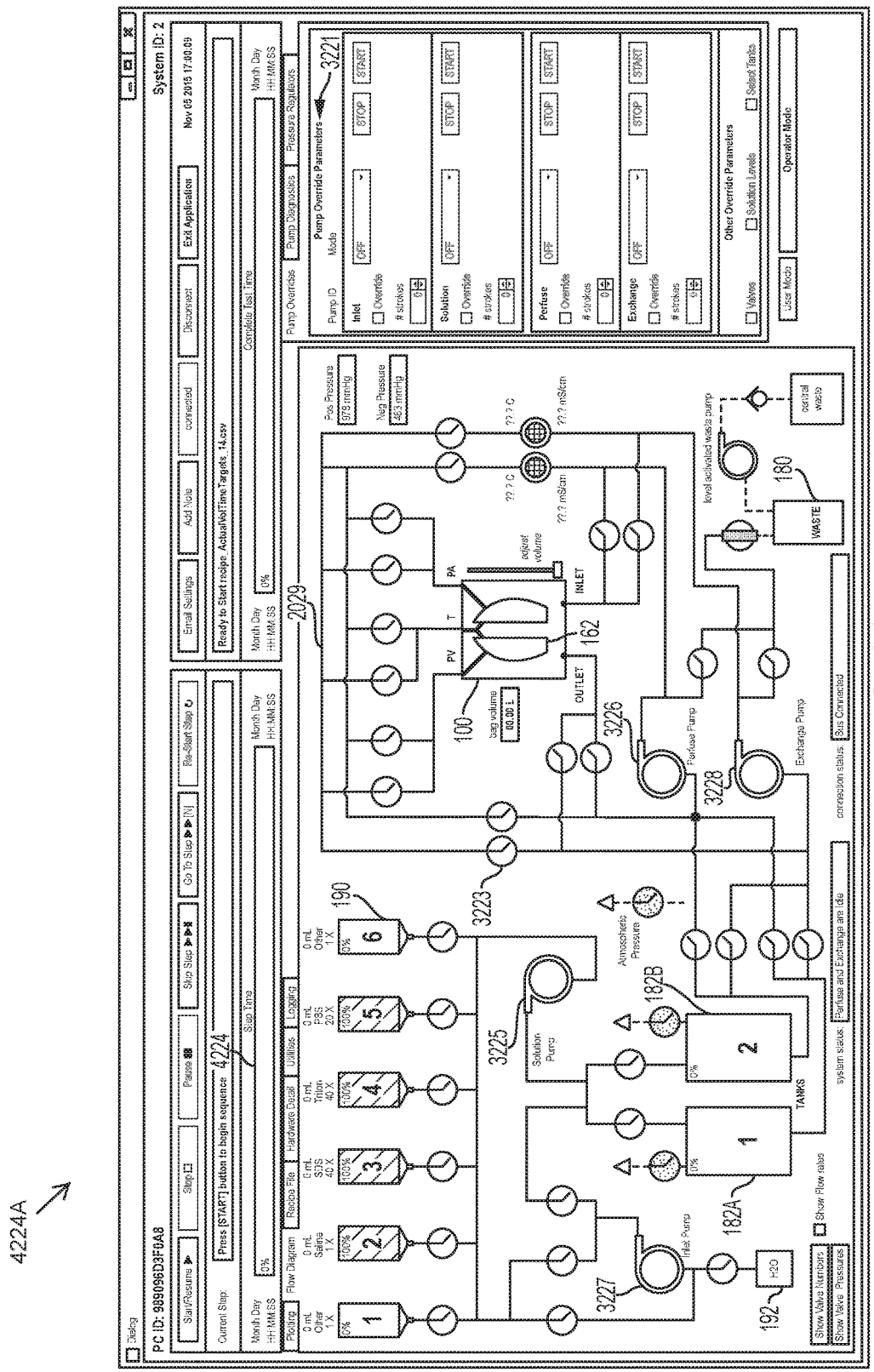
FIG. 31F is a graphical user interface of the components of an operational system of the present teachings.
Figure 31G:
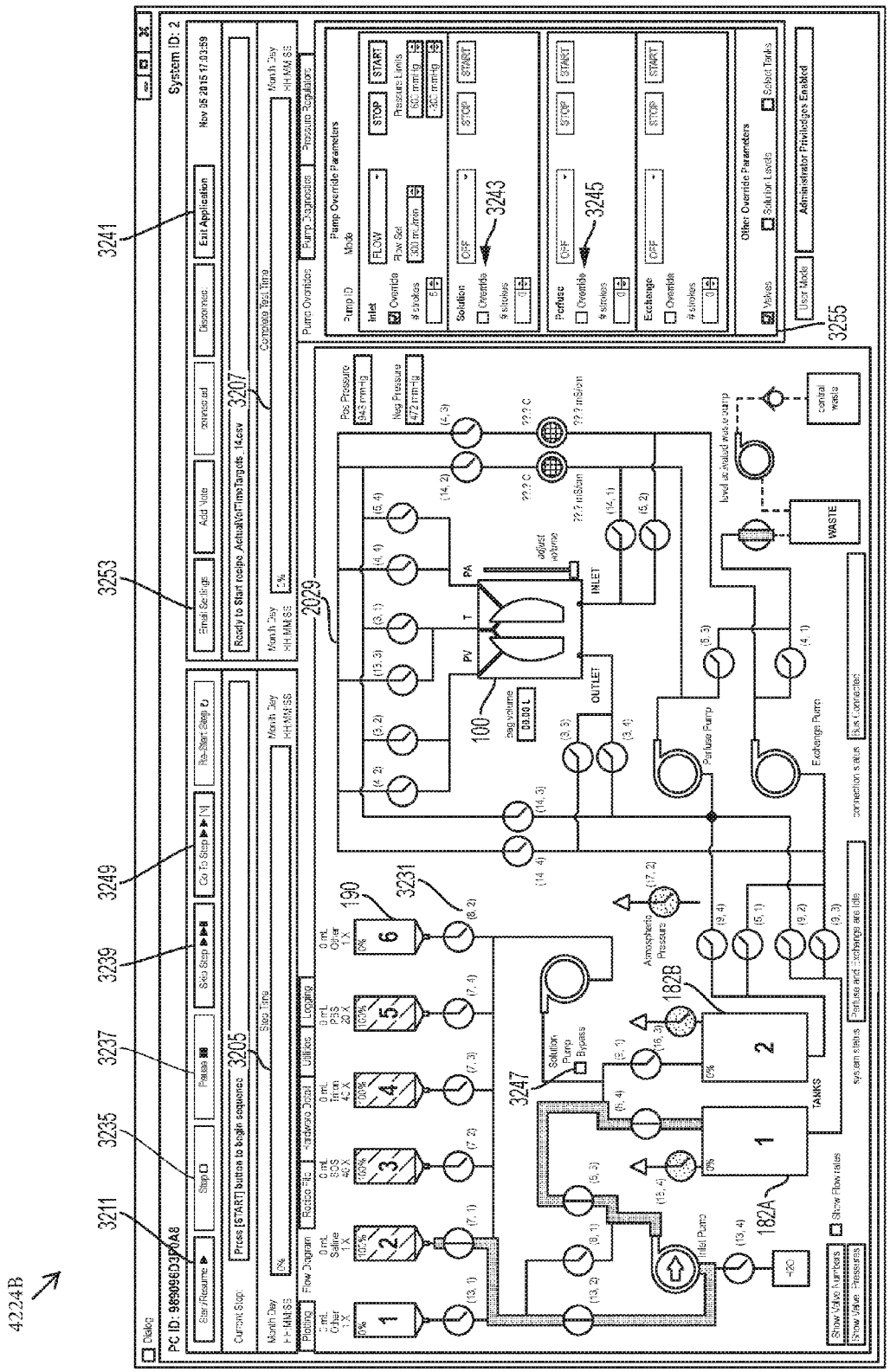
FIG. 31G is a graphical user interface of the components of an operational system as fluid is proceeding through the system.

Referring again to FIG. 31B, controller 2047 can update an active sequence to, for example, periodically update a step change in recipe 2047A (FIG. 31A) as well as update pause information and updates to progress bars 3205 (FIG. 31G). Controller 2047 may not complete the update if active state 3051 is pause or prime state and if next state 3049 is not not-connected and not connected. If the step of recipe 2047A (FIG. 31A) has changed and the start time of the step is not zero, controller 2047 can set the step end time to be the step start time plus the time the step is to require. If system 2048B is in time mode, controller 2047 can direct GUI 2037 to display, for example, a first progress label. If system 2048B is in volume mode, controller 2047 can direct GUI 2037 to display a second progress label. If system 2048B is in bolus mode, controller 2047 can direct GUI 2037 to display a third progress label. Otherwise, controller 2047 can direct GUI 2037 to display an alert message and complete recipe time label 3207 (FIG. 31G). If system 2048B is paused, controller 2047 can compute an end time of the step as the current time plus the time left to complete the step, and the end time of recipe 2047A (FIG. 31A) as the time the step started plus the total remaining time in the step plus the total time the step was paused. If system 2048B is in mirror mode, controller 2047 can determine and flag conditions that froze both pumps or in which system 2048B was not able to be resumed. Controller 2047 can determine and log actual volumes reported by any of pumps 202, 204, 206, 208, 210, 212, 214 (FIG. 2).

Referring still primarily to FIG. 31B, if a first of pumps 202, 204, 206, 208, 210, 212, 214 (FIG. 2) is ahead of a second of pumps 202, 204, 206, 208, 210, 212, 214 (FIG. 2), controller 2047 can unfreeze the second of pumps 202, 204, 206, 208, 210, 212, 214 (FIG. 2) by resuming processing of system 2048B and vice versa. Controller 2047 can reduce the mirror-delta to a 1-pod size delta at the end of the step of recipe 2047A (FIG. 31A) (when almost at the target volume), and then compare the flow rates of the first and second of pumps 202, 204, 206, 208, 210, 212, 214 (FIG. 2) to a freeze set amount (mirror delta limit) to decide if either of the first or second pumps 202, 204, 206, 208, 210, 212, 214 (FIG. 2) should be frozen. Controller 2047 can then resume processing when one of pumps 202, 204, 206, 208, 210, 212, 214 (FIG. 2) is frozen. In some configurations, both of the first and second of pumps 202, 204, 206, 208, 210, 212, 214 (FIG. 2) may not be frozen at the same time. Controller 2047 can reduce mirror delta limit by half (preventing the reduced limit from being less than one pod volume). When the second of pumps 202, 204, 206, 208, 210, 212, 214 (FIG. 2) is ahead and is frozen, then controller 2047 can wait for the second of pumps 202, 204, 206, 208,

210, 212, 214 (FIG. 2) to be half way ahead. When the first of pumps 202, 204, 206, 208, 210, 212, 214 (FIG. 2) is ahead and frozen, controller 2047 can wait for the first of pumps 202, 204, 206, 208, 210, 212, 214 (FIG. 2) to be half way behind. Controller 2047 can issue a warning if the volume error is greater than a mirror alarm delta spin box value (not shown). Controller 2047 can direct GUI 2037 (FIG. 31A) to update progress bars 3205/3207 (FIG. 31G) managed by GUI 2037 (FIG. 31A) based on volume or time control modes, update a bolus progress bar managed by GUI 2037 (FIG. 31A) based on bolus state (bolus init stopping pumps 3101 (FIG. 31C), bolus partial drain reservoir 3103 (FIG. 31C), bolus deliver solution 3107 (FIG. 31C), bolus flush 3111 (FIG. 31C), bolus delivery complete 3109 (FIG. 31C)), compute time to complete step 3201 (FIG. 31F) of recipe 2047A (FIG. 31A) based on progress bar 3205/3207 (FIG. 31G) managed by GUI 2037, and update step table display 3047 (FIG. 31F) managed by GUI 2037 (FIG. 31A) if a row of the recipe table has changed.

Referring still primarily to FIG. 31B, controller 2047 can receive from GUI 2037 direction to force a step state. If system 2048B had been in ready state and is moved to run state, controller 2047 can execute actions according to a depression of start button 3211 (FIG. 31F) and pause button actions. Also, controller 2047 can disable the override stop buttons 3213A (FIG. 31D) when system 2048B is started or resumed. To complete the forcing of a step state, controller 2047 can set an initial start time of step 1, set active state 3051 to process running, set a sleep time, freeze all of pumps 202, 204, 206, 208, 210, 212, 214 (FIG. 2), pause from process running, skip the step that had been selected before start was selected, set the non-mixing valve so that it is not overridden, pause from running, stop/abort all of pumps 202, 204, 206, 208, 210, 212, 214 (FIG. 2), change to a specific step, and set the requested of states 3051. In some configurations, controller 2047 can load, save, update, and restore a last saved of states 3051/3049.

Referring again primarily to FIG. 31B, controller 2047 can set system 2048B in an update not ready to proceed substate for as long as active state 3051 is not ready to proceed, and can issue a warning if active state 3051 is ready to proceed. To update the not ready to proceed substate, if active state 3051 is prime operations state, or if active state 3051 is process pause state, system 2048B may not enter the update not ready to proceed substate. For updating the not ready to proceed substate, automatic state changes can be blocked if system 2048B is in pause state. Further, controller 2047 can set substate 3053 to idle and active state 3051 to ready to proceed if next state 3049 in recipe 2047A (FIG. 31A) is either connected or ready to run, and if control system state 3063 is ready and CANbus 2043 is connected, which can be the prerequisite conditions for changing to a connected state (normal flow) or a ready to run state (if recipe 2047A (FIG. 31A) is loaded before connecting). Otherwise controller 2047 can set active state 3051 to not ready to proceed and substate 3053 to waiting on hardware. If next state 3049 in recipe 2047A (FIG. 31A) is the pause state, other state processing can be blocked. Controller 2047 can check for an empty of reservoirs 182 (FIG. 1), a situation that can further stop all of pumps 202, 204, 206, 208, 210, 212, 214, 216 (FIG. 2) that are active according to recipe 2047A (FIG. 31A) if one or more of reservoir(s) reservoirs 182A/B (FIG. 31F) has just been emptied. Further, controller 2047 can also check if reservoirs 182A/B (FIG. 31F) are full and can also set flags but may not start mixing. Still further, controller 2047 can further mark reservoirs 182A/B (FIG. 31F) as currently filling and the same reservoir 182A/B (FIG. 31F) or a different reservoir 182B/A (FIG. 31F) as currently being used.

Continuing to refer primarily to FIG. 31B, controller 2047 can process step 3201 in recipe 2047A (FIG. 31A) by executing the following steps. (1) Initialize, while system 2048B is idle, active step 3201 in recipe 2047A (FIG. 31A), the maximum number of steps 3201 in recipe 2047A (FIG. 31A), the total processing time in recipe 2047A (FIG. 31A), the elapsed step time of active step 3201, the last saved time of active step 3201, and the times per step 3201 (duration 3213) to completion of step 3201. (2) Reset data, while system 2048B (FIG. 31A) is idle, for example, reset total processing time 3213 of step 3201, reset the total number of steps 3201, reset the elapsed step time, reset the last saved time, reset active step 3201, reset the maximum number of steps 3201, reset the times per step 3201 to completion of step 3201, reset step target volume to one (for example, initialize the step target volume to above the step actual volume 3215). Controller 2047 can determine the step volume % complete, and can reset step actual volume 3215. (3) Set/get the maximum number of steps 3201 (system 2048B is idle when setting the maximum number of steps 3201. (4) Change active step 3201: (a) set the elapsed step time to zero and set the last saved time to the current time. (b) If the number of active steps 3201 is lower than the maximum number of steps 3201, set active step 3201. (c) If the same step 3201 is being restarted, reset the start time. (d) When step 3201 is either being changed or restarted, controller 2047 can set up GUI 2037 (FIG. 31A), clear a solution pump blocked flag on every step change, set the actual step volume to zero, reset all of pumps 202, 204, 206, 208, 210, 212, 214, 216 (FIG. 2) and valves 216A-Z, 218A-R (FIG. 2) that may have been left in an indeterminate state from the previous of steps 3201, and check preconditions 3203 for the next step of recipe 2047A (FIG. 31A), and update the progress of step 3201.

Continuing to still refer primarily to FIG. 31B, controller 2047 can also perform utility functions such as, for example, but not limited to, (1) determine active step 3201 of recipe 2047A (FIG. 31A), (2) perform certain tasks when system 2048B is in a particular substate, such as, for example, logging system status when system 2048B is in substate idle, waiting on hardware, emptying reservoirs 182A/B (FIG. 31F), filling single reservoir 182A or 182B (FIG. 31F), filling multiple reservoirs 182A/B (FIG. 31F), running single reservoirs 182A or 182B (FIG. 31F), using first reservoir 182A (FIG. 31F) and filling second reservoir 182B (FIG. 31F), and using second reservoir 182B (FIG. 31F) and filling first reservoir 182A (FIG. 31F), (7) determine the current sub state, (8) determine the next active step of recipe 2047A (FIG. 31A), (9) move system 2048B to the next active step of recipe 2047A (FIG. 31A), (10) move system 2048B to a specific step 3201, (11) restart the active step of recipe 2047A (FIG. 31A), (12) perform step time and number of steps accounting, (13) set step 3201 as complete, (14) determine total remaining time, not including pause time, in the step of recipe 2047A (FIG. 31A), (15) determine the total elapsed time, (16) get the elapsed time taken by the step of recipe 2047A (FIG. 31A), (17) determine the percent complete of the step in terms of time, (18) set the time step 3201 completed, (19) determine the percent complete of step 3201 in terms of volume, (20) determine step target volume, (21) set step target volume, (22) determine the step actual volume 3215, (23) set step actual volume 3215, (24) determine total processing time for all steps 3201 of recipe 2047A (FIG. 31A), (25) determine the total percent complete of recipe 2047A (FIG. 31A) based on elapsed time, (26) determine the amount of time that step 3201 required, and (27) restart step 3201 of recipe 2047A (FIG. 31A) by disabling sequence edit, disabling the sequence edit push button, restarting active step 3201 of recipe 2047A (FIG. 31A), checking if e-mail needs to be sent, and resuming from a paused state.

Referring to FIG. 31B, in some configurations, controller 2047 (FIG. 31A) can receive log data 3061 such as, for example, but not limited to, of valve pressure, pump stroke count, mixing count, and fluid flow rate. Valve pressure refers to the pressure sensed by at least one of sensors 2027 of valves 216A-Z, 218A-S (FIG. 2). In some configurations, the number of valves can be thirty-five, and the number of pump valves can be twenty-eight. Pump stroke count refers to the number of strokes required for a pump to take to support the fluid flow required by recipe 2047A (FIG. 31A). Pump stroke count can be initialized to a particular value and can vary throughout the duration of step 3201 of recipe 2047A (FIG. 31A). Mixing count refers to the number of strokes required of solution/inlet pumps 3225/3227 (FIG. 31F) to create a fluid required by recipe 2047A (FIG. 31A). In some configurations, the number of pumps, not including, for example, a waste pump, can be four. Mixing count can be initialized to a particular value and can vary throughout the duration of step 3201 of recipe 2047A (FIG. 31A). Fluid flow rate refers to the rates of fluid flow through the system based on the requirements of recipe 2047A (FIG. 31A). Fluid flow rate can be initialized to a particular value and can vary throughout the duration of step 3201 of recipe 2047A (FIG. 31A).

Referring primarily again to FIG. 31B, when controller 2047 determines that a first type of error has occurred, controller 2047 can enter an error processing state in which current activity can be stopped, an indication that stopping is complete can be requested and received, and the user can be notified that an error has occurred, for example, by email. When controller 2047 determines that a second type of error has occurred, controller 2047 can enter a warning processing state in which controller 2047 can, for example, but not limited to, pause the system and await user interaction. Controller 2047 can perform such housekeeping as clearing filtering on reservoir levels to prevent a reservoir over-full condition from immediately posting after the clearing as a result of hysteresis in the signal produced by the sensor detecting the reservoir level. Other alerts can include, but are not limited to including, overfull tank, mixing error, CAN-bus error, solution error, recipe file error, state error, connection timeout, communications problem, operation problem, unexpected state, and excessive volume.

Referring primarily to FIG. 31C, controller 2047 (FIG. 31B) can process a bolus sequence. Controller 2047 (FIG. 31B) can manage delivery of the bolus in a configuration in which there are multiple of reservoirs 182A/B (FIG. 31F). Bolus delivery 3100 can include steps such as, for example, but not limited to, initializing 3101 bolus delivery 3100 including stopping pumps in which pumps 202, 204, 206, 208, 210, 212, 214 (FIG. 2) can be stopped, and system 2048B (FIG. 31B) can pause while the effect of the stopping pumps completes. Bolus delivery 3100 can include partially draining 3103 reservoir 182A/B (FIG. 31F). If the bolus can fit into available space in reservoirs 182A/B (FIG. 31F), controller 2047 (FIG. 31B) can direct 182A/B (FIG. 31F) to be drained. Bolus delivery 3100 can include configuring 3105 any of valves 216A-Z, 218A-S (FIG. 2) for a bolus. Configuring 3105 can include closing all open mixing valves including reservoir-in valves, setting up accounting of solution 190 (FIG. 31G) for the bolus, and displaying valves 216A-Z, 218A-S (FIG. 2) in their correct states on the display of GUI 2037 (FIG. 31A)). Configuring 3105 can include flushing a bolus. Flushing a bolus can include configuring a bolus flush, waiting for valves 216A-Z, 218A-S (FIG. 2) to be updated, flushing the bolus, and waiting for valves 216A-Z, 218A-S (FIG. 2) to complete processing. Bolus delivery can include delivering 3107 the bolus solution. If the bolus volume and rinse volume can fit into 182A/B (FIG. 31F) without overflow, the number of strokes to deliver the volume of the bolus can be determined, and mixing to reservoirs 182A/B (FIG. 31F)) can be started. Bolus delivery can include completing 3109 the bolus delivery by updating the volume to indicate that the bolus is done. Delivering 3111 a bolus flush, for example, using a first of pumps 202, 204, 206, 208, 210, 212, 214 (FIG. 2) only, not a second of pumps 202, 204, 206, 208, 210, 212, 214 (FIG. 2), can include, but is not limited to including, configuring strokes=(volume of flush after bolus+pod size)/2/pod size, flushing the bolus based on first pump strokes in and second pump strokes in, mixing to reservoirs 182A/B (FIG. 31F), computing the first pump flow rate and the second pump flow rate, opening the inlet valve, configuring the bolus flush, setting the second pump start time, and starting mixing. Mixing can be started directly because the correct of valves 216A-Z, 218A-S (FIG. 2) are open. The first of pumps 202, 204, 206, 208, 210, 212, 214 (FIG. 2) can be pre-configured for bypass mode. Bolus states 3100 do not have to occur in the order set out in FIG. 31C.

Continuing to refer primarily to FIG. 31C, determining the number of strokes to deliver the volume can include calculating a first pump stroke in as (target volume+pod size)/2/pod size, delivering the bolus based on the first pump stroke in and a second pump stroke in, setting first and second pump flow rates, closing selected of valves 216A-Z, 218A-S (FIG. 2) associated with second of pumps 202, 204, 206, 208, 210, 212, 214 (FIG. 2), updating the first pump start time, and starting mixing based on the first and second pump flow rates. Updating flow rate values can include determining stroke numbers for each of pumps 202, 204, 206, 208, 210, 212, 214 (FIG. 2). Before the last stroke, controller 2047 can compute the solution flow rate filter ml/min=((stroke count−last reported stroke count)*pod size*60)/(current time−stroke start time)) for solution pump 3225 (FIG. 31F) and update display 4224A (FIG. 31F), for example. Controller 2047 (FIG. 31B) can a compute solution flow rate in ml/min. If the current pump stroke number is smaller than last pump stroke number, controller 2047 can reset the flow rate and associated flow rate parameters. Controller 2047 (FIG. 31B) can update the flow rates for all of pumps 202, 204, 206, 208, 210, 212, 214 (FIG. 2), update all last stroke numbers, and set flow rate to zero for pumps 202, 204, 206, 208, 210, 212, 214 (FIG. 2) that are idle.

Continuing to refer to FIG. 31C, configuring a bolus flush can include, but is not limited to including, closing all of valves 216A-Z, 218A-S (FIG. 2) that have been open from bolus delivery 3100 including reservoir-in valves. Configuring a bolus flush can also include setting a bypass of solution 190 (FIG. 31F), opening selected of valves 216A-Z, 218A-S (FIG. 2) pre-selected for this step, setting system 2048B (FIG. 31B) in bypass mode so pumping can be done through a second of pumps 202, 204, 206, 208, 210, 212, 214 (FIG. 2) such as, for example, inlet pump 3227 (FIG. 31F), for dual reservoirs 182A/B (FIG. 31F), delivering the bolus into reservoir 182A/B (FIG. 31F), setting up accounting for solution 190 (FIG. 31F), and displaying valves 216A-Z, 218A-S (FIG. 2) in their correct states. The accounting usage for solution 190 (FIG. 31F) can be configured using a first of pumps 202, 204, 206, 208, 210, 212, 214 (FIG. 2), such as solution pump 3225 (FIG. 31F), so the flush is not counted as the bolus solution.

Referring now primarily to FIG. 31D, and with respect to recipe 2047A (FIG. 31A) and recipe override, recipe 2047A (FIG. 31A) can be displayed as a list of steps 3201, for example, as shown in GUI recipe display 3047. Controller 2047 (FIG. 31B) can select/load/save a file that includes recipe 2047A (FIG. 31A) that can be, but is not limited to being, a comma-separated values file. Controller 2047 (FIG. 31B) can read a loaded file that includes recipe 2047A (FIG. 31A) and can interpret from recipe 2047A (FIG. 31A) actions that controller 2047 (FIG. 31B) can take to complete, for example, decellularization of biological specimen 162 (FIG. 31F). Each step of recipe 2047A (FIG. 31A) can, but does not always, require preconditions 3203 to be met.

Continuing to refer primarily to FIG. 31D, controller 2047 (FIG. 31B) can access, from recipe 2047A (FIG. 31A), from which port 3214 to draw liquid in order to fulfill the requirements of step 3201. Liquids can include solutions or sources 190 (FIG. 31F), for example, as set out in Table I. Controller 2047 (FIG. 31B) can access, from recipe 2047A (FIG. 31A), pump information such as fluid sources 4214 and fluid targets 4216 of pumps 3226/3228 (FIG. 31F), and fill pressure 4220 and delivery pressures 4222 of pumps 3226/3228 (FIG. 31F). Pump sources 4214 can include, but are not limited to including, fluid from enclosure 100 (FIG. 31F) and fluid from storage reservoirs 182A/B (FIG. 31F). Pump targets 4216 can include, but are not limited to including waste reservoir 180 (FIG. 31F) and a port of biological specimen 162 (FIG. 31F). Recipe 2047A (FIG. 31A) can also set pump mode 4218 which can include mirror mode in which pumps 3226/3228 (FIG. 31F) operate cooperatively.

Continuing to still further refer primarily to FIG. 31D, controller 2047 can receive recipe override information from recipe display 3047. Pump and valve instructions can be overridden, depending on the states of buttons and boxes on recipe display 3047, for example. Selection of reservoir 182A/B (FIG. 31F), level of solution 190 (FIG. 31F), pump valve, chemical levels, and pump actions can also be overridden by setting override parameters 3221 (FIG. 31F). Examples of pump override parameters can include inlet pump stop 3213A and perfuse pump stop 3249. If inlet pump stop 3213A is selected from recipe display 3047, and if step 3201 of recipe 2047A (FIG. 31A) requires an action of inlet pump 3227 (FIG. 31F), the action of recipe 2047A (FIG. 31A) can be overridden. If perfuse pump stop 3249 is selected from recipe display 3047, and if step 3201 of recipe display 3047 requires an action of one of pumps 3226/3228 (FIG. 31F) that is perfusing biological specimen 162 (FIG. 31F), the action of recipe 2047A (FIG. 31A) can be overridden. Inlet pump 3227 (FIG. 31F) and pumps 3226/3228 (FIG. 31F) can be restarted through recipe display 3047, again overriding recipe 2047A (FIG. 31A). Recipe 2047A (FIG. 31A) can be overridden with respect to, for example, but not limited to, valves 216A-Z, 218A-S (FIG. 2), solution levels of sources 190 (FIG. 31F), and storage reservoirs 182A/B (FIG. 31F).

Continuing to refer primarily to FIG. 31D, controller 2047 (FIG. 31B) can test the integrity of the recipe and the current configuration, for example, but not limited to, the following tests. Controller 2047 (FIG. 31B) can check that steps 3201 are in a correct sequence order, and that port 3214 is not set to "no tanks" when one of pumps 3226-3228 (FIG. 31F) needs to draw from at least one of reservoirs 182A/B (FIG. 31F). Controller 2047 (FIG. 31B) can check that both of pumps 3226/3228 (FIG. 31F) are not set to mirror mode, or that one of pumps 3226/3228 (FIG. 31F) is set to mirror mode and the other of pumps 3226/3228 (FIG. 31F) is off. Controller 2047 (FIG. 31B) can check that bolus volume is not excessive compared to a pre-selected value, and that the bolus is not configured in a step of recipe 2047A (FIG. 31A) that has a fill precondition 3203. Controller 2047 (FIG. 31B) can check that required parameter fields are not set to zero, that mixing is not disabled, and that pumps 3226-3228 (FIG. 31F) that are configured to use reservoirs 182A/B (FIG. 31F) are not part of a bolus. Controller 2047 (FIG. 31B) can check that a bolus into reservoir 182A/B (FIG. 31F) for recipe step n and recipe step n+1 does not empty reservoir 182A/B (FIG. 31F) as a pre-condition to prevent emptying the bolus before using it. Controller 2047 (FIG. 31B) can insure that valves 216A-Z, 218A-S (FIG. 2) are open to empty reservoirs 182A/B (FIG. 31G).

Continuing to still further refer to FIG. 31D, controller 2047 (FIG. 31B) can enable and disable editing of the sequence of recipe 2047A (FIG. 31A). In some configurations, editing can be accomplished through recipe display 3047. In some configurations, editing can happen automatically as a by-product of system activity. In some configurations, GUI (FIG. 31A) can accept, and controller 2047 (FIG. 31B) can automatically process, several types of instructions such as, for example, but not limited to, instructions with respect to state/substate 3049/3051/3053, solution 190 (FIG. 31G), valves 216A-Z, 218A-S (FIG. 2), recipe 2047A (FIG. 31A), pumps 3225-3228, reservoirs 182A/B (FIG. 31G), and display features. GUI (FIG. 31A) can accept instructions to set the system in, for example, ready to run state and process complete state, and can report the state the system is in. GUI (FIG. 31A) can also accept instructions to set the level of solution 190, and to block a manual override of active of reservoirs 182A/B (FIG. 31G). Through GUI 2037 (FIG. 31A), a user can close the open ones of valves 216A-Z, 218A-S (FIG. 2), enable/disable display push buttons, and stop the usage of enclosure 100 (FIG. 31G). GUI 2037 (FIG. 31A) can further accept instructions to stop pumps 3225-3228. This list is not exhaustive, GUI 2037 (FIG. 31A) can accept a wide variety of instructions, a subset of which is described herein.

Referring still primarily to FIG. 31D, controller 2047 (FIG. 31B) can insure that preconditions 3203 for each of steps 3201 have been met. For example, after moving to step 3201, controller 2047 (FIG. 31B) can test if step 3201 requires changing solutions 190 (FIG. 31F) in reservoir 182A/B (FIG. 31F), get active step 3201, get target volume 3215 for step 3201 if in volume or bolus of modes 3055, if in time control of modes 3055 set duration 3213, set substate to idle, set ready to proceed to false. After all preconditions 3203 are met, controller 2047 (FIG. 31B) can start mixing if needed and start the active states 3051 (FIG. 31B) of selected of valves 216A-Z, 218A-S (FIG. 2) and pumps 202, 204, 206, 208, 210, 212, 214 (FIG. 2). If in bolus of modes 3055, controller 2047 (FIG. 31B) can disable mixing, use the same of reservoirs 182A/B (FIG. 31F) for filling and using, and set up for dual or single of reservoirs 182A/B (FIG. 31F). Controller 2047 (FIG. 31B) can also bypass preconditions 3203 if, for example, the system is starting from a saved state.

Referring now primarily to FIG. 31E, controller 2047 (FIG. 31B) can manage priming by performing functions as set out in TABLE V.

TABLE V

| Priming operation | Actions taken by controller 2047 (FIG. 31A) |
|---|---|
| Set state 3051/3029 (FIG. 31B) for priming | Set active of states 3051 (FIG. 31B) to prime operation state if active of states 3051 (FIG. 31B) is either ready to run or connected |
| Update prime status | Unblock solution pump 3225 (FIG. 31F) and insure that valves are closed if the prime operation succeeded<br>Unblock solution pump 3225 (FIG. 31F) and insure that valves are closed if the prime operation failed |
| Update solution only prime status | Update clock if mixing is running<br>Unblock solution pump 3225 (FIG. 31F) and insure that valves are closed if mixing is not running |
| Update empty fill reservoir prime status | If a drain and fill operation beginning through, for example, but not limited to, a click on drain then fill button 3405, and if any of reservoirs 182A/B (FIG. 31F) is not empty, drain reservoirs 182A/B (FIG. 31F)<br>If draining multiple reservoirs 182A/B (FIG. 31F), multiple of pumps 3226/3228 (FIG. 31F) can be used<br>If any of pumps 3226/3228 (FIG. 31F) are frozen, close open non-mixing of valves 216A-Z, 218A-S (FIG. 2)<br>Fill reservoirs 182A/B (FIG. 31F) and unblock solution pump 3227 (FIG. 31F)<br>If reservoirs 182A/B (FIG. 31F) are not full, close open of valves 216A-Z, 218A-S (FIG. 2) and set up for failure notice |
| Prime mixing fill reservoir 182A/B (FIG. 31F) | Determine flow rates of solution pump 3227 (FIG. 31F) and inlet pump 3225 (FIG. 31F)<br>Insure that open of mixing valves 216A-Z, 218A-S (FIG. 2) are closed including reservoir-in valves<br>If water 192 (FIG. 31F), compute inlet pump strokes as 1000/inlet pump size<br>Insure that valves for reservoir 182A/B (FIG. 31F) are open<br>If water 192 (FIG. 31F) and solution 190 (FIG. 31F), start mixing<br>If water only start inlet pump 3225 (FIG. 31F) |
| Prime lines changed | If GUI 2037 (FIG. 31A) receives certain signals (representing, for example, user input), the status (for example, connected and clamped) of prime lines to enclosure 100 (FIG. 31F) can be updated |
| Prime pre-reservoir lines | If GUI 2037 (FIG. 31A) receives certain signals (representing, for example, user input through selecting prime pre-tank lines button 3401), controller 2047 (FIG. 31A) can start priming through a pre-reservoir circuit |
| Prime solution lines | If GUI 2037 (FIG. 31A) receives certain signals (representing, for example, user input through selecting prime solution lines button 3403), controller 2047 (FIG. 31A) can prime lines connecting solutions 190 (FIG. 31F) to pumps 3226-3228 (FIG. 31F) |
| Prime post-reservoir lines that do not feed enclosure 100 (FIG. 31F) | If GUI 2037 (FIG. 31A) receives certain signals, controller 2047 (FIG. 31A) can prime selected post-reservoir lines that do not feed enclosure 100 (FIG. 31F) |
| Prime enclosure lines | If GUI 2037 (FIG. 31A) receives certain signals, controller 2047 (FIG. 31A) can prime lines connecting selected lines to enclosure 100 (FIG. 31F) |

Referring primarily to FIG. 31F, controller 2047 (FIG. 31B) can load a solution configuration file that can set the names of solutions 190, set the concentrations of solutions 190, set the capacities of solutions 190, and set the defaults (not shown) of solutions 190 as set out for example in TABLE VI.

TABLE VI

| Chemical | Concentration | Capacity |
|---|---|---|
| SDS | 1X | 100 |
| Heparin | 10X | 100000 |
| Triton | 10X | 100000 |
| PBS | 10X | 100000 |
| Saline | 10X | 100000 |
| Other | 10X | 100000 |

Controller 2047 (FIG. 31B) can update the solution file by allowing names, concentrations, and capacities of solutions 190 to be set, and controller 2047 (FIG. 31B) can save the solution file. Controller 2047 (FIG. 31B) can resize the solution tanks and can update the solution file with the new sizes, if desired. Controller 2047 (FIG. 31B) can determine solutions 190 that are currently in use by determining current step 3201 (FIG. 31D) of recipe 2047A (FIG. 31A), and determining a temporary mixing state (for example, mixing disabled, mixing Di water only, and mixing chemicals and Di water). If the system is in bolus control mode, controller 2047 (FIG. 31B) can discontinue determining solutions 190 that are currently in use. If the system is not in bolus control mode, controller 2047 (FIG. 31B) can set mix parameters for solution 190 for current step 3201 (FIG. 31D) of recipe 2047A (FIG. 31A), and set up accounting information for the current of solutions 190. Controller 2047 (FIG. 31B) can also set mix parameters for solution 190 for the current step of recipe 2047A (FIG. 31A) by, if not in bolus control mode, determining the active step of recipe 2047A (FIG. 31A), computing a residual reservoir level, computing a current volume in strokes as, and computing inlet strokes. Controller 2047 (FIG. 31B) can exit without setting the mixing parameters if the difference between the inlet strokes and current volume in strokes is less than zero.

Continuing to refer primarily to FIG. 31F, controller 2047 (FIG. 31B) can also set solution mix parameters by blocking solution pump 3225 if source concentration is 1×. Controller 2047 (FIG. 31B) can determine a residual % of reservoir 182A/B, a current volume in strokes at least based on the volume of reservoir 182A/B and the pod size of inlet pump 3227, and the current inlet strokes based on volume of reservoir 182A/B and the pod size of inlet pump 3227. Controller 2047 (FIG. 31B) can compute the difference between the inlet strokes and the current volume in strokes and the volume. If the source concentration is not 1×, controller 2047 (FIG. 31B) can unblock solution pump 3225 if necessary and access values of inlet strokes, solution strokes, and volume. Controller 2047 (FIG. 31B) can update levels of solutions 190 periodically to, for example, update solution reservoir usage against a maximum capacity that can be, for example, user configured. In some configurations, if next state 3049 (FIG. 31B) is process running or ready to run or connected, controller 2047 (FIG. 31B) can determine and display levels of solutions 190. Controller 2047 (FIG. 31B) can update the levels of solutions 190 by computing the remaining of solution 190. Controller 2047 (FIG. 31B) can also update the tank ratios of solutions 190 when, for example, a user selection has been made. Controller 2047 (FIG. 31B) can further set for which solution 190 accounting should be done. Solution pump 3225 and/or inlet pump 3227 can be used for accounting.

Referring primarily to FIG. 31F, controller 2047 (FIG. 31A) can direct GUI 2037 (FIG. 31A) to update valve images 3223 and diagnostic display images at the display of GUI 2037. For example, the display of images of valves 216A-Z, 218A-S (FIG. 2) can vary depending upon whether any of valves 216A-Z, 218A-S (FIG. 2) are open or closed, for example, or whether any of valves 216A-Z, 218A-S (FIG. 2) are in unexpected states. Controller 2047 (FIG. 31A) can update the states of valves 216A-Z, 218A-S (FIG. 2) after the hardware is connected, i.e. when active state 3051 is not either connected or not connected. Controller 2047 (FIG. 31A) can determine the state of any of valves 216A-Z, 218A-S (FIG. 2) in system 2048B (FIG. 31B), for example, atmospheric pressure valves, reservoir pressure valves, or fluid valves. Controller 2047 (FIG. 31A) can toggle valves 216A-Z, 218A-S (FIG. 2) between open and closed states. GUI 2037 (FIG. 31A) can update valve diagnostic images if the display of valve pressures is enabled. In some configurations, the current valve diagnostic image can be updated periodically. Valves 216A-Z, 218A-S (FIG. 2) can be set to open/closed states based on, for example, pre-selected thresholds, and the type of valve. The valve display images can be updated after valves 216A-Z, 218A-S (FIG. 2) have been toggled. Controller 2047 can, for example, check if pumps 202, 204, 206, 208, 210, 212, 214 (FIG. 2) have been running for greater than a pre-selected time.

Referring again primarily to FIG. 31F, controller 2047 (FIG. 31A) can direct GUI 2037 (FIG. 31A) to update chamber image displays depending on, for example, but not limited to, pumps 202, 204, 206, 208, 210, 212, 214 (FIG. 2), the pump valve state (open or closed), and whether overrides for pumps 202, 204, 206, 208, 210, 212, 214 (FIG. 2) are allowed. Pump images can be updated depending on, for example, but not limited to, the type of pump 202, 204, 206, 208, 210, 212, 214 (FIG. 2) (for example, but not limited to, inlet, solution, exchange, perfuse), whether pump 202, 204, 206, 208, 210, 212, 214 (FIG. 2) is responsive, whether pump 202, 204, 206, 208, 210, 212, 214 (FIG. 2) is running, whether the status of pump 202, 204, 206, 208, 210, 212, 214 (FIG. 2) has changed, and whether pump 202, 204, 206, 208, 210, 212, 214 (FIG. 2) is frozen. Solution pump 3225 can have more states than, for example, inlet pump 3227 (FIG. 31F). In some configurations, GUI 2037 (FIG. 31A) can update the display periodically, for example, but not limited to, about 3.33 times/second, and can update the animation of fluid line 2029 if there have been changes. In some configurations, GUI 2037 (FIG. 31A) can periodically update, for example, but not limited to, about every 1.7 seconds, displays and graphics of pressure readings and solution levels, can check for reservoir 182A/B over full, flow rate values, flow rate display, diagnostic images, step progress, volume of enclosure 100, mixing valves (if system 2048B (FIG. 31B) is in process running state, preconditions state, prime operations state, ready to run state, or process pause state), last saved state (if active state 3051 is process running or preconditions). In some configurations, GUI 2037 (FIG. 31A) can alert an operator if active of states 3051 (FIG. 31B) is connected and more than, for example, two seconds have elapsed since a valve command or a pump command has issued. In some configurations, GUI 2037 (FIG. 31A) can test for a low memory event by testing against a low memory limit every, for example, ten minutes, and can take remedial action, for example, but not limited to, adjusting the rate of logging system events.

Referring again primarily to FIG. 31F, controller 2047 (FIG. 31B) can update the volume of enclosure 100 if the volume is being changed by one of pumps 3226/3228 and if system 2048B (FIG. 31B) is not in pause state. The volume of enclosure 100 can be reset, perhaps after a delay, in some configurations to zero, when controller 2047 (FIG. 31B) sends a new command as the result of a next step in recipe 2047A (FIG. 31A) or an override through GUI 2037 (FIG. 31B). Controller 2047 (FIG. 31B) can compute the volume of enclosure 100 based on the reported volumes of pumps 3226/3228 and whether or not fluid is flowing from 3226/3228 to or from enclosure 100. Controller 2047 (FIG. 31B) can recompute the fluid direction from/to enclosure 100 and toggle the status of pumps 3226/3228 depending on whether pumps 3226/3228 are the source of fluid to enclosure 100 or the target of fluid from enclosure 100.

Referring again primarily to FIG. 31F, pumps 202, 204, 206, 208, 210, 212, 214, 216 (FIG. 2) can be set to several states that can include, but are not limited to including, dual pump state, single pump state, idle, start pumping, deliver chamber x or y, fill chamber x or y, deliver from chamber x or y while filling chamber y or x, filling chamber y while delivering to chamber x, EOS delay, frozen, initial fill, fill chamber state, filling, initial delivery, pump inactive, pump running, solution pump normal, solution pump bypass, solution pump blocked, and delivering. In some configurations, the volume of pumps 202, 204, 206, 208, 210, 212, 214, 216 (FIG. 2) can be, for example, 308 ml, which can require seven strokes to fill for a 43 ml pod. Controller 2047 (FIG. 31B) can update the pump start time, enable or disable pump diagnostics, and configure mixing. In some configurations, controller 2047 (FIG. 31B) can, when mixing is not running, configure mixing by configuring solution pump 3225 and inlet pump 3227, setting pressure limits, configuring pump commands based on mode flow, inlet pump fill pressure, and solution pump delivery pressure, and setting mixing configuration strokes for selected of valves 216A-Z, 218A-R (FIG. 2) based on solution pump strokes in and inlet pump strokes in.

Referring again primarily to FIG. 31F, controller 2047 (FIG. 31B) can start mixing pumps by starting mixing of deionized (Di) water 192 and/or solutions 190 to reservoirs 182A/B. Controller 2047 (FIG. 31B) can set inlet pump 3227 and solution pump 3225 flow rates, and set pumps 3227/3225 in flow mode. If mixing is disabled, controller 2047 (FIG. 31B) can discontinue setting up mixing. If mixing Di water only, controller 2047 (FIG. 31B) can update inlet pump start time, and start inlet pump 3227 at an inlet flow rate. If mixing chemicals and Di water, controller 2047 (FIG. 31B) can set pump start times for solution pump 3225 and inlet pump 3227, and start mixing at a solution flow rate and an inlet flow rate. If mixing directly from chemicals, controller 2047 (FIG. 31B) can set inlet pump start time, start inlet pump 3227, and block solution pump 3225. Controller 2047 (FIG. 31B) can pause to give mixing time to start.

Continuing to refer primarily to FIG. 31F, controller 2047 (FIG. 31B) can stop pumps 3226-3228. If a stop is in progress, controller 2047 (FIG. 31B) can discontinue trying to stop pumps. If a stop is not in progress, controller 2047 (FIG. 31B) can stop the ongoing recipe sequence and pause while pumps 3226-3228 receive the message. Controller 2047 (FIG. 31B) can test if any of pumps 3226-3228 are running and, if they are, controller 2047 (FIG. 31B) can abort each of pumps 3226-3228 individually because any of pumps 3226-3228 that are not responding to a stop command could be frozen. To make sure pumps 3226-3228 have stopped, controller 2047 (FIG. 31B) can check pump states by messaging over CANbus 2043 (FIG. 31B) and setting up an error path if any of pumps 3226-3228 have not stopped.

Continuing to refer primarily to FIG. 31F, controller 2047 (FIG. 31B) can freeze pumps 3226-3228, if a freeze is not in progress, and can pause to give pumps 3226-3228 time to respond to the freeze command. Controller 2047 (FIG. 31B) can determine pump states by messaging CANbus 2043 (FIG. 31B) to determine if any of pumps 3226-3228 is running, and exit if none of pumps 3226-3228 is running. Controller 2047 (FIG. 31B) can freeze running pumps 3226-3228, get the status of pumps 3226-3228 by messaging over CANbus 2043 (FIG. 31B) test to make sure the freeze worked, and report errors if necessary. Controller 2047 (FIG. 31B) can also resume frozen of pumps 3226-3228 if a resume is not in progress, and if there are frozen of pumps 3226-3228. Controller 2047 (FIG. 31B) can pause to give the frozen of pumps 3226-3228 time to respond to the resume command. If the frozen of pumps 3226-3228 are non-mixing pumps, but the pumps are in mirror mode and set as non-frozen, controller 2047 (FIG. 31B) can resume pumps 3226/3228 regardless of their status in mirror mode.

Referring again primarily to FIG. 31F, controller 2047 can manage reservoir activity based on recipe 2047A (FIG. 31A), GUI 2037, and the automatic processing of controller 2047. Some functions that controller 2047 can perform and the automatic processing performed by controller 2047 with respect to the functions are set out in TABLE VII.

TABLE VII

| Reservoir function | Automatic processing |
| --- | --- |
| Partially drain reservoirs | (1) if a sequence is running or the control system state is not control system ready then stop all pumps 202, 204, 206, 208, 210, 212, 214 (FIG. 2) and compute the number of strokes to drain the reservoir (2) if the number of strokes to drain reservoir 182A/B is greater than the maximum number of strokes from reservoir 182A/B then set the number of strokes to drain reservoir 182A/B to the maximum number of strokes (3) open a selection of valves 216A-Z, 218A-S (FIG. 2) that have to do with emptying reservoir 182A/B (4) update pump start time (5) start emptying reservoir 182A/B (6) set configuration data for freeze and resume states while emptying reservoirs 182A/B |
| Empty reservoirs | (1) if a sequence is running or the control system state is not control system ready then stop all pumps 202, 204, 206, 208, 210, 212, 214 (FIG. 2) and compute the number of strokes to empty reservoirs 182A/B to be the maximum number of strokes times the filtered reservoir level divided by 90 plus pad empty strokes (2) if the number of strokes to drain reservoirs 182A/B is greater than the maximum number of strokes from reservoir 182A/B then set the number of strokes to drain reservoir 182A/B to the maximum number of strokes (3) open a selection of valves 216A-Z, 218A-S (FIG. 2) that have to do with emptying reservoir 182A/B (4) update pump start time (5) start emptying reservoir 182A/B (6) set configuration data for freeze and resume states while emptying reservoirs 182A/B |
| Empty multiple reservoirs at the same time | (1) if a sequence is running or the control system state is not control system ready then stop all pumps 202, 204, 206, 208, 210, 212, 214 (FIG. 2) and compute the number of strokes to empty both reservoirs 182A/B (2) if the number of strokes to drain reservoir 182A/B is greater than the maximum number of strokes from reservoirs 182A/B then set the number of strokes to drain reservoirs 182A/B to the maximum number of strokes (3) open a selection of valves 216A-Z, 218A-S (FIG. 2) that have to do with emptying reservoir 182A/B (4) update pump start time (5) start emptying reservoir 182A/B (6) set configuration data for freeze and resume states while emptying reservoirs 182A/B using multiple of pumps 208, 210, 212, 214 (FIG. 2) simultaneously |

TABLE VII-continued

| Reservoir function | Automatic processing |
|---|---|
| Empty active reservoirs | (1) close any open of valves 216A-Z, 218A-S (FIG. 2) that are mixing valves<br>(2) close all non-mixing valves that are open<br>(3) command reservoirs 182A/B to drain<br>(4) wait .25 seconds to give pumps 208, 210, 212, 214 (FIG. 2) time to start to prevent filling reservoirs 182A/B before the empty starts, |
| Configure reservoir-in valves and mixing | (1) close all solution valves that may be open<br>(2) get current solutions<br>(3) if not mixing chemicals and if reservoir level is too high then exit<br>(4) open reservoir inputs, for example, open valves 216A-Z, 218A-S (FIG. 2) for input from a select one of reservoirs 182A/B if multiple of reservoirs 182A/B and the current filling of reservoirs 182A/B is the select one of reservoirs 182A/B<br>(5) open selected of valves 216A-Z, 218A-S (FIG. 2) for solution 190 (FIG. 31G)<br>(6) open inlet pump to mixing valves and water solenoid valves<br>(7) configure mixing for solution pump stroke in and inlet pump strokes in if mixing one solution and state is mixing chemicals and Di water<br>(8) if not mixing direct DiRO (i.e. the mixing state is mixing DI water only), open inlet pump to mixing valves and water solenoid valves and configure mixing for solution pump stroke in and inlet pump strokes in<br>(9) if not mixing but instead drawing directly from solution 190 (FIG. 31G) (i.e. the mixing state is mixing direct from chemicals) then open inlet pump from solutions valves and inlet pump to mixing valves and configure mixing for solution pump stroke in and inlet pump strokes in<br>(10) then start mixing pumps (i.e. starts mixing to reservoirs 182A/B<br>(11) either start mixing or start inlet pump only for direct solution and direct DiRO water |

Continuing to refer primarily to FIG. 31F, during processing, controller 2047 (FIG. 31B) may check for when reservoir 182A/B is full. Controller 2047 (FIG. 31B) may wait for reservoir 182A/B to be full, for example, if controller 2047 is not also waiting for reservoir 182A/B to be empty, for example, in the case of drain before refill. Controller 2047 (FIG. 31B) may reset flags that indicate waiting for either reservoir 182A or 182B to be full if controller 2047 (FIG. 31B) is both waiting for reservoir 182A/B to be full and checking for the level of reservoir 182A/B to be full. Controller 2047 (FIG. 31B) can also (1) test if the reservoir level of a particular of reservoirs 182A/B is below a threshold to restart mixing if the mixing state is not mixing disabled, (2) test against an empty reservoir pre-selected threshold, (3) test against a full reservoir pre-selected threshold, (4) test if reservoir 182A/B is overfull and issue a warning if (a) system 2048B is neither in a connected state or a not connected state, and if a filtered level of reservoir 182A/B is greater than an alarm threshold, (5) test if reservoir 182A/B is empty if controller 2047 (FIG. 31B) is waiting for reservoir 182A/B to be empty, and controller 2047 (FIG. 31B) can stop all pumps if reservoirs 182A/B are emptied. Controller 2047 (FIG. 31B) can insure that reservoir valves are reset to a known state. Possible considerations for resetting reservoir valves can include, but are not limited to including, atmosphere pressure, reservoir half pressure, and reservoir half in.

Referring now to FIG. 31G, in some configurations, GUI 2037 (FIG. 31A) can process selected user button depressions as laid out in TABLE VIII.

TABLE VIII

| Button | Automatic actions |
|---|---|
| Start 3211 | (1) disable pump override stop buttons that may have been enabled on any start or resume<br>(2) restart certain of pumps 208, 210, 212, 214 (FIG. 2) if they were paused<br>(3) allow the user to reset all non-mixing of valves 216A-Z, 218A-S (FIG. 2) to the previous state, i.e. the state before the pause<br>(4) resume all frozen of mixing pumps 204, 206 (FIG. 2)<br>(5) resume the process running state if the state before the pause state is process running state and if the state before the pause was not modified by an override command<br>(6) restore the running state before the pause state that had been modified by an override command<br>(7) restore the state that was not modified by an override command by, for example, resuming all of pumps 202, 204, 206, 208, 210, 212, 214 (FIG. 2) |

TABLE VIII-continued

| Button | Automatic actions |
|---|---|
| | (8) resume from prime operations when state 3051 is prime operations state<br>(9) set the solution pump bypass and block state to solution pump normal<br>(10) set an initial start time of the first step of recipe 2047A (FIG. 31A)<br>(11) move system to a process running state |
| Stop 3235 | (1) prompt the user for verification that a system stop is desired<br>(2) send an e-mail or another form of electronic communication<br>(3) move system to a process complete state |
| Pause 3237 | (1) clear any valve override change flag<br>(2) trigger a pop-up window on valve state change<br>(3) save the state before the paused state<br>(4) freeze all pumps<br>(5) send an email<br>(6) move system to pause from running state |
| Skip step 3239 | (1) get next step to determine step to skip<br>(2) disable sequence edit<br>(3) check email<br>(4) process specially if skip step button was pressed before start button<br>(5) move to the active step after the step to skip if the maximum number of steps of recipe 2047A (FIG. 31A) have not been performed |
| Exit application 3241 | (1) if active state 3051 (FIG. 31B) is anything but not connected, verify that the user wants to exit the application<br>(2) stop all activity by pumps 202, 204, 206, 208, 210, 212, 214 (FIG. 2) and valves 216A-Z, 218A-S (FIG. 2)<br>(3) disable the usage of enclosure 100<br>(4) retry stopping all of pumps 202, 204, 206, 208, 210, 212, 214 (FIG. 2) |
| Override solution levels 3243 | (1) set sliders to reservoir default positions<br>(2) configure solution level equal to resize bottles<br>(3) update defaults from GUI 2037 if they have not been overridden manually<br>(4) configure the chemical reservoir size based on % in reservoirs |
| Override pumps 3245 | (1) stop all activity of pumps 202, 204, 206, 208, 210, 212, 214 (FIG. 2) and valves 216A-Z, 218A-S (FIG. 2) OR<br>(2) override pumps 202, 204, 206, 208, 210, 212, 214 (FIG. 2) and compute inlet flow rate<br>(3) update pump start time and start inlet pump at flow rate |
| Override solution and/or inlet pump 3243/3243A | (1) set all pump configuration values to user-selected values<br>(2) if solution or inlet pump is running then prompt user to verify that a reconfiguration is desired<br>(3) stop all activity of pumps 202, 204, 206, 208, 210, 212, 214 (FIG. 2) and valves 216A-Z, 218A-S (FIG. 2)<br>(4) if active state 3051 is not running, then override any of pumps 202, 204, 206 (FIG. 2)<br>(5) start mixing to reservoirs<br>(6) set flow rates<br>(7) update pump start time<br>(8) start mixing |
| Override perfuse/exchange pumps 3245 | (1) set configuration values of all of pumps 208, 210, 212, 214 (FIG. 2) to user-selected values<br>(2) compute the current volume pumped plus any earlier volume pumped<br>(3) if any of pumps 208, 210, 212, 214 (FIG. 2) are running, then prompt the user to verify that a reconfiguration is desired<br>(4) configure a selected of pumps 208, 210, 212, 214 (FIG. 2) by supplying any of type, fill pressure, delivery pressure, minimum pressure, maximum pressure<br>(5) update pump start time<br>(6) start either perfuse or exchange function<br>(7) set function start time |
| Generic override pump parameters | (1) set the enable/disable state of the UI pump override controls<br>(2) hide the pump override controls that are not used in the selected mode<br>(3) configure any of pumps 208, 210, 212, 214 (FIG. 2) |
| Solution pump bypass and block state 3247 | (1) If the system is in any of states solution pump bypass, solution pump blocked, and solution pump normal, set solution pump operating state<br>(2) bypass solution pump |
| Generate mouse click to table center | (1) keep recipe 2047A (FIG. 31A) active step row highlighted over step changes if the bioreactor window is not the application with the mouse/keyboard input focus<br>(2) generate the mouse click event if the current active tab is associated with recipe 2047A (FIG. 31A) |
| Stop perfuse/exchange and update display | (1) stop running the process if a stop is in progress<br>(2) stop all pump and valve actions<br>exit if no pumps are running, abort all pumps, send stop to all frozen pumps, exit if CANbus reports pumps are not running, test again if pumps are running and report an error if true |

Continuing to refer primarily to FIG. 31G, other functions that GUI 2037 (FIG. 31A) can process can include, but are not limited to including, going to step N 3249, jumping to step N via a pop-up window, adding a button, processing an e-mail setting button 3253, overriding pumps/valves 3255, overriding reservoir configurations, overriding reservoir selections, enabling/disabling specific valve state controls, modifying recipe 2047A (FIG. 31A), filling (on a graphical display) reservoirs 182A/B in use, graphing functions, calibrating pressure preconditions push button, CANbus 2043 (FIG. 31B) and connection status display, updating (on a graphical display) the status of the system, and processing various push buttons. GUI 2037 (FIG. 31A) can manage a reservoir active check box by setting the current filling reservoir and the current using from reservoir to be the same in a multiple reservoir system where only a single reservoir is running. GUI 2037 (FIG. 31A) can, for example, set the active of reservoirs 182A/B to blue, the inactive of reservoirs 182A/B to grey. GUI 2037 (FIG. 31A) can also update fluid lines 2029 on a graphical display. In some configurations, flow diagram lines can fall into categories such as, but not limited to, line active, line frozen, and line inactive. These lines can, for example, be assigned colors to distinguish them from each other in a graphical display. Controller 2047 (FIG. 31A) can begin determining how to direct GUI 2037 (FIG. 31A) to update the graphical display by determining, through queries to CANbus 2043 (FIG. 31B), the states of various features on the flow diagram. Flow diagram lines can be updated based at least on the lines from valves 216A-Z, 218A-S (FIG. 2) to end items, for example, but not limited to, reservoir 182A/B, drain 226, and DiRO water 192. Lines between two of valves 216A-Z, 218A-S (FIG. 2), and from valves 216A-Z, 218A-S (FIG. 2) to pumps 202, 204, 206, 208, 210, 212, 214 (FIG. 2) can also be constructed. Active lines from pumps 202, 204, 206, 208, 210, 212, 214 (FIG. 2) to valves 216A-Z, 218A-S (FIG. 2), frozen lines from valves 216A-Z, 218A-S (FIG. 2) to pumps 202, 204, 206, 208, 210, 212, 214 (FIG. 2), and lines that have changed since the last update can further be constructed.

Figure 31H:
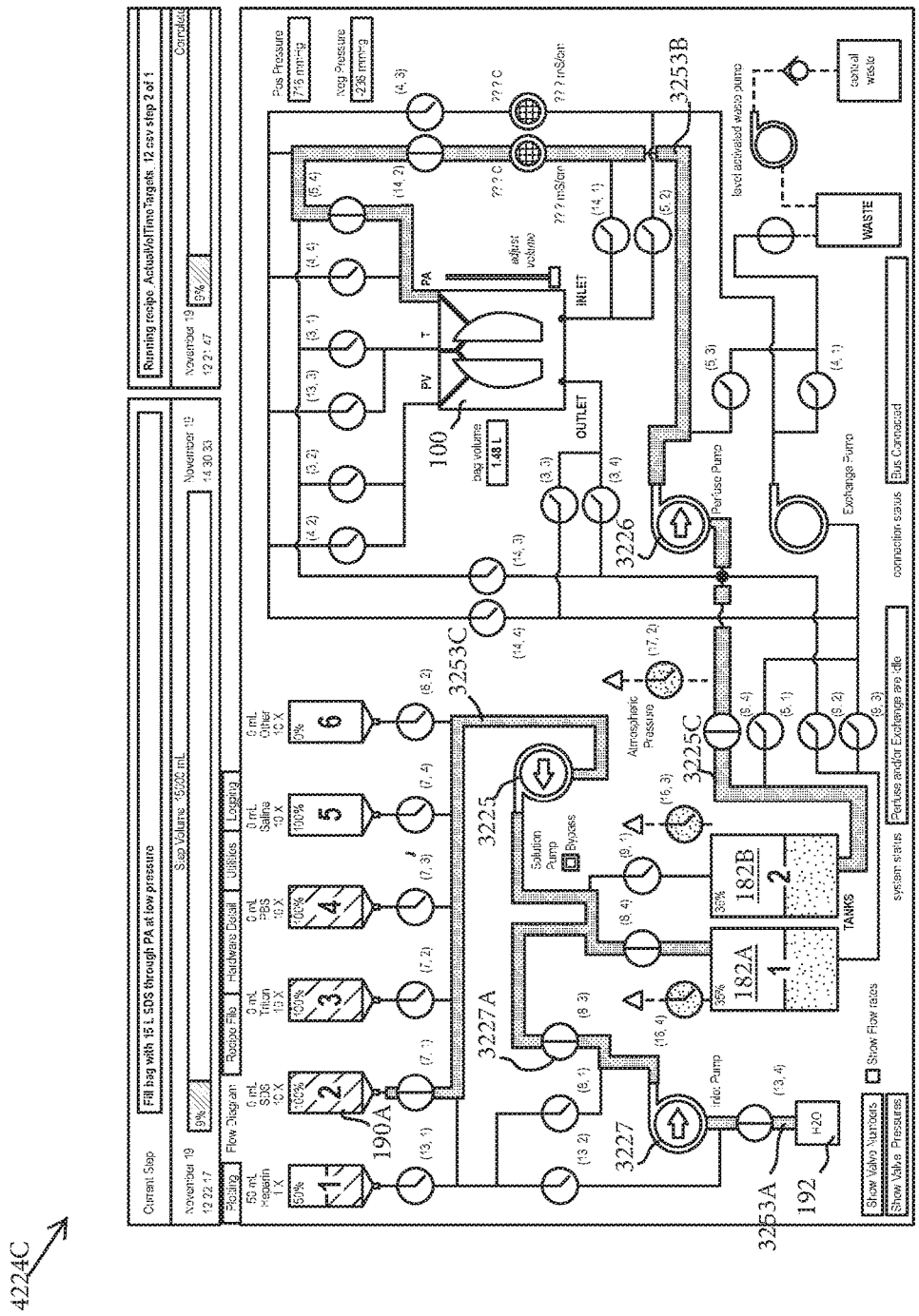
FIG. 31H is a graphical user interface of the components of an operational system as fluid is proceeding through the system.

Referring now primarily to FIG. 31H, in flow diagram 4224C, water 192 can be drawn into flow path 3253A by inlet pump 3227, traverse open valve 3227A (among others), and follow fluid path 3253A to reservoir 182A. At the same time, solution 190A can be drawn into solution pump 3225, and follow fluid path 3253A to join water 192 in reservoir 182A. Fluid from reservoir 182B can be drawn into fluid path 3225C by perfuse pump 3226 to eventually end up in fluid path 3253B and within enclosure 100, for example perfusing a pulmonary artery. Controller 2047 (FIG. 31B) can stop drawing from reservoirs 182A/B (FIG. 31F) if the level of fluid in reservoirs 182A/B (FIG. 31F) is below a threshold. Controller 2047 (FIG. 31B) can also manage reservoir low conditions and frozen of pumps 202, 204, 206, 208, 210, 212, 214 (FIG. 2). Controller 2047 (FIG. 31B) can test and swap reservoirs 182A/B (FIG. 31F). Controller 2047 (FIG. 31B) can begin by updating substate 3053 (FIG. 31B) when recipe 2047A (FIG. 31A) is ready to proceed unless, for example, system 2048B (FIG. 31B) is in pause state. Controller 2047 can log occurrences of when system 2048B (FIG. 31B) finds itself in substate 3053 (FIG. 31B). Controller 2047 (FIG. 31B) can maintain data structures that can include appropriate state-substate and state-state transitions, as well as appropriate state-mode and substate-mode relationships. To proceed with testing and swapping reservoirs 182A/B (FIG. 31F), if a single reservoir 182A or 182B (FIG. 31F) is being used, if mixing is not running, and if the level of a current filling reservoir 182A or 182B (FIG. 31F) is empty, then controller 2047 (FIG. 31B) can configure reservoir-in valves and mixing to be running to restart mixing to a single of reservoirs 182A/B (FIG. 31F). Controller 2047 (FIG. 31B) can test and swap reservoirs 182A/B (FIG. 31F) and restart mixing if reservoir 182A or 182B (FIG. 31F) is below thresholds, if system 2048B (FIG. 31B) is running and using a first of reservoirs 182A/B (FIG. 31F) while filling a second of reservoirs 182A/B (FIG. 31F), and if mixing is not disabled. In some configurations, controller 2047 (FIG. 31B) may not test and swap reservoirs 182A/B (FIG. 31F) and restart mixing if reservoirs 182A/B (FIG. 31F) are below thresholds, if reservoir 182A/B (FIG. 31F) that is currently being used is not empty, or if reservoir 182A or 182B (FIG. 31F) that is currently filling and reservoir 182A or 182B (FIG. 31F) that is currently being used are the same, if mixing is disabled, and if the step of recipe 2047A (FIG. 31A) requires a bolus. When mixing is enabled, and when the level of reservoir 182A or 182B (FIG. 31F) that is currently being used is low, and when mixing is not running, controller 2047 (FIG. 31B) can swap reservoirs 182A/B (FIG. 31F) and enable mixing. For this situation, controller 2047 (FIG. 31B) can verify that system 2048B (FIG. 31B) is in normal mode. Normal mode is when system 2048B (FIG. 31B) is using liquid from one reservoir 182A or 182B (FIG. 31F), filing another reservoir 182A or 182B (FIG. 31F), and mixing is not active. If mixing is not active, controller 2047 (FIG. 31B) can swap dual reservoir use from ports, configure reservoir-in valves and mixing, for example, when system 2048B (FIG. 31B) is running, start mixing to reservoir 182A/B (FIG. 31F) (dual reservoirs), and exit when mixing is not running and a swap of reservoirs 182A/B (FIG. 31F) has been configured. If mixing is active, controller 2047 may not complete the swap of reservoirs 182A/B (FIG. 31F).

Referring again primarily to FIG. 31H, when swapping dual reservoir use from ports, controller 2047 (FIG. 31B) can set output valves of reservoir 182A or 182B (FIG. 31F), and can swap reservoir 182A or 182B (FIG. 31F) that is currently being used with reservoir 182B or 182A (FIG. 31F) that is currently filling, which can modify mixing when configuring reservoir-in valves and mixing. In some configurations, controller 2047 (FIG. 31B) may not, for example, change reservoir-in valves or reservoir-out valves at this time, nor may controller 2047 start or stop the mixing pumps. In some configurations, controller 2047 (FIG. 31B) may not swap dual reservoir 182A/B (FIG. 31F) use if mixing is running. In some configurations, if no reservoirs 182A/B (FIG. 31F) are active (this can occur on initial filling of reservoirs 182A/B (FIG. 31F) before starting active processing), controller 2047 (FIG. 31B) may not swap reservoirs 182A/B (FIG. 31F). Controller 2047 can (1) swap reservoir 182A or 182B (FIG. 31F), that is being used, with reservoir 182A or 182B (FIG. 31F) that is being filled, (2) set substates 3053 (FIG. 31B) accordingly, (3) save the last states of reservoir-out valves, (4) swap the states of reservoir-out valves, (5) set the valves to the updated swapped states, and (6) set expected valve states to match the change.

Figure 31I:
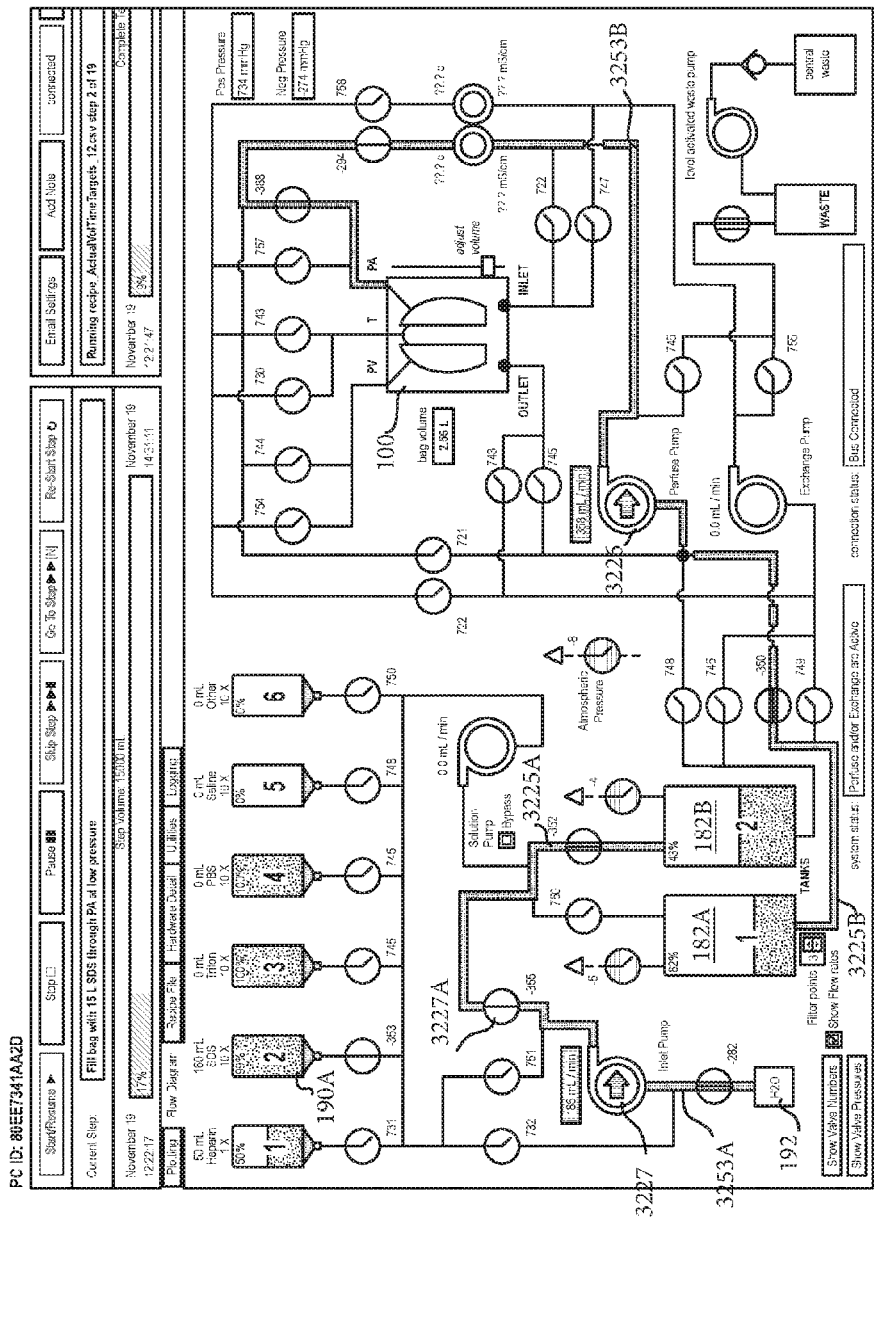
FIG. 31I is a graphical user interface of the components of an operational system as fluid is proceeding through the system.

Referring now to FIG. 31I, in flow diagram 4224D, water 192 can be drawn into flow path 3253A by inlet pump 3227, traverse open valve 3227A (among others), and follow fluid path 3225A to reservoir 182B. In flow diagram 4224D, solution 190A is not being drawn by solution pump 3225, and, at this snapshot, no solution is joining water 192 in reservoir 182B. Fluid from reservoir 182A can be drawn into fluid path 3225B by perfuse pump 3226 to eventually end up in fluid path 3253B and within enclosure 100, for example perfusing a pulmonary artery. GUI 2037 (FIG. 31A) can display a flow diagram and pump diagnostic valve numbers 3231 (FIG. 31G) and pressures, which can be hidden. GUI 2037 (FIG. 31A) can display flow rates and a flow rate filter changed indication when pre-selected thresholds have been met.

Referring again primarily to FIG. 31, the fluid pumped through system 2100 may be drawn from a number of sources. In some configurations, first fluid source 2012 and second fluid source 2015 can provide fluid to fluid circuit 2029. Fluid sources 2012, 2015 may be any of a variety of fluid sources such as any of those described in Table I. Fluid sources 2012, 2015 may be user selected to suit the needs of a specific procedure performed by system 2100. One or more of fluid sources 2012, 2015 may be passed through deaerator 2013 before entering the rest of fluid circuit 2021. In some configurations, fluid sources 2012, 2015, may pass through one or more filter (e.g. 230, 234 (FIG. 2)) or regulator (e.g. 232 (FIG. 2)) before reaching the rest of fluid circuit 2021. Filters 220, 234 (FIG. 2) and regulator 232 (FIG. 2) may be included alone or in addition to deaerator 2013. In some configurations, filtered water can enter fluid circuit 2029 through deaerator 2013 and can be mixed, in fluid circuit 2029, with concentrates to, for example, dilute concentrates to a pre-selected or dynamic concentration appropriate for a procedure.

Continuing to refer to FIG. 31, power supply 2017 may be included to provide appropriate power to various components of the system 2100. Power supply 2017 may, for example, supply power at multiple voltages as suitable for different components of system 2100 (e.g. 24V, 12V, etc.). Power supply 2017 in some configurations can supply power to deaerator 2013, pressure source 2011, and valve module 2019. Enclosure 100 can reside in container 174. In some configurations, container 174 can be 24"×18"×18", though container 174 dimensions may vary. Fluid circuit 2029 can be in fluidic communication with biological specimen 162 (FIG. 1) within enclosure 100 through at least one fluid path 2021 including, but not limited to, enclosure inlet and outlet paths, and specimen-specific paths. If biological specimen 162 (FIG. 1) is a lung, for example, the specimen-specific paths may include a path between the fluid circuit and the trachea, the pulmonary artery, and the pulmonary vein.

Figure 32:
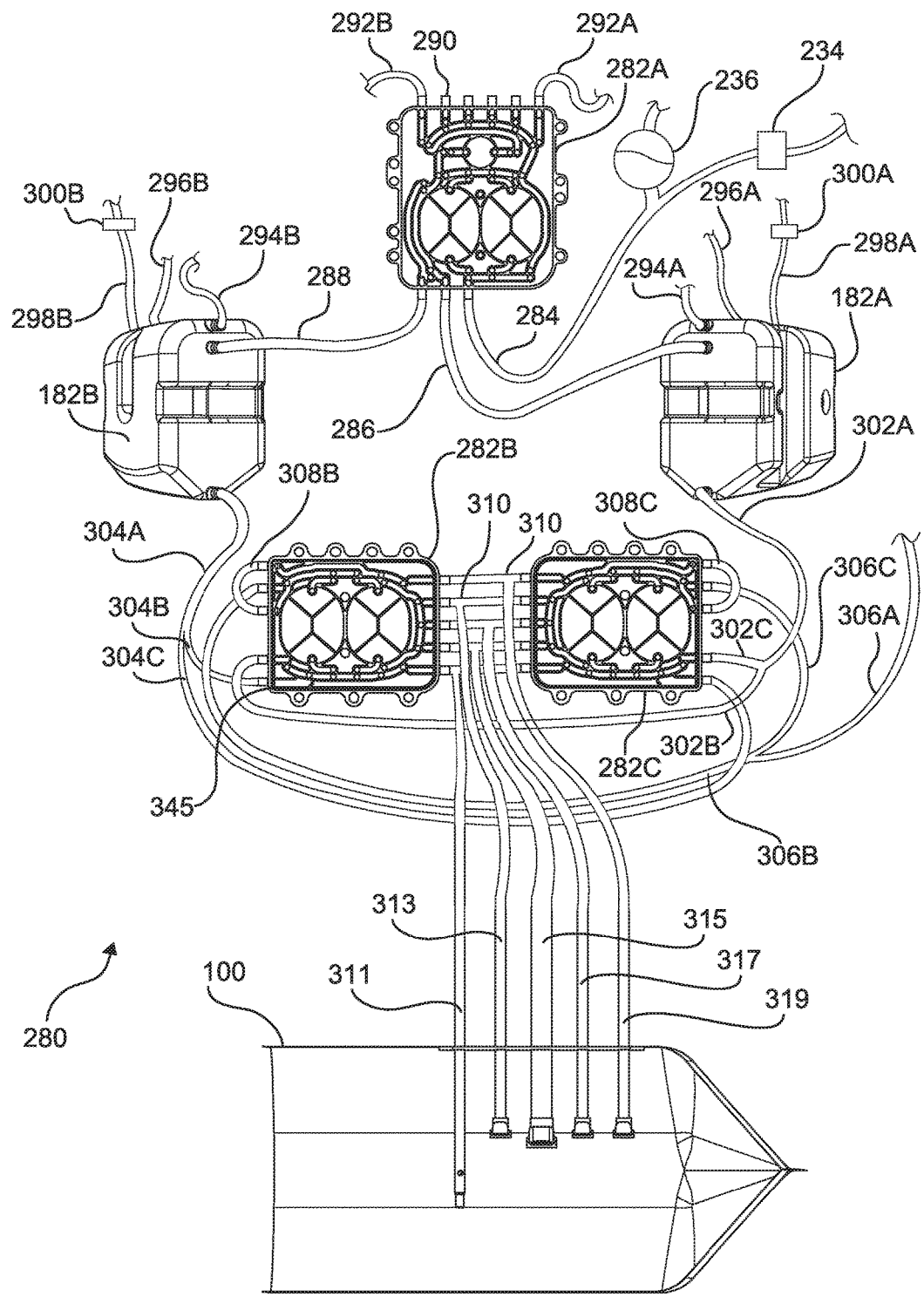
FIG. 32 is a schematic diagram of an example of a fluid handling set of the present teachings.

Referring now to FIG. 32, fluid handling set 280 can provide a fluid circuit similar to that of FIG. 2. Fluid handling set 280 can include, but is not limited to including, a number of fluid handling cassettes 282A, 282B, 282C. Each fluid handling cassette 282A, 282B, 282C may include pumps, incoming and outgoing ports, valves, and fluid paths between valves and pumps allowing the fluid circuit to be relatively simple and compact. Pumping and directing of fluid through the fluid handling cassette 282A, 282B, 282C may be driven, e.g., pneumatically as described in, for example, U.S. Pat. No. 5,350,357, filed Mar. 3, 1993, and entitled PERITONEAL DIALYSIS SYSTEMS EMPLOYING A LIQUID DISTRIBUTION AND PUMPING CASSETTE THAT EMULATES GRAVITY FLOW, which is hereby incorporated by reference herein in its entirety or as described in U.S. patent application Ser. No. 11/787,212, U.S. Pat. No. 8,292,594, filed Apr. 13, 2007, issued Oct. 23, 2012, entitled "Fluid Pumping Systems, Devices and Methods," (E78) incorporated herein by reference in its entirety. In some configurations, fluid handling set 280 can include storage reservoirs 182A, 182B and enclosure 100. Any suitable enclosure 100 may be used such as, but not limited to, any of those described above with reference to FIGS. 4-20. Fluid handling set 280 may be disposable for single use to, for example, streamline sterilization and/or cleaning of fluid handling set 280.

Continuing to refer primarily to FIG. 32, first cassette 282A may be in fluid communication with a number of fluid sources (such as any of those shown in Table I) via a number of attached fluid lines 284, 292A, 292B. For example, first cassette 282A can draw fluid from first line 284. First cassette 282A may also draw fluid from a source connected to any of solution ports 290 and source lines 292A, 292B of first cassette 282A. In some configurations, any or all of solution ports 290 may be connected to a source line. In some configurations, one or more port may be blocked or sealed and not used. In some configurations, one or more solution port 290 may include spike port 320 (FIG. 36) for attachment of a vial or other source. In some configurations, a vial of source fluid may, for example, be spiked directly onto solution port 290 and source lines 292A, 292B may not be necessary. Solution ports 290 may also include other fittings such as luer locks or similar fittings to which source lines 292A, 292B may be attached. In some configurations, solution port 290 may be replaced by vent port 322 (FIG. 36) which may allow pressure build up in a source in communication with the solution ports 290 to be relieved.

Continuing still further to refer to FIG. 32, first cassette 282A may draw in fluid via the solution ports 290 and first line 284. This fluid may then be expelled from cassette 282A through reservoir inlet lines 286, 288 to fluid reservoirs 182A, 182B. In some configurations, fluid may be drawn in from select sources in predetermined ratios to create a fluid mixture. The mixture may, in some configurations, be created within first cassette 282A or may be created by pumping the constituent fluids of the mixture to fluid reservoirs 182A, 182B and allowing the constituent fluids to mix within storage reservoirs 182A, 182B. A fluid mixture may, for example, be an admixture "cocktail" of the contents of a number of different sources which are in communication with first cassette 282A. Additionally, a fluid mixture may be created via first cassette 282A by drawing in fluid from a concentrated fluid source as well a diluent source. Again, mixing may occur within first cassette 282A or after pumping of these fluids to fluid reservoirs 182A, 182B. To achieve a desired concentration of the concentrate in the diluted mixture, fluid may be pumped from the concentrate source and diluent source in a predetermined ratio.

Continuing to refer to FIG. 32, in some configurations, first line 284 may place first cassette 282A in fluid communication with a diluent source such as a water source (e.g. reverse osmosis, deionized, or distilled water). Solution ports 290 may be connected to concentrates or additional diluent sources via a vial spike or source lines 292A, 292B. Any of attached fluid lines 284, 292A, 292B may include filter 234 attached to line 284 to filter incoming fluid. Filter 234 can be, but is not limited to being, a 0.2 μm filter. Incoming fluid may also be subjected to multiple filters 220, 234 (FIG. 2) or redundant filtration, deaeration in deaerator 230 (FIG. 2), and/or subjected regulator 232 (FIG. 2) which may ensure fluid is at a desired pressure. Though these components may be included within fluid handling set 280 in some configurations, these components may be included in partitioned portion 222 (FIG. 2) to which fluid handling set 280 connects. Any of attached fluid lines 284, 292A, 292B may also include fluid accumulator 236. In some configurations, accumulator 236 can be attached to first line 284. Accumulator 236 may be any suitable type of accumulator 236. Accumulator 236 can be, but is not limited to being, sized according to various specifications of first cassette 282A such as maximum estimated fluid throughput, pump chamber volume, etc. In some configurations, accumulator 236 can be sized to accommodate between 25-100 ml (e.g. 50 ml) of fluid.

Figure 33:
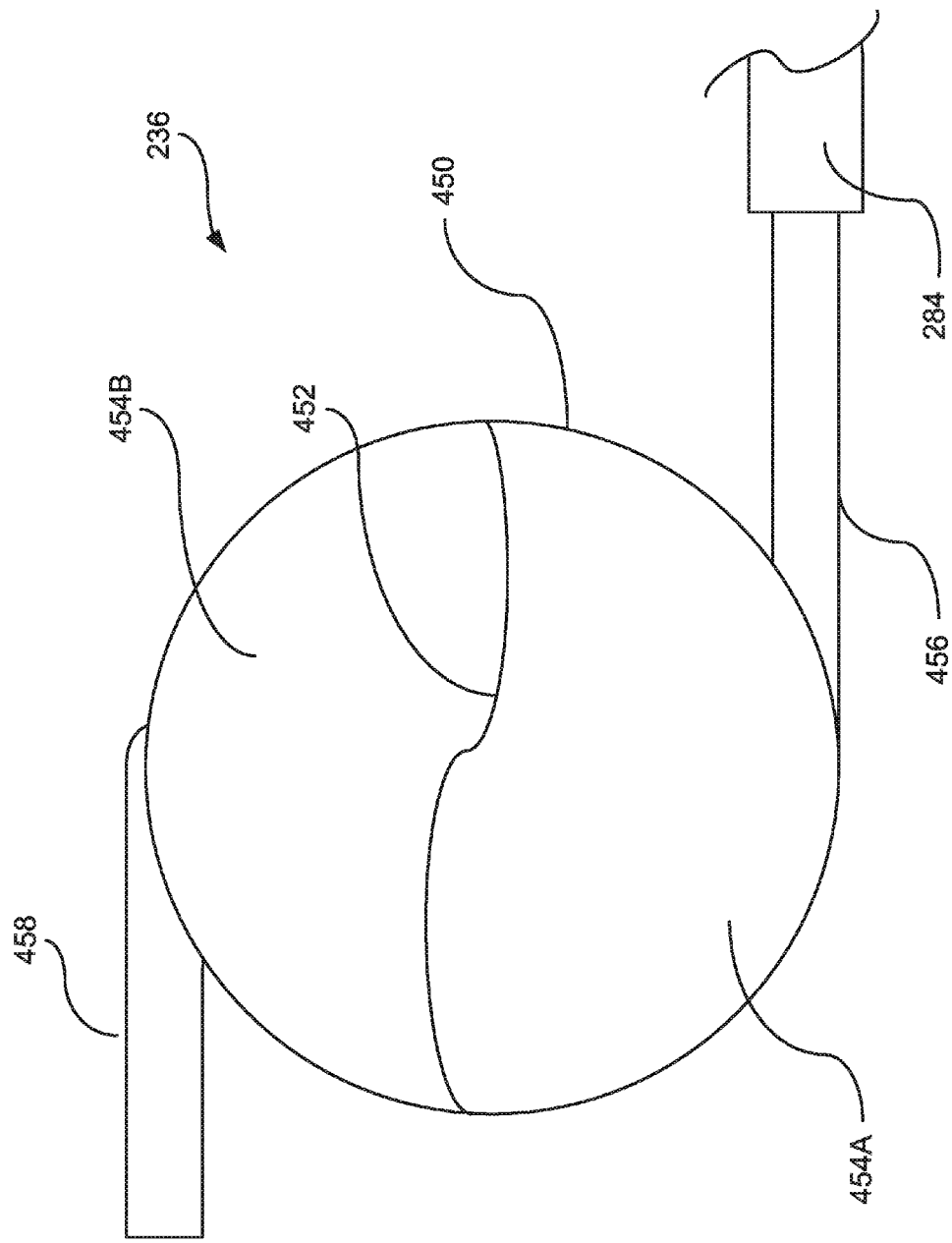
FIG. 33 is a representational illustration of an example of an accumulator of the present teachings.

Referring now primarily to FIG. 33, in some configurations, accumulator 236 can include, but is not limited to including, rigid housing 450 with a displaceable flexible membrane or barrier 452 therein. Flexible membrane 452 may be constructed of an elastomeric material, flexible plastic, or other substantially impermeable barrier. Rigid housing 450 may be constructed of a rigid plastic. Flexible membrane 452 may define two variable volume chambers 454A, 454B within rigid housing 450. The volume of each variable volume chamber 454A, 454B may change as flexible membrane 452 displaces with one volume increasing and the other decreasing in direct proportion. In some configurations, first variable volume chamber 454A may be a wet chamber in communication with first line 284 via first accumulator port 456. Flexible membrane 452 may create a seal between first variable volume chamber 454A and second variable volume chamber 454B. Second variable volume chamber 454B may be in communication with the atmosphere via vent port 458. Fluid in first line 284 may be at a pressure higher than atmospheric pressure. In the event that fluid throughput of first cassette 282A (FIG. 32) is lower than a fluid supply rate to first line 284, first variable volume chamber 454A may increase in volume and air may be displaced out of second variable volume chamber 454B via vent port 458. Thus accumulator 236 may accumulate a reserve of fluid. This reserve of fluid may help ensure that there is extra fluid available for first cassette 282A if first cassette 282A is drawing fluid from first line 284 at a rapid rate (e.g. a rate higher than the supply rate).

Referring again to FIG. 32, storage reservoirs 182A, B may be included in fluid handling set 280. In some configurations, two storage reservoirs 182A, B are included though the number of storage reservoirs 182A, B may differ. Storage reservoirs 182A, B may include one or more port to which a fluid line may be connected. Each of storage reservoirs 182A, B may be in fluid communication with each cassette 282A, 282B, 282C of fluid handling set 280. Storage reservoirs 182A, B may, for example, receive fluid from first cassette 282A respectively via reservoir inlet lines 286, 288. In some configurations, cassette 282A may also be capable of drawing fluid from storage reservoirs 182A, B via lines 286, 288. Storage reservoir 182A may be in communication with cassettes 282B, 282C respectively via reservoir outlet lines 302B, 302C. Reservoir outlet lines 302B, 302C may split from common line 302A at a Y-site in some configurations. Storage reservoir 182B may be in communication with second cassettes 282B, 282C respectively via reservoir outlet lines 304B, 304C. These lines 304B, 304C may also split from a common line 304A at a Y-site in some configurations. In some configurations, second cassettes 282B, C may each have a dedicated storage reservoir. In some configurations, storage reservoir 182A can feed second cassette 282B, and storage reservoir 182B can feed second cassette 282C. In some configurations, the storage reservoirs 182A, B may be shared between cassettes 282B, C and each cassette 282B, C may draw from each storage reservoir 182A, B. Any configuration that can accommodate providing fluid to second cassettes 282B, C can be included within the scope of the present teachings.

Continuing to refer to FIG. 32, storage reservoirs 182A, B can include ports for air vent lines 298A, B, overflow lines 294A, B, and level lines 296A, B. Air vent lines 298A, B may allow air to escape or enter storage reservoirs 182A, B as the level of fluid in storage reservoirs 182A, B changes. This may help ensure no pressure build up occurs within a storage reservoirs 182A, B. Air vent lines 298A, B can optionally include filters 300A, B. Filters 300A, B may be a 0.2 micron filter. Overflow lines 294A, B may be in fluid communication with an overflow reservoir (not shown) which may hold excess fluid in the event that storage reservoirs 182A, B are over-filled. Level lines 296A, B may be in communication with a sensor which is configured to provide a determination of the fluid level within storage reservoirs 182A, B. Level lines 296A, B will be described elsewhere in the specification.

Continuing to refer primarily to FIG. 32, second cassettes 282B, C can be, for example, mirror images of each other. In some configurations, second cassettes 282B, C may be identical and the arrangement of fluid lines may differ. In some configurations, second cassettes 282B, C may differ from one another. Each second cassette 282B, C may, for example, each be specialized or optimized to perform a specific task. Second cassettes 282B, C may be in communication with a number of fluid lines to/from which fluid may be drawn or pumped. Second cassettes 282B, C may be in communication with one or more storage reservoirs 182A, B. Second cassettes 282B, C may each be in communication with loop lines 308B, 308C respectively. In some configurations, only one or neither of second cassettes 282B, C may be in communication with loop lines 308B, 308C. Loop lines 308B, 308C will be described elsewhere in the specification. Second cassettes 282B, 282C may be in communication with lines 306B, 306C of waste line 306A which may lead to waste reservoir 180 (FIG. 1). Air bubbles and used, excess, spent, or otherwise unacceptable fluid, for example, may be pumped by second cassettes 282B, 282C to waste line 306A, possibly, but not limited to, for disposal.

Continuing to still further refer to FIG. 32, second cassettes 282B, 282C may also be in communication with a number of fluid buses 310. Fluid buses 310 may be attached to a number of fluid lines extending to one or more enclosure 100. In some configurations, first fluid line 319, second fluid line 311, and a number of specimen fluid lines 313, 315, 317 can be connected to at least one of fluid buses 310. Fluid may be pumped into or drawn from fluid lines 311, 313, 315, 317, 319 through the fluid buses 310 to transfer fluid to/from enclosure 100 or biological specimen 162 (FIG. 1) within enclosure 100. In some configurations, such as those where second cassettes 282A, B are not mirror images, but identical, shared fluid buses 310 may not be included. Instead fluid lines 311, 313, 315, 317, 319 may include branches that can be associated with each second cassette 282A, 282B. The branches may, for example, resemble drain line 306A which can include drain lines 302B, 306C. In some configurations, multiple of each of fluid lines 311, 313, 315, 317, 319 may be included in fluid handling set 280 and each second cassette 282B, 282C may be associated with its own dedicated fluid lines 311, 313, 315, 317, 319. In configurations with a plurality of enclosures 100 included in fluid handling set 280, each second cassette 282B, C may be associated with fluid lines 311, 313, 315, 317, 319 from one of enclosures 100. Additional cassettes 282A, 282B, 282C and/or other types of cassettes may be included in fluid handling set 280.

Continuing to still further refer primarily to FIG. 32, operationally, fluid handling set 280 can circulate specific fluids through biological specimen(s) 162 (FIG. 1) and enclosure 100 according to an automatic process, a manual process, or a combination of both. A recipe including, for example, but not limited to, ingredients and valve positions as a function of, for example, time, can be constructed that can facilitate an automatic process which can be overridden manually. First cassette 282A can be operated to provide sufficient fluid to storage reservoirs 182A, B, and second cassettes 282B, 282C can allow continuous flow into enclosure 100 without risking the integrity of enclosure 100. For example, second cassette 282B can be delivering fluid to enclosure 100 via first fluid line 311 while second cassette 282C can be draining enclosure 100 via second fluid line 319. Fluid drained from enclosure 100 may be pumped to waste line 306A or, if recirculation is desired may be pumped back to enclosure 100.

Continuing to refer to FIG. 32, if it is desired to pump air into enclosure 100 or to biological specimen(s) 162 (FIG. 1) within enclosure 100, storage reservoirs 182A, B, for example, can be emptied of contents, leaving air behind. Second cassettes 282B, 282C can then draw air from storage reservoirs 182A, B and pump the air through fluid lines 313, 315, 317 to specimen(s) 162 (FIG. 1). In some configurations, second cassettes 282B, 282C may include vent port 322 (FIG. 36) which may be used to draw in air for pumping. Fluid handling set 280 can be operated partially or entirely manually through a graphical user interface 2037 (FIG. 31) in which valves that control fluid flow can be toggled individually or in predefined groups to move fluid throughout fluid handling set 280 and/or biological specimen 162 (FIG. 1) in enclosure 100. In some configurations, fluid handling set 280 may be partially manually operated based on information provided to graphical user interface 2037 (FIG. 31). The commands may be associated with predefined control functions which can accomplish a desired pumping task. For example, a manually input command may be in the form of "pump 'X' volume of fluid from 'A' to 'B' at rate 'Y' using cassette 'Z'" where the variable parameters may be manually defined.

Figure 34:
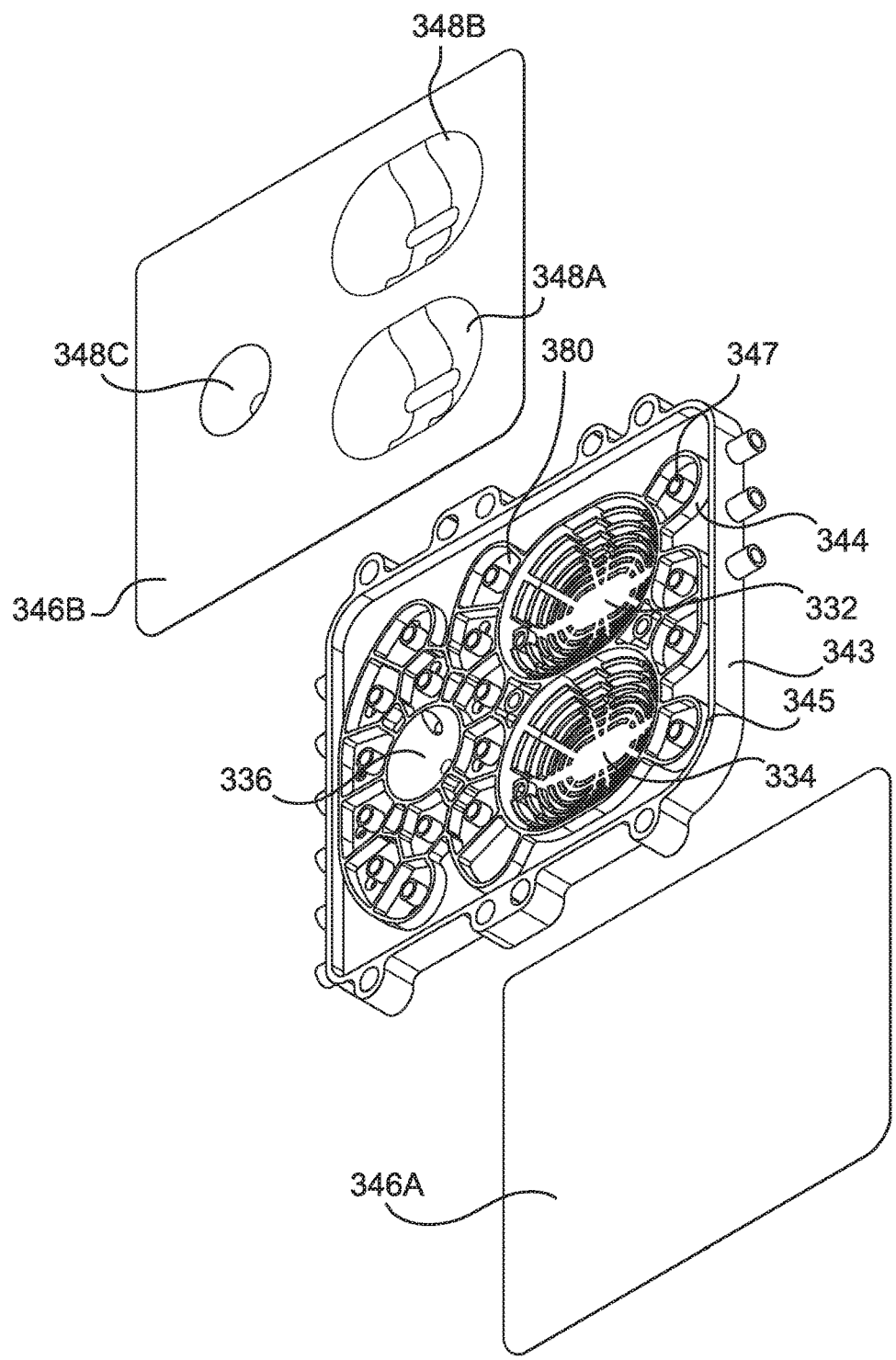
FIG. 34 is a perspective diagram of an example of a first cassette of the present teachings having sheeting exploded away from the cassette.

Referring now primarily to FIG. 34, first cassette 282A may be operated to deliver desired fluids to storage reservoirs 182A, B (FIG. 32) and may function as a mixing cassette to create desired fluid mixtures. First cassette 282A may include cassette body 343. Cassette body 343 may be a rigid member which can be, for example, but not limited to, constructed from a hard plastic or other hard material. Cassette body 343 may be manufactured in any number of suitable manners such as molding, machining, etc. Cassette body 343 may be, for example, but not limited to, a generally planar structure from which a number of walls 344 and perimeter wall 345 project. Walls 344, 345 may project at an angle that can be substantially perpendicular from the plane of cassette body 343. First cassette 282A can also include a number of valve seats 347 which can project away from cassette body 343, for example, similar to walls 344, 345. Each valve seat 347 may be surrounded by walls 344 which can define valve well 380A. Walls 344, 345 of cassette 282A may extend proud of valve seats 347.

Continuing to refer to FIG. 34, first cassette 282A may also include cassette sheeting or membrane 346A, 346B. Cassette sheeting 346A, 346B may be generally planar pieces of material. Cassette sheeting 346A, 346B may be, for example, but not limited to, substantially impermeable and flexible, for example a flexible plastic or elastomeric material. Cassette sheeting 346A, 346B may be attached to each side of cassette body 343 at perimeter wall 345, and can overlay walls 344 of cassette 282A. Cassette sheeting 346A, 346B may be positioned on first cassette 282A and attached to first cassette 282A e.g., by heat bonding, adhesive, ultrasonic welding or other means. Cassette sheeting 346A, 346B can be a flexible polymer film made from, for example, polyvinyl chloride (PVC), that is cast, extruded or otherwise formed. Alternatively, the cassette sheeting 346A, 346B may be formed as a laminate of two or more layers of poly-cyclohexylene dimethylene cyclohexanedicarboxylate (PCCE) and/or ULDPE, held together, for example, by a coextrudable adhesive (CXA). Urethane may also be used. The thickness of cassette sheeting 346A, 346B may be any suitable thickness, and in some configurations, in the range of approximately 0.002 to 0.020 inches thick. In one configuration, the thickness may be in the range of approximately 0.012 to 0.016 inches thick, and in one configuration, can be approximately 0.014 inches thick.

Continuing to still further refer to FIG. 34, when pressure is applied to each side of cassette body 343, cassette sheeting 346A, 346B may be forced against walls 344 of cassette body 343. The pressure can, for example, form fluidically sealed chambers and pathways in first cassette 282A. Cassette sheeting 346A, 346B may be, but is not limited to being, prevented from being forced against each of valve seats 347 because walls 344 may be, for example, proud of valve seats 347. Positive pressure (pressure may be exerted mechanically or by a control fluid pneumatically, hydraulically, etc.) applied to cassette sheeting 346A, 346B over valve seat 347 may displace cassette sheeting 346A, B into contact with valve seat 347. Negative pressure may displace cassette sheeting 346A, B away from valve seat 347. One or more piece of cassette sheeting 346A, 346B may optionally include one or more preformed region 348A, 348B, 348C. Preformed regions 348A, 348B, 348C may be, but are not limited to being, depression-like features in cassette sheeting 346A, 346B which can generally conform to the contours of various portions of first cassette 282A. Preformed regions 348A, 348B, 348C may be added to cassette sheeting 346A, 346B during manufacture. Cassette sheeting 346A, 346B may be, for example, generally formed as a flat member and preformed regions 348A, 348B, 348C may later be thermoformed. In some configurations, preformed regions 348A, 348B, 348C can correspond to pump chambers 332, 334, 336 of first cassette 282A. The dome-like preformed shapes can, for example, conform to pump chamber 332, 334, 336 depressions of first cassette 282A. The dome-like shape of preformed portions 348A, 348B, 348C may be constructed, for example, by heating and forming cassette sheeting 346A, 346B over a vacuum form mold. The vacuum form mold can press a sheet of cassette sheeting 346A, 346B against first cassette 282A and bond them together.

Continuing to refer primarily to FIG. 34, when first cassette 282A is assembled, each pump chamber 332, 334, 336 can be, for example, defined in part by cassette sheeting 346A, B. Each of pump chambers 332, 334, 336 can, for example, be defined in part by walls 344 extending from cassette body 343 to create depressions in pump chambers 332, 334, 336. Application of pressure to cassette sheeting 346A, 346B over pump chambers 332, 334, 336 may cause the volume of pump chambers 332, 334, 336 to vary. Negative pressure can draw cassette sheeting 346A, 346B away from cassette body 343 and can increase the volume of pump chamber 332, 334, 336. If, in communication with a fluid source such as, for example, but not limited to, source 190 (FIG. 1) and/or storage reservoirs 182 (FIG. 1), fluid may be drawn into one or more of pump chambers 332, 334, 336 when negative pressure is applied, executing a fill pump stroke. Positive pressure can force cassette sheeting 346A, 346B toward cassette body 343 and decrease the volume of one or more of pump chambers 332, 334, 336. When one or more of pump chambers 332, 334, 336 contains fluid, the application of positive pressure may cause the fluid to be expelled from one or more of pump chambers 332, 334, 336, executing a deliver pump stroke.

As with cassette sheeting 346A, 346B over valve seat 347, pressure may be applied in any of a variety of ways (e.g. mechanically or by a control fluid pneumatically, hydraulically, etc.). In configurations where cassette sheeting 346A, 346B includes preformed regions 348A, 348B, 348C, preformed regions 348A, 348B, 348C may displace to conduct pumping action without requiring significant (or any) stretching of cassette sheeting 346A, 346B, even when a region of cassette sheeting 346A, 346B is at a maximum excursion point (e.g. when an associated pump chamber 332, 334, 336 is at minimum or maximum volume).

Figure 36:
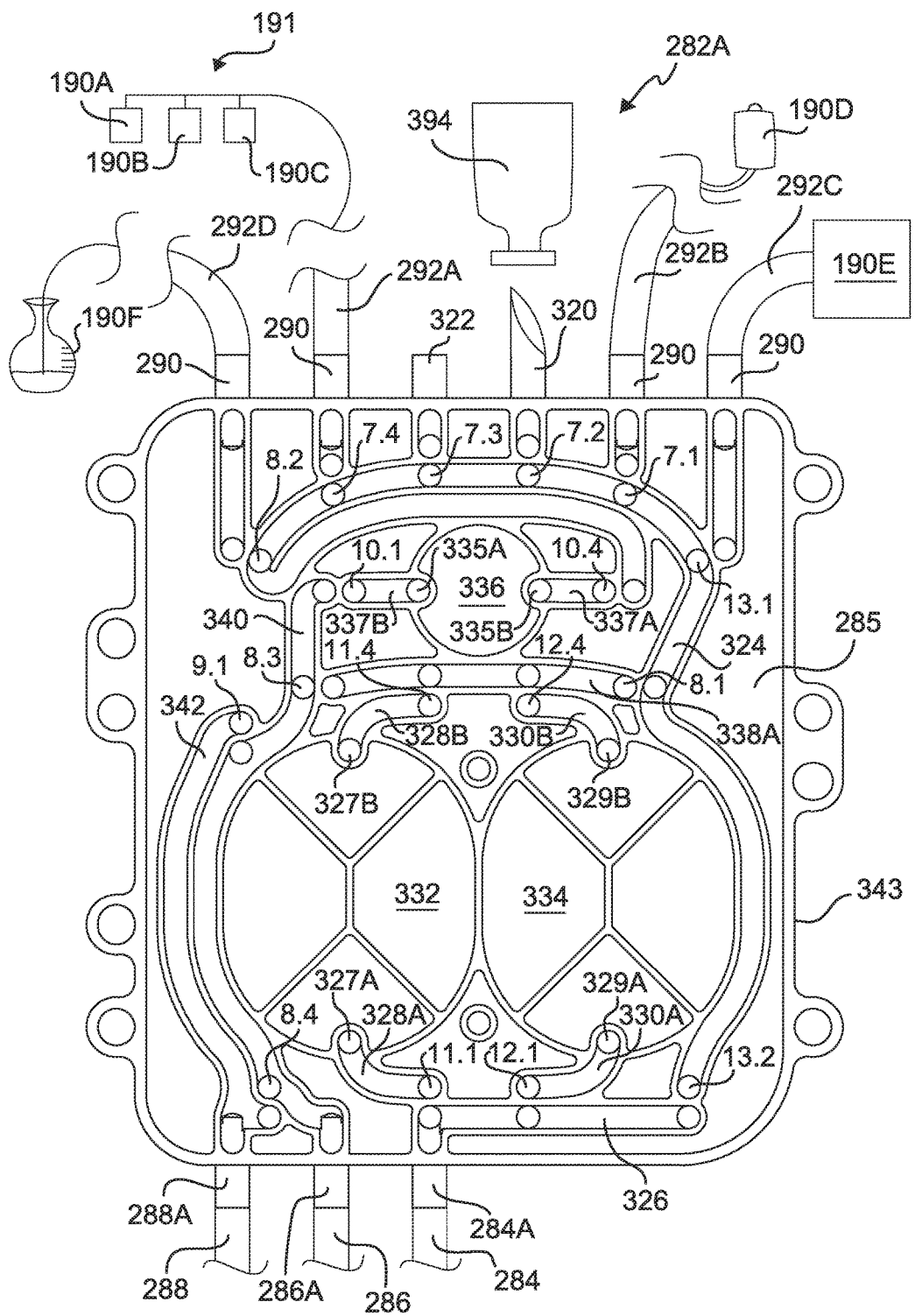
FIG. 36 is a schematic diagram of an example of a second side of the first cassette of FIG. 35.

Continuing to refer to FIG. 34, in some configurations, cassette sheeting 346A, 346B (also referred to as flexible sheeting) may also be bonded to walls 344 of first cassette 282A. For example, cassette sheeting 346A, B may be bonded to walls 344 that form various pathways or buses within first cassette 282A and can cover at least one pump chamber 332, 334, 336 (FIG. 36). At least one piece of cassette sheeting 346A, 346B may be formed of a rigid sheet of material that is bonded or otherwise made integral with first cassette 282A. Thus, at least one piece of cassette sheeting 346A, 346B need not necessarily be, or include, a flexible member. Similarly, cassette sheeting 346A, 346B need not be flexible over its entire surface, but instead may include one or more flexible portions to permit pump and/or valve operation, and one or more rigid portions, e.g., to close fluid buses of first cassette 282A. In some configurations, first cassette 282A can include fluid buses or pathways that can be otherwise sealed or fully enclosed within first cassette 282A without cassette sheeting 346A, 346B.

Figure 35:
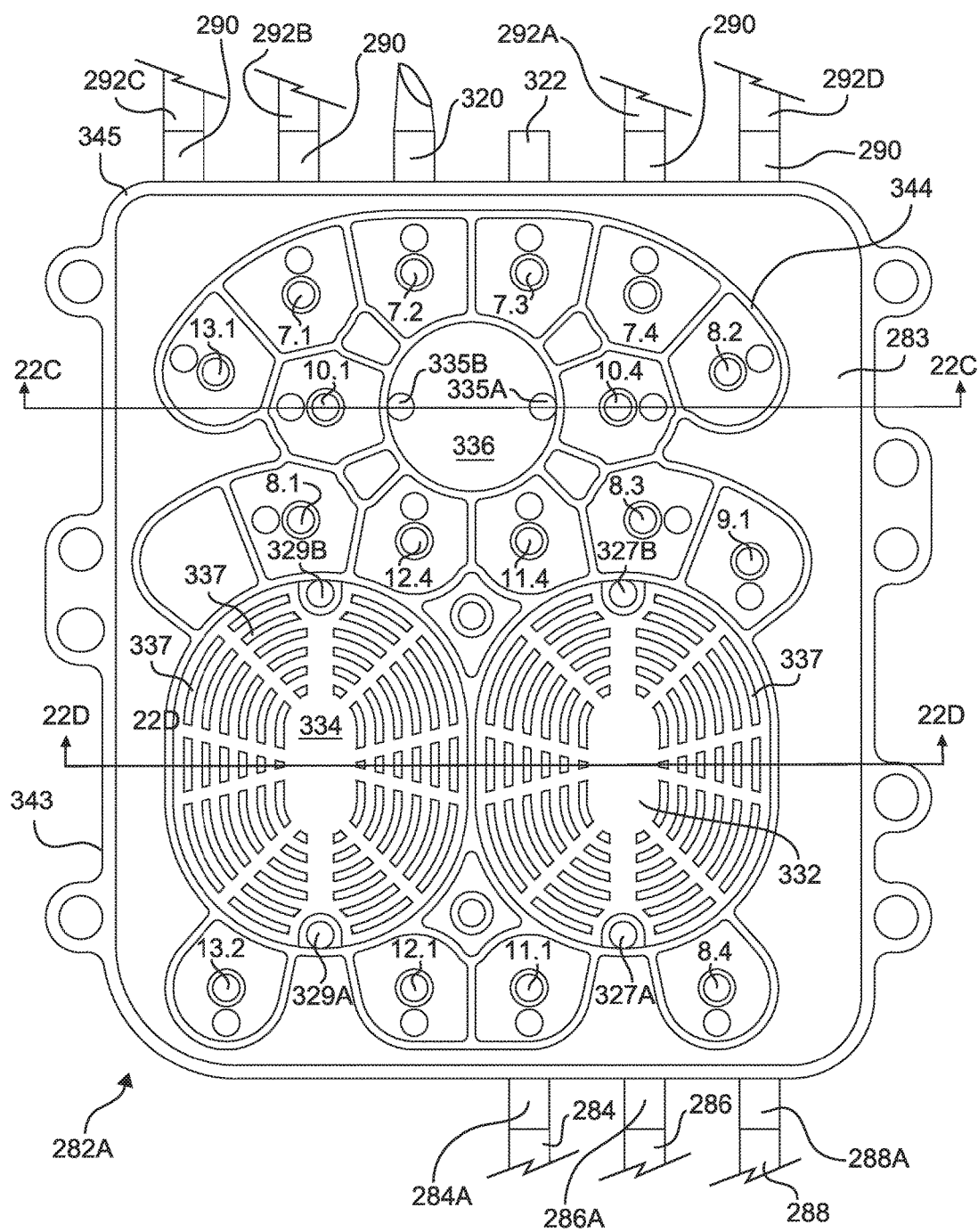
FIG. 35 is a schematic diagram of an example of a first side of a first cassette of the present teachings.
Figure 38:
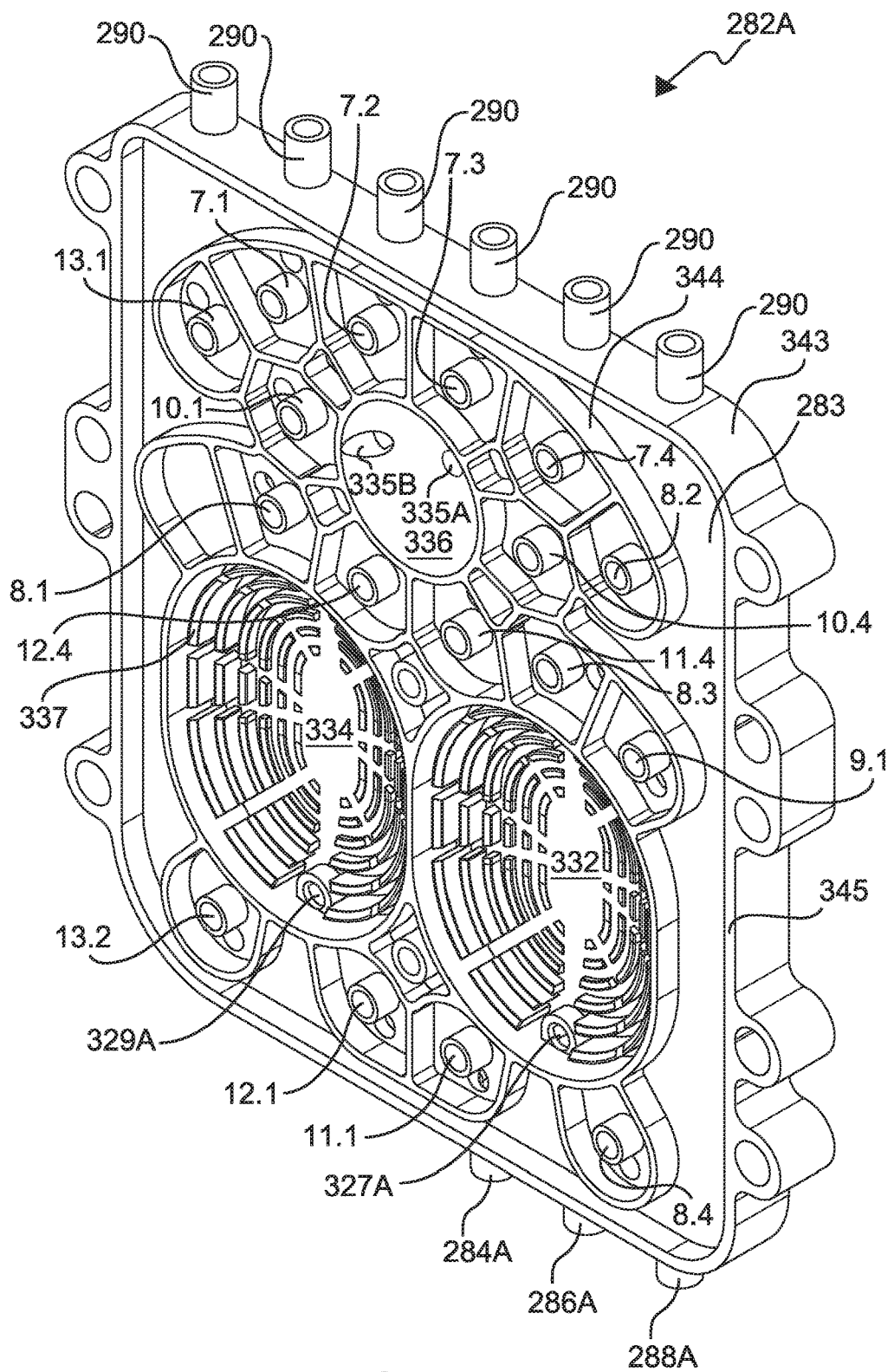
FIG. 38 is a perspective view of a first side of the first cassette of FIG. 35.

Referring now primarily to FIGS. 35, 36, and 38, first cassette 282A can include, but is not limited to including, first side 283 (FIG. 35) and second side 285 (FIG. 36). First cassette 282A may also include one or more pump chamber, for example, first pump chamber 332, second pump chamber 334, and solution pump chamber 336. Each of pump chambers 332, 334, 336 may be a variable volume chamber which may be defined in part by cassette sheeting 346A, 346B (FIG. 34) which may act as a displaceable diaphragm. Pressure applied to one or more pump chambers 332, 334, 336 may cause fluid to be drawn into or forced out of one or more pump chambers 332, 334, 336. First cassette 282A may include, but is not limited to including a number of fluid valves 13.1, 7.1-7.4, 10.1, 10.4, 8.1-8.4, 12.4, 11.4, 9.1, 13.2, 12.1, 11.1 (e.g. volcano valves) which may be independently opened and closed to make and break fluid communication with fluid pathways 324, 326, 328A, 328B, 330A, 330B, 338A, 340, 342 (FIG. 36) on second side 285 (FIG. 36) of first cassette 282A. Each of fluid valves 13.1, 7.1-7.4, 10.1, 10.4, 8.1-8.4, 12.4, 11.4, 9.1, 13.2, 12.1, 11.1 in first cassette 282A may be associated with valve seats 347 (FIG. 34). Cassette sheeting 346A, 346B (FIG. 34) may be forced against or pulled away from valve seats 347 (FIG. 34) associated with valves 13.1, 7.1-7.4, 10.1, 10.4, 8.1-8.4, 12.4, 11.4, 9.1, 13.2, 12.1, 11.1 to respectively close or open valves 13.1, 7.1-7.4, 10.1, 10.4, 8.1-8.4, 12.4, 11.4, 9.1, 13.2, 12.1, 11.1. Valves 13.1, 7.1-7.4, 10.1, 10.4, 8.1-8.4, 12.4, 11.4, 9.1, 13.2, 12.1, 11.1 can be opened and closed to direct fluid flow when fluid is pumped via one or more of pump chambers 332, 334, 336. Fluid in valve well 380A (FIG. 34) may, for example, flow through valve 12.1 to a flow path on the opposing side of the cassette 282A if the sheeting 346A, 346B (FIG. 34) is not pressed against valve seat 347 (FIG. 34) of valve 12.1.

Continuing to refer primarily to FIGS. 35, 36, and 38, cassette sheeting 346A, 346B (FIG. 34) may also serve to create a fluid tight seal for fluid pathways 324, 326, 328A, 328B, 330A, 330B, 338A, 340, 342 (FIG. 36) such that fluid in fluid pathways 324, 326, 328A, 328B, 330A, 330B, 338A, 340, 342 (FIG. 36) can be confined within each of fluid pathways 324, 326, 328A, 328B, 330A, 330B, 338A, 340, 342 (FIG. 36). First cassette 282A may also include a number of fluid ports 290, 322, 284A, 286A, 288A, 320. Each of ports 290, 322, 284A, 286A, 288A, 320 may be connected to fluid lines, or conduits leading to fluid sources 190 (FIG. 1) or reservoirs 182 (FIG. 1). Operation of pump chambers 332, 334, 336, and valves 13.1, 7.1, 7.2, 7.3, 7.4, 8.2, 10.1, 10.4, 8.1, 12.4, 11.4, 8.3, 9.1, 13.2, 12.1, 11.1, 8.4 may allow fluid to be pumped into or out of first cassette 282A through one or more of ports 290, 322, 284A, 286A, 288A, 320. Closing all of valves 13.1, 7.1, 7.2, 7.3, 7.4, 8.2, 10.1, 10.4, 8.1, 12.4, 11.4, 8.3, 9.1, 13.2, 12.1, 11.1, 8.4 which are not associated with a desired of fluid pathways 324, 326, 328A, 328B, 330A, 330B, 338A, 340, 342 (FIG. 36) to one or more of ports 290, 322, 284A, 286A, 288A, 320 may allow one or more pump chambers 332, 334, 336 to be in exclusive communication with the desired ports 290, 322, 284A, 286A, 288A, 320. Depending on how valves 13.1, 7.1, 7.2, 7.3, 7.4, 8.2, 10.1, 10.4, 8.1, 12.4, 11.4, 8.3, 9.1, 13.2, 12.1, 11.1, 8.4 are actuated in relation to the actuation of pump chambers 332, 334, 336, fluid may be pumped either in a first direction, or in a second direction. That is, one or more of pump chambers 332, 334, 336 may transfer fluid into and out of one or more ports 290, 322, 284A, 286A, 288A, 320 of first cassette 282A such that one or more ports 290, 322, 284A, 286A, 288A, 320 may behave as inlets and outlets.

Referring now to FIG. 36, in some configurations, solution ports 290 may be attached to solution lines 292A-D providing fluid from various sources 190A-F. Sources 190A-F may differ and a non limiting number of example sources 190A-F are shown in FIG. 36. In some configurations, manifold 191 for, for example, sources 190A-C may be attached to solution port 290 by solution line 292A which can be used by manifold 191 as a common inlet to first cassette 282A. Each type of source 190A-C on manifold 191 may be different or, in some configurations, at least two sources 190A-C on manifold 191 may be the same. In some configurations, solution line 292B may be connected to solution bag 190D. Any size solution bag 190D may be used to provide the source fluid. In some configurations, solution line 292C may be in communication with reservoir 190E which can be, for example, a drum or other bulk size container. Solution line 292D may be placed in communication with flask 190F or other laboratory vessel. Flask 190F may be desirable in scenarios where the incoming fluid is manually produced or produced on site. Other source 190A-F types may also be used.

Continuing to refer to FIG. 36, in some configurations, first cassette 282A may include one or more spike(s) or spike port(s) 320. Spike port 320 can include, but is not limited to including, a needle or hollow spike that can pierce a seal or septum of source vial 394 or other source reservoir. Spike port 320 may be formed from, for example, but not limited to, plastic, or a metal such as stainless steel. In some configurations, spike port 320 may be made from a sterilizable material which may be able to withstand sufficiently high temperatures and/or chemical/radiation exposure related to a sterilization process. Spike port 320 may be used to spike source vial 394 such that fluid may be drawn through spike port 320 into first cassette 282A. In some configurations, spike 320 may be omitted. For example, spike port 320 may be replaced by solution port 290. Some configurations may include additional spike ports 320 which may be in addition to or substituted for one or more of solution ports 290.

Continuing to refer to FIG. 36, in some configurations, first cassette 282A may include vent port 322. Vent port 322 can allow pressure build up in sources 190A-F or source vials 394 to be relieved. Source 190A-F and source vial 394 may be placed in communication with vent port 322 to equalize the pressure of source 190A-F and source vial 394 with ambient pressure as fluid is drawn into first cassette 282A. Vent port 322 may also be used to pump or purge undesired fluid such as air out of first cassette 282A. Vent port 322 may include a filter, such as a 0.2 micron filter. Vent port 322 may include a hydrophobic filter. In some configurations, air may be introduced from vent port 322 into first cassette 282A through operation of at least one of pump chambers 332, 334, 336. The air may, for example, be pumped throughout first cassette 282A to purge first cassette 282A of a first fluid before re-priming first cassette 282A with another fluid. In some configurations, vent port 322 may be omitted. For example, vent port 322 may be replaced by solution port 290. Some configurations may include additional vent port(s) 322 which may be in addition to or substituted for one or more of solution ports 290.

Continuing to refer primarily to FIG. 36, among the fluid pathways of first cassette 282A may be solution bus 324. Solution bus 324 may be a common bus for solution drawn into first cassette 282A through solution ports 290 and spike ports 320. Valves 7.4, 7.2, 7.1, 8.2, 13.1 may be opened and closed to make and break fluid communication between solution bus 324 and one or more of ports 290, 320, 322. For example, opening valve 7.2 while closing valves 7.4, 7.1, 8.2, 13.1 could place spike port 320 in communication with solution bus 324 while isolating solution ports 290 and vent port 322 from solution bus 324. Fluid may then be transferred between solution bus 324 and spike port 320.

Additional ports including, though not limited to, first line port 284A, first reservoir port 286A, and second reservoir port 286A may be included in first cassette 282A. These ports may be connected to various fluid lines leading to fluid sources 190 (FIG. 1) and reservoirs 182 (FIG. 1). For example, first line port 284A may be connected to first line 284 leading to a diluent source in some configurations. First and second reservoir port 286A, 288A may be respectively connected to first reservoir line 286 and second reservoir line 288 leading to storage reservoirs 182A, 182B (FIG. 32) of fluid handling set 280 (FIG. 32).

Continuing to refer primarily to FIG. 36, among the fluid pathways of first cassette 282A may be pump chamber bus 326, first reservoir inlet path 340 and second reservoir inlet path 342. Pump chamber bus 326 may allow fluid to be transferred between first cassette 282A and first line 284. The fluid may, for example, be a diluent such as purified water in some configurations. First reservoir inlet path 340 and second reservoir inlet path 342 may allow fluid to be transferred between first cassette 282A and first and second reservoir lines 286, 288. Central bus 338A (though it may be included anywhere on the cassette 282A and not necessarily near the cassette 282A center) may also be included among the flow pathways. First cassette 282A may include first pump chamber 332, second pump chamber 334, and solution pump chamber 336. In some configurations, first cassette 282A may be configured such that any of pump chambers 332, 334, 336 may be placed in fluid communication with any of ports 290, 320, 284A, 286A, 288A. While in fluid communication with a desired of ports 290, 320, 284A, 286A, 288A, negative pressure may be applied to sheeting 346A (FIG. 34) over one or more pump chambers 332, 334, 336 to fill one or more pump chambers 332, 334, 336 with fluid from fluid source 190 (FIG. 1) or reservoirs 182 (FIG. 1) connected to one or more of ports 290, 320, 284A, 286A, 288A. Positive pressure may be applied to expel fluid within one or more of pump chambers 332, 334, 336 to one or more fluid lines connected to one or more of ports 290, 320, 284A, 286A, 288A. Each of pump chambers 332, 334, 336 may be placed in communication with one another. Thus, the flow of fluid from any of ports 290, 320, 284A, 286A, 288A through first cassette 282A may be controlled by any of pump chambers 332, 334, 336. Only one of pump chambers 332, 334, 336 need be operable to draw fluid into itself. Other of pump chambers 332, 334, 336 may be left inoperable and closed off to flow by closing the appropriate valves.

Continuing to still further refer to FIG. 36, with respect to first pump chamber 332, communication with first line port 284A may be established by opening valve 11.1 creating a fluid pathway from pump chamber bus 326 to first pump chamber inlet/outlet path 328A and into first pump chamber 332 via pump chamber inlet/outlet 329A. Communication with solution line bus 324 may be established by opening valves 8.1 and 11.4. Opening valves 8.1 and 11.4 may generate a fluid pathway from solution bus 324 to central bus 338A and from central bus 338A to first pump chamber inlet/outlet path 328B. First pump chamber inlet/outlet path 328B is in communication with first pump chamber 332 via pump chamber inlet/outlet 329B. Communication with first reservoir port 286A may be established by opening valves 8.3 and 11.4. Opening valves 8.3 and 11.4 may generate a fluid pathway from first reservoir path 340 to central bus 338A and from central bus 338A to first pump chamber inlet/outlet path 328B. Communication with first pump chamber inlet/outlet path 328B may be established by opening valves 9.1, 8.3, and 11.4. Opening valves 9.1, 8.3, and 11.4 may generate a fluid pathway from second reservoir path 342 to first reservoir path 340 onto central bus 338A and into pump chamber 332 through first pump chamber inlet/outlet path 328B.

Continuing to refer to FIG. 36, with respect to second pump chamber 334, communication with first line port 284A may be established by opening valve 12.1 creating a fluid pathway from pump chamber bus 326 to second pump chamber inlet/outlet path 330A and into second pump chamber 334 via pump chamber inlet/outlet 327A. Communication with solution line bus 324 may be established by opening valve 8.1 and 12.4. Opening valve 8.1 and 12.4 may generate a fluid pathway from solution bus 324 to central bus 338A and from central bus 338A to second pump chamber inlet/outlet path 330B. Second pump chamber inlet/outlet path 330B may be in communication with pump chamber inlet/outlet 327B. Communication with first reservoir port 286A may be established by opening valves 8.3 and 12.4. Opening valves 8.3 and 12.4 may generate a fluid pathway from first reservoir path 340 to central bus 338A and from the central bus 338A to second pump chamber inlet/outlet path 330B. Communication with second reservoir port 328A may be established by opening valves 9.1, 8.3, and 12.4. Opening valves 9.1, 8.3, and 12.4 may generate a fluid pathway from second reservoir path 342 to first reservoir path 340 onto central bus 338A and into second pump chamber 334 through second pump chamber inlet/outlet path 330B.

Continuing to refer to FIG. 36, with respect to solution pump chamber 336, communication with solution line bus 324 may be established by opening valve 10.1 establishing a pathway from solution bus 324 to solution pump chamber inlet/outlet path 337A. Solution pump chamber inlet/outlet path 337A is in communication with solution pump chamber 336 via solution pump chamber inlet outlet 335A. Communication with first line port 284A may be established by opening valves 13.2 and 10.1. Opening valves 13.2 and 10.1 may create a fluid pathway from pump chamber bus 326 to solution bus 324 and on to solution pump chamber inlet/outlet path 337A. Communication with first reservoir port 286A may be established by opening valve 10.4. Opening valve 10.4 may generate a fluid pathway from first reservoir path 340 to solution pump chamber inlet/outlet path 337B. Solution pump chamber inlet/outlet path 337B is in communication with solution pump chamber 336 via solution pump chamber inlet/outlet 335B. Communication with second reservoir port 228A may be established by opening valves 9.1 and 10.4. Opening valves 9.1 and 10.4 may generate a fluid pathway from second reservoir path 342 to first reservoir path 340 onto solution pump chamber inlet/outlet path 337B.

Continuing to refer to FIG. 36, the fluid pathways described herein for placing pump chambers 332, 334, 336 in communication with specific ports 290, 320, 284A, 286A, 288A are merely exemplary. More than one pathway can be established by opening and closing of valves of first cassette 282A to place one or more of pump chambers 332, 334, 336 in communication with a desired of ports 290, 320, 284A, 286A, 288A. Multiple of pump chambers 332, 334, 336 may be placed in communication with the same of ports 290, 320, 284A, 286A, 288A at the same time. By opening valves 12.4, 11.4, 8.3, and 10.4 all of pump chambers 332, 334, 336 may, for example, be operated to deliver fluid to first reservoir port 286A.

In some configurations, first line 284 may be connected to a diluent source. Each of solution ports 290 and spike ports 320 may be connected to a variety of sources 190A-F and vial 394 which can contain a concentrate or number of concentrates. If the concentrate in source 190A-F and vial 394 requires reconstitution, one or more of pump chambers 332, 334, 336 may be placed in communication with first line port 284A and filled with diluent. The diluent may then be expelled from one or more of pump chambers 332, 334, 336 to source 190A-F and vial 394 through one or more of ports 290, 320 associated with source 190A-F and vial 394. In some configurations, one or more of pump chambers 332, 334, 336 may be operated to pump the partially reconstituted concentrate back and forth between one or more of pump chambers 332, 334, 336, and source 190A-F and vial 394. Pumping the partially reconstituted concentrate back and forth may help to facilitate reconstitution. In some configurations, reconstitution may be performed similar to as described in U.S. Pat. No. 6,726,656, filed Oct. 8, 2002, and entitled System For Controlling Flow Through a Line During Intravenous Drug Delivery, which is incorporated by reference herein in its entirety.

Still further referring primarily to FIG. 36, in some configurations, diluent may be pumped via one or more of pump chambers 332, 334 from first line port 284A through first cassette 282A to one or more of reservoir ports 286A, 288A. The diluent may then proceed through reservoir inlet line 286, 288 to one or more storage reservoirs 182A, 182B (FIG. 32). Concentrate fluid from a desired of sources 190A-F and vial 394 may be pumped via solution pump chamber 336 from solution bus 324 to one or more of reservoir ports 286A, 288A. The concentrate fluid may then proceed through reservoir inlet line 286, 288 to one or more storage reservoirs 182A, 182B (FIG. 32). With the concentration of the concentrate in source 190A-F, 394 known, the ratio of diluent to concentrate pumped may be altered such that the fluid mixture delivered to one or more storage reservoirs 182A, 182B (FIG. 32) is at a desired concentration. In some configurations, the ratio of diluent to concentrate may, for example, be one full solution pump chamber 336 delivered for every ten full deliveries from any of pump chambers 332, 334. If a full delivery of one of pump chambers 332, 334 is five times the volume of a full delivery of solution pump chamber 336, the ratio would be 50:1. For finer control of the ratio, partial deliveries of any of pump chambers 332, 334, 336 may also be performed. In some configurations, partial deliveries may be done by calculating the volume of fluid transferred between one or more of pump chambers 332, 334, 336 and one or more of sources 190A-F, vial 394, and reservoir ports 286A, 288A as the pump stroke is in progress. When the desired volume of fluid has been pumped, the stroke may be terminated. Such displaced volume accounting as a stroke is in progress may be conducted as described in U.S. patent application Ser. No. 14/732,564, filed Jun. 5, 2015, and entitled Medical Treatment System and Method Using a Plurality of Fluid Lines, which is incorporated by reference herein in its entirety. In some configurations, dilution may be performed within first cassette 282A. Two fluids, e.g. a diluent and a concentrated source fluid may be mixed similarly to as described in U.S. Pat. No. 7,461,968, filed Oct. 30, 2003, and entitled System, Device, and Method for Mixing Liquids, which is incorporated by reference herein in its entirety.

Referring now specifically to FIG. 35, first cassette 282A can include one or more pump chambers. Each of pump chambers 332, 334, 336, may be identical or may differ from one another. For example, solution pump chamber 336 can have a different design from pump chambers 332, 334. Solution pump chamber 336 may be a small volume chamber, e.g. 5-20 ml or in some configurations 10 ml in volume when fully filled. Pump chambers 332, 334 may or may not be of equal volume and may be larger in volume than solution pump chamber 336 when fully filled. In some configurations, pump chambers 332, 334 may be about 3.5-7 times (e.g. 5 times) larger in volume when fully filled than solution pump chamber 336. In some configurations, pump chambers 332, 334 may each be about 40-50 ml (e.g. 50 ml) in volume when fully filled.

Each of pump chambers 332, 334, 336 may be of different or identical geometry. For example, solution pump chamber 336 may have a generally circular footprint while pump chambers 332, 334 can be, for example, but not limited to, ovoid, elliptical, oblong, and stadium shaped. In some configurations, solution pump chamber 336 may be at least partially formed as a generally hemispherical or spherical cap like depression in first cassette 282A. Pump chambers 332, 334 may be defined at least partially by flat bottomed depressions in first cassette 282A. One or more of pump chambers 332, 334, 336 may include spacers 337. For example, pump chambers 332, 334 may include spacers 337 while solution pump chamber 336 can be devoid of spacers 337. Spacers 337 may be similar to those described in U.S. Pat. No. 6,302,653, filed Jul. 20, 1999, and entitled METHODS AND SYSTEMS FOR DETECTING THE PRESENCE OF A GAS IN A PUMP AND PREVENTING A GAS FROM BEING PUMPED FROM A PUMP, and, U.S. patent application Ser. No. 13/667,696, filed Nov. 2, 2012, and entitled MEDICAL TREATMENT SYSTEM AND METHODS USING A PLURALITY OF FLUID LINES, both of which are incorporated herein by reference in their entireties. Spacers 337 will be described further herein.

Continuing to refer to FIG. 35, each pump chamber 332, 334, 336 may have pressure applied in a different manner (e.g. mechanically v. with a control fluid) or with different control fluids. In some configurations, pressure may be applied to pump chambers 332, 334, 336 in a different manner than it is applied to sheeting over valve seats 347 (FIG. 34). For example, the pressure may be applied to pump chambers 332, 334, 336 with a control fluid while sheeting 346A, 346B may be mechanically pressed against valve seats 347.

Figure 37A:
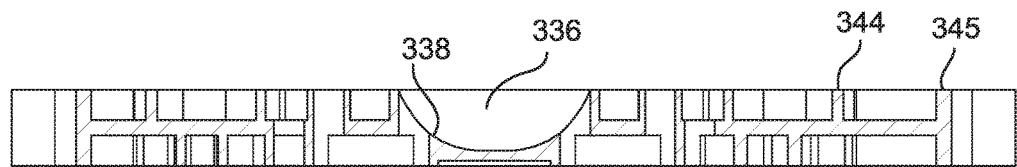
FIG. 37A is a cross section diagram taken at line 22C-22C of FIG. 35.
Figure 37B:
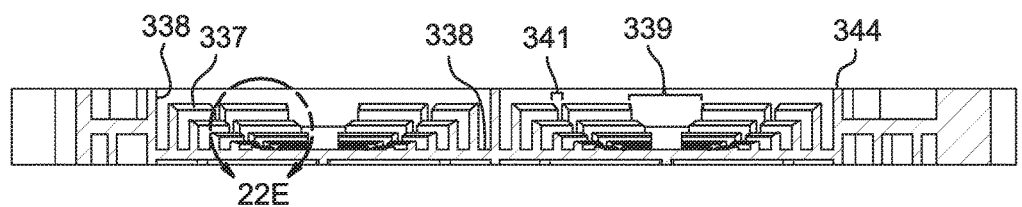
FIG. 37B is a cross section diagram taken at line 22D-22D of FIG. 35.

Referring now to FIGS. 37A and 37B, cross sectional views of an example first cassette 282A taken at lines 22C-22C and 22D-22D of FIG. 36 are shown. In some configurations, the pump chambers 332, 334, 336 depressions may be defined by chamber depression faces 338.

Referring now primarily to FIG. 37A, spacers 337 may be omitted from at least one pump chamber 332 (FIG. 36), 334 (FIG. 36), 336 of first cassette 282A. Solution pump chamber 336, for example, may be defined by a relatively featureless or bald depression face 338.

Figure 37C:
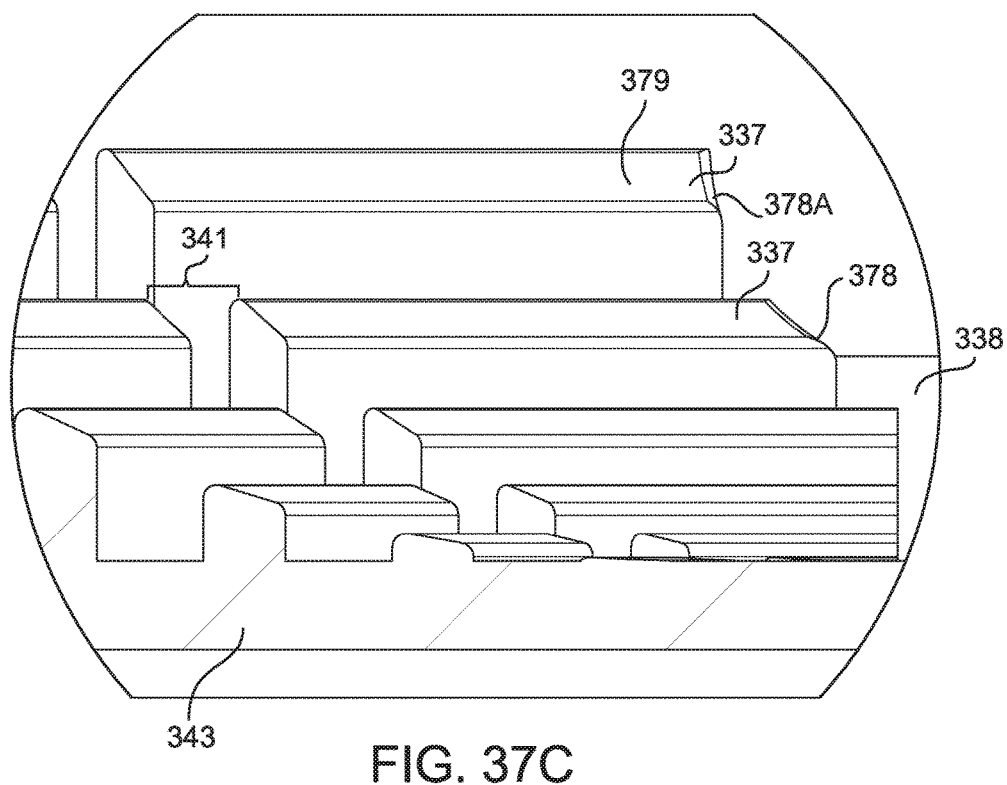
FIG. 37C is an enlarged detailed view of the spacers of FIG. 37B.

Referring now primarily to FIGS. 37B and 37C (which is an enlarged view of region 22E in FIG. 37B), depression face 338 (FIG. 37A) of pump chambers 332, 334 (FIG. 36) can include spacers 337 which can project away from depression face 338. Spacers 337 may extend, for example, but not limited to, in a manner substantially perpendicular from depression face 338 or in a manner parallel to walls 344 (FIG. 37B) of first cassette 282A (FIG. 36). Spacers 337 can be spaced, for example, but not limited to, an equal distance apart from one another. The height of spacers 337 may be equal or may progressively increase or decrease in size within pump chambers 332, 334, 336 (FIG. 36). In one configuration, spacers 337 can be arranged in a kind of "stadium seating" arrangement such that spacers 337 can be arranged in a concentric elliptical pattern with ends of spacers 337 increasing in height from one portion of depression face 338 to another to form a semi-elliptical domed shaped region. Spacers 337 may have, for example, but not limited to, top face 379A (FIG. 37C) that is, for example, but not limited to, flat or sloped. Edges 378A (FIG. 37C) of top face 379A (FIG. 37C) may be beveled, rounded, or chamfered. Top face 379A (FIG. 37C) of each spacer 337 may serve as a contact face for cassette sheeting 346A, 346B (FIG. 34) when cassette sheeting 346A, 346B (FIG. 34) travels into pump chambers 332, 334 (FIG. 36). Spacers 337 may at least partially define the shape or curvature of cassette sheeting 346A, 346B (FIG. 34) at an excursion into pump chambers 332, 334 (FIG. 36).

Continuing to refer primarily to FIGS. 37B and 37C, by preventing contact of cassette sheeting 346A, 346B (FIG. 34) with depression face 338, spacers 337 can provide a dead space (or trap volume or tidal volume) which can trap an undesired fluid such as air or other gas in pump chambers 332, 334 (FIG. 36) during pumping. The trap volume may aid in inhibiting undesired fluid from being pumped out of pump chambers 332, 334 (FIG. 36) unless desired. Also, spacers 337 can prevent cassette sheeting 346A, 346B (FIG. 34) from sticking to depression faces 338. In addition, spacers 337 can prevent cassette sheeting 346A, 346B (FIG. 34) from contacting pump chamber inlet/outlets 329A, 329B, 327A, 327B (FIG. 36). Spacers 337 may also be arranged so as to allow undesired fluid to move toward a location of pump chambers 332, 334 where it may be easily discharged to, for example, but not limited to, waste line 306A (FIG. 32), vent port 322 (FIG. 35), or other location. Discharging fluid may be accomplished, for example, by providing fluidic communication between spacers 337 such that fluid may pass between spacers 337 near depression face 338. When spacers 337 are positioned in a "stadium seating" arrangement, "aisles" or breaks 339, 341 in the elliptical pattern, for example, can be included. Density of the fluids may be leveraged to aid in moving fluid toward a discharge point. For example, first cassette 282A (FIG. 36) may be used in a prescribed orientation. Aisles 339 (FIG. 37B), 341 and the discharge point (e.g. one of ports 327A, 327B, 329A, 329B (FIG. 35)) may be arranged such that the undesired fluid may sink or rise to the discharge point based density properties. If, for example, the undesired fluid is air, the air may automatically rise toward the highest point in one or more of pump chambers 332, 334. Aisles 339 (FIG. 37B), 341 may be positioned to facilitate this and the discharge point may be disposed at or near that location. In some configurations, cassette sheeting 346A, 346B (FIG. 34) may have spacer elements or other features, such as, for example, but not limited to, ribs, bumps, tabs, grooves, and channels, in addition to, or in place of spacers 337.

Referring now to FIG. 38, first side of first cassette 282A can include pump chambers 332/334, spacers 337, walls 344, valve wells, and ports.

Figure 39:
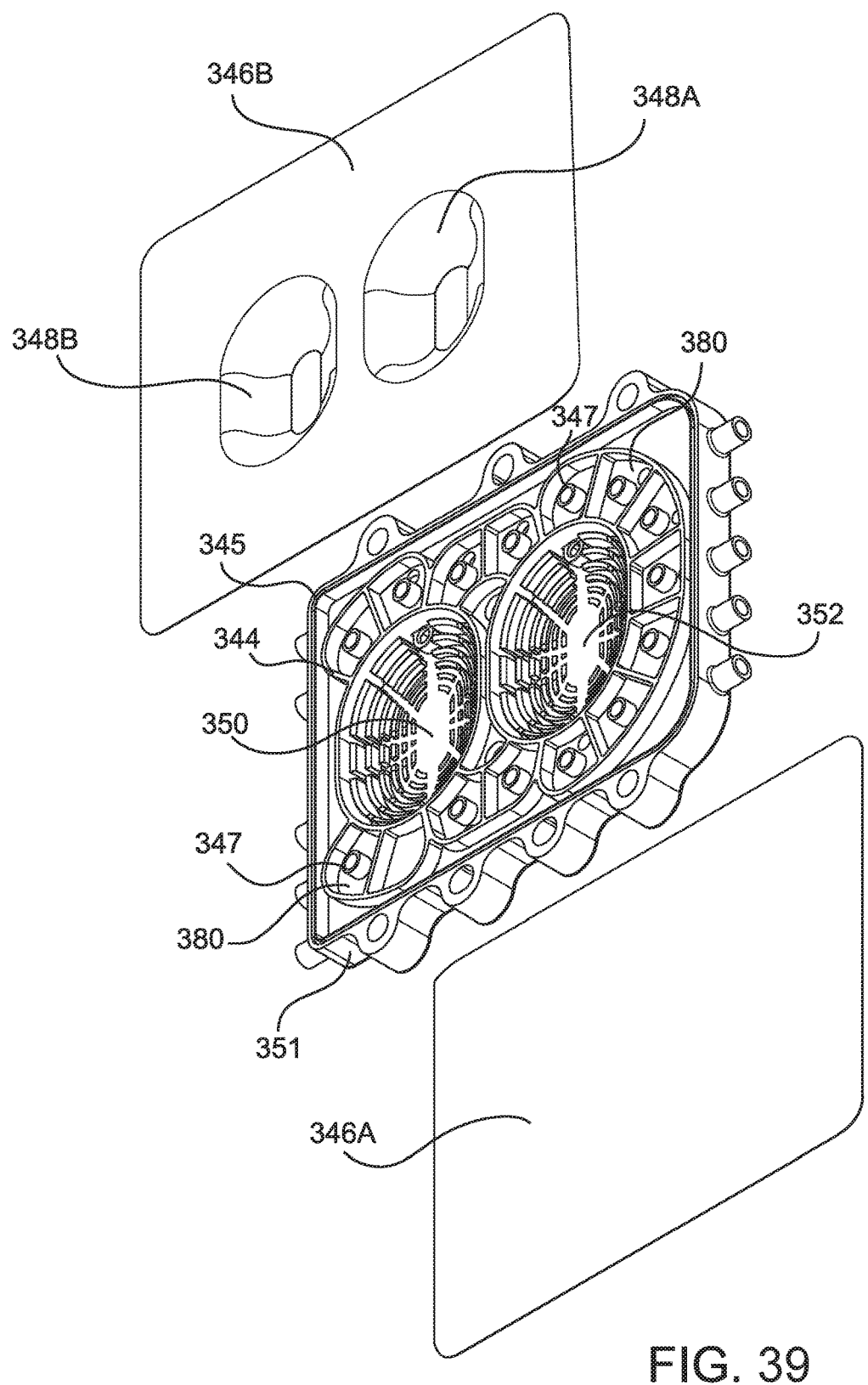
FIG. 39 is a perspective view of a second cassette and cassette sheeting.

Referring now primarily to FIG. 39, second cassette 282C may be operationally similar to the first cassette 282A (FIG. 36), but may have a different layout. Second cassette 282C may include one or more pump chambers, for example, first pump chamber 350 and second pump chamber 352. Second cassette 282C can also include spacers 337 described elsewhere herein. Walls 344 (FIG. 34) and perimeter wall 345 (FIG. 34) may be included and may project from cassette body 351. Walls 344 (FIG. 34) may define various fluid pathways in second cassette 282C and may also form valve wells 380A (FIG. 34). Valve seat 347 (FIG. 34) may be included in each valve well 380A (FIG. 34). Cassette sheeting 346A, 346B may be included as part of second cassette 282C. Cassette sheeting 346A, 346B for second cassette 282C may include preformed regions 348A, 348B for each pump chamber 350, 352. Application of pressure to cassette sheeting 346A, 346B of second cassette 282C may be coordinated to pump fluid via pump chamber 350, 352 through a desired flow pathway or pathways. Pushing cassette sheeting 346A, 346B into or pulling cassette sheeting 346A, 346B away from valve seats 347 may allow a desired flow pathway or pathways to be established.

Fill and deliver strokes may be performed in a manner which mimics a physiological characteristic or condition of a biological specimen 162 (FIG. 1). For example, the fill and deliver strokes may be synchronized in a manner which generates a pulsatile flow of the fluid(s) being pumped. The rate at which fill strokes and deliver strokes are performed may allow for the pulse rate of the flow to be adjusted. Such adjustment may allow a cassette to mimic physiological perfusion of a biological specimen 162 (FIG. 1). The pressure used to execute fill and delivery strokes may also be varied. This pressure may be set to a value which causes the pressure of the pumped fluid to mimic physiological perfusion pressures.

Figure 40:
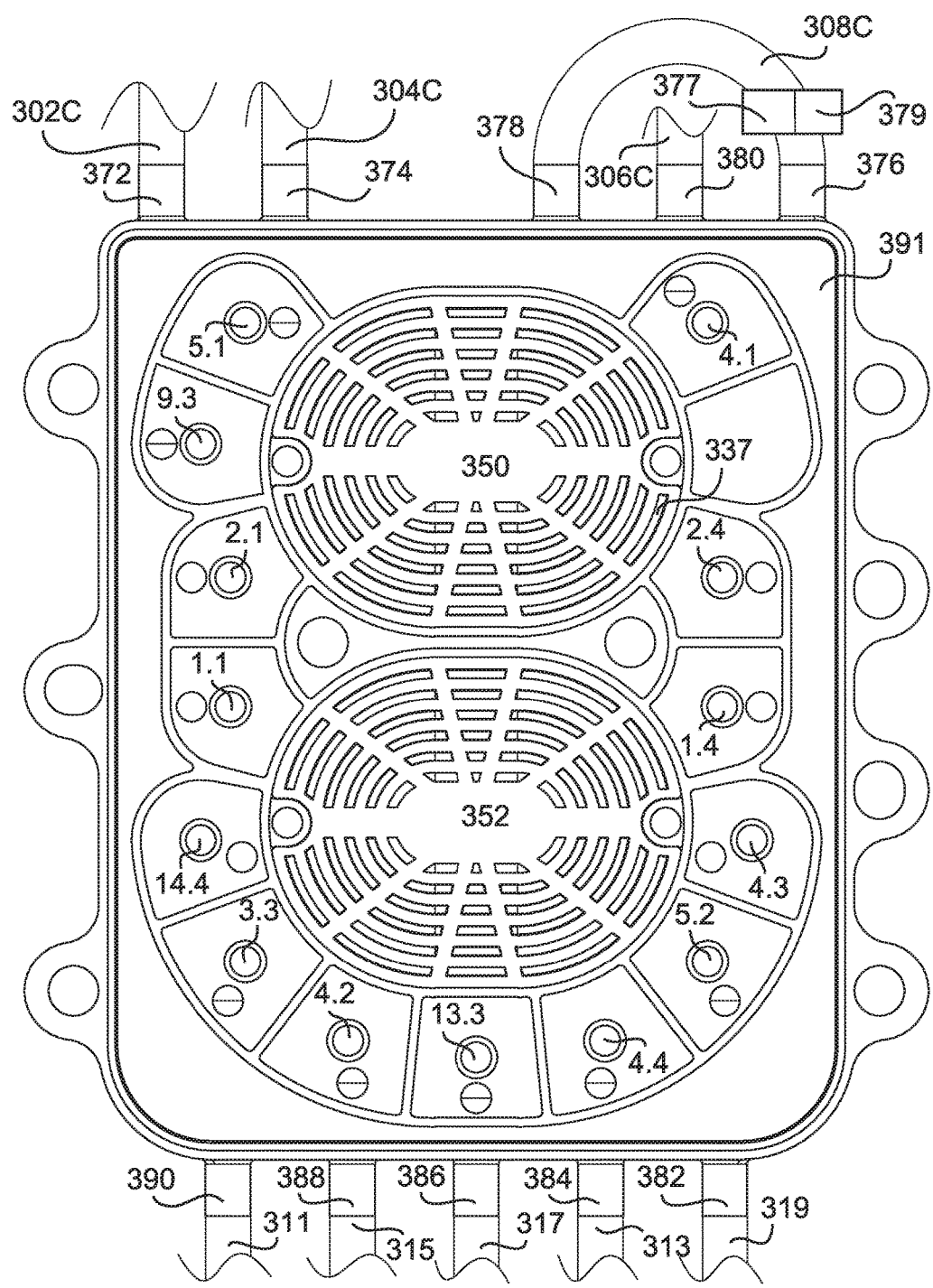
FIGS. 40 and 41 are plan views of two sides of one cassette of the present teachings.
Figure 41:
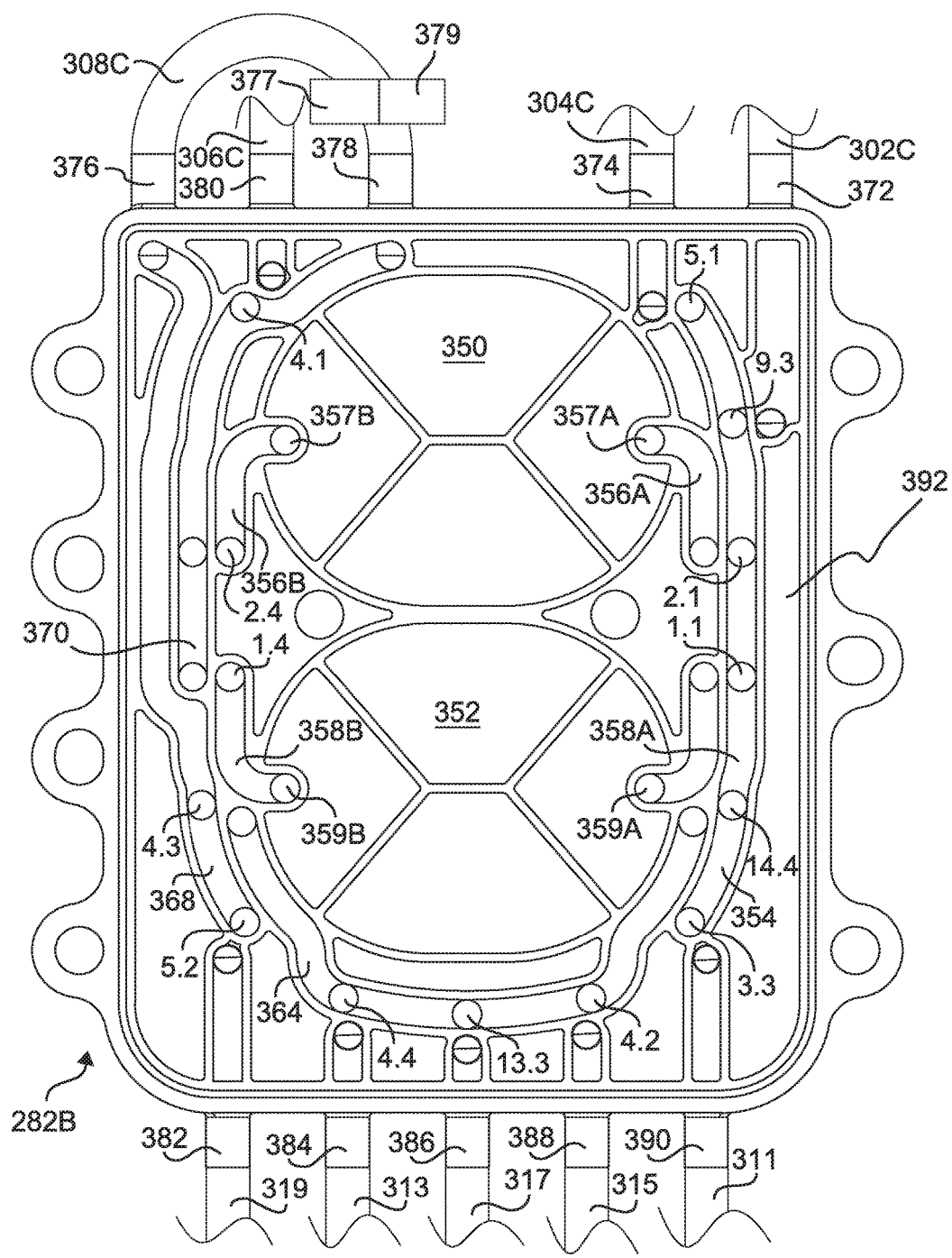

Referring now primarily to FIGS. 40 and 41, second cassette 282C can include, but is not limited to including, first side 391 (FIG. 40) and second side 392 (FIG. 41). Second cassette 282C can include, but is not limited to including, valves 3.3, 4.1-4.4, 5.1, 5.2, 9.3, 13.3, 2.4, 1.4, 2.1, 1.1, and 14.4. Valves 3.3, 4.1-4.4, 5.1, 5.2, 9.3, 13.3, 2.4, 1.4, 2.1, 1.1, 14.4 which may, for example, be similar to those in first cassette 282A and may be independently opened and closed to make and break fluid communication with fluid pathways 370, 368, 364, 354, 358A, 358B, 356A, 356B (FIG. 41) second side 392 of second cassette 282C. Fluid in valve well 380A (FIG. 24G), for example, may flow through valve 2.1 to fluid pathway 354 on second side 392 of cassette 282C if cassette sheeting 346A, 346B (FIG. 34) is not pressed against valve seat 347 (FIG. 39) of valve 2.1. Second cassette 282C may also include fluid ports 390, 388, 386, 384, 382, 372, 374, 376, 378, and 380. Each fluid port

390, 388, 386, 384, 382, 372, 374, 376, 378, 380 may be connected to a fluid line or conduit leading to fluid source 190 (FIG. 1), reservoir 182 (FIG. 1), enclosure 100 (FIG. 1) or biological specimen 162 (FIG. 1). Operation of pump chambers 350, 352 and valves 3.3, 4.1-4.4, 5.1, 5.2, 9.3, 13.3, 2.4, 1.4, 2.1, 1.1, 14.4 may allow fluid to be pumped into or out of second cassette 282C through any desired ports 390, 388, 386, 384, 382, 372, 374, 376, 378, 380. Additionally, in some configurations, second cassette 282C may be configured such that any of pump chambers 350, 352 may be placed in fluid communication with any of ports 390, 388, 386, 384, 382, 372, 374, 376, 378, 380.

Continuing to refer primarily to FIGS. 40 and 41, at least one storage reservoir port 372, 374 may be included on second cassette 282C. Storage reservoir ports 372, 374 may be in communication with reservoir outlet lines 302C, 304C. Loop out port 378 and loop return port 376 may be in communication with ends of a loop line 308C. At least one inlet port 382, at least one outlet port 390 may also be included. Inlet port 382 may be in communication with enclosure line 319 which can transfer fluid into/out of enclosure 100 (FIG. 1). Outlet port 390 may be in communication with an enclosure line 311 which may transfer fluid into/out of enclosure 100 (FIG. 1). At least one specimen port 384, 386, 388 may be included on second cassette 282C. Specimen ports 384, 386, 388 may be in communication with specimen lines 313, 315, 317. Specimen lines 313, 315, 317 may allow transfer of fluid to biological specimen 162 (FIG. 1). At least one waste port 380 may be in communication with line 306C of waste line 306A (FIG. 32).

Continuing to further refer primarily to FIGS. 40 and 41, among the fluid pathways of second cassette 282C may be pump chamber bus 354 (FIG. 41), loop out bus 370 (FIG. 41), loop return bus 368 (FIG. 41), and specimen bus 364 (FIG. 41). Pump chamber bus 354 (FIG. 41) may allow fluid to be transferred between second cassette 282C and reservoir outlet lines 302C, 304C. The fluid may, for example, be a diluted concentrate or fluid admixture delivered to storage reservoirs 182A, 182B (FIG. 32) from first cassette 282A (FIG. 36). Loop out bus 370 (FIG. 41) and loop return bus 368 (FIG. 41) may allow fluid to flow through loop line 308C from one portion of second cassette 282C to another. Specimen bus 364 (FIG. 41) may allow fluid to be transferred between second cassette 282C and specimen lines 313, 315, 317.

Continuing to refer primarily to FIGS. 40 and 41, second cassette 282C may include first pump chamber 350 and second pump chamber 352 which may be placed in fluid communication with any of ports 390, 388, 386, 384, 382, 372, 374, 376, 378, 380. While in fluid communication with desired port(s) 390, 388, 386, 384, 382, 372, 374, 376, 378, 380, negative pressure may be applied to sheeting 346A, 346B (FIG. 39) over pump chamber 350, 352 to fill pump chamber 350, 352 with fluid from fluid source 190 (FIG. 1) connected to the desired of ports 390, 388, 386, 384, 382, 372, 374, 376, 378, 380. Positive pressure may be applied to expel fluid within pump chamber 350, 352 to one or more of lines 311, 313, 315, 317, 319, 308C, 306C, 304C, 302C connected to the desired port(s) 390, 388, 386, 384, 382, 372, 374, 376, 378, 380. Additionally, each pump chamber 350, 352 may be placed in communication with one another. Thus, the flow of fluid from any of ports 390, 388, 386, 384, 382, 372, 374, 376, 378, 380 through second cassette 282C may be controlled by any of pump chambers 350, 352. Only one pump chamber 350, 352 need be operable to draw fluid into itself. The other pump chamber 350, 352 may be left inoperable and closed off to flow by closing the appropriate of valves 3.3, 4.1-4.4, 5.1, 5.2, 9.3, 13.3, 2.4, 1.4, 2.1, 1.1, 14.4.

Referring primarily to FIG. 41, with respect to pump chamber 350, communication with reservoir inlet port 372, may be established by opening valve 9.3 creating a pathway from reservoir inlet port 372 to pump chamber bus 354. Opening valve 2.1 can create a pathway from pump chamber bus 354 to first pump chamber inlet/outlet path 356A which is in communication with pump chamber 350 via inlet/outlet 357A. Communication with reservoir inlet port 374 may be established by opening valve 5.1 creating a pathway from reservoir inlet port 374 to pump chamber bus 354. Opening valve 2.1 can create a pathway from pump chamber bus 354 to first pump chamber inlet/outlet path 356A. Communication with loop out port 378 may be established by opening valve 2.4 creating a pathway from first pump chamber inlet/outlet path 356B to loop out bus 370. Inlet/outlet path 356B can be in communication with first pump chamber 350 via inlet/outlet 357B. Communication with waste port 380 may be established by opening valve 2.4 creating a pathway from first pump chamber inlet/outlet path 356B to loop out bus 370. Opening valve 4.1 can create a pathway from loop out bus 370 to waste port 380. Communication with inlet port 382 may be established by opening valve 2.4 creating a pathway between first pump chamber inlet/outlet path 356B and loop out bus 370. Opening valve 5.2 to place loop return bus 368 in communication with inlet port 382 may complete the pathway since loop out bus 370 may be in communication with loop return bus 368 via loop line 308C. Communication with outlet port 390 may be established by opening valve 3.3 creating a pathway between outlet port 390 and pump chamber bus 354. Opening valve 2.1 would then create a pathway from the pump chamber bus 354 to first pump chamber inlet/outlet path 356A. Communication with specimen bus 364 may be established by opening valve 2.4 creating a pathway between first pump chamber inlet/outlet path 356B and loop out bus 370. Opening valve 4.3 to place loop return bus 368 in communication with specimen bus 364 may then complete the pathway since loop out bus 370 may be in communication with loop return bus 368 via loop line 308C. Valves 4.2, 13.3, 4.4 may then be opened to establish communication between the desired specimen ports 384, 386, 388 and specimen bus 364.

Continuing to refer to FIG. 41, with respect to pump chamber 352, communication with reservoir inlet port 372, may be established by opening valve 9.3 creating a fluid pathway from reservoir inlet port 372 to pump chamber bus 354. Opening valve 1.1 could create a fluid pathway from pump chamber bus 354 to second pump chamber inlet/outlet path 358A via inlet/out 359A. Communication with reservoir inlet port 374 may be established by opening valve 5.1 creating a fluid pathway from reservoir inlet port 374 to pump chamber bus 354. Opening valve 1.1 could create a fluid pathway from pump chamber bus 354 to second pump chamber inlet/outlet path 358A. Communication with loop out port 378 may be established by opening valve 1.4 creating a fluid pathway from second pump chamber inlet/outlet path 358A to the loop out bus 370. Second pump chamber inlet/outlet path 358B is in communication with second pump chamber 352 via inlet/outlet 359B. Communication with waste port 380 may be established by opening valve 1.4 creating a fluid pathway from second pump chamber inlet/outlet path 358B to loop out bus 370. Opening valve 4.1 can create a fluid pathway from loop out bus 370 to waste port 380. Communication with inlet port 382 may be established by opening valve 1.4 creating a fluid pathway between second pump chamber inlet/outlet path 358B and loop out bus 370. Opening valve 5.2 to place loop return bus 368 in communication with inlet port 382 may complete the fluid pathway since loop out bus 370 may be in communication with loop return bus 368 via loop line 308C. Communication with outlet port 390 may be established by opening valve 3.3 creating a fluid pathway between outlet port 390 and pump chamber bus 354. Opening valve 1.1 could create a fluid pathway from pump chamber bus 354 to second pump chamber inlet/outlet path 358A. Communication with specimen bus 364 may be established by opening valve 1.4 creating a fluid pathway between second pump chamber inlet/outlet path 358B and loop out bus 370. Opening valve 4.3 to place loop return bus 368 in communication with specimen bus 364 may then complete the fluid pathway since the loop out bus 370 may be in communication with loop return bus 368 via loop line 308C. Valves 4.2, 13.3, 4.4 may then be opened to establish communication between the desired specimen ports 384, 386, 388 and specimen bus 364.

Continuing to still further refer primarily to FIG. 41, the fluid pathways for placing pump chambers 350, 352 in communication with specific of ports 390, 388, 386, 384, 382, 372, 374, 376, 378, 380 can be formed in many possible sequences of valve openings/closings. More than one pathway can be established by opening and closing of valves 3.3, 4.1-4.4, 5.1, 5.2, 9.3, 13.3, 2.4, 1.4, 2.1, 1.1, 14.4 of second cassette 282C to place a pump chamber 350, 352 in communication with a desired port(s) 390, 388, 386, 384, 382, 372, 374, 376, 378, 380. Additionally, multiple pump chambers 350, 352 may be placed in communication with the same port(s) 390, 388, 386, 384, 382, 372, 374, 376, 378, 380 at the same time. By opening valves 3.3, 1.1, and 2.1, all of pump chambers 350, 352 may, for example, be operated to draw fluid from the outlet port 390. In some configurations, specimen ports 384, 386, 388 can allow for transfer of fluid between second cassette 282C and specimen 162 (FIG. 1). If specimen 162 (FIG. 1) is a lung, specimen port 384, for example, may be in communication with a pulmonary artery of the lung via specimen line 317. Specimen port 386 may be in communication with a trachea of the lung via specimen line 315. Specimen port 388 may be in communication with a pulmonary vein of the lung via specimen line 313. Fluid or a mixture of fluid such as any fluid or any combination of those in Table I may be delivered to specimen 162 (FIG. 1) via second cassette 282C from storage reservoir 182A, 182B (FIG. 32). Fluid may also be delivered to enclosure 100 (FIG. 1) in which specimen 162 (FIG. 1) is housed via enclosure lines 319, 311 attached to inlet and outlet ports 382, 390. Once the fluid is spent, the fluid may be removed from the specimen 162 (FIG. 1) and pumped, via second cassette 282C, to waste line 306C.

Continuing to still further refer to FIG. 41, in some configurations, fluid can, for example, proceed from a first at least one loop port 376, 378 through loop line 308C, to another port such as a second at least one loop port 376, 378. At least one sensor 377 may sense a characteristic of interest of the fluid as it passes through loop line 308C. Temperature, conductivity, turbidity, spectrophotometric characteristics, flow rate, viscosity, color, dielectric properties, acoustic impedance, dissolved gas content (e.g. dissolved oxygen), fluorescence, dissolved organic matter, flow cytometrics or any other characteristic of interest may be sensed by sensor 377 monitoring fluid in loop line 308C. Sensor 377 may be, but is not limited to being, a thermocouple, thermistor, resistance thermometer, conductivity sensor or probe, turbidity sensor or probe, spectrophotometer, flow sensor, flow meter, velocimeter, viscosity sensor, optical sensor, capacitance probe or sensor, ultrasonic sensor, dissolved oxygen sensor, fluorescence sensors, colored dissolved organic matter sensors (CDOM), fluorescent dissolved organic matter sensors (fDOM), and flow cytometers. Sensor 377 may also monitor for a particular condition of interest. For example, sensor 377 may monitor for air bubbles in loop line 308C. In some configurations, sensor 377 may be, for example, an ultrasonic air bubble detection sensor, or may be a sensor similar to any of those described in U.S. Patent Publication No. US 2015/0033823, filed Jul. 25, 2014, and entitled System, Method, and Apparatus for Bubble Detection in a Fluid Line Using a Split-Ring Resonator, which is hereby incorporated by reference in its entirety.

Continuing to refer to FIG. 41, in some configurations, sensor 377 may be a part of a sorting system or apparatus. For example, sensor 377 may be included in a fluorescence-activated cell sorting flow cytometer. In some configurations, a heterogeneous mixture of cells may be separated into constituent parts using the fluorescence-activated cell sorting (FACS) flow cytometer.

Continuing to refer primarily to FIG. 41, in some configurations, fluid can also be subject to temperature regulation as it passes through loop line 308C. For example, temperature regulator 379 may be placed against or in proximity to loop line 308C such that the fluid is regulated to a desired temperature as it passes through loop line 308C. At least one sensor 377 may be included to provide feedback as to the temperature of the fluid in loop line 308C. Temperature regulator 379 may, for example, include any of a variety of suitable heating elements such as a resistive heater or number of resistive heaters. Temperature regulator 379 may also include cooling elements as well for lowering the temperature of the fluid. Any temperature regulating elements 379, sensors 377, and other components associated with loop line 308C can be optional parts of fluid handling set 280 (FIG. 32), or can be coupled to or otherwise associated with loop line 308C. For example, sensor 377 may clip onto loop line 308C or loop line 308C may be seated in a receiving structure of sensor 377 during set up.

Figure 42:
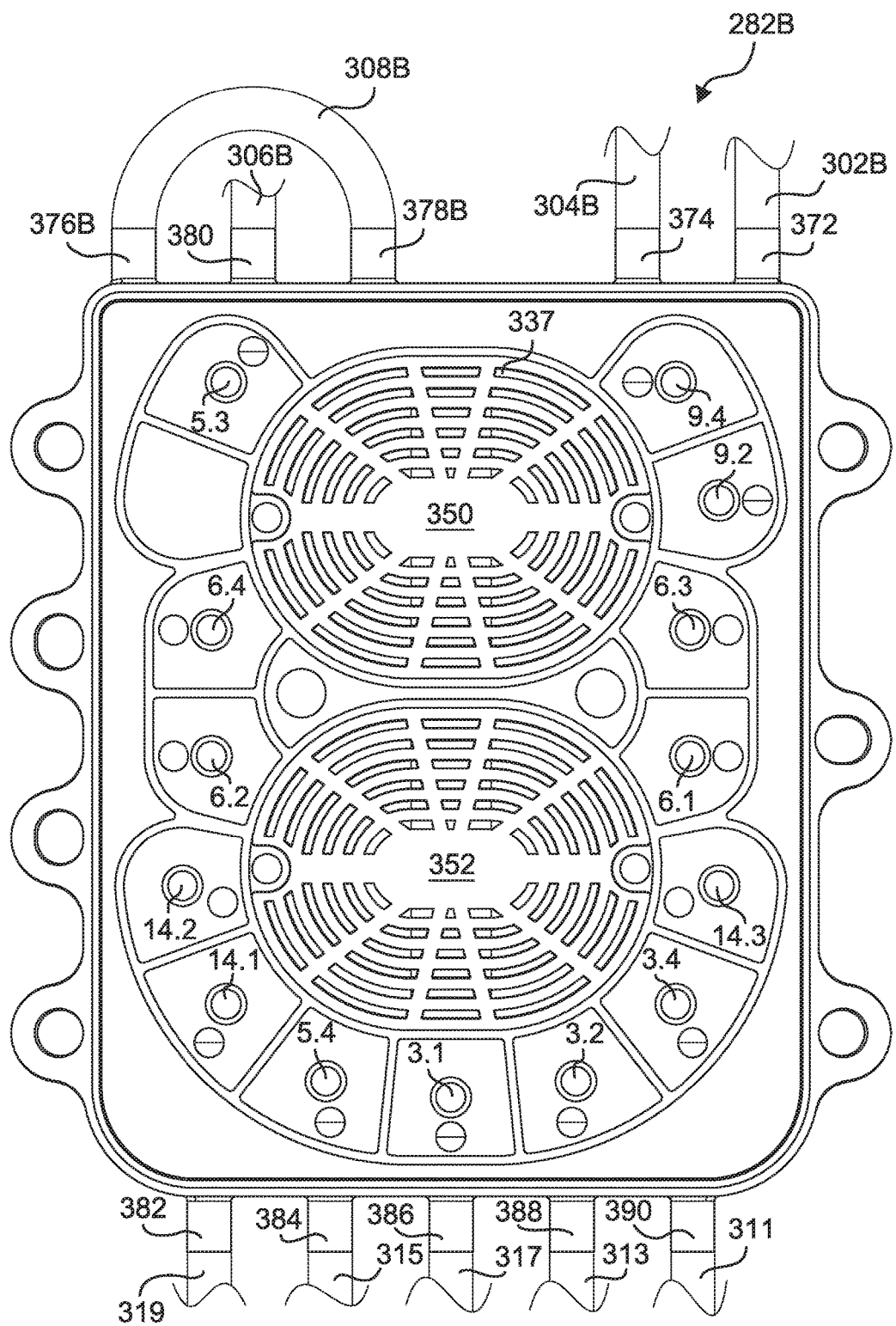
FIGS. 42 and 43 are plan views of two sides of another cassette of the present teachings.
Figure 43:
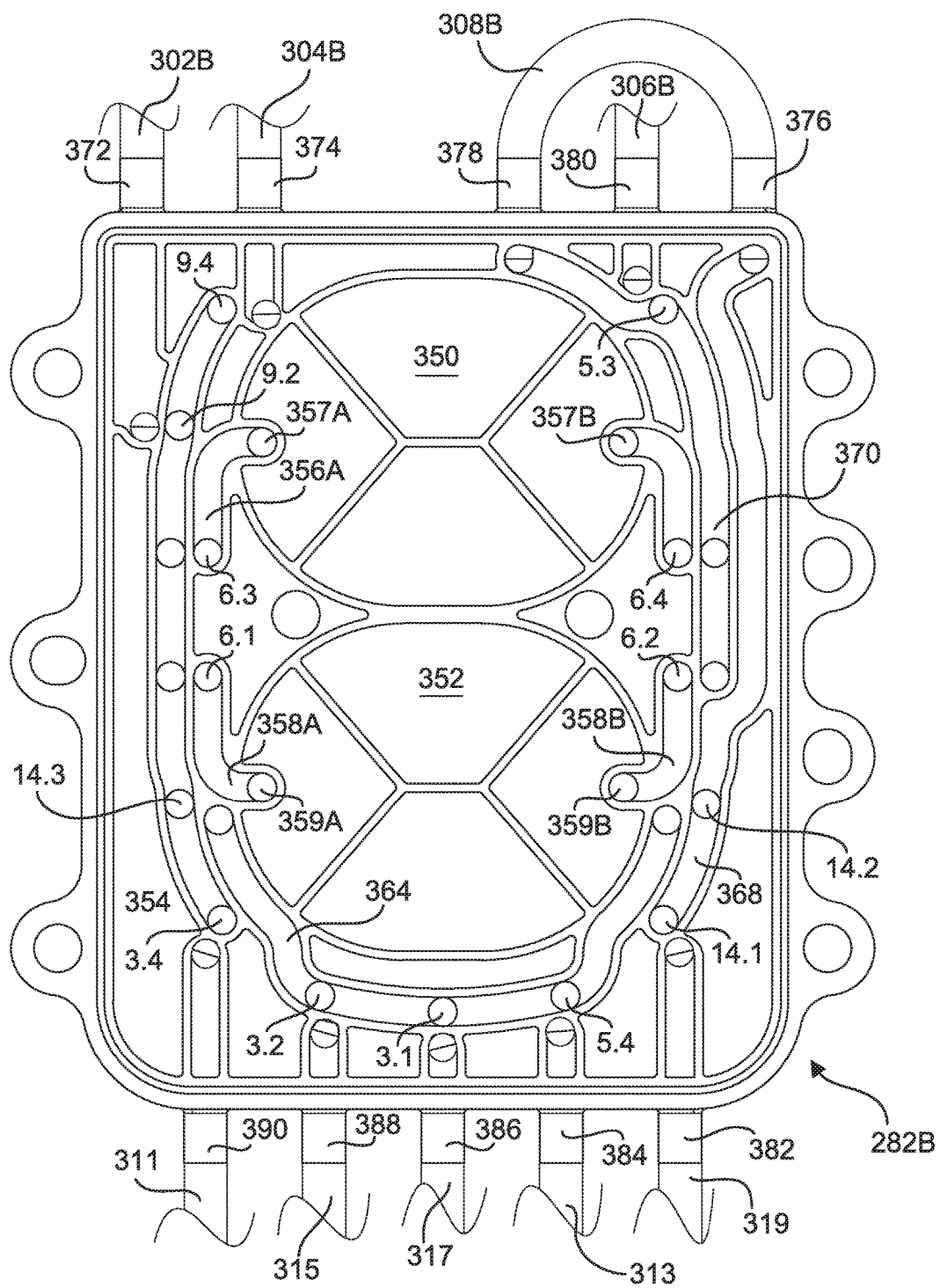

Referring now to FIGS. 42 and 43, second cassette 282B can be, for example, but not limited to, a mirror image of second cassette 282C, can be identical to cassette 282C, or may differ, perhaps substantially, from second cassette 282C. Second cassette 282B can include, but is not limited to including, valves 3.1, 3.2, 3.4, 9.2, 9.4, 5.3, 6.1-6.4, 14.1-14.3, 5.4. In some configurations, each valve 3.1, 3.2, 3.4, 9.2, 9.4, 5.3, 6.1-6.4, 14.1-14.3, 5.4 in second cassette 282B may have a corresponding sister valve on second cassette 282C. In some configurations, the same fluid pathways between cassette ports 390, 388, 386, 384, 382, 372, 374, 376, 376B, 378, 378B, 380 and pump chambers 350, 352 described in relation to second cassette 282C may be established in second cassette 282B by operating valves 3.1, 3.2, 3.4, 9.2, 9.4, 5.3, 6.1-6.4, 14.1-14.3, 5.4 in the same manner as their sister valves on second cassette 282C. For the configuration shown FIGS. 45 and 46, valves 3.1, 3.2, 3.4, 9.2, 9.4, 5.3, 6.1-6.4, 14.1-14.3, 5.4 of second cassette 282B and their counterpart or corresponding sister valves on second cassette 282C are provided in Table IX as follows:

TABLE IX

| Cassette 282B | Cassette 282C |
|---|---|
| 3.1 | 13.3 |
| 5.4 | 4.4 |

TABLE IX-continued

| Cassette 282B | Cassette 282C |
|---|---|
| 14.1 | 5.2 |
| 14.2 | 4.3 |
| 6.2 | 1.4 |
| 6.4 | 2.4 |
| 5.3 | 4.1 |
| 9.4 | 5.1 |
| 9.2 | 9.3 |
| 6.3 | 2.1 |
| 6.1 | 1.1 |
| 14.3 | 14.4 |
| 3.4 | 3.3 |
| 3.2 | 4.2 |

Figure 44:
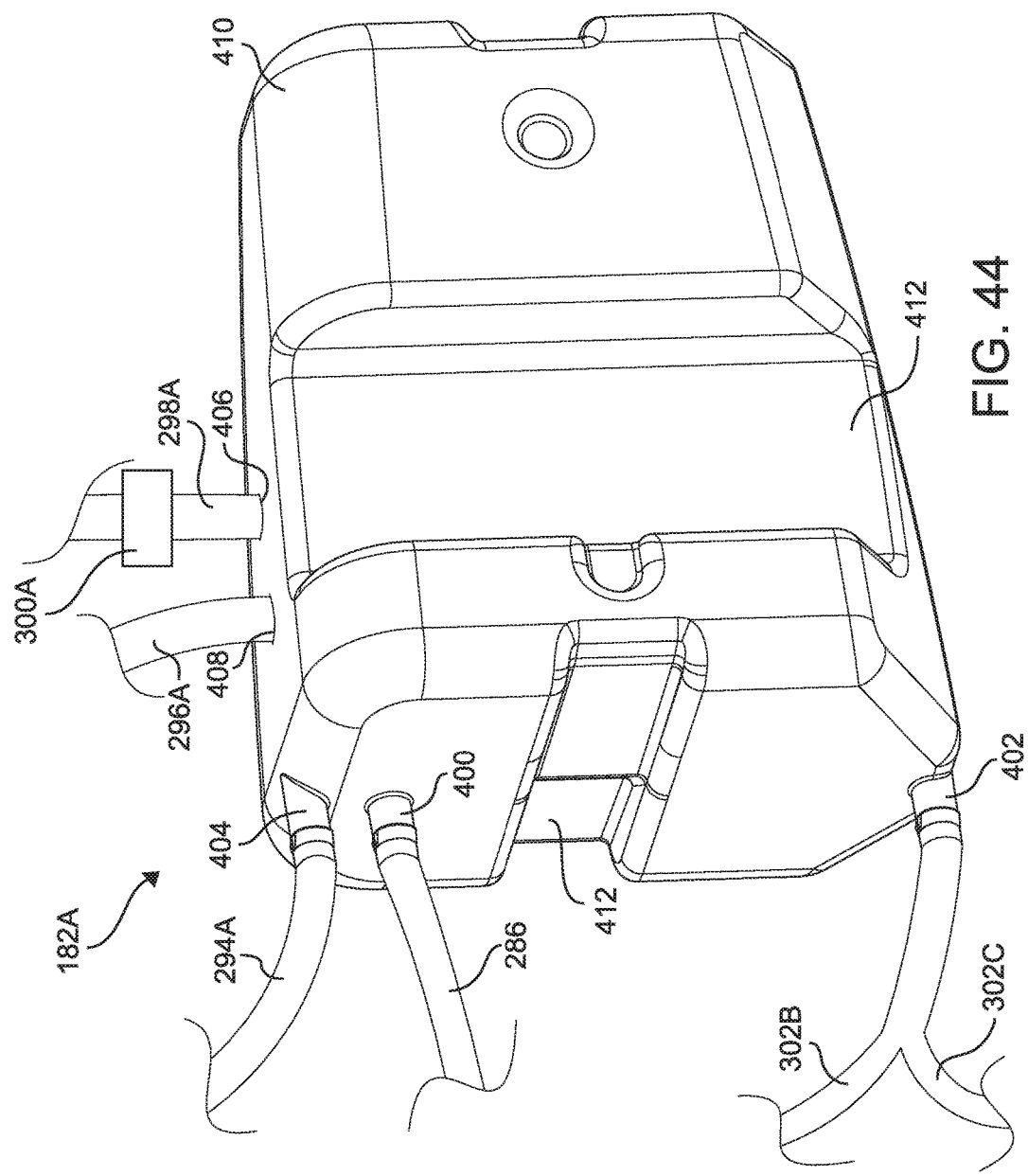
FIG. 44 is a perspective view of a storage reservoir of an example of the present teachings.

Referring now to FIG. 44, upstream cassette 282A (FIG. 36) can pump fluid to storage reservoir 182A. The pumped fluid may be mixed inside of first cassette 282A (FIG. 36) or mixed as it is pumped into storage reservoir 182A. The fluid stored within storage reservoir 182A may be for used by any component of fluid handling set 280 (FIG. 32) that can be in the fluid pathway of storage reservoir 182A, for example. In some configurations, first cassette 282A (FIG. 36) may also draw fluid from storage reservoir 182A. Storage reservoir 182A can include inlet port 400. Inlet port 400 may attach to first reservoir inlet line 286 through which fluid may be pumped into storage reservoir 182A. Storage reservoir 182A may also include reservoir outlet port 402. Outlet port 402 may be attached to reservoir outlet lines 302B, 302C through which fluid may exit storage reservoir 182A. Fluid may, for example, be drawn from storage reservoir 182A, by second cassette 282B, 282C (FIG. 36). The interior volume of storage reservoir 182A may vary depending on the configuration or biological specimen 162 (FIG. 1) being processed. In some configurations, storage reservoir 182A may have an interior volume of 0.5-10 liters (e.g. 1.4 liters). In some configurations, storage reservoir 182A can have a different interior volume from storage reservoir 182B (FIG. 36).

Continuing to refer to FIG. 44, storage reservoir 182A may include a number of other ports or orifices. For example, storage reservoir 182A may include overflow port 404. Overflow port 404 may connect to overflow line 294A. Overflow line 294A may be in fluid communication with an overflow reservoir (not shown) which may hold excess fluid in the event that storage reservoir 182A is over filled. Overflow port 404 may include a sensor (not shown) which may provide data indicating whether the fluid level in storage reservoir 182A has reached overflow port 404. In some configurations overflow port 404 may include a conductivity sensor, for example. Storage reservoir 182A may also include at least one vent port 406. In some configurations, the overflow port 404 may double as a vent port 406. In some configurations, vent port 406 can be connected to vent line 298A which can include filter 300A. Vent port 406 may allow air to be displaced into or out of storage reservoir 182A as the liquid level within storage reservoir 182A changes. Filter 300A on vent line 298A may, for example, but not limited to, filter biological material or organisms from entering into storage reservoir 182A. Filter 300A may be a 0.2 micron filter in some configurations. Filter 300A may be a hydrophobic filter in some configurations.

Continuing to still further refer to FIG. 44, storage reservoir 182A may also include sensor port 408. Sensor port 408 may allow for data related to the liquid level within storage reservoir 182A to be collected. In some configurations, the type of sensor used may vary. In some configurations, sensor port 408 may allow for electrical communication with a sensor in storage reservoir 182A. The sensor may, for example, be a float sensor or any other liquid level sensor. Sensor port 408 may provide pass-through for sensor line 296A or may provide a pass-through for a fluid conduit for a manometer type sensing arrangement. Storage reservoir 182A may include a number of features which aid in mounting of storage reservoir 182A. For example, body 410 of the storage reservoir 182A may include various projections or recesses 412 therein which can facilitate attachment of storage reservoir 182A to another structure. Body 410 may include recesses which can accommodate clips (not shown) which can hold storage reservoir 182A in place on a holding structure.

Figure 45:
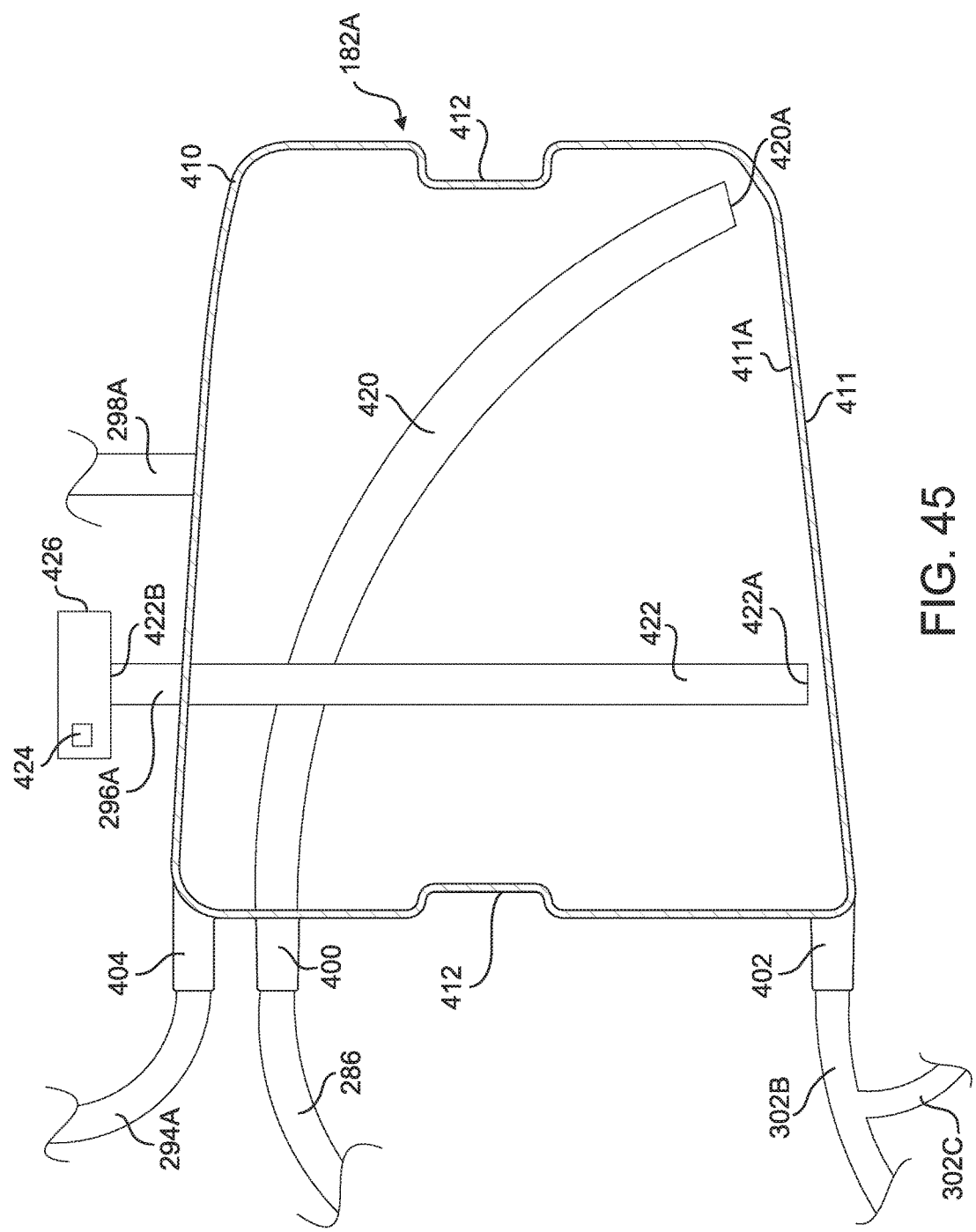
FIG. 45 is a medial cross-section view of a storage reservoir of FIG. 39.

Referring now to FIG. 45, first side 411 of body 410 of storage reservoir 182A may be sloped to enable gravity to move fluid within storage reservoir 182A toward outlet port 402 of storage reservoir 182A. The sloping may, for example, facilitate full emptying of storage reservoir 182A when fluid is transferred out of storage reservoir 182A through outlet port 402. In some configurations, interior inlet line 420 may extend into the interior volume of storage reservoir 182A from inlet port 400. Interior inlet line 420 may extend nearly to interior first side 411A of storage reservoir 182A. Fluid entering storage reservoir 182A may pass from reservoir inlet line 286 through inlet port 400 to interior inlet line 420. By placing the inlet line end 420A of interior inlet line 420 near interior first side 411A of storage reservoir 182A, any splashing and mixing with air in storage reservoir 182A may be minimized. Minimizing splashing and mixing in air may, for example, reduce and/or eliminate foaming or bubbling if the fluid in storage reservoir 182A contains a surfactant, for example. In some configurations, the inlet line end 420 may be positioned so as to be on the opposite side of the interior first side 411A than the outlet port 402. This may help to maximize mixing of various fluids entering the storage reservoir 182A. Interior inlet line 420 and reservoir inlet line 286 may be continuous in some configurations, and in some configurations, may be two separate fluid conduits.

Continuing to refer to FIG. 45, interior sensor line 422 can be included within the interior volume of storage reservoir 182A. In some configurations, interior sensor line 422 may be continuous with sensor line 296A, and in some configurations, interior sensor line 422 may be a separate fluid conduit from sensor line 296A. Interior sensor line 422 can extend towards and nearly to interior first side 411A of storage reservoir 182A. In some configurations, a gap (e.g. 3-10 mm) may exist between interior sensor line end 422A of interior sensor line 422 and interior first side 411A of storage reservoir 182A. Alternatively, interior sensor line 422 may touch interior first side 411A and a notch, fenestration, or other void may be cut out of interior sensor line end 422A. Sensor line exterior end 422B of sensor line 296A may be closed such that fluid may not enter or exit sensor line exterior end 422B of sensor line 296A. In some configurations, sensor line exterior end 422B may be in communication with closed volume 426 in which pressure sensor 424 can reside. Pressure sensor 424 and closed volume 426 may be optionally included in fluid handling set 280 (FIG. 32). Sensor line 296A of storage reservoir 182A may be coupled to closed volume 426 during set up of fluid handling set 280 (FIG. 32) and the closed volume 426 and pressure sensor 424 may be parts a separate durable component with which the fluid handling set 281 interfaces. In some configurations an additional pressure sensor (not shown) may be included to sense ambient pressure and the ambient pressure reading may be used in conjunction with the reading from pressure sensor 424. When the fluid level in storage reservoir 182A has covered the interior sensor line end 422A, the air (or another compressible fluid) within the conduit of interior sensor line 422 can become compressed as the fluid level rises. The rise in pressure within interior sensor line 422 and sensor line 296A may be monitored by pressure sensor 424. The pressure data output from pressure sensor 424 may be used to determine the liquid level within storage reservoir 182A. The pressure values associated with a specific liquid level may be mathematically or empirically derived.

Figure 46A:
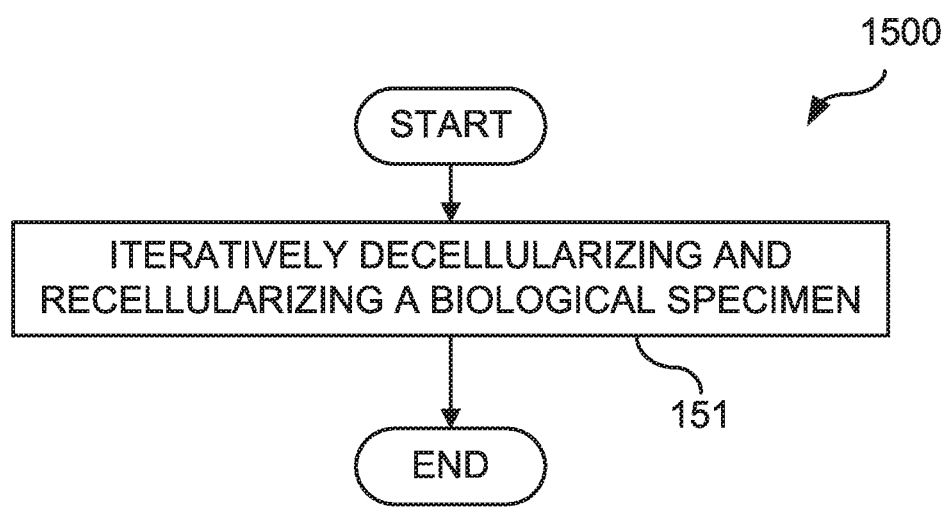
FIGS. 46A-46D are flowcharts of methods for iteratively decellularizing and recellularizing a biological specimen.

Referring now to FIG. 46A, method 1500 for generating a tissue for transplant may include, but is not limited to including, iteratively decellularizing and recellularizing 1502 a biological specimen (a synthetic scaffold may be used and will be understood to be included under the term biological specimen). A biological specimen may be a grouping of cells and the associated extra cellular matrix including, but not limited to, a tissue, group of tissues, organ, organ system, or group of organs. The biological specimen may, in some configurations, be porcine tissue, bovine tissue, non-human primate tissue, harvested human transplant tissue found unsuitable for transplantation, and tissue from any other source. The biological specimen may, in some configurations, be a porcine lung or lungs. The biological specimen may, in some configurations, be decellularized and recellularized for research purposes, for example, but not limited to biological and biochemical research, or for the purpose of generating a transplant. The term biological specimen may be used interchangeably herein with donor tissue.

Continuing to refer to FIG. 46A, the protocol used to decellularize and the protocol used to recellularize the biological specimen may each be any protocol such as any known protocol. The protocol may involve delivering/removing a variety of agents, such as, for example, but not limited to, different solutions, mediums, fluids, biological agents, and cells to/from the biological specimen or the area around the biological specimen. A non-limiting list of potential agents which may be used in any suitable combination is provided in Table I.

Continuing to refer to FIG. 46A, in some configurations, the protocol may be any of those described in: Weymann, A. et al., *Perfusion-Decellularization of Porcine Lung and Trachea for Respiratory Bioengineering, International Center for Artificial Organs and Transplantation and Wiley Periodicals, Inc.*, 2015 (Weymann); Price, A., et al., *Development of a Decellularized Lung Bioreactor System for Bioengineering the Lung: The Matrix Reloaded, Tissue Eng Part A*, 2010, August: 16(8):2581-2591 (Price, 2010); Price, A., et al., *Automated Decellularization of Intact, Human-Sized Lungs for Tissue Engineering, Tissue Engineering: Part C*, Vol. 21, No. 1, 2015 (Price 2015); Urbano, J. J. et al., *Lung Scaffolds for Bioengineered Organ, XXIV Congresso Brasiliero de Engenharia Biomedia*, CBEB 2014, pp. 2814-2816 (Urbano); Taylor and Kren, United States Patent Publication #2013/0156744, entitled Methods of Recellularizing a Tissue or Organ for Improved Transplantability, filed Feb. 28, 2013 (Taylor); Gratzer, P. F. et al., *Matrix Alteration and Not Residual Sodium Dodecyl Sulfate Cytotoxicity Affects the Cellular Repopulation of a Decellularized Matrix, Tissue Engineering*, 2006, October: 12(10):2975-83 (Gratzer); and/or Sumitran-Holgersson et al, United States Patent Publication #2014/0377864, entitled Biogenic Allogeneic Blood Vessel, filed Jun. 12, 2014 (Sumitran) each of which is incorporated by reference herein in its entirety. Any protocol described herein is merely exemplary and non-limiting.

Continuing to refer to FIG. 46A, in some configurations, decellularization and recellularization protocols for a biological specimen such as a pulmonary system may include (a) perfusing the lung(s) with deionized water and subsequently harvesting lung(s), (b) incubating the lung(s) in deionized water for 1 hour, (c) injecting deionized water into the trachea and right ventricle, (d) injecting a Triton series detergent into the trachea and right ventricle and incubating for 24 hours, (e) rinsing as in step (c), (f) injecting deoxycholate into the trachea and right ventricle, (g) incubating for 24 hours, (h) rinsing as in step (c), (i) injecting sodium chloride into the trachea and right ventricle, (j) incubating for 1 hour, (k) rinsing as in step (c), (l) injecting deoxyribonuclease (DNase) into the trachea and right ventricle, (m) incubating for 1 hour, (n) rinsing as in step (c) using PBS, (o) submerge lung(s) in growth medium, (p) infusing cells through the trachea, and (q) connecting the lung(s) to a ventilator in an incubator. In some configurations, the decellularization protocol for a biological specimen such as a lung or lungs may include the steps of (a) perfusing PBS enriched with penicillin-streptomycin through the lung(s) and trachea for 24 hours, (b) perfusing the lung(s) with SDC and a Triton series detergent in PBS for five days, (c) immersing the trachea in SDS and agitating for 72 hours and changing the solution at 24 hours, (d) washing and agitating the lung(s) with peracetic acid and ethanol for six hours, (e) washing the lung(s) and trachea with PBS once daily during the steps of (a)-(d), and (f) perfusing the lung(s) with PBS for 24 hours.

Continuing to refer to FIG. 46A, in some configurations, the decellularization protocol for a biological specimen such as a lung or lungs may include the steps of (a) freezing the lung(s) in PBS until the lung(s) is/are needed, (b) freezing/thawing the lung(s) in cycles of ten minutes each, (c) washing the lung(s) 6-8 times in PBS, (d) rinsing the lung(s) in deionized water, (e) instilling SDS in the lung(s) and agitating for 24 hours in a bath of SDS, (f) maintaining the lung(s) in SDS overnight without agitation, (g) rinsing and agitating the lung(s) in PBS for 24 hours, and (h) maintaining the lung(s) in PBS without agitation. In some configurations, the recellularization protocol for a biological specimen such as, for example, but not limited to, a lung or lungs may include re-endothelialization of a scaffold which has been previously perfused with a buffer solution. The recellularization protocol may further include introduction of epithelial cells, clara cells, goblet cells, alveolar type I, and/or alveolar type II cells into or onto a scaffold. The cells may be allowed to adhere to the scaffold for a period of time, such as, for example, but not limited to, 30 to 180 minutes. Further, the scaffold may be naturally recellularized in vivo through the migration of cells from the adjacent tissue.

Continuing to refer to FIG. 46A, in some configurations, the recellularization protocol for a biological specimen may include, but is not limited to including, expanding and differentiating a population of cells. The cell population may be differentiated into endothelial cells and smooth muscle cells in vitro. Introduction of the population of cells to the biological specimen may include perfusion of endothelial cells and smooth muscle cells. Perfusion of an endothelial cell medium and smooth muscle cell medium may be administered in alternating fashion. Method 1500 can optionally include preparing the supplied tissue by decellularizing the supplied tissue a plurality of times, and refining the tissue for transplant by decellularizing the iteratively decellularized and recellularized supplied tissue a plurality of times. Method 1500 can also optionally include introducing at least one agent to the supplied tissue, removing an undesired component of the supplied tissue with the at least one agent, and rinsing the supplied tissue. Rinsing the supplied tissue can optionally include rinsing the supplied tissue with an isotonic solution, and/or phosphate buffered solution. The at least one agent can optionally include a detergent, a Triton series detergent, sodium dodecyl sulfate, peracetic acid, ethanol, an enzyme solution, a nuclease, DNase, RNase, water, deionized water, and/or distilled water. Method 1500 can optionally include freezing the supplied tissue, and alternately freezing and thawing the supplied tissue.

Continuing to still further refer to FIG. 46A, method 1500 can optionally include, but is not limited to including, introducing the biological specimen to at least one agent for a period of time. The at least one agent may include, but is not limited to including, a detergent (e.g. a Triton series detergent such as Triton X-100), enzyme (e.g. a nuclease such as DNase or RNase), enzyme inhibitor, chelating agent, cell lysing agent, osmotically incompatible agent, antimicrobial agent (e.g. anti-biotic, Peracetic acid), water, alcohol (e.g. ethanol), and any suitable agent from Table I. The biological specimen may be introduced to the at least one agent in any of a number of ways. In some configurations, the at least one agent may be perfused through an anatomical passageway of the biological specimen and/or the biological specimen may be bathed in the at least one agent. Method 1500 may optionally include preparing the biological specimen for decellularization. Preparation may include cleaning and rinsing the biological specimen and/or readying anatomical structures of the biological specimen for decellularization by, for example, but not limited to, attaching tubing and ligating vasculature. In some configurations, method 1500 may further include agitating, for example, but not limited to, mechanical and through sonication, the biological specimen. In some configurations, method 1500 may further include regulating the temperature of the biological specimen and/or at least one agent before, during, and after decellularization.

Continuing to refer to FIG. 46A, recellularization can optionally include introducing a cell culture to the decellularized supplied tissue, introducing endothelial cells, epithelial cells, clara cells, ciliated cells, goblet cells, alveolar type I, and/or alveolar type II cells to the decellularized supplied tissue, and/or introducing stem cells or cells of at least one tissue specific phenotype to the decellularized supplied tissue. Recellularizing can also optionally include introducing cells to an acellular scaffold which may be, but is not limited to being, an isolated ECM scaffold or a synthetic scaffold. In some configurations, the scaffold may be created via method 1500. Introducing cells may be done in any of a number of ways. In some configurations, the cells may be perfused through an anatomical passageway of the biological specimen and/or the biological specimen may be bathed in the cells. In some configurations, introducing cells may include perfusing different types of cells through assigned anatomical passages. In some configurations, the cells introduced may be epithelial cells, endothelial cells, mesothelial cells, mesenchymal cells, etc. Depending on the biological specimen, more specific specialized cell types or cells with tissue specific phenotypes may be introduced which are appropriate to the specimen. In a lung, in some configurations, clara cells, ciliated cells, goblet cells, alveolar type I, and/or alveolar type II cells, may be introduced. In some configurations, hepatocytes may be introduced if the biological specimen is a liver for example. In some configurations, cardiomyocytes may be introduced if the biological specimen is a heart. Other varieties of cells may also be introduced such as lineage uncommitted or pluripotent cells such as stem cells, progenitor cells, precursor cells, and/or fetal associated cells. Introducing cells may include introducing cells which are autologous to the intended recipient or non-immunogenic to the intended recipient. Method 1500 may optionally Method 1500 may optionally include regulating the temperature of the biological specimen and/or at least one recellularization agent before, during, and after recellularization. In some configurations, method 1500 may optionally include simulating a physiological condition. In some configurations, pulsatile blood flow or breathing may be simulated.

Figure 46B:
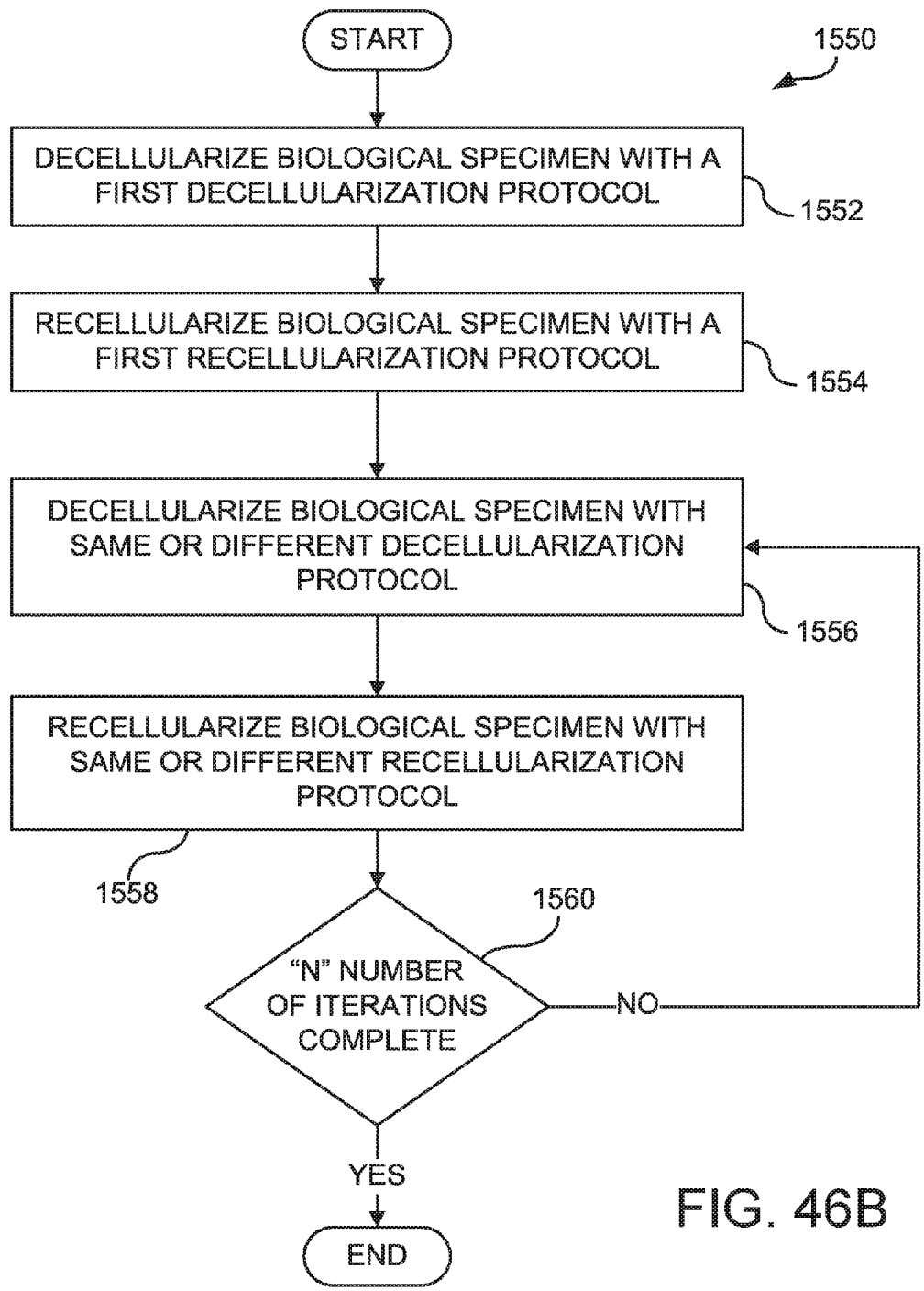

Referring now to FIG. 46B, method 1550 for decellularizing and recellularizing a biological specimen may include, but is not limited to including, decellularizing 1552 a biological specimen with a first decellularization protocol. Method 1550 may further include recellularizing 1554 the biological specimen with a first recellularization protocol. Method 1550 may also include decellularizing 1556 the biological specimen with a second decellularization protocol. Method 1550 may include recellularizing 1558 the biological specimen with a second recellularization protocol. The second decellularization protocol and the second recellularization protocol may differ in whole or in part respectively from the first decellularization protocol and first recellularization protocol. The first and second decellularization protocols and the first and second recellularization protocols may optionally each use the same agents or may use at least one different, some different, or all different agents. In some configurations, one of the first decellularization protocol or the first recellularization protocol may be used a second time when decellularizing 1556 or recellularizing 1558.

Continuing to refer to FIG. 46B, the first decellularization protocol may use at least one of a first set of decellularization agents, and the second decellularization protocol may use at least one of a second set of decellularization agents. The first set of decellularization agents can optionally include at least one decellularization agent, and the second set of decellularization agents can optionally include at least one decellularization agent. The first set of decellularization agents can optionally be substantially the same as or identical to the second set of decellularization agents or the first set of decellularization agents can optionally be different from the second set of decellularization agents. The first recellularization protocol may use at least one of a first set of recellularization agents, and the second recellularization protocol may use at least one of a second set of recellularization agents. The first set of recellularization agents can optionally include at least one recellularization agent, and the second set of recellularization agents can optionally include at least one recellularization agent. The first set of recellularization agents can optionally be substantially the same as to the second set of recellularization agents or the first set of recellularization agents can optionally be different from the second set of recellularization agents. The protocols may be defined by differing temporal parameters. In some configurations, the protocols may include steps which can be performed for greater or lesser periods of time and/or steps within a protocol may be temporally rearranged and performed in various orders.

Continuing to refer to FIG. 46B, if 1560 "n" number of iterations have been completed, method 1550 may terminate. The variable "n" may be any number of iterations and may be predefined or determined dynamically by, for example, but not limited to, examining the status of the processed biological specimen. If 1560 "n" number of iterations have not been completed the biological specimen may be decellularized 1556 and recellularized 1558 again until the number of iterations completed is equal to "n". In some configurations, each iteration may use protocols which are different from any previously used protocol. A first iteration may use the first decellularization protocol and the first recellularization protocol, a second iteration may use the second decellularization protocol and the second recellularization protocol, and so on. In some configurations, each iteration may use a previously used protocol or a different protocol. In some configurations, the protocols used in method 1550 may alternate based on which part of method 1550 is being executed. For example, the protocols used in 1552, 1554 and 1556, 1558 may be used in alternating fashion throughout multiple iterations. In some configurations, a select number of different decellularization protocols and recellularization protocols may be scheduled for use on specific iterations. The number of different decellularization protocols may differ from the number of different recellularization protocols.

Continuing to still further refer to FIG. 46B, in some configurations, the protocol used for decellularization in each iteration may remain the same while the protocol used for recellularization in each iteration can be changed (or vice versa). In some configurations, the protocol used for decellularization in each iteration may be altered at a first rate (e.g. after every first number of iterations) while the protocol used for recellularization can be altered at a second rate (e.g. after every second number iterations).

Figure 46C:
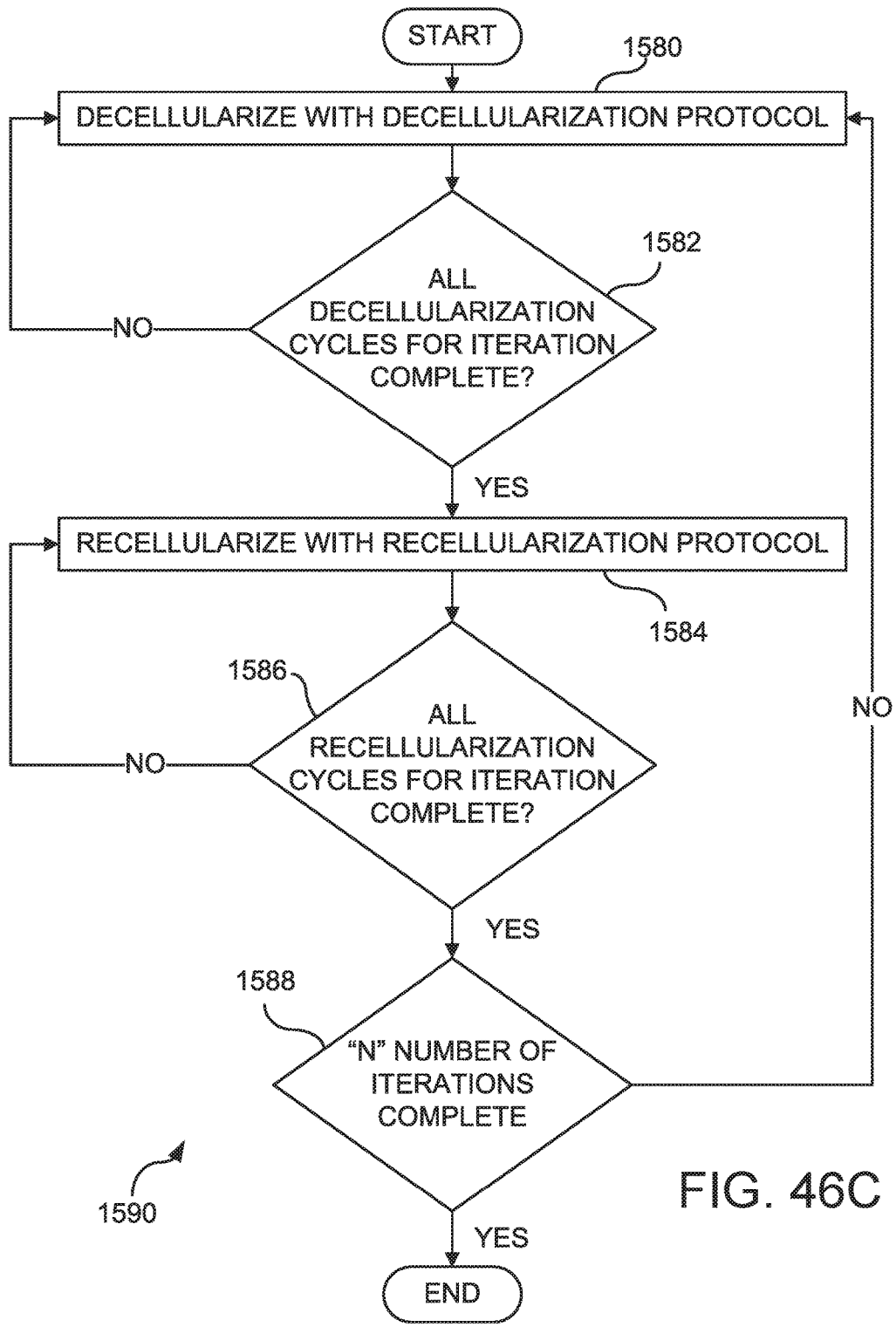

Referring now to FIG. 46C, method 1590 for decellularizing and recellularizing a biological specimen may include, but is not limited to including, decellularizing 1580 a biological specimen with a decellularization protocol. If 1582 all decellularization cycles for the current iteration of method 1590 have not been completed, decellularization 1580 of the biological specimen may be repeated. If 1582 all decellularization cycles for the current iteration have of method 1590 have been completed, method 1590 may include recellularization 1584 of the biological specimen with a recellularization protocol. If 1586 all recellularization cycles for the current iteration of method 1590 have not been completed, recellularization 1584 of the biological specimen may be repeated. If 1586 all recellularization cycles for the current iteration of method 1590 have been completed, and if 1588 "n" iterations of method 1590 have been completed, method 1590 may terminate. If 1586 all recellularization cycles for the current iteration of method 1590 have been completed, and if 1588 "n" iterations of method 1590 have not been completed, method 1590 may return to decellularizing 1580. The variable "n" may be any desired number of iterations and may be predefined or dynamically determined based on, for example, but not limited to, the status of the biological specimen.

Continuing to refer to FIG. 46C, protocols in each iteration of method 1590 may differ from each other, for example, similarly to as described above in relation to FIG. 63. In some configurations, within each iteration, decellularization and recellularization may each (though not necessarily both) be done multiple times and the number of times for each may be predefined or determined dynamically based on, for example, but not limited to, the status of the processed biological specimen. In some configurations, each time a decellularization protocol or recellularization protocol is performed within an iteration, the protocol used may be the same as at least one or differ from each protocol performed previously. The protocols may use at least one different, some, or all different agents, for example. In some configurations, protocols which differ from one another may be defined by differing temporal parameters. In some configurations, the protocols may include steps which are performed for greater or lesser periods of time and/or steps within a protocol may be temporally rearranged and performed in a different order. In some configurations, there may be multiple cycles of both decellularization and recellularization protocols within an iteration. In some configurations, one of the protocols for decellularization and recellularization may differ from cycle to cycle, while the other may be constant or maintained. In some configurations, the decellularization protocol may be maintained, while the cell type(s) introduced in the recellularization protocol may differ from cycle to cycle. In some configurations, a select number of different decellularization protocols and recellularization protocols may be scheduled for use on specific cycles. Different protocols for decellularization and recellularization may be used in alternating fashion over a number of cycles. In some configurations, the protocol used for decellularization in each cycle may be altered at a first rate (e.g. after every first number of cycles) while the protocol used for recellularization is altered at a second rate (e.g. after every second number cycles).

Figure 46D:
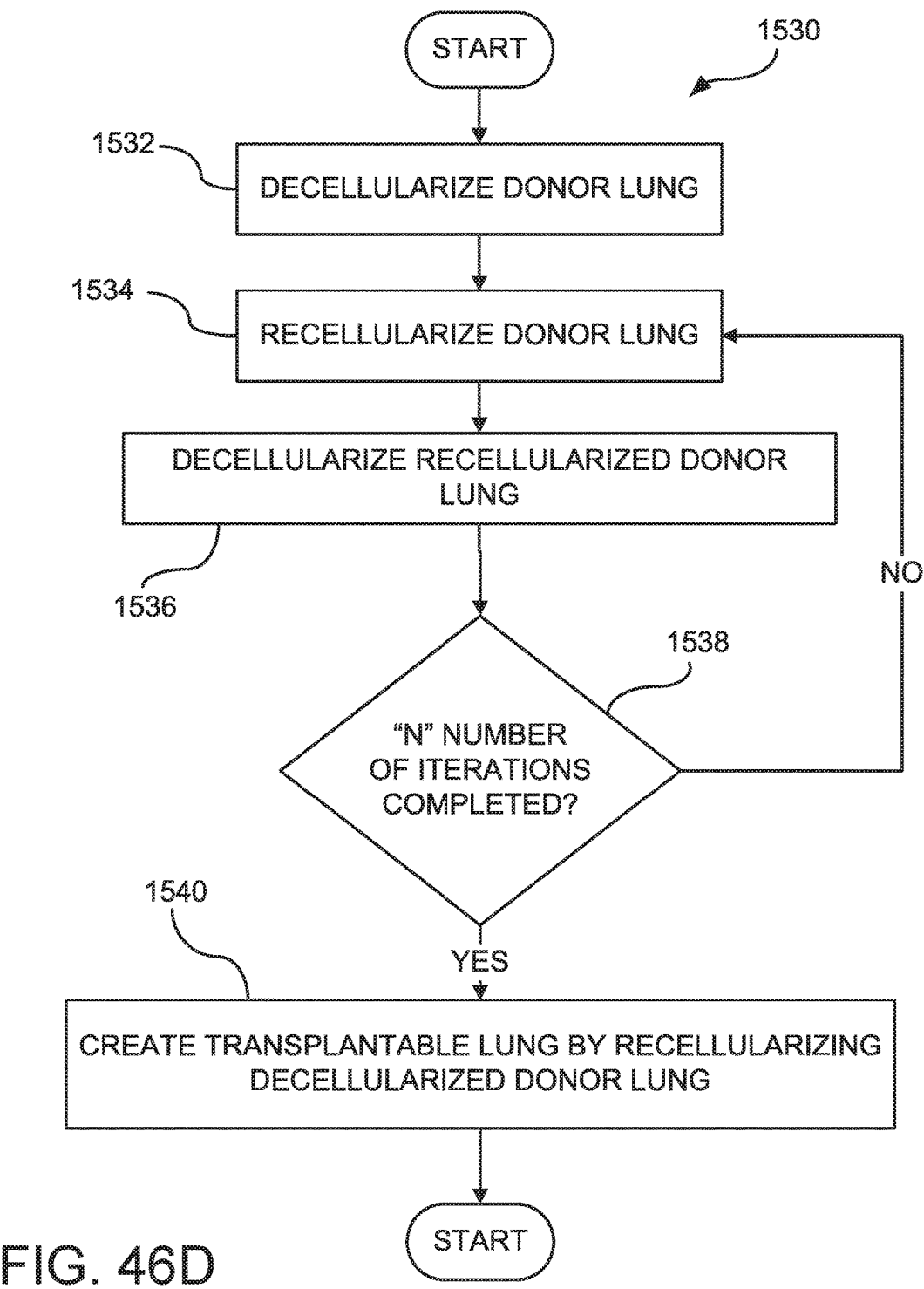

Referring now to FIG. 46D, method 1530 for a generating a transplantable lung from a donor lung may include, but is not limited to including, decellularizing 1532 the donor lung. Method 1530 may include recellularizing 1534 the decellularized lung. Method 1530 may include decellularizing 1536 the recellularized lung. Method 1530 may include creating 1540 the transplantable lung by recellularizing the lung from 1536 if 1538 "n" number of iterations have been completed. The variable "n" may be any number of desired iterations and may be predefined or determined dynamically based on, for example, but not limited to, the status of the processed donor lung. Method 1530 may include repeating recellularizing 1534 the lung and decellularizing 1536 the lung if 1538 "n" number of iterations have not been completed. In some configurations, method 1530 may also be used for other biological specimens. In some configurations, the iterations may be conducted as described in relation to FIGS. 63 and 64.

Figure 47:
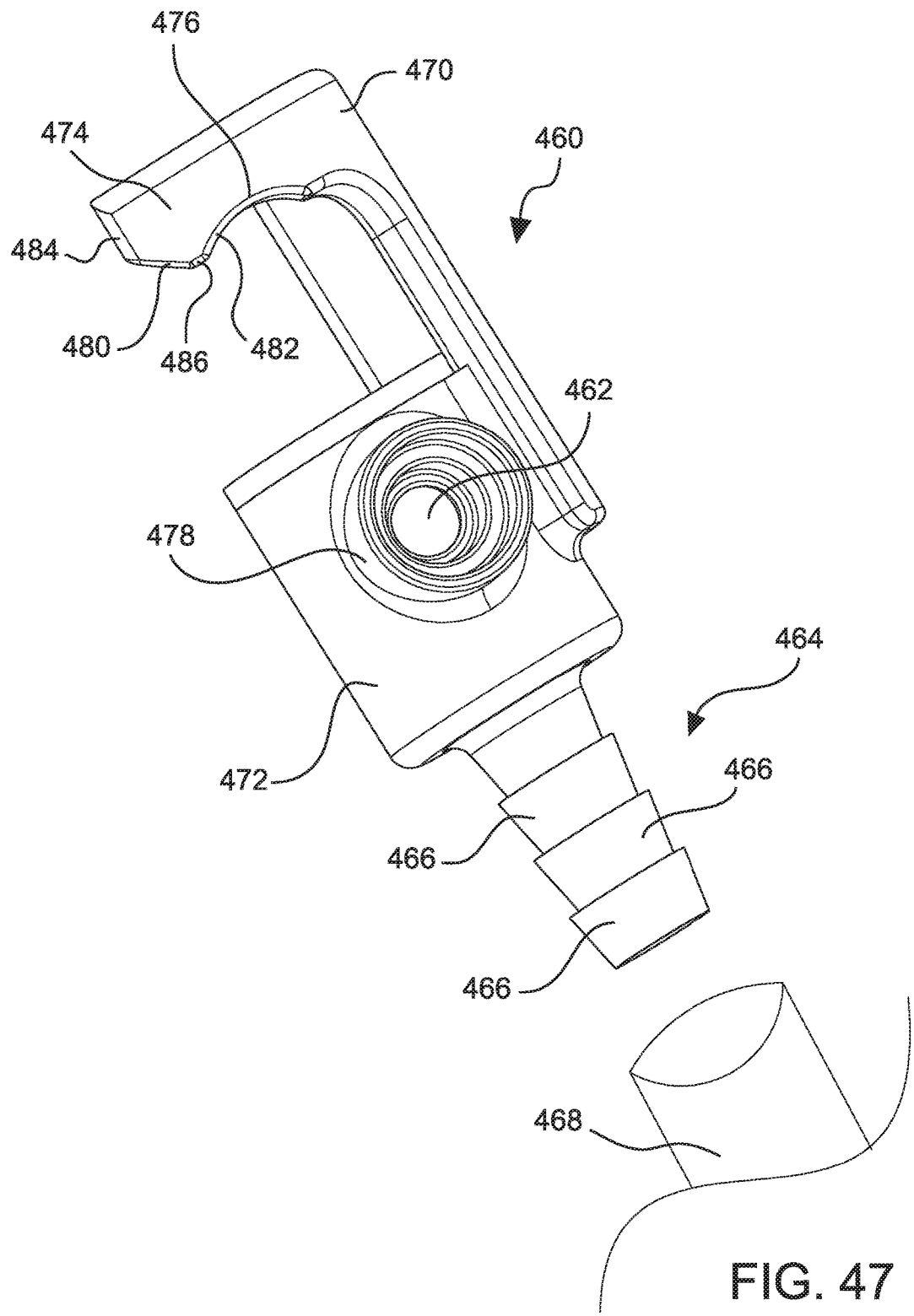
FIG. 47 is a perspective diagram of an example of a fitting of the present teachings.

Referring now to FIG. 47, fitting 460 can include, but is not limited to including, sensor well 462. Sensor well 462 can form a pathway leading to the interior of fitting 460. Sensor well 462 can be, but is not limited to being, located on the main portion or body 472 of fitting 460 and can be defined in part by surrounding wall 478 that can, for example, project away from main portion 472. Surrounding wall 478 may, for example, but not limited to, project from main portion 472 in a manner substantially perpendicular to the long axis of fitting 460. In some configurations, main portion 472 may be elongated and may include multiple sensor wells 462.

Fitting 460 can also include connector projection 464 which may optionally, but not necessarily, include a number of barbs 466. In some configurations connector projection 464 may be Luer-lock like connector projections. Fluid conduit 468 may couple onto connector projection 464 such that fluid may pass from conduit 468 into the interior of fitting 460. In some configurations, fluid conduit 468 may be permanently attached to connector projection 464 via e.g. solvent bonding.

Continuing to refer to FIG. 47, fitting 460 can also include mating body 470 which can extend from main portion 472 of fitting 460. Mating body 470 may be configured to mate and lock onto another, possibly identical, fitting 460. For example, mating body 470 may include arm 474 which can have mating face 476 that can mate and lock to another fitting 460. Mating face 476 may include ramp 480 which can begin at end 484 of arm 474. Ramp 480 may progressively increase the thickness of arm 474 in a direction toward main portion 472 of fitting 460 as the ramp 480 extends away from the end 484. Mating face 476 may also include a detent region or dwell 482 which can be separated from ramp 480 by transition region 486 at which the thickness of arm 474 can be greatest. Detent region 482 may be a depression into arm 474 which can decrease the thickness of arm 474. Detent region 482 may be a curved shape depression, or in some configurations may be defined by a lip or step down from transition region 486. In some configurations, the thinnest part of detent region 482 of arm 474 may be thicker than the thinnest part of ramp 480. Fitting 460 can also include gasket 488. Gasket 488 may be any of a variety of suitable sealing members. Gasket 488 may be constructed of a compliant, compressible material such as an elastomeric material. Gasket 488 may be, for example, but not limited to, a planar gasket or an o-ring. In some configurations, when two fittings 460 are mated to one another, gasket 488 of each fitting 460 may abut and be compressed to create a fluid tight seal between fittings 460.

Figure 48A:
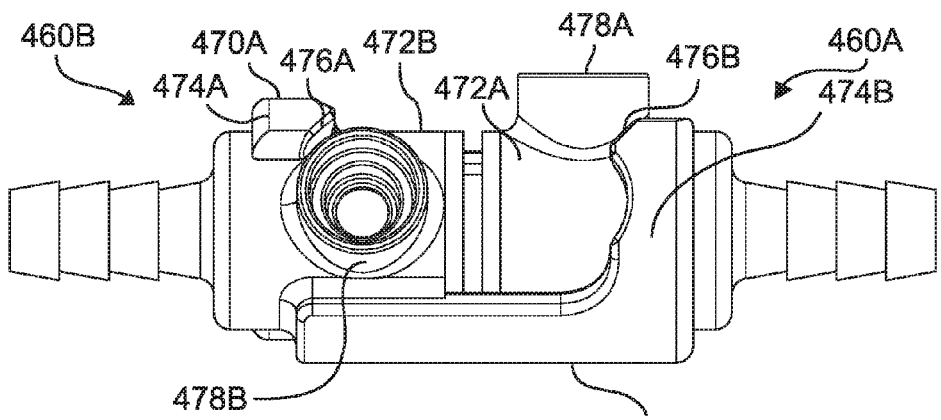
FIGS. 48A-C are perspective diagrams of example fittings of the present teachings in various stages of mating with one another.
Figure 48B:
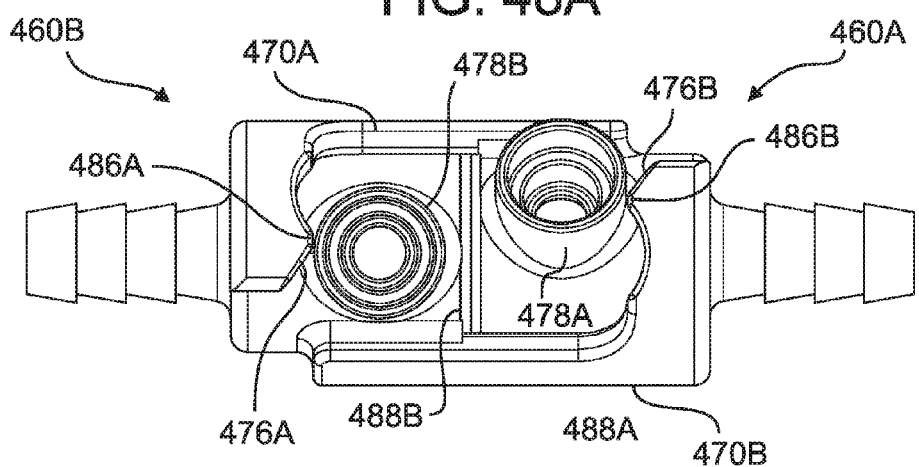

Referring now to the progression of FIGS. 48A and 48B, two fittings 460A, 460B are shown being mated together. In the first stage of mating shown in FIG. 48A, fittings 460A, 460B may be brought into proximity with one another. Main portions 472A, 472B of each fitting 460A, 460B may be cradled in mating body 470A, 470B of the other. One of fittings 460A, 460B may be rotated until ramps 480A, 480B of fittings 460A, 460B abuts surrounding walls 478A, 478B of the other of fittings 460A, 460B. Fittings 460A, 460B may be rotated in opposite directions or one of fittings 460A, 460B may be held stationary while the other of fittings 460A, 460B is rotated.

Referring now primarily to FIG. 48B, when ramps 480A, 480B abut surrounding walls 478A, 478B, fittings 460A, 460B may continue to be rotated in the second stage of mating. In some configurations, the increase in thickness of ramps 480A, 480B, may cause ramps 480A, 480B to act in a cam-like manner. Ramps 480A, 480B may convert the rotational displacement into a linear displacement by applying a force against surrounding walls 478A, 478B of fittings 460A, 460B urging them toward one another. As compared to FIG. 48A, gaskets 488A, 488B in FIG. 48B are compressed against one another as a result of the further rotation. At the end of the second stage of mating, surrounding walls 478A, 478B may be in contact with transition region 486B of the arm 474A, 474B (FIG. 48A).

Figure 48C:
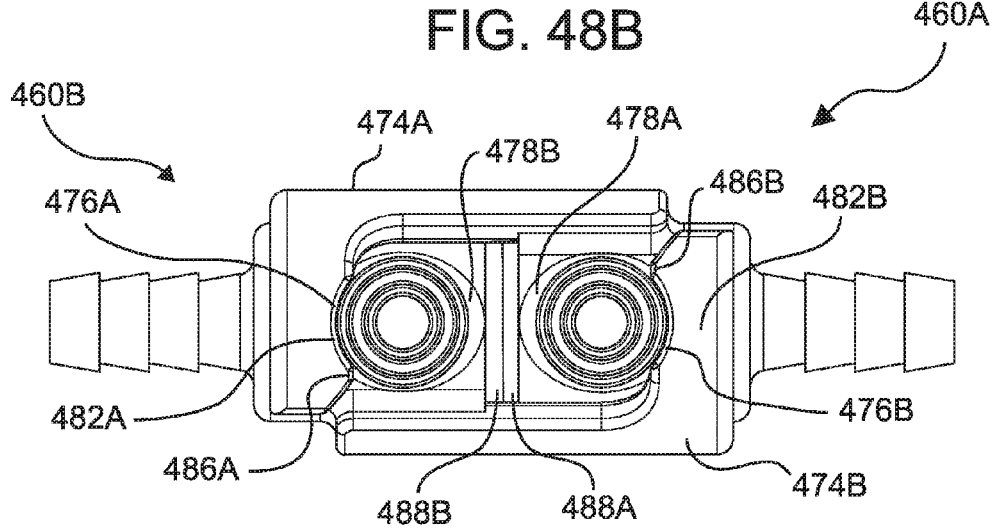

Referring now to FIG. 48C, fittings 460A, 460B may continue to be still further rotated into a fully mated and locked state. The further rotation of fittings 460A, 460B may cause detent region 482A, 482B of each arm 474A, 474B to rest against a portion of surrounding walls 478A, 478B of the opposing fitting 460A, 460B. In this position, mating faces 476A, 476B may apply a force against surrounding walls 478A, 478B which can compress gaskets 488A, 488B of each fitting 460A, 460B. The compression of gaskets 488A, 488B may form a fluid tight seal between the environment and the interior of fittings 460A, 460B. Detent regions 482A, 482B may be shaped complimentarily to surrounding walls 478A, 478B to allow detent regions 482A, 482B to cradle surrounding walls 478A, 478B.

Continuing to refer to FIG. 48C, the interaction of detent region 482A, 482B and surrounding walls 478A, 478B may serve to help protect against inadvertent disassociation of fittings 460A, 460B or may lock them together. In order to disassociate fittings 460A, 460B from one another, a rotational force may be applied which can force fittings 460A, 460B toward one another and compress gaskets 488A, 488B. Detent regions 482A, 482B and transition regions 486A, 486B may be shaped to tune the amount of force required to disassociate fittings 460A, 460B from one another. The thicker are transition regions 486A, 486B in comparison to detent regions 482A, 482B, the greater the force required to disassociate fittings 460A, 460B from one another. The amount of force desired may be chosen to allow fittings 460A, 460B to be separated without undue effort, but with enough force that accidental disassociation is unlikely. Alternatively, the amount of force required may be selected such that it is very hard to disassociate two mated fittings 460A, 460B to, for example, dissuade against reuse.

Continuing to refer primarily to FIG. 48C, fittings 460A, 460B can be permanently associated after they are mated by using additional or alternative mating structures. In some configurations, fittings 460A, 460B may include features which render them inoperative if disassociated after being mated. In some configurations, arms 474A, 474B may include a cable tie-like projection which can include an integrated gear rack. Each of mating bodies 470A, 470B (FIG. 48B) may include a pawl or ratcheting mechanism which can be sized to accept the rack projection of the opposing of arms 474A, 474B. When joined, the ratcheting mechanism may prevent disassociation of fittings 460A, 460B. Any other arrangement to prevent disassociation may also be used.

Referring now to FIGS. 49A-D, a number of views of fittings 460A, 460B which have been mated and locked together are shown. Each of fittings 460A, 460B may include sensor well 462 (FIG. 47) which can be defined at least in part by surrounding walls 478A, 478B. Sensor 490 may be placed or housed in each sensor well 462 (FIG. 47). Sensor 490 may be any of a variety of sensors. Temperature, conductivity, turbidity, spectrophotometric, flow rate, color, dielectric property, air bubble, acoustic impedance sensors, or any other sensors mentioned herein may, for example, be used. In some configurations, sensors 490 can be conductivity sensors. In some configurations, when multiple of sensors 490 are used, sensors 490 can be different from one another. In some configurations, sensor 490 may only be included for one of fittings 460A, 460B. In some configurations, fittings 460A, 460B can have an elongated of main bodies 472A, 472B (FIG. 49E) including multiple sensor wells 462 (FIG. 47). Single fittings 460A, 460B may have sensors 490 for multiple different characteristics of interest.

Referring now primarily to FIG. 49E, a cross sectional view of two mated fittings 460A, 460B taken at line 26I-26I of FIG. 49A is shown. Connector projections 464A, 464B may each include connector fluid conduits 492A, 492B extending therethrough and leading to sensing volumes 494A, 494B. When fittings 460A, 460B are mated and locked together, the seal created by gaskets 488A, 488B may join sensing volumes 494A, 494B in a fluidically sealed manner creating sensing chamber 496. Fluid may pass from fluid line or conduit 468 (FIG. 47) attached to one of connector projections 464A, 464B through connector conduits 492A, 492B and sensing chamber 496 to another of fluid line 468 (FIG. 47) attached to the other of connector projections 464A, 464B. Sensors 490 may be introduced to sensing chamber 496 via sensor wells 462A, 462B. A characteristic of the fluid may be sensed by sensors 490 while the fluid is within sensing chamber 496. If sensors 490 are conductivity sensors, sensing chamber 496, may for example, be sized such that the working portion of probe 498 of sensor 490 may be completely bathed in the fluid being sensed. In some configurations, dimensions of fittings 460A, 460B may be selected to place sensors 490 a desired distance apart from one another. In some configurations, gaskets 488A, 488B may be altered or swapped out to alter the distance between sensors 490. In some configurations, the distance between sensors 490 may be about 0.4-0.8 inches apart. In some configurations, the distance between sensors 490 (from center point to center point) may be about 0.6 inches. Alternatively, the distance may be greater, for example between 3.5-2 inches. The distance chosen may be dependent on the concentration ranges expected. Generally, if the expected concentration ranges are lower the distance may be shorter. In some configurations, a light source can be included as part of sensor 490 or within the sensing chamber 496. In some configurations, the light source may, for example, be an LED light source.

Continuing to refer primarily to FIG. 49E, in some configurations, connector projections 464A, 464B may be of differing sizes allowing mated fittings 460A, 460B to act as adapters between different diameter fluid lines 468 (FIG. 47). One of connector projections 464A, 464B may be sized to fit a first diameter line while the other can be sized to fit a second, different size, diameter line. Sensor wells 462 (FIG. 47) and sensors 490 can be optional in some configurations where fittings 460A, 460B serve as adapters.

Figure 50:
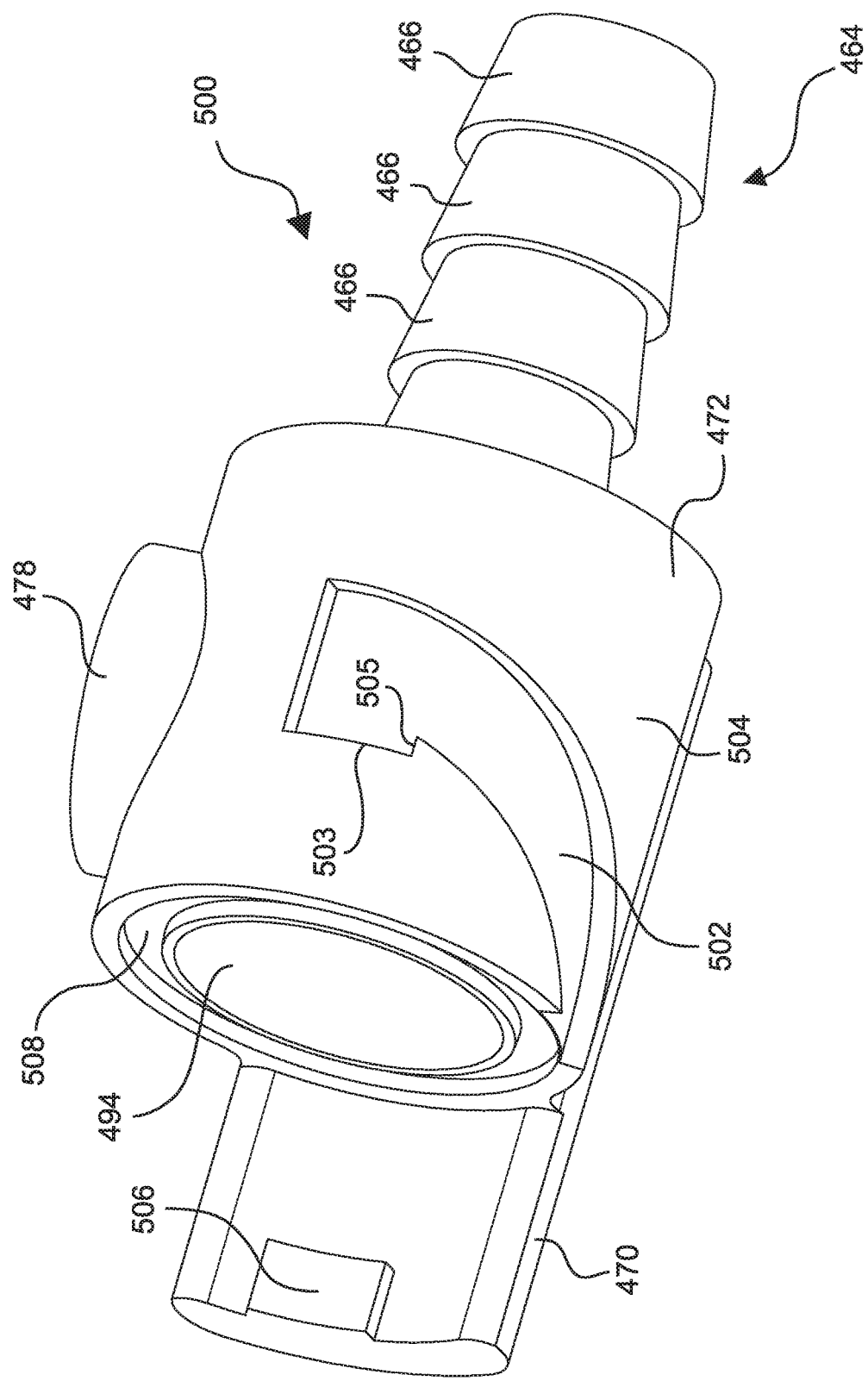
FIG. 50 is a perspective diagram illustration of another example of a fitting of the present teachings.

Referring now primarily to FIG. 50, fitting 500 can include, but is not limited to including, connector projection 464 which can optionally include barbs 466, though other varieties may also be used. Connector projection 464 may be attached to fluid line or conduit 468 (FIG. 47). Fitting 500 may include main body 472 and mating body 470. Main body 472 may include sensor well 462 (FIG. 47) which can be defined at least in part by surrounding wall 478. Sensor well 462 (FIG. 47) may be in communication with sensing volume 494 on the interior of fitting 500. Main body 472 may include track 502 which can be recessed into outer face 504 of main body 472. Track 502 may have, for example, but not limited to, a detent or dwell region 503. Mating body 470 may be configured to mate and lock with another fitting 500 which may be identical to fitting 500. Mating body 470 may include projection 506 which can be sized to fit within track 502 of another fitting 500. When projection 506 is engaged with track 502 of another fitting 500, two fittings 500 may be rotated and mated. As projection 506 rides along track 502 toward detent region 503, the rotational displacement of two fittings 500 can be translated to a linear displacement. The linear displacement may force two fittings 500 toward one another. When projection 506 reaches detent region 503, two fittings 500 may be fully mated and locked. Lip 505 that can define the boundary between track 502 and detent region 503 may help lock fittings 500 together and may protect against inadvertent disassociation of two fittings 500. In some configurations, an undercut (not shown) may be included along at least one wall of the track 502. Projection 506 may include a cooperating feature which mates into the undercut and helps secure two fittings 500 together. Gasket 488 (FIG. 47) may be placed in recess 508. Gasket 488 may become compressed which can create a fluid-tight seal between two fittings 500 during mating.

Figure 51A:
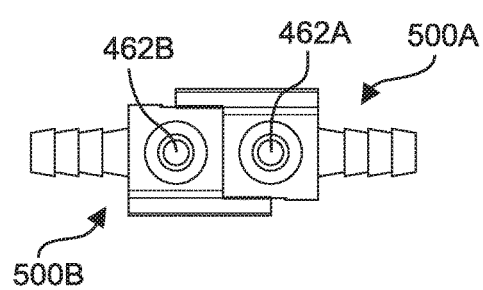
FIG. 51A is a plan view of a first side of another example of fittings of the present teachings mated together.
Figure 51B:
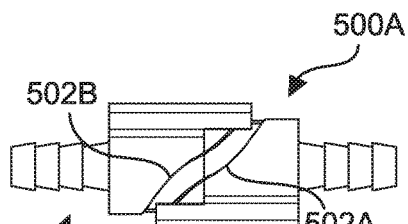
FIG. 51B is a plan view of a second side of another example of fittings of the present teachings mated together.
Figure 51C:
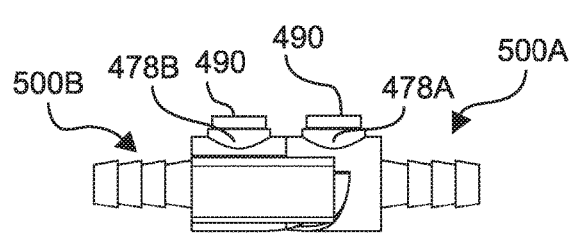
FIG. 51C is a plan view of a third side of another example of fittings of the present teachings mated together.
Figure 51D:
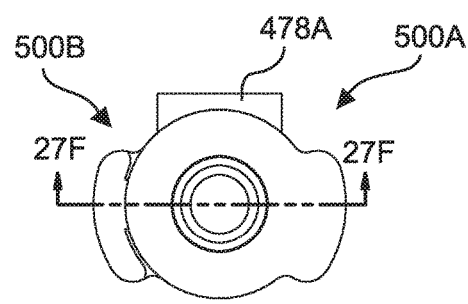
FIG. 51D is a plan view of a fourth side of another example of fittings of the present teachings mated together.

Referring now to FIGS. 51B-D, a number of views of two fittings 500A, 500B which have been mated and locked together are shown. Each of fittings 500A, 500B may include sensor well 462 which can be defined at least in part by surrounding wall 478A, 478B. Sensor 490 may be placed or housed in each sensor well 462. Sensor 490 may be any of a variety of sensors, for example, but not limited to, sensors described herein. Sensors 490 in each sensor well 462 can differ from one another. In some configurations, sensor 490 may be included for only one of fittings 500A, 500B.

Figure 51E:
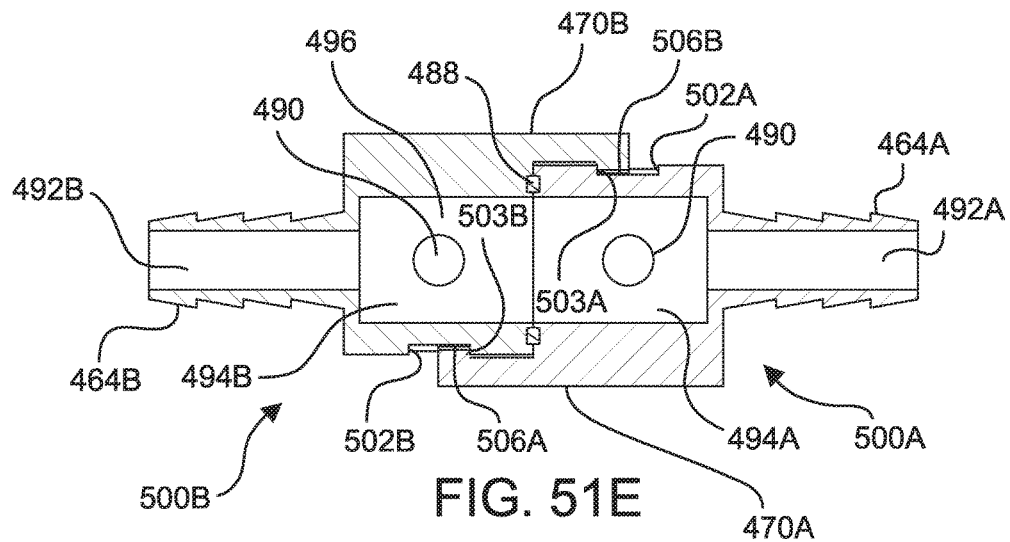
FIG. 51E is a cross-sectional view of the fittings of FIG. 51E at line 27F-27F.

Referring now primarily to FIG. 51E, a cross sectional view of two mated fittings 500A, 500B taken at line 27F-27F of FIG. 51D is shown. Projections 506A, 506B of each mating body 470A, 470B may be in contact with the detent region 503A, 503B of the opposing fitting 500A, 500B track 502A, 502B. Thus, the fittings 500A, 500B may be fully mated and locked together. Gasket 488 may be compressed, joining sensing volumes 494A, 494B in a fluidically sealed manner creating sensing chamber 496. Connector projections 464A, 464B may each include connector fluid conduit 492A, 492B extending therethrough and leading to respective sensing volumes 494A, 494B. Fluid may pass from fluid line or conduit 468 (FIG. 47) attached to one connector projection 464A, 464B through the connector conduits 492A, 492B and sensing chamber 496 to another fluid line 468 (FIG. 47) attached to the other connector projection 464A, 464B.

Continuing to refer to FIG. 51E, Sensors 490 may be introduced to sensing chamber 496 via sensor wells 462A, 462B. A characteristic of the fluid may be sensed by sensors 490 while the fluid is within sensing chamber 496. If sensors 490 are conductivity sensors, sensing chamber 496, may, for example, be sized such that the working portion of sensor 490 may be completely bathed in the fluid being sensed. Dimensions of fittings 500A, 500B may be selected to place sensors 490 a desired distance apart from one another. In some configurations, the distance between sensors 490 (from center point to center point) may be about 0.4-0.8 inches. In some configurations, the distance between sensors 490 may be about 0.6 inches. Alternatively, the distance may be greater, for example between 3.5-2 inches. The distance chosen may be dependent on the concentration ranges expected. Generally, if the expected concentration ranges are lower the distance may be shorter.

Figure 52A:
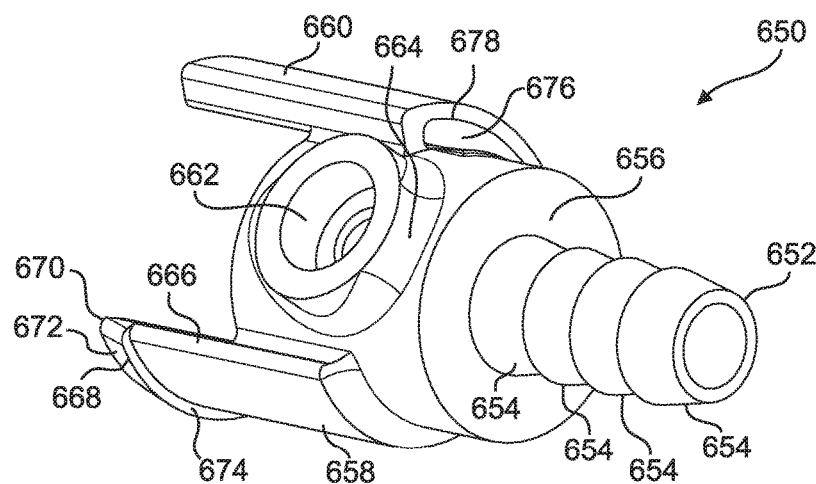
FIG. 52A is a perspective view of another example of a fitting.

Referring now to FIG. 52A fitting 650 can include, but is not limited to including, connector projection 652 which can optionally include barbs 654, though other varieties may also be used. Connector projection 652 may be attached to fluid line or conduit 468 (FIG. 47). Fitting 650 may include main body 656, first mating body 658 and second mating body 660. Main body 656 may include sensor well 662 which can be defined at least in part by surrounding wall 664. Sensor well 662 may be in communication with a sensing volume on the interior of fitting 650.

Continuing to refer to FIG. 52A, first mating body 658 may include cantilevered beam 666 which can extend from main body 656 substantially parallel to the long axis of fitting 650. Cantilevered beam 666 may include a catch or latching structure 668. The catch 668 may be at an end 670 of the first mating body 650. The end 670 may be distal to the main body 656. In some configurations, the catch 668 may include a sloped portion which increases the thickness of the cantilevered beam 666 as it extends from end 670 proximally toward main body 656. The catch 668 may also include a lip 674 which defines the end of the sloped portion 672. The sloped portion 672 may have a gentle slope or slope between 30-50 degrees, though the slope may differ in other configurations.

Continuing to still further refer to FIG. 52A, fitting 650 may mate with a second fitting which may, in some configurations, be an identical fitting. Second mating body 660 may, for example, be configured to receive a first mating body 658 of another fitting 650. The second mating body 660 may include a slot or bay 676 into which a first mating body 658 of another fitting 650 may be introduced. In some configurations, the bay 676 may completely surround the first mating body 658 when the first mating body 658 has been introduced. The bay 676 may include an opening 678 through which the end 670 of a first mating body 658 may protrude.

Figure 52B:
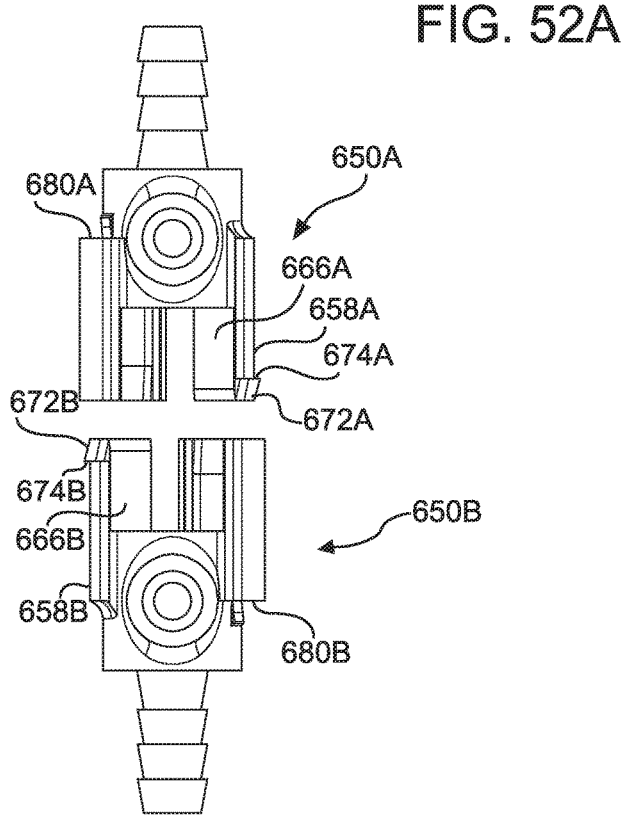
FIG. 52B is a plan view of two exemplary fittings aligned for mating.
Figure 52C:
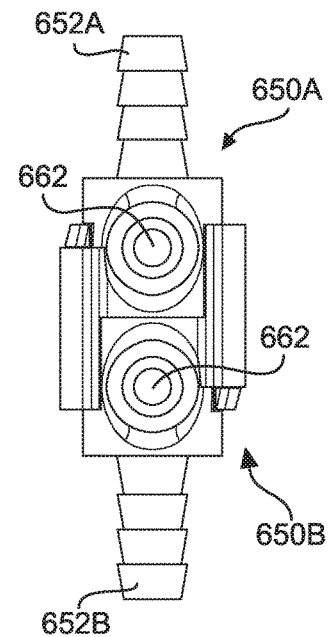
FIG. 52C is a plan view of two exemplary fittings which have been mated together.

Referring now to FIGS. 52B-C, during mating of two fittings 650A,B, the fittings 650A,B may be aligned such that the first mating bodies 658A,B of fittings 650A,B are in line with second mating bodies 660A,B of the opposing fitting 650A, B. When the first mating bodies 658A,B begin to enter the receiving second mating bodies 660A,B, the sloped portions 672A,B may cause the cantilevered beams 666A,B to be deflected inward toward the long axis of fittings 650A, B. The two fittings 650A,B may continue to be brought together until they reach the position shown in FIG. 52C.

Still referring to FIGS. 52B-C, once the two fittings 650A,B are fully mated together, the ends 670A,B of first mating bodies 658A,B may project through openings 678 (FIG. 52A) of their receiving second mating bodies 660A,B. When the sloped portions 672A,B have cleared opening 678 (FIG. 52A) cantilevered beams 666A, B may restore to a resting or undeflected position. In this position, lips 674A,B may abut against walls 680A, B of their respective second mating bodies 660A, B locking the two fittings 650A,B together. As in above configurations, a gasket 488 (FIG. 47) may be placed in between the two fittings 650A,B when they are mated and locked together. Gasket 488 (FIG. 47) may become compressed which can create a fluid-tight seal between two fittings 650A,B during mating.

Referring now to FIG. 52C, a sensor 490 (FIG. 49E) may be placed or housed in each sensor well 662. Sensor 490 may be any of a variety of sensors, for example, but not limited to, sensors described herein. Sensors 490 (FIG. 49E) in each sensor well 662 can differ from one another. In some configurations, sensor 490 (FIG. 49E) may be included for only one of fittings 650A, 650B. Fluid may pass from fluid line or conduit 468 (FIG. 47) attached to one connector projection 652A, 652B through the fittings 650A, 650B to another fluid line 468 (FIG. 47) attached to the other connector projection 652A, 652B. Sensors 490 (FIG. 49E) may sense at least one characteristic of the fluid as the fluid passes through the fittings 650A, B. The fittings 650A, B may be configured to accommodate or space apart sensors 490 as described above.

Figure 53A:
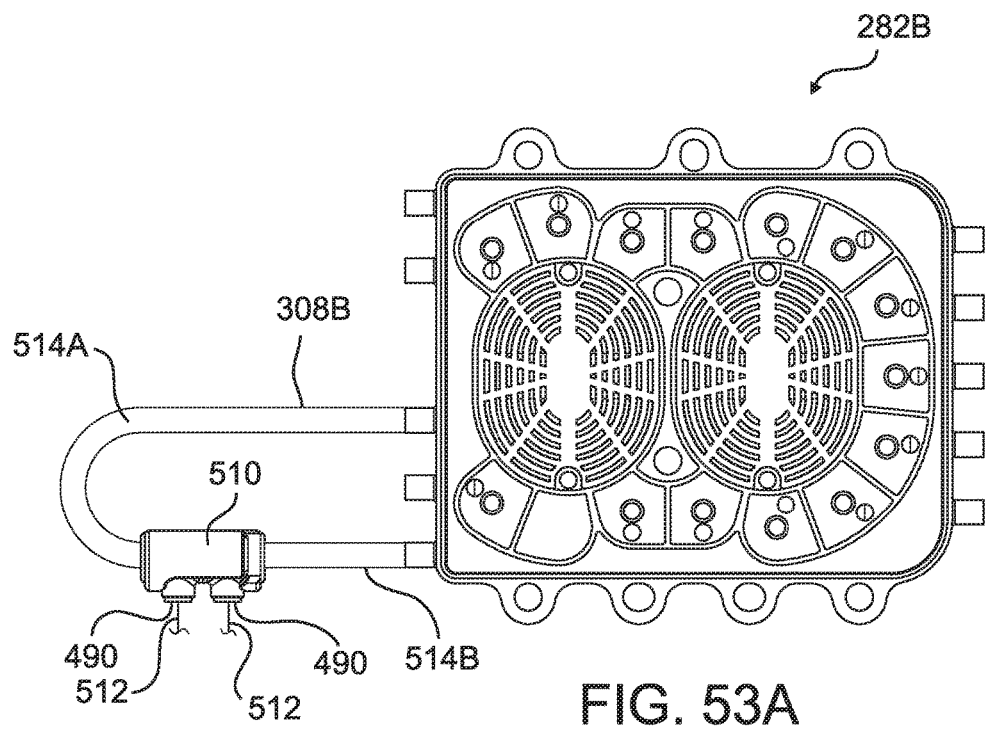
FIG. 53A is a plan view of an example of a second cassette of the present teachings including a fitting assembly on a loop line.

Referring now to FIG. 53A, an example of second cassette 282C which can include a loop line 308B is shown. Fitting assembly 510 can include, for example, but not limited to, a pair of mated fittings 460A, 460B (FIG. 48C) between first loop portion 514A and second loop portion 514B of loop line 308C. Fitting assembly 510 can include, but is not limited to including, two sensors 490 from which electrical communication lines 512 can extend. Sensors 490 may sense a characteristic of fluid passing through loop line 308C such as the conductivity of the fluid. Any other characteristic and/or condition may also be sensed. A signal representative of a sensed value for the characteristics and/or condition of interest may be reported via electrical communication lines 512.

Figure 53B:
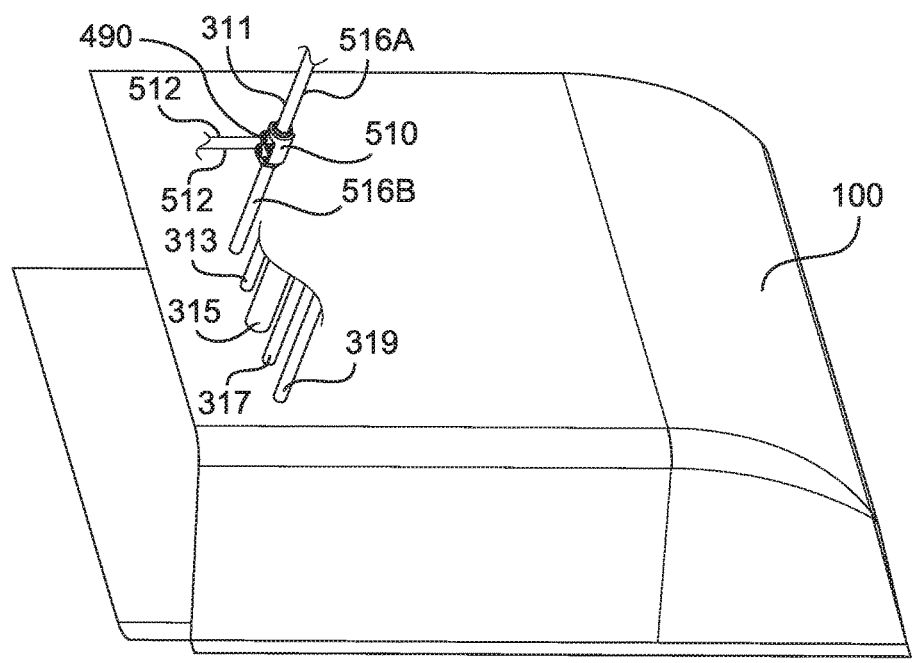
FIG. 53B is a perspective view of an example of an enclosure of the present teachings including a fitting assembly on a line leading to the enclosure.

Referring now primarily to FIG. 53B, enclosure 100 can include, but is not limited to including, fluid lines 311, 313, 315, 317, 319 that may be attached to or extend into a bag containing specimen 162 (FIG. 1) as described elsewhere herein. In some configurations, one of lines 311, 313, 315, 317, 319 may include a first portion and a second portion which are separated by fitting assembly 510. Fitting assembly 510 may serve as an adapter between tubing of differing sizes in some configurations. Fitting assembly 510 may include sensors 490 which may sense a characteristic and/or condition of the fluid entering or exiting enclosure 100 or biological specimen 162 (FIG. 1) in enclosure 100. In some configurations, line 319 may include first portion 516A and second portion 516B which can be separated by and attached to fitting assembly 510 including sensors 490. Sensors 490 may sense any characteristics and/or condition of interest of the fluid passing through fitting assembly 510, for example, conductivity. A signal representative of a sensed value for the condition of interest may be reported via electrical communication lines 512.

Figure 54:
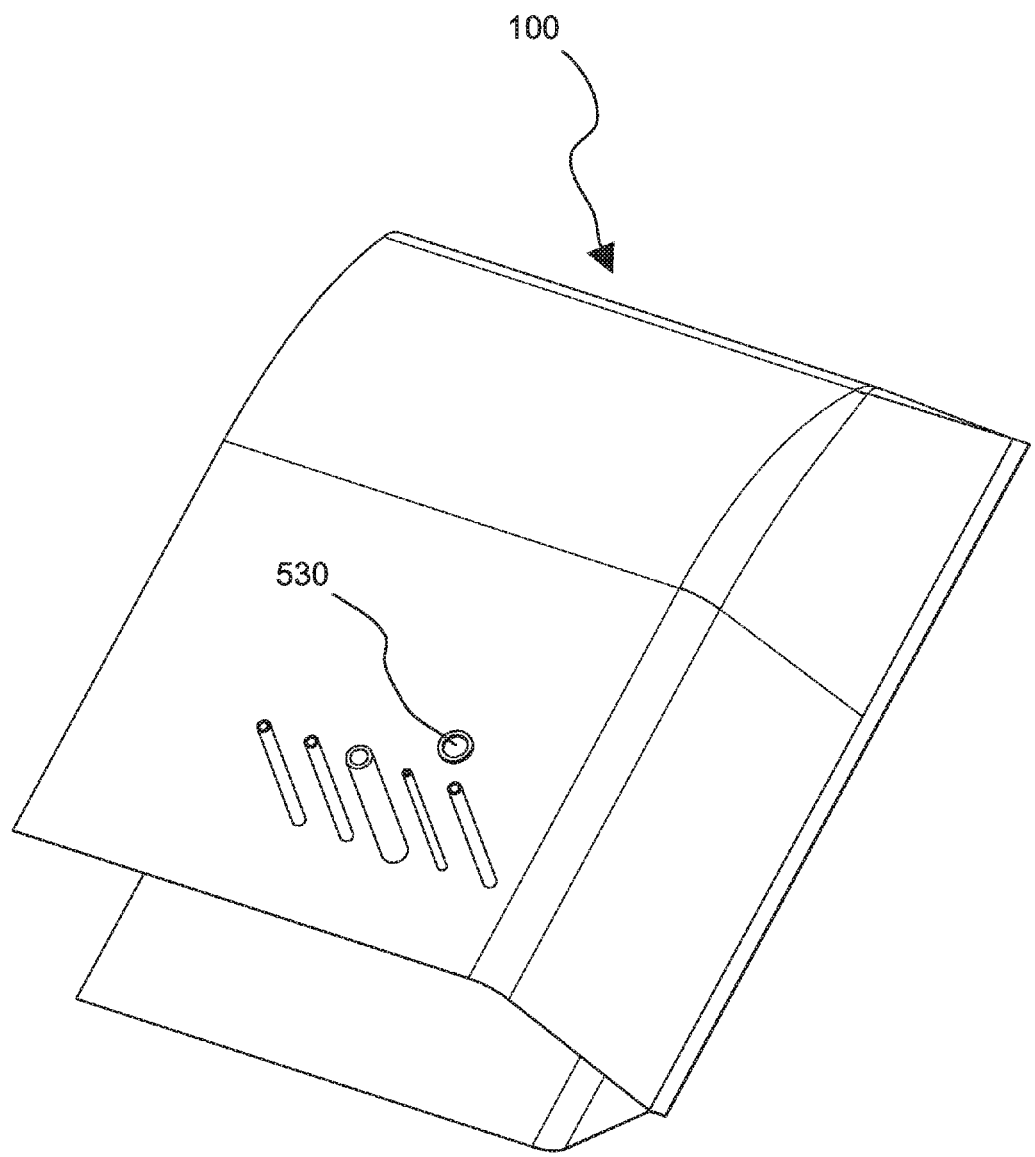
FIG. 54 is a perspective diagram of an enclosure of the present teachings having a septum.

Referring now to FIG. 54, in some configurations, an example fluid handling set 280 (FIG. 32) may include one or more pierceable septum 530. Septum(s) 530 may be made of a self closing or sealing material such as a rubber or elastomer which may be pierced by a sharp instrument such as a needle. Septum(s) 530 may form a fluid tight seal between the surrounding environment and the interior of fluid handling set 280 (FIG. 32). Septum(s) 530 may serve as sampling ports through which a sample of fluid or biological specimen 162 (FIG. 1) within fluid handling set 280 (FIG. 32) may be drawn. After drawing the sample, the hole in septum 530 may close and septum 530 may again provide a fluid tight barrier. The sample may then be analyzed to determine various characteristics of the sample. For example, a cell count may be taken or components of the sample may be separated and stained for later analysis. In some configurations, at least one septum 530 may be included as part of enclosure 100. Septum 530 may be attached to a piece of material which is then heat bonded, solvent bonded, attached with adhesive, ultrasonically welded, or otherwise attached to enclosure 100. Septum 530 may allow sampling of the contents of enclosure 100. In some configurations, fluid may be drawn from enclosure 100 or part of biological specimen 162 (FIG. 1) contained within enclosure 100. Septum 530 may be placed at any suitable location on enclosure 100. In some configurations, septum 530 may be placed near adapter 23 (FIG. 3).

Figure 55A:
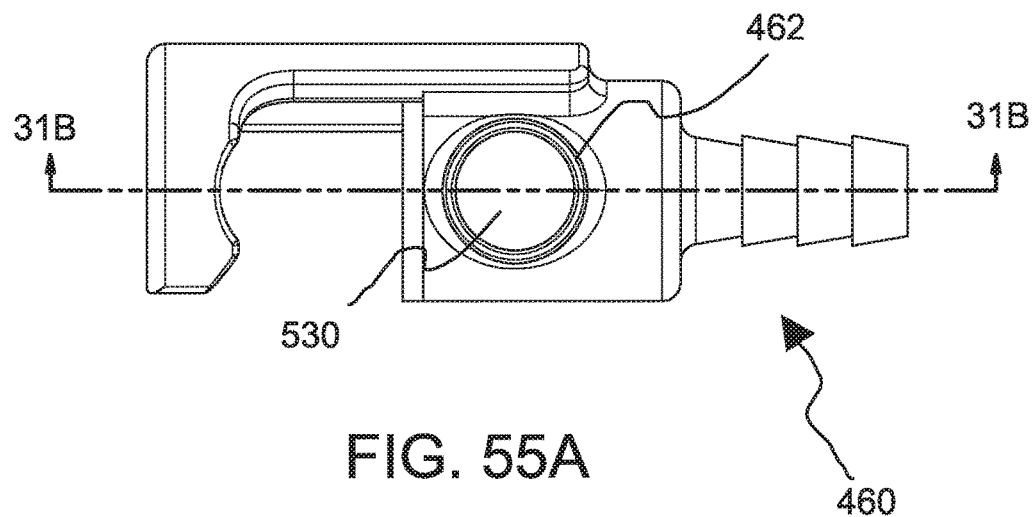
FIG. 55A is a plan view of a fitting of the present teachings having a septum.

Referring now primarily to FIG. 55A, at least one septum 530 may be disposed in other portions of fluid handling set 280 (FIG. 32). In some configurations, septum 530 may provide access to fluid flowing through a fluid line of fluid handling set 280 (FIG. 32). Any fluid line within fluid handling set 280 (FIG. 32) may be in communication with septum 530 which may be used as a sampling port. In some configurations, in lieu of or in addition to sensor 490 (FIG. 51E), fitting 460 may include septum 530. Septum 530 may, in some configurations, be placed in sensor well 462 of fitting 460. In some configurations, a needle or other sharp instrument may pierce through septum 530 to gain access to the fluid within fitting 460. Septum 530 may be made of a self healing material and may re-seal itself upon withdrawal of the piercing instrument.

Figure 55B:
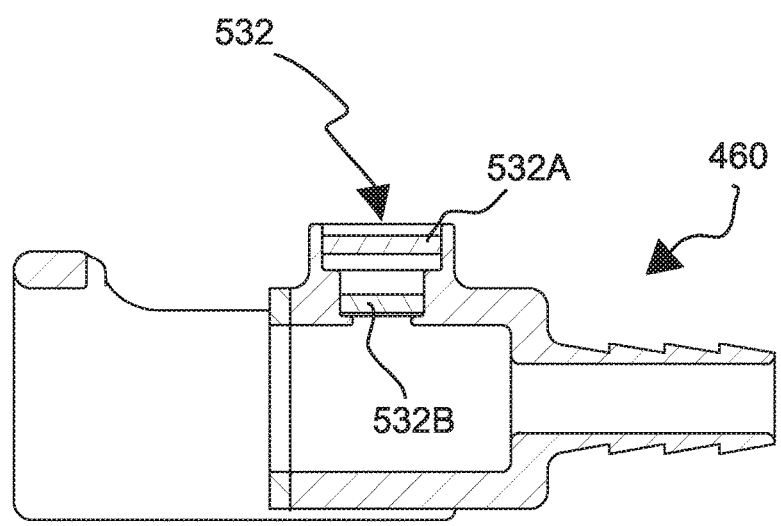
FIG. 55B is a cross sectional view of the fitting of FIG. 55A.

Referring now to FIG. 55B, in some configurations, a dual (or triple, quadruple, so on) septum 532 may be included as part of fluid handling set 280 (FIG. 32). In some configurations, a plurality of septa 532A, 532B may be placed in series with one another. Each septum 532A, 532B may be pierced to gain access to the fluid to be sampled. Multiple septa 532A, 532B can provide redundant fluid tight seals between the environment and the fluid. In some configurations, a plurality of septa 532 may be included in many places in fluid handling set 280 (FIG. 32) such as in enclosure 100 (FIG. 32).

Figure 55C:
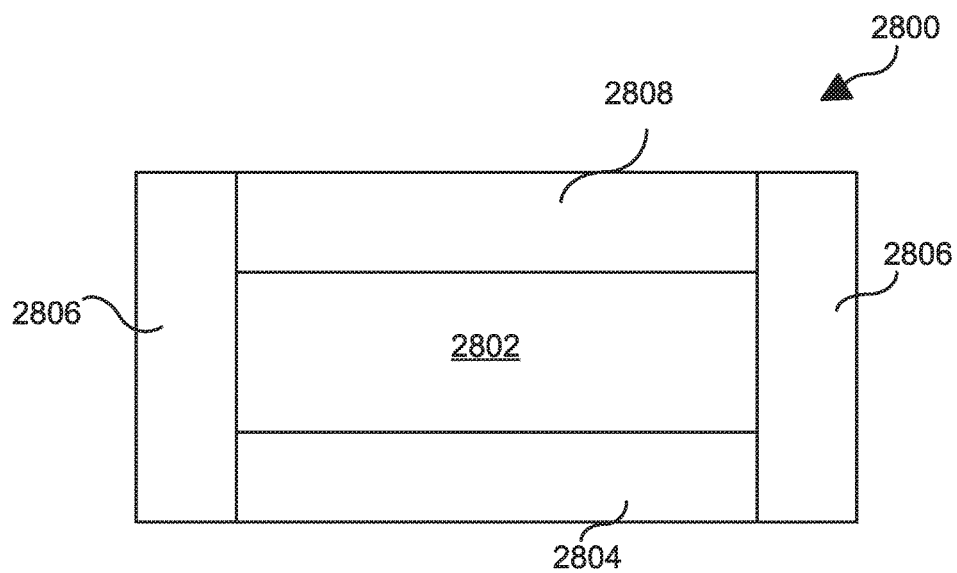
FIG. 55C is a schematic block diagram of a valve module of the present teachings.

Referring now to FIG. 55C, valves and pump chambers of cassettes 282A-C (FIG. 32) may be actuated by any suitable type of pneumatic valves. In some configurations, the valves may be included in valve modules which may each comprise one or more valves. Additionally, each valve module may contain all of the electronic components necessary to operate the valves included in that valve module. A valve module may thus be an assembly of one or more valves attached to one or more PCBs populated with electronic components suitable for operating the valves autonomously or semi-autonomously with respect to main or central controller 2047 (FIG. 31). This may help to offload some of the computing resources necessary to run the valves from a main processor of a device. Controller 2047 (FIG. 31) may then only need to send a valve module high level commands. These high level commands may include start commands, stop commands, pause/resume commands, and commands to perform template functions pre-programmed on the PCB. Alternatively, the PCB may allow a valve module perform a valve function in an entirely autonomous manner without the need for an external controller. Still further, control may be centralized in the main processor. Any of the example methods, systems, and valves described in U.S. patent application Ser. No. 14/967,093, filed Dec. 11, 2015, and entitled Modular Valve Apparatus and System, incorporated herein in its entirety, may, for example, be used.

Continuing to refer to FIG. 55C, valves such as binary valves, vari-valves, or any of the valves described herein may, in some configurations, be supplied as modular that can be plugged into a manifold frame or base to provide pneumatic, hydraulic or electrical control of external devices, such as fluid flow control devices, heaters, motors, or hydraulic or pneumatic devices. Each valve module 2800 can include one or more valves 2802. Each valve module 2800 may include electronic components necessary to operate valves 2802 included in valve module 2800. The electronic components can include an electronic controller equipped to perform a number of programmed commands to the valves to allow valve module 2800 to actuate or control an external device in at least a partially autonomous manner. Valve module 2800 can include an assembly of one or more valves 2802 connected to one or more on-board PCBs 2808 populated with electronic components suitable for operating the valves autonomously or semi-autonomously with respect to a main or central controller. Some of the computing resources necessary to run valves 2802 can be performed by the on-board PCBs 2808, and others can be performed by a main processor of the controlled device, for example. The main processor can supply high level commands to valve module 2800 such as, for example, but not limited to, start commands, stop commands, pause/resume commands, commands to perform a measurement, commands to reverse liquid flow in an associated flow control device, commands to properly sequence the operation of on-board valves, commands to coordinate valve actions among a local group of modules, and commands to perform template functions pre-programmed on PCB 2808. PCB 2808 can command valve module 2800 to perform a valve function (e.g., opening or closing a port in a prescribed sequence or at a prescribed rate) in an autonomous manner without further input from an external controller.

Continuing to refer to FIG. 55C, in some configurations valve manifold module 2800 can include a plurality of valve assemblies 2802, and PCB 2808 may be configured such that all of the valves 2802 in the module 2800 may be operated using a common power source or bus. In some configurations, module 2800 can include multiple valve assemblies 2802, each of the valve assemblies 2802 being mounted on modular manifold base 2804 which can include or can be operably connected to manifold fluidic (hydraulic or pneumatic) flow paths (fluid buses) for valves 2802. An integrated manifold assembly can include a plurality of concatenated valve manifold modules 2800 that can be assembled (attached or connected together, for example by fasteners) and configured for control or operation of an external device, such as a liquid flow control device (e.g. pump and valve device for transfer of a liquid). A modular valve/manifold assembly can permit maintenance, repair or replacement of individual valve modules 2800 by plugging in or unplugging the valve module 2800 from the manifold. Each valve module 2800 can include a bank of valve assemblies 2802. Value assemblies can include ports and electrical connections and housing dimensions that can be sufficiently identical to be interchangeable among the designated receptacles in module 2800. Valve manifold module 2800 can be configured for operation of an external device having various features or functions, for example, but not limited to, various arrays of fluid flow control pumps and valves, and/or systems with various electronic, electrical, hydraulic or pneumatic functions.

Continuing to still further refer to FIG. 55C, each PCB 2808 may include, for example, a pressure sensor which is configured to read the pressure of a fluid volume in the module. In some configurations, the pressure sensors may read the pressure from wells in the module manifold or block 2804 where the wells can fluidically communicate with the fluid pathways in module block 2804. O-rings, gasketing, and/or another suitable seal, for example, may sealably isolate the volume of the wells in module block 2804 from the ambient environment. In some configurations, one or more o-rings and/or gaskets may be compressed to create the seal as PCB 2808 is coupled to module block 2804. In other configurations, the pressure sensors of PCB 2808 may communicate with the interior valve cavities of valves 2802 via any suitable fluid path. In some configurations, pressure sensors may be, for example, in fluid communication with the interior valve cavities directly through a fluid path in each of the respective valves 2802. In some configurations, pressure sensors may be in communication with the flow paths leading from outlets of values 2802 via a flow path through end blocks 2806 on the ends of module 2800. Other arrangements may also be used.

Continuing to refer to FIG. 55C, sensors, such as, for example, but not limited to, current sensors, may also be included on PCB 2808. Current sensors may be configured to sense the current running through the electromagnetic coils of valve 2802, for example. Data provided by the current sensors may allow for a determination to be made about whether or not valve 2802 is functioning properly. PCB 2808 may also be equipped to receive electronic signals from remote sensors, and to convert these signals to digital form using any suitable A/D converter mounted to on PCB 2808. Remote sensor signals may be received from remote pressure sensors, conductivity sensors, temperature sensors, air-in-line sensors, fluid level sensors, flow sensors, as well as other types of sensors depending on the application to which the valve/controller module is directed. A processor or processing components may be included on PCB 2808 and may allow valve module 2800 to autonomously execute various valve-related applications. Module 2800 may require little or no direction from an external processor included in the device in which module 2800 is installed. The processor or processing components of PCB 2808 may make use of and analyze data collected from other components (e.g. pressure sensors) of PCB 2808 to meet the needs of a particular application.

Continuing to refer to FIG. 55C, modules 2800 can be configured and programmed for particular applications. Modules 2800 may be programmed to perform a multiplicity of tasks. In some configurations, valve(s) 2802, PCB 2808, and other components of valve module 2800 may be overmolded together such that all of the components of module 2800 are physically attached to one another and form a single unit. In some configurations, module 2800 may be programmed to perform basic functions (e.g. coordinating the opening and closing of inlet and outlet valves while driving a pump, regulating the flow or pumping rate of the pump, detecting aberrant flow conditions, etc.), but may be automatically assigned more specific or detailed tasks upon connection of module 2800 to a communications control bus, such as a controller area network ('CAN') bus.

Figure 55D:
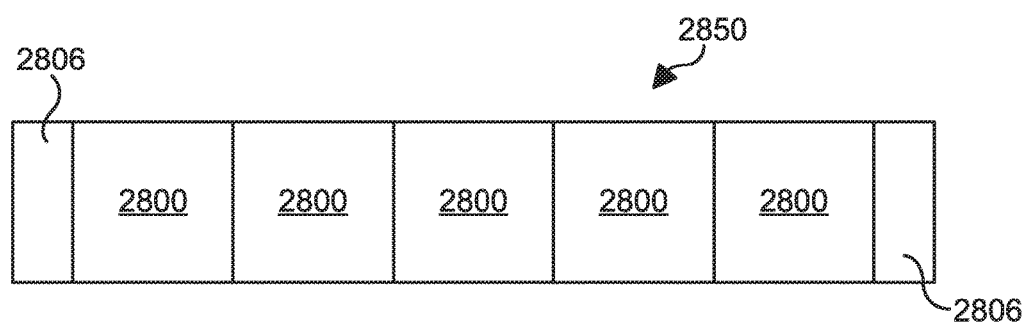
FIG. 55D is a schematic block diagram of a manifold including the valve modules of the present teachings.

Referring now to FIG. 55D, each module 2800 may be configured such that it may be connectable to another module 2800, allowing assembly of manifold 2850 configured for a particular application. Valve modules 2800 may be arranged such that fluid pathways of each module 2800 may be connectable or coupleable to fluid pathways of another module 2800. End blocks 2806 may be placed on the ends of manifold 2850 to allow assembled manifold 2850 to interface with other components such as a pressure reservoir or bus of a device, and electronic communication bus of a device, and/or a power bus of a device. An o-ring, gasket, and/or seal may be provided to ensure integrity of the fluid paths within manifold 2850.

Continuing to refer to FIG. 55D, the electronic components of each connected module 2800 may be placed into communication with one another, allowing connected modules 2800 to utilize power from a single source, for example, but not limited to, a device power bus. Connected modules 2800 can share and/or synchronize data such as, for example, valve state and pressure data. Modules 2800 that include various types of electronic components can operably communicate with each other and with controllers and other devices using any communication scheme, including, but not limited to, a CANbus. Each module 2800 may include a component (not shown) such as, for example, but not limited to, a resistor that can terminate manifold 2850 if module 2800 is located at a terminating position such as, for example, but not limited to, at the end of manifold 2850 and/or at the end of the CAN-bus communications chain.

Continuing to still further refer to FIG. 55D, manifold 2850 may communicate with other components of a device wirelessly or via wired connection to a device communication bus. In some configurations, manifold 2850 can be controlled remotely or wirelessly, and communications among modules 2800 can be wireless. In some configurations, each valve module 2800 may be configured to perform a full set of valve-related tasks or applications, but without a preset assigned functionality. Tasks may include, but are not limited to, synchronization of inter-modular operations, functioning as a master device of modules 2800 for multi-module manifold 2850, functioning as a pumping device of modules 2800 by supplying pressure to a pneumatically or hydraulically driven fluid pump, and/or functioning as a pneumatic or hydraulic valve controller by supplying pressure to a pneumatic/hydraulic valve interface. In some configurations, tasks may include, but are not limited to including, supplying pressure to an interface for a pumping cassette to effect pumping of fluid in the pumping cassette, supplying pressure to an interface for a pumping cassette to actuate valves of the pumping cassette, and/or supplying pressure to an interface for a pumping cassette to direct fluid flow through the pumping cassette.

Continuing to refer to FIG. 55D, as modules 2800 are added onto manifold 2850 that carries hydraulic or pneumatic supply lines, modules 2800 may be specialized to particular tasks and/or applications. The tasks and/or applications may be automatically determined by the location of module 2800 along an interconnected chain of modules 2800 on a communications bus. Further specialization may also be imposed during operation by a system controller as required by particular applications. For example, module 2800 that can act as a pumping module may be programmed to pump at a specific pressure or flow rate. In some configurations, the specific task assigned to a first of modules 2800 may be automatically assigned to a second of modules 2800 by (1) locating the second of modules 2800 in the same position along the chain of modules 2800 on the communications bus as the first of modules 2800 had been located, and/or (2) alerting a system controller to the location on the communications bus, for example, of the second of module 2800 by providing, for example, but not limited to, a unique identifier.

Continuing to refer to FIG. 55D, in some configurations, modules 2800 may self-identify and may be assigned a unique identifier after installation onto manifold 2850. A processor included on PCB 2808 of a master of modules 2800 may take a census of modules 2800 connected to one another in manifold 2850. Any module 2800 may be assigned as the master of modules 2800. The processor can update the census as additional modules 2800 are added to and removed from manifold 2850. The processor of the master of modules 2800 may also assign one or more specialization(s) to each module 2800 in manifold 2850. The specialization assigned may depend on the physical position of module 2800 on manifold 2850. In some configurations, when the census of is taken, each module 2800 may be assigned a unique identifier. The census may also determine the spatial arrangement of modules 2800. For example, a processor of the master of modules 2800 may determine, during the census, that a first of modules 2800 is first side of a second of modules and adjacent a first side of a third of modules 2800. The spatial arrangement can aid in automatic assignment of tasks to modules 2800. In some configurations, the spatial arrangement may be implied from identities of modules 2800.

Continuing to refer to FIG. 55D, in some configurations, modules 2800 that are added to manifold 2850 either to replace modules 2800 or add modules to manifold 2850 may automatically self-identify. For example, if a first of modules 2800 needs to be replaced with a second of modules 2800, the processor of the master of modules 2800 may detect when the second of modules 2800 has been installed, and may automatically assign the identity, including the tasks, of the first of modules 2800 to the second of modules 2800. The second of modules 2800 may determine its own identity and tasks. The second of modules 2800 can execute commands issued for the first of modules 2800, and can communicate with others of modules 2800. In some configurations, fault conditions may be communicated between modules 2800 within manifold 2850, and manifold 2850 can adapt to faults. In some configurations, a processor of a master of modules 2800 may command that manifold 2850 operate in a "limp home" mode if particular fault conditions occur. For example, if manifold 2850 includes a first and a second of modules 2800 and the first of modules 2800 has a fault, the processor of the master of modules 2800 may command modules 2800 of manifold 2850 to continue pumping with the second of modules 2800.

Continuing to refer to FIG. 55D, if a communications bus of manifold 2850 has a fault and is interrupted, and if the power bus remains functional, modules 2800 of manifold 2850 may identify the fault and switch to operation in a fail safe mode. Fluid valves may, for example, be commanded to automatically close. Any other desirable fail safe mode could also be implemented. For example, module 2800 could be programmed to continue pumping of fluid at a previously programmed or commanded flow rate. In this way, the failure of one of modules 2800 in manifold 2850 may allow the system to wind down in an orderly manner. For example, a blood pump module could be allowed to continue to operate for a designated period of time if a dialysate pump module were to fail in a hemodialysis system.

Continuing to refer to FIG. 55D, in some configurations, modules 2800 may detect and react to various conditions. For example, in configurations where at least one of modules 2800 of manifold 2850 is a pumping module, a processor of module 2800 may detect flow condition-related information. If an abnormal flow condition, for example, but not limited to, reduced flow or no flow, is detected, module 2800 may arrange for and/or perform troubleshooting, and/or may request that the processor of the master of modules 2800 command that troubleshooting be performed. Troubleshooting may determine, for example, if an occlusion exists. Manifold 2850 may then cease pumping and signal that an error condition exists if an occlusion is detected.

Figure 55E:
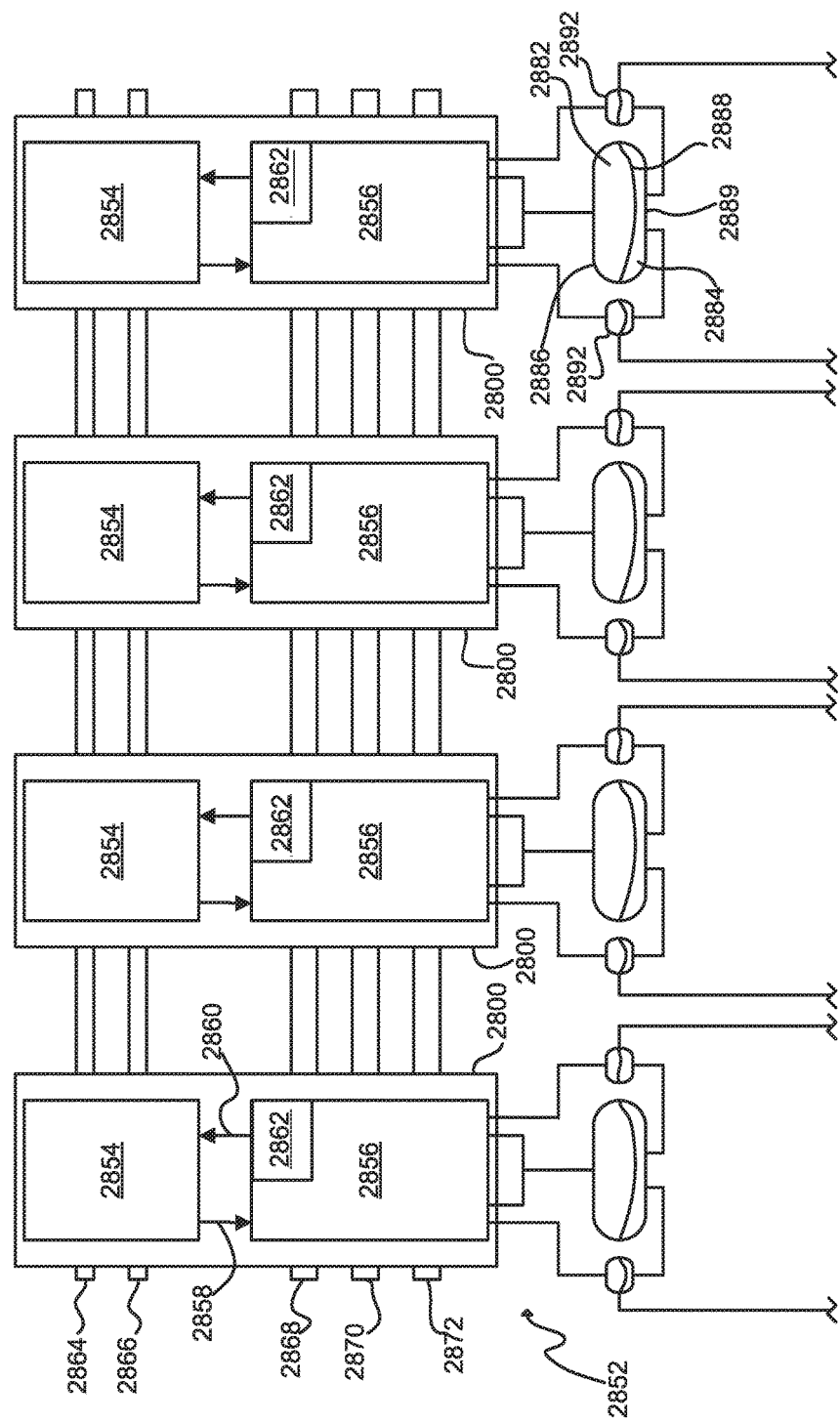
FIG. 55E-55I are a schematic block diagrams of a pneumatic pump/valve systems controlled by the manifold assemblies of the present teachings.

Referring now to FIG. 55E, pneumatic system 2852 can include a number of valve modules 2800. Each module 2800 can include controller 2854 which may be included on PCB 2808 (FIG. 55C) of module 2800. Each module 2800 can include pneumatic block 2856. Pneumatic block 2856 may include various pneumatic components of module 2800 such as one or more valves 2802 (FIG. 55C), module block 2804 (FIG. 55C) including fluid flow paths, and end block 2806 (FIG. 55C) if module 2800 is at the end of multi-module manifold 2850 (FIG. 55D). Each module 2800 may connect to various buses of a device. Data/communications bus 2864 may allow for data and/or commands to be communicated from module 2800 to module 2800 within multi-module manifold 2850 (FIG. 55D) to enable synchronization and coordination of module 2800 activities in multi-module manifold 2850 (FIG. 55D). Commands and/or data may be conveyed to/from manifold 2950 (FIG. 55D) to an external board or processor via data/communications bus 2864. Power bus 2866 may supply power to modules 2800 in manifold 2850 (FIG. 55D). Power may pass to manifold 2850 (FIG. 55D) via power bus 2866 from a source external to manifold 2850 (FIG. 55D). Data/communication bus 2864 and power bus 2866 may be operably coupled to PCB 2808 (FIG. 55C).

Continuing to refer to FIG. 55E, first pneumatic buses 2868, second pneumatic buses 2870, and third pneumatic bus 2872 may each be connected to a pressure reservoir. The pressure of the pressure reservoir can be different from the pressure of pneumatic busses 2868, 2870, 2872. Pneumatic buses 2868, 2870, 2872 may be operably coupled to end block 2806 (FIG. 55C) of multi-module manifold 2850 (FIG. 55D). Pneumatic buses 2868, 2870, 2872 may be operably coupled with pneumatic block 2856 of module 2800. The connection between module 2800 and pneumatic busses 2868, 2870, 2872 can be plug and play. If module 2800 includes operable connection with any of pneumatic buses 2868, 2870, 2872, an identity for module 2800 may be determined and module 2800 can be ready for operation.

Continuing to refer to FIG. 55E, As represented by the buses of the FIG. 55E running through each module 2800 and on to the next, each bus may be conveyed through the modules 2800 of a multi-module manifold. Electrical power and data communication may be conveyed through a module to module connector on a PCB 2808 (see, for example, FIG. 55C) of each module 2800. Pneumatic buses 2868, 2870, 2872 may be conveyed through bus flow paths in a first of pneumatic blocks 2856. The bus flow paths can align with bus flow paths on a second of pneumatic blocks 2856. Each module 2800 in manifold 2850 (FIG. 55D) may be individually connected to any of pneumatic buses 2868, 2870, 2872. In some configurations, pneumatic buses 2868, 2870, 2872 may be in fluid communication with selected of modules 2800 of manifold 2850 (FIG. 55D). In some configurations, modules 2800 may have occludable ports to pneumatic block 2856, or may be constructed with a limited array of ports. Controller 2854 of each module 2800 may issue valve commands 2858 to control valve(s) 2802 (FIG. 55C) of module 2800. Controller 2854 may receive data 2860 from one or more sensor(s) 2862 in module 2800. Sensor(s) 2862 can, for example, but not limited to, sense the pressure of flow paths within pneumatic block 2856. Sensor data 2860 may be used by controller 2854 to inform control of valve(s) 2802 (FIG. 55C). In some configurations, each module 2800 can identify as a pumping module, and controller 2854 may control module 2800 to cause fluid to be pumped by pneumatic system 2852.

Continuing to refer to FIG. 55E, a change in volume of first variable volume 2882 may cause a change in volume of second variable volume 2884. An increase in volume of first variable volume 2882 may cause a corresponding decrease in volume of second variable volume 2884. A decrease in volume of first variable volume 2882 may cause an increase in volume of second variable volume 2884. Two pneumatically driven inlet/outlet valves 2892 for second variable volume 2884 may be actuated to allow variable volumes 2882, 2884 to change in volume.

Continuing to refer to FIG. 55E, first variable volume 2882 and two inlet/outlet valves 2892 can be operably connected to the outputs of their respective modules 2800. Valves 2802 (FIG. 55C) of each module 2800 may be actuated to increase or decrease the volume of first variable volume 2882. When the volume of first variable volume 2882 is decreased, one inlet/outlet valve 2802 is open, and the other inlet/outlet valve 2892 is closed, fluid will be drawn into second variable volume 2884. When the volume of first variable volume 2882 is increased, one inlet/outlet valve 2892 is closed, and inlet/outlet valve 2892 is open, fluid will be forced out of second variable volume 2884. Pumping of fluid in either direction may be accomplished by appropriate actuation of inlet/outlet valves 2892.

Continuing to refer to FIG. 55E, first and second variable volumes 2882, 2894 may be configured in any suitable arrangement which would allow a change in volume in one to be tied to a change in volume of the other. For example, first variable volume 2882 may surround or be surrounded by second variable volume 2884. In some configurations, first variable volume 2882 may be separated from second variable volume 2884 by a displaceable intermediary structure which can act on second variable volume 2884 as first variable volume 2882 increases or decreases in volume. The intermediary structure can include, but is not limited to including, a piston, an arm, and a lever. First and second variable volume 2882, 2884 may be separated from one another by displaceable wall 2888 that can include, but is not limited to including, a diaphragm and a membrane made of a flexible material.

Continuing to refer to FIG. 55E, there can be any number of variable volumes, and, in some configurations, a change in volume of first variable volume 2882 may cause a change in volume of a plurality of other variable volumes. Likewise, change in volume of a plurality of variable volumes may cause a change in volume of, for example, but not limited to, first variable volume 2882. First variable volume 2882 can be defined by fixed wall 2886 and displaceable wall 2888. Second variable volume 2884 can be adjacent to first variable volume 2882 and can be defined by second fixed wall 2889 and displaceable wall 2888. As the volume of first variable volume 2882 increases, displaceable wall 2888 can be pushed toward second fixed wall 2889. As the volume of first variable volume 2882 decreases, displaceable wall 2888 can be pulled toward first fixed wall 2886.

Figure 55F:
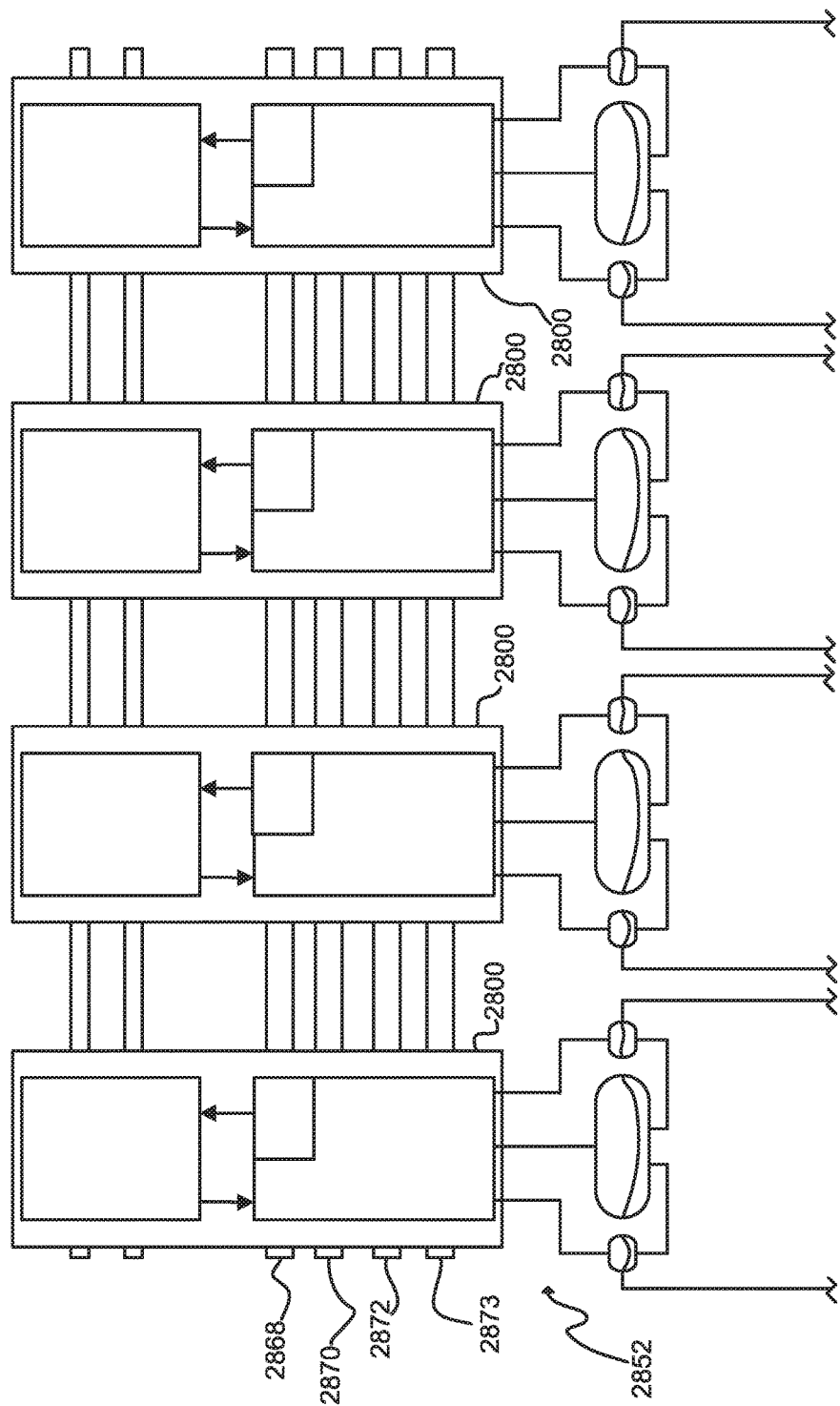

Referring now to FIG. 55F, fourth pneumatic bus 2873 may be connected to a vent reservoir such as the atmosphere. Pneumatic buses 2868, 2870, 2872 may be connected to pressure reservoirs. In some configurations, first pneumatic bus 2868 may be connected to a negative pressure reservoir, second pneumatic bus 2870 may be connected to a low positive pressure reservoir, and third pneumatic bus 2872 may be connected to a high positive pressure reservoir. Fourth pneumatic bus 2873 acting as a vent to the atmosphere may minimize the amount of pumping necessary to maintain reservoirs for buses 2868, 2870, 2872. For example, when switching a volume from positive pressure to a negative pressure or vice versa, it may be desirable to vent the volume to ambient pressure to lower the pressure difference between the volume and the reservoir. Any number of pneumatic and electrical buses may be included in various configurations.

Figure 55G:
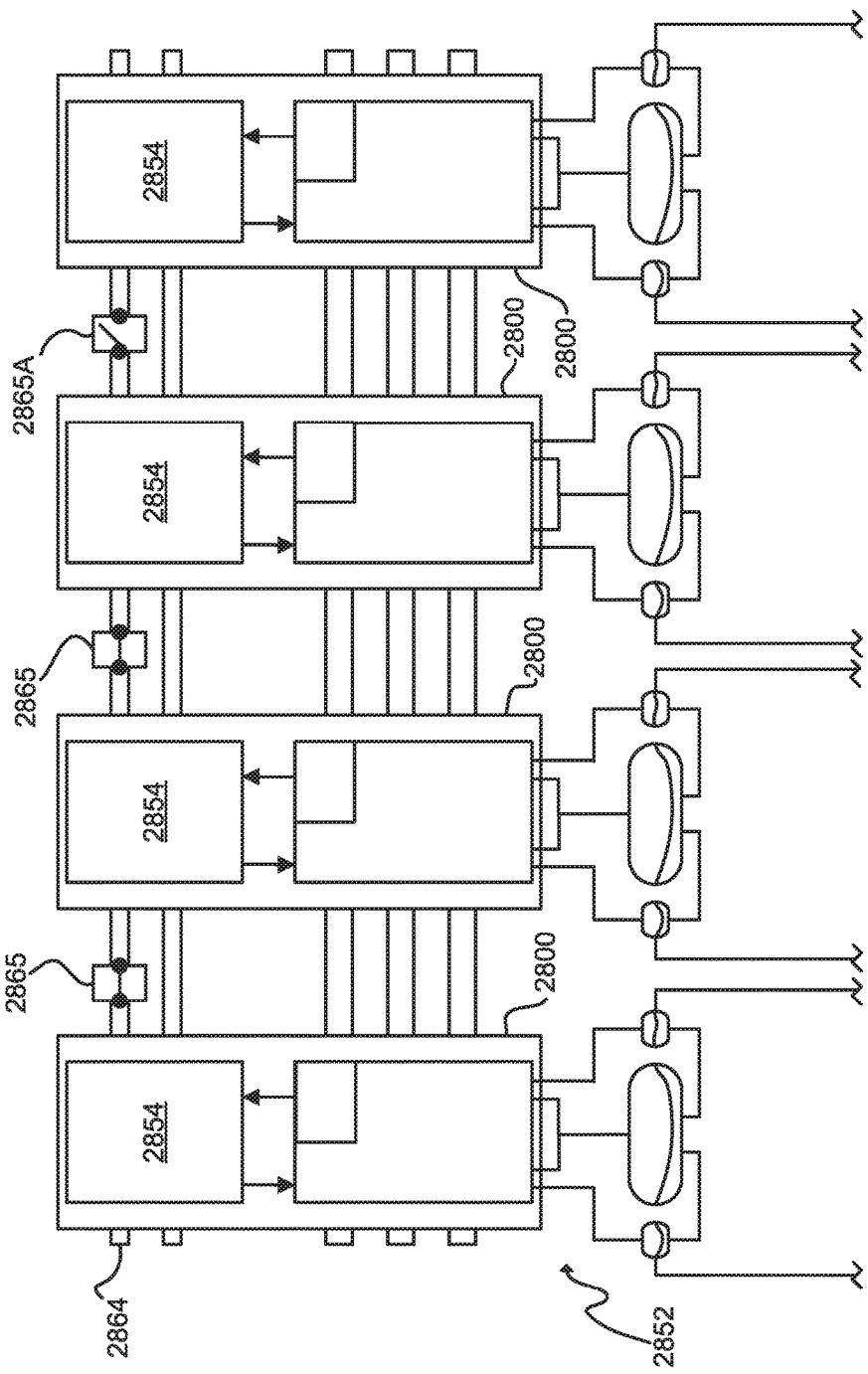

Referring now to FIG. 55G, module to module connectors 2865 on data/communication bus 2864 can include cooperating pieces of hardware on each module 2800. Connectors 2865 can create an electrical communication pathway between modules 2800. Controller 2854 can interrupt communications between modules 2800 by toggling switch 2865A. Communications can be interrupted when, for example, but not limited to, a manifold is self-defining or when a new of modules 2800 is being installed in the manifold. In some configurations, module 2800 may interrupt communications in a first direction while maintaining communications in a second direction. Communications may be interrupted as a default configuration of module 2800 upon installation into a manifold. When communication has been interrupted, in some configurations, a terminating resistor on module 2800 may also be switched in.

Continuing to refer to FIG. 55G, each message sent on the data/communication bus 2864 may be uniquely marked according to the module 2800 from which it originated. After interrupting communications, module 2800 may then poll modules 2800 on the portion of the manifold that module 2800 is still in communication with. Modules 2800 may respond to new module 2800 and new module 2800 can determine its identity or function based upon the responses received. For example, if module 2800 only receives responses from modules 1 and 2, new module 2800 can determine that it must be module 3. Messages addressed with the unique marker for module 3 may be received and acted upon by new module 2800. Communication with the rest of the manifold may be reestablished and next module 2800 may repeat the process to determine its identity or function, and so on. When communications are reestablished, a terminal resistor included on newly self-identified module 2800 may also be switched off.

Continuing to refer to FIG. 55G, after module 2800 interrupts communications to one side of the manifold, module 2800 may wait for a period of time and receive messages sent across data/communication bus 2864. Module 2800 may determine its identity or function based upon the unique markers of the messages sent across the data/communication bus 2864. If new module 2800 receives messages from module 1 and 2, new module 2800 may determine that it is module 3. As above, communication with the rest of the manifold may be reestablished and this process may repeat until each module 2800 in a manifold has self-identified. A terminal resistor which may be switched in and out may be included on each module 2800. Any other process involving interruption of the communication bus to facilitate self-identification of modules 2800 in a multi-module manifold may also be used. In some configurations, the process may be conducted or coordinated by a master controller in the manifold.

Figure 55H:
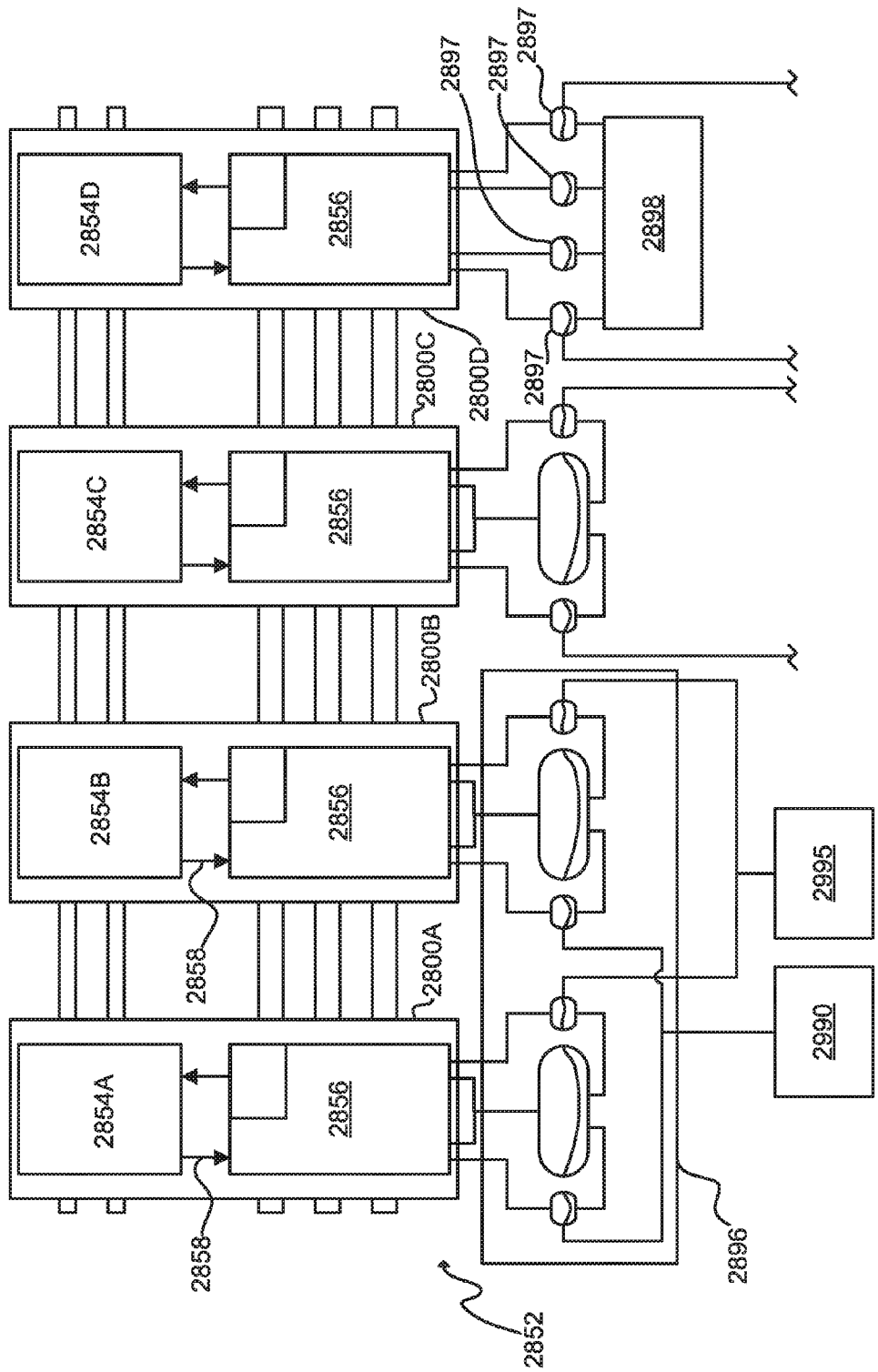

Referring now to FIG. 55H, a number of modules 2800 can perform a plurality of different valve-related tasks. Module 2800C can include a pumping module. Modules 2800A and 2800B can control two-chamber fluid pump 2896. Controllers 2854A and 2854B may operate in tandem, coordinating or synchronizing pumping operations between one another to optimize fluid throughput and/or achieve substantially continuous pumping, for example. Controllers 2854A, 2854B, 2854C, 2854D may communicate over the data/communication bus 2864 to synchronize with one another. Each of controllers 2854A, 2854B may send commands 2858 to pneumatic blocks 2856A, 2856B to effect pumping of fluid in chambers of the fluid pumps of modules 2800A, 2800B. In some configurations, controller 2854A, for example, may be synchronized to command filling of its associated chamber while the controller 2854B commands delivery of its associated chamber. Thus fluid may be pumped to one of first reservoir 2890 or second reservoir 2895 substantially continuously from one of second reservoir 2895 or first reservoir 2890. Modules 2800A, 2800B, 2800C, 2800D may coordinate to synchronize operations between a greater number of fluid pumping chambers as well. For example, a three chamber fluid pump may be controlled by modules 2800A, 2800B, 2800C that can communicate over data/communication bus 2864 to synchronize pumping.

Figure 55I:
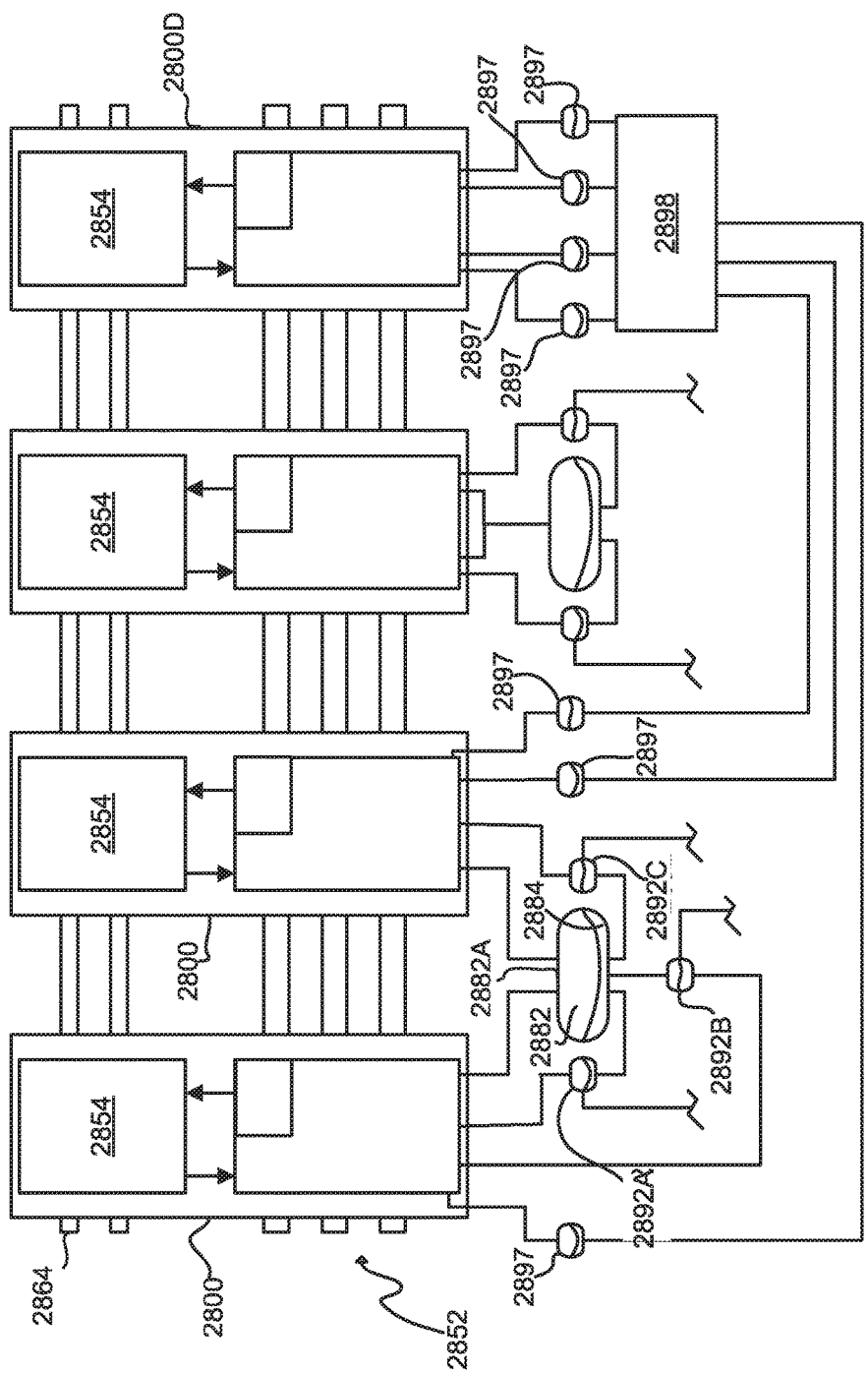

Referring now to FIG. 55I, module 2800D can be configured as a pneumatic (or, in some configurations, hydraulic) valve module that can control valves. The outputs of module 2800D can be connected to a number of fluid valves 2897 that can control fluid communication to various fluid pathways 2898 in the pneumatic system. Any number of fluid valves 2897 can be included. Depending on the number of valves included in module 2800, the number of fluid valves 2897 that module 2800D can control independently can depend on the number of valves in module 2800. System can include modules 2800A, 2800B, 2800C, 2800D that can perform a plurality of exemplary valve related tasks including fluid pumping and actuation of pneumatic fluid valve 2897. Modules 2800A, 2800B can cooperatively control fluid pump 2882A. For example, module 2800A may provide fluid at a first negative pressure and a second negative pressure while module 2800B may provide fluid at a first positive pressure and a second positive pressure. Module 2800A can control the state of inlet/outlet valves 2892A, 2892B of the second variable volume 2884 of fluid pump 2882A. Module 2800A can control a pressure input to first variable volume 2882 of fluid pump 2882A. Module 2800B can control another pressure input to first variable volume 2882 as well as inlet/outlet valve 2892C of second variable volume 2884. To coordinate pumping operations for the fluid pump, processor 2854 of modules 2800A, 2800B may synchronize valve activity related to fluid pump 2882A over data/communication bus 2864. Synchronization can allow a manifold assembled from modules 2800A, 2800B each including four valves 2802 (FIG. 55C) to run a fluid pump requiring five valves 2802 (FIG. 55C). Modules 2800 (FIG. 55C) may be modified to control a wide range of components or devices, for example, but not limited to, hydraulically actuated pumps and/or valves, in which manifold valve module 2800 can make a hydraulic connection to one or more pressurized hydraulic lines in a system, using, for example, quick-connect fittings.

Figure 55J:
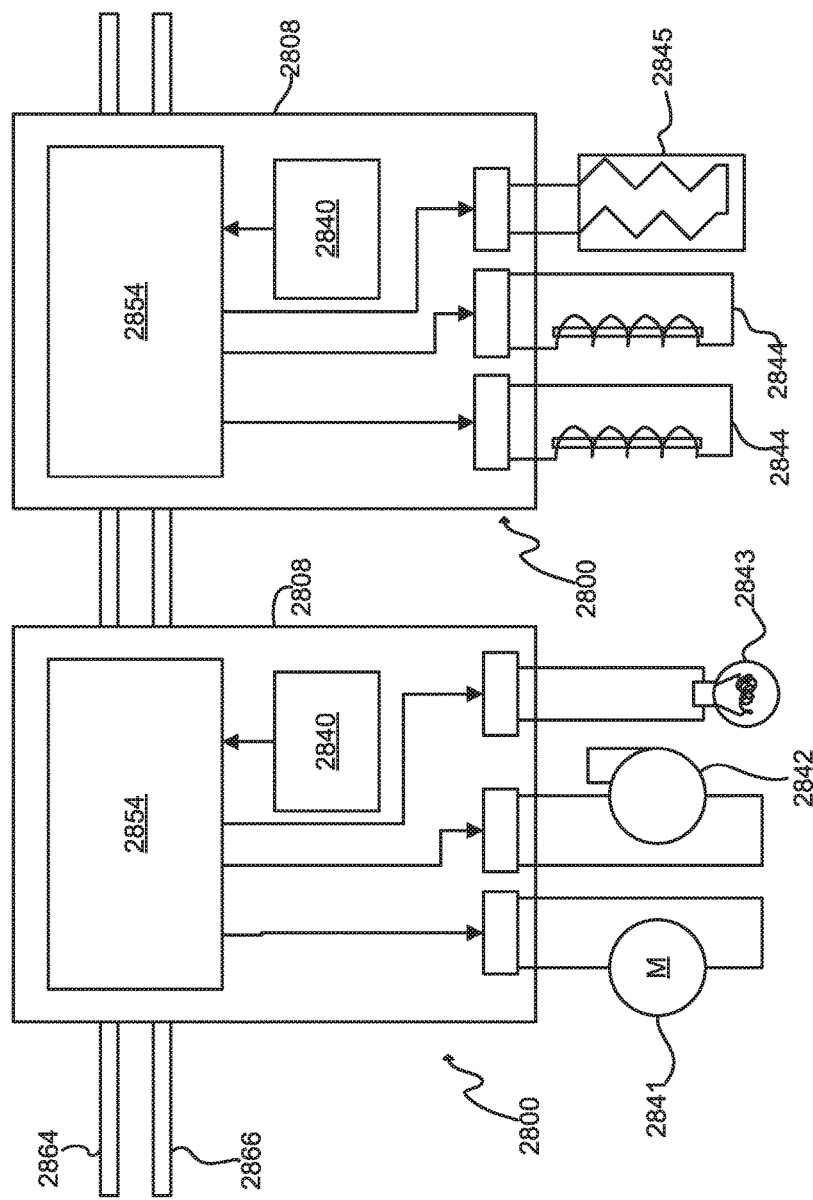
FIG. 55J is a schematic block diagram of a manifold assembly controlling a variety of electrical and/or electronic components and/or devices.

Referring now to FIG. 55J, module 2800 may include PCB 2808. PCB 2808 can include, but is not limited to including, processor 2854 that can be programmed to automatically command operation of one or more motors 2841. PCB 2808 may include electrical outputs to each winding of motor 2841. In some configurations, motor 2841 and PCB 2808 may be included as a single package and the PCB 2808 may be overmolded onto a portion of the motor 2841. Module 2800 may automatically control operation of one or more pump 2842. PCB 2808 may include electrical outputs which can interface with pump 2842. In some configurations, pump 2842 and PCB 2808 may be included as a single package and PCB 2808 may be overmolded onto a portion of pump 2842. Module 2800 may be programmed to control illumination of one or more light emitters 2843.

Continuing to refer to FIG. 55J, PCB 2808 can include controller 2854 that can be programmed to control operation of one or more electromagnets 2844 based. PCB 2808 may include an electrical output that can interface with the contacts of electromagnets 2844 to energize electromagnets 2844. Modules 2800 may automatically control operation of one or more heater elements 2845. In some configurations, PCB 2808 can include controller 2854 that can switch current flow through heater element 2845 on and off based upon a pre-defined program or commands from an external main controller. For example, the main controller may command heater element 2845 to warm a surface to a temperature set point. Module 2800 may execute the necessary control functions to raise the temperature of the surface to the commanded temperature set point using heater element 2845 and feedback signals from a temperature sensor. Controller 2854 can provide analog control of heater element 2845, or digital control through, for example, application of pulse-width-modulated current to the heater element 2845. In some configurations, module 2800 may control a relay making or breaking a connection between a current source and heater element 2845. This may be desirable in scenarios in which heater element 2845 is run at high voltages (e.g. mains voltage). Modules 2800 may control relays such as high speed digital devices, for example, thyristors, TRIACS, or silicon controlled rectifiers.

Continuing to refer to FIG. 55J, PCB 2808 can interface with and/or include a variety of sensors 2840 suited for particular applications. For example, sensors 2840 may include current sensors, temperature sensors, pressure sensors, encoders, optical sensors, magnetic sensors, inertial sensors, or any other sensor required by an application executing on module 2800. Modules 2800 used for control of other devices or components can share power transmitted through shared power bus 2866. Modules 2800 can coordinate or synchronize operation via shared data/communication bus 2864. Coordination may be between similar and/or dissimilar devices or components. Coordination may limit and/or manage peak power loads.

Figure 55K:
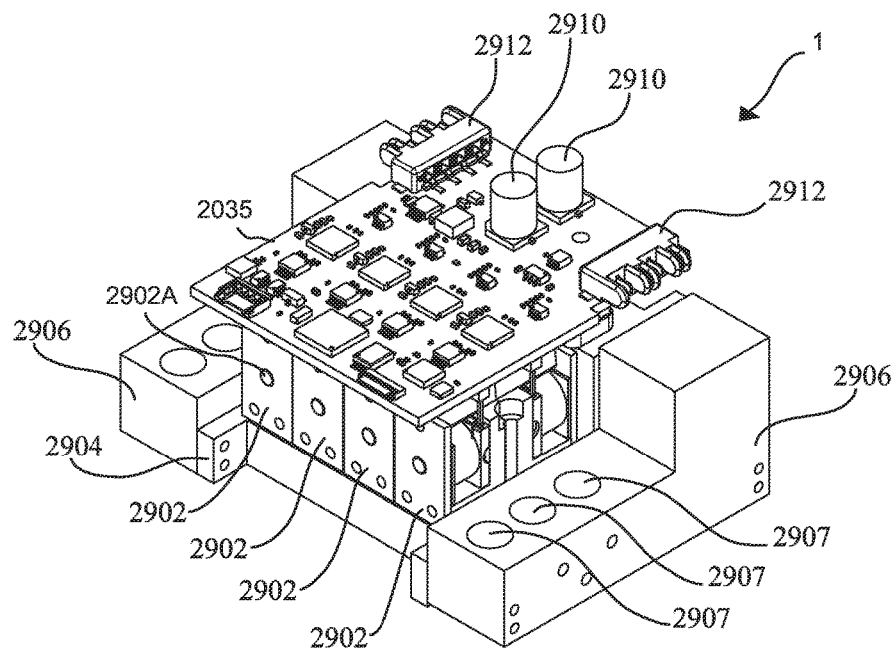
FIG. 55K is a perspective view of a programmable valved manifold module.

Referring now to FIG. 55K, in some configurations, module 1 (and any of modules 1-17 (FIG. 55P)) can include, for example, four valve assemblies 2902, but any number of valve assemblies 2902 can be included. Valve assemblies 2902 can include any of a variety of types of valves including binary valves, variable valves, or bi-stable valves. Valve assemblies 2902 can be mounted on manifold module base or block 2904. Module block 2904 can include a number of fluid channels or flow paths that can interface with the fluid inlets and outlets of each valve assembly 2902. Module block 2904 can form a manifold for valve assembly 2902. In some configurations, one of the inlet ports for one or more valve assemblies 2902 can be blocked. If valve assembly 2902 includes a bi-stable valve, blocking valve assembly 2902 can allow the bi-stable valve to function as a two-way valve. Module base or block 2904 may include one or more flow paths that can convey pressurized fluid (e.g. pneumatic or hydraulic) from a pressurized fluid source line to a series of interconnected manifold modules. The one or more flow paths can also be known as fluid busses. Any number of modules 1-17 (FIG. 55P) can be concatenated or connected, for example, in series. Each of modules 1-17 (FIG. 55P) can have a fluid bus connecting a pressure line inlet port 2907 on one side of the module to a pressure line outlet port 2907 on another side of the module. Modules 1-17 (FIG. 55P) can be connected together by standard fasteners, with inlet and outlet ports 2907 joined via gaskets or O-rings, for example. Manifold module end blocks 2906 can be operably connected to manifold 700 (FIG. 55P) that can be assembled from a number of valve modules 1-17 (FIG. 55P). End blocks 2906 can include connection ports 2907 connecting one or more pressure line inputs or outputs 706/708/710 (FIG. 55P) to corresponding pressure line input or output ports 2907 of each of valve modules 1-17 (FIG. 55P). In some configurations, connection ports 2907 may enable connection to pressurized fluidic components such as, for example, but not limited to, pneumatic lines and/or buses from one or more positive pressure sources or reservoirs, negative pressure reservoirs, a vented source or reservoir (e.g. atmosphere), or other reservoir. Any suitable connector fitting may be incorporated into connection ports 2907, including, for example, but not limited to, quick-connect fittings. Unused of connection ports 2907 may be plugged, blocked, or otherwise sealed off. In some configurations, three connection ports 2907 can be included. In some configurations, any number of connection ports 2907 can be included. In some configurations, module end blocks 2906 may terminate a series or bank of connected of modules 1-17 (FIG. 55P), and connection ports 2907 can be closed or blocked. In some configurations, connection ports 2907 including end blocks 2906 that terminate connected of modules 1-17 (FIG. 55P) can include connections to one or more fluid lines leading to one of end blocks 2906 forming an input block of another bank of manifolds 700 (FIG. 55P) in a larger manifold assembly.

Continuing to refer to FIG. 55K, controller board (PCB) 2035 can include capacitors 2910 that can have a capacitance sufficient to power valves 2902 to a known or desired state in the event that power to any of modules 1-17 (FIG. 55P) is lost. If the electrical power and/or communications bus voltage of a device operably connected to PCB 2035 drops below a predetermined level, valve(s) 2902 may be transitioned to a pre-determined configuration, for example, but not limited to, a valve state that closes a specified fluid port or opens a specified fluid port. The pre-determined configuration can represent a fail-safe configuration for an apparatus controlled by any of modules 1-17 (FIG. 55P). The apparatus can include, but is not limited to including, a fluid flow control device such as a pump and/or valves in a medical device. Capacitors 2910 can transition valve(s) 2902 to the pre-determined configuration if power is lost.

Figure 55L:
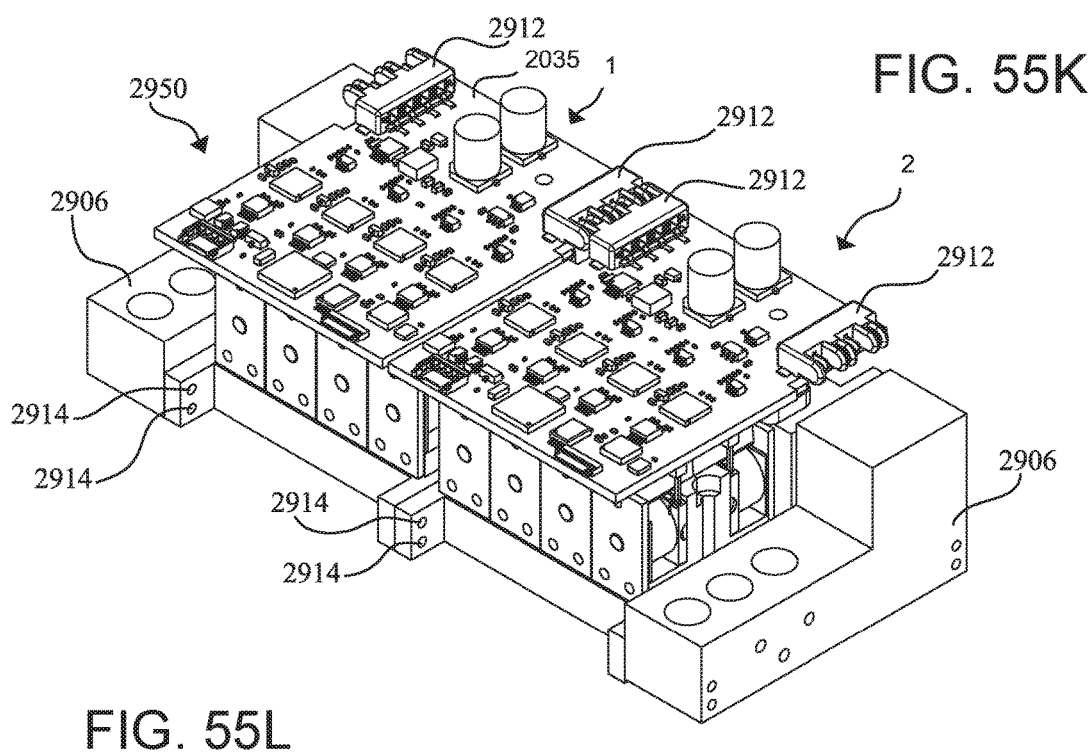
FIG. 55L is a perspective view of two connected or concatenated programmable valved manifold modules.

Referring now primarily to FIG. 55K, each module block 2904 may include one or more coupling features that can facilitate connecting modules 1-17 (FIG. 55P) together to form a bank of modules 1-17 (FIG. 55P) or manifold assembly 2950 (FIG. 55L). In some configurations, module blocks 2904 can include holes 2914 (FIG. 55L) through which a fastener (not shown) may be placed to couple module blocks 2904 together. The fastener may be any variety of fastener. A fastener may also be used to couple end blocks 2906 of manifold 2950 (FIG. 55L) to any of valve modules 1-17 (FIG. 55P). Where various fluid pathways between valves 2902, module blocks 2904, and/or end blocks 2906 interface with one another, a sealing member such as an o-ring, gasket, or the like may be used to ensure leak-free connections. In some configurations, module bases or blocks 2904 can be operably configured side-to-side, aligning pressure line input ports (not shown) and pressure line output ports (not shown) of adjacent of blocks 2904. Blocks 2904 can be fastened together using, for example, but not limited to, gaskets and/or O-rings to form a seal between the input and output ports (not shown). One or more valve assemblies 2902 can be installed in each of modules 1-17 (FIG. 55P), either before or after modules 1-17 (FIG. 55P) are concatenated. Valve assemblies 2902 can be positioned in operable communication with receiving stations (not shown) on manifold base or block 2904. Inlets (not shown) of valve assemblies 2902 can be aligned with pressure ports (not shown) that can enable communication with a fluidic pressure bus in module block 2904. Outlet (not shown) of each valve assembly 2902 can be aligned with a port (not shown) on module block 2906 that can enable fluid communication with an outlet of module block 2904. A gasket can be interposed between a face of valve assembly 2902 and a mating receiving face of module block 2904. In some configurations, the gasket can include a variable number of ports. In some configurations, module blocks 2904 can be interconnected, valve assemblies 2902 can be installed, and PCB 2035 can be mounted on each of modules 1-17 (FIG. 55P) and valve assemblies 2902. In some configurations, each PCB 2035 can be installed on module block 2906 before any of modules 1-17 (FIG. 55P) are interconnected, forming an expandable assemblage 2950 having standardized fluidic and electronic inputs, outputs, valve mating dimensions and similar of PCBs 2035.

Referring now to FIG. 55L, a series of interconnected (or bank) of manifold modules 1,2 can include interconnected PCBs 2035 through connector 2912 that can enable data and/or power communications and/or power bus between modules 1,2. Each of manifold modules 1,2 can be assigned a specific task or set of tasks, and/or PCBs 2035 can establish a 'master-slave' or primary-secondary hierarchical relationship. Through the transmission of identifying data to or from each PCB 2035, any or all of the PCBs 2035 can detect the presence of and/or function of any other module 1,2 in the bank or in an entire manifold assembly 2950. If a controlled device has a plurality of functions or plurality of pump/valve combinations, a primary PCB 2035 can be assigned, which can then coordinate or synchronize the functions of a group of secondary modules 1,2 with respect to the controlled device. In some configurations, a linked group of modules 1,2 can include a subset of manifold modules 1-17 (FIG. 55P) in a bank or manifold assembly 2950.

Figure 55M:
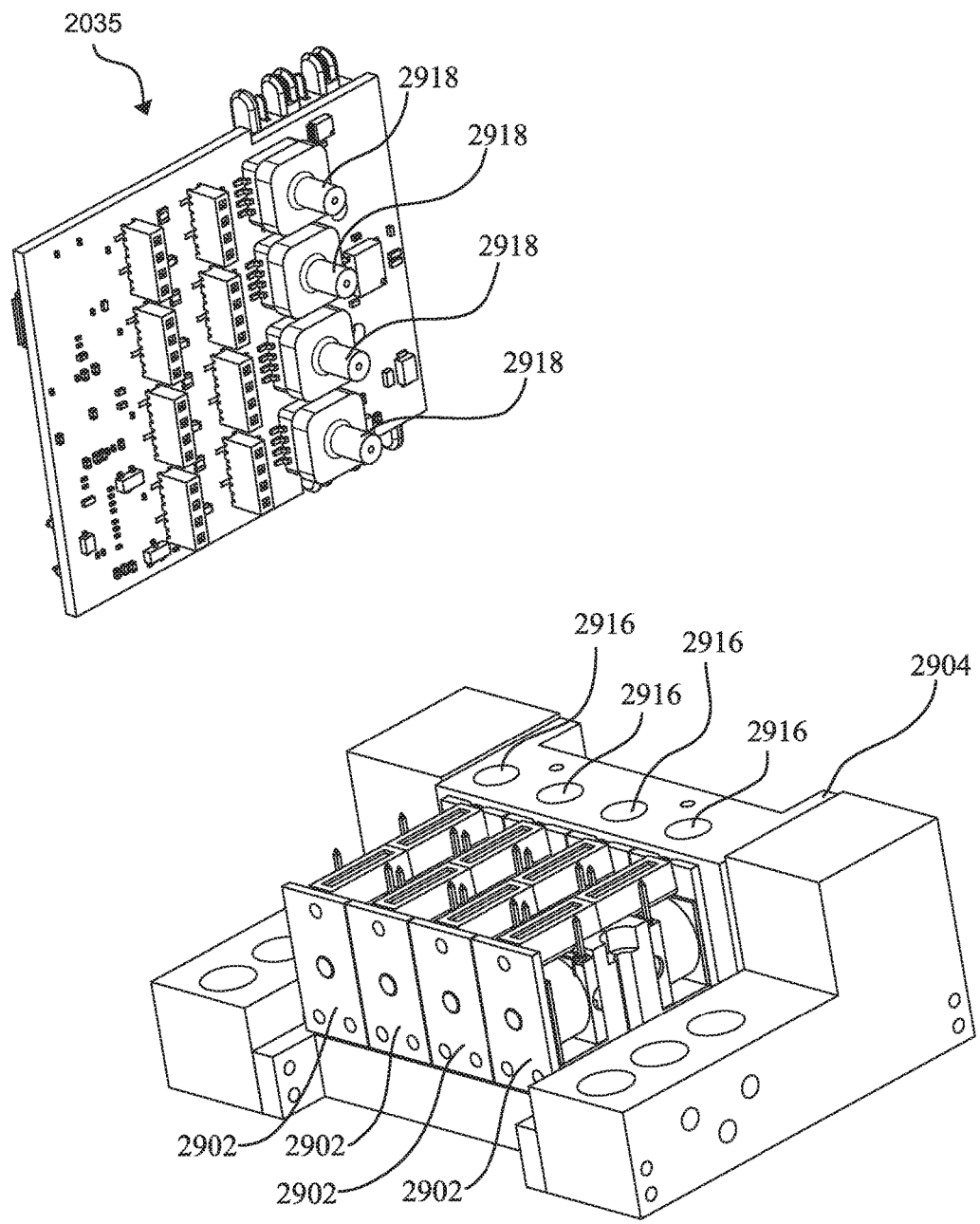
FIG. 55M is a perspective view of a programmable valved manifold module with the controller board disconnected from the valve assemblies and the module base.

Referring now to FIG. 55M, PCB 2035 can include components such as, for example, but not limited to, field programmable gate arrays, microprocessor chips, and/or a combination thereof. The components are can provide, for example, but not limited to, pressure data from on-board pressure sensors 2918 connectable to ports 2916 providing an interface with valve cavities 2902A (FIG. 55K) of valve assemblies 2902 (FIG. 55K). Pressure sensors 2918 can be aligned with pressure sensing ports or wells 2916 on module block 2904. Pressure sensors 2918 can communicate with the cavity (not shown) of valve assembly 2902. If electromagnetic coils are mounted on valve assembly 2902, electrodes on PCB 2035 can be aligned with corresponding receptacles or electrodes connected to the coils. Valve assemblies 2902 can be securely fastened to module block 2904, and PCB 2035 can be securely fastened to module block 2904 using fasteners, for example, but not limited to, screws. In some configurations, each of modules 1-17 (FIG. 55P) can have four valve receiving stations 2916 onto which PCB 2035 can position four pressure sensors 2918—one for each installed valve assembly 2902. Each of modules 1-17 (FIG. 55P) can have a fewer or greater number of receiving stations.

Continuing to refer to FIG. 55M, each of sensing wells 2916 can be in fluid communication with the interior valve cavity (not shown) of one of valves 2902. Sensing wells 2916 can enable pressure sensors 2918 on PCB 2035 to sense the pressure of the interior cavity (not shown) of valves 2902. The valve cavity pressure may be measured periodically or monitored in real time, acquired and stored by PCB 2035, and/or used by PCB 2035 to control valves 2902. Valves 2902 can be directed to perform tasks such as, for example, but not limited to, selected delivery of one or another pressurized fluid (e.g. air) to a device, such as a pump and/or valve. If valve 2902 controls a single pressure line, or if valve 2902 can simultaneously block more than one pressure line, PCB 2305 can receive pressure data that can represent the pressure present in a device, for example, the valve cavity (not shown) can be in fluid communication with a control chamber, for example, of a controlled membrane pump. Any of valve modules 1-17 (FIG. 55P) can be assigned the task of a pumping module. In some configurations, the pressure data can be used to determine, among other things, an amount of liquid transferred and a flow rate of the liquid being transferred in the liquid flow control apparatus.

Figure 55N:
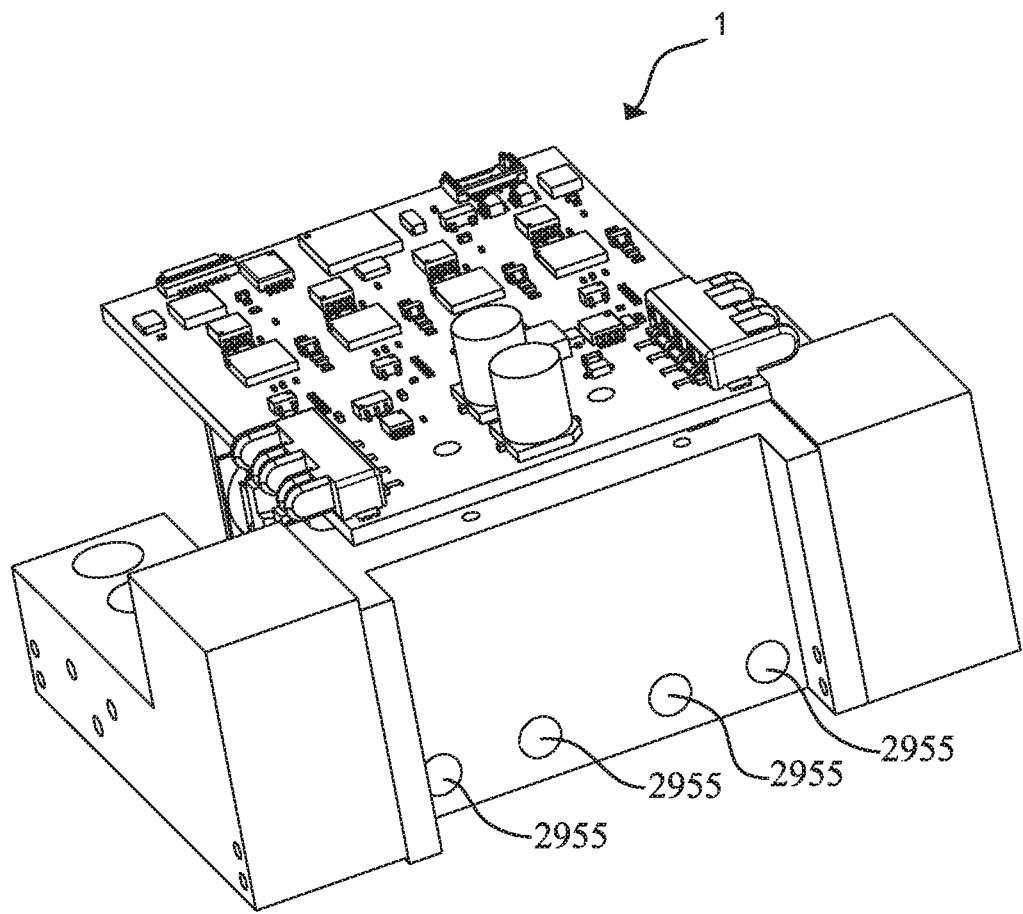
FIG. 55N is a perspective view of a programmable valved manifold module having pneumatic output lines of the module.

Referring now primarily to FIG. 55N, four-valve manifold modules 1-17 (FIG. 55P) can function independently to operate a single pump. For example, a liquid inlet valve and outlet valve of the pump can each be assigned and connected to the output of a separate manifold valve assembly 2902 (FIG. 55K), which can toggle between a positive fluidic pressure bus and negative fluidic pressure bus in any of modules 1-17 (FIG. 55P) to either close or open the inlet/outlet pump valve. Third manifold valve 2902 (FIG. 55K) can be arranged to toggle on or off a connection of the positive pressure bus to the pump control chamber to perform a pump deliver stroke, and fourth manifold valve 2902 (FIG. 55K) can be arranged to toggle on or off a connection of the negative pressure bus to the pump control chamber to perform a pump fill stroke. The pump control manifold valves can be converted to two-way valves (on/off) by installing them on module block 2904 (FIG. 55K) using a gasket having no port to the positive pressure bus if used as a fill control valve, or having no port to the negative pressure bus if used as a deliver control valve. PCB 2035 (FIG. 55M) can operate the liquid pump/valve unit by coordinating the inlet and outlet pump valves to permit filling the pump chamber with liquid and then expelling the liquid from the pump chamber in the direction assigned by PCB 2035 (FIG. 55M). PCB 2035 (FIG. 55M) can receive pressure data from the pump control chamber to determine rate of fluid volume movement and end-of-stroke conditions. PCB 2035 (FIG. 55M) can vary the rate or amount of pressure delivered to the pump control chamber. PCB 2035 (FIG. 55M) can receive command sets locally from other manifold modules PCB 2035 (FIG. 55M), or from an external main or system controller.

Continuing to refer to FIG. 55N, module 1 can include output ports 2955 that can enable tubing to be connected to module 1. The tubing can supply a conduit to a destination for outputs from module 1. In some configurations, the destination may be, for example, but not limited to, a fluid pump, a pneumatic valve, and/or a fluid reservoir. Any suitable connector fitting may be included as part of output ports 2955. Unused output ports 2955 can be plugged, blocked, or otherwise sealed off.

Figure 55O:
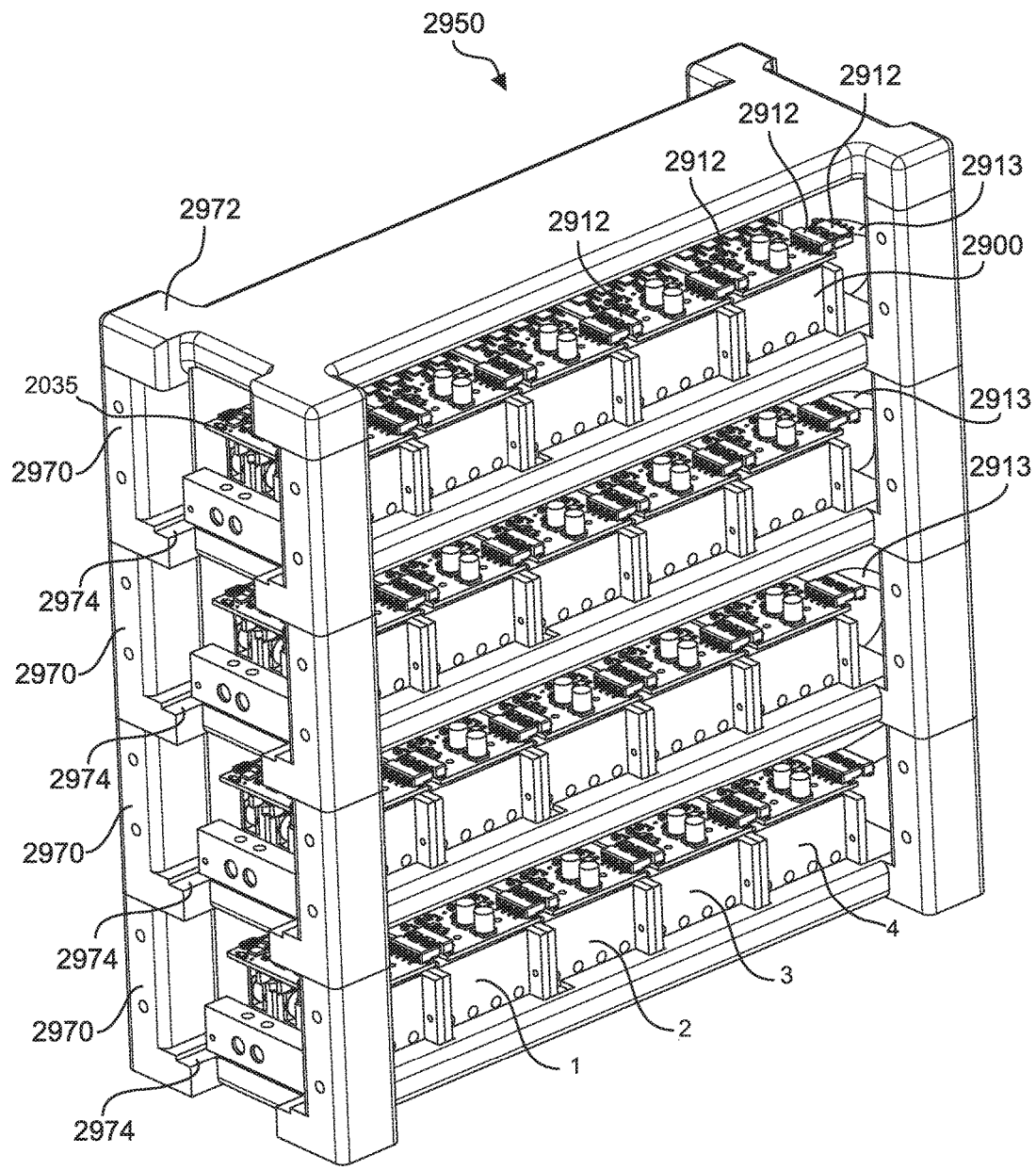
FIG. 55O is a perspective view of manifold assembly having a stack of four banks of grouped or concatenated programmable valved manifold modules.
Figure 55P:
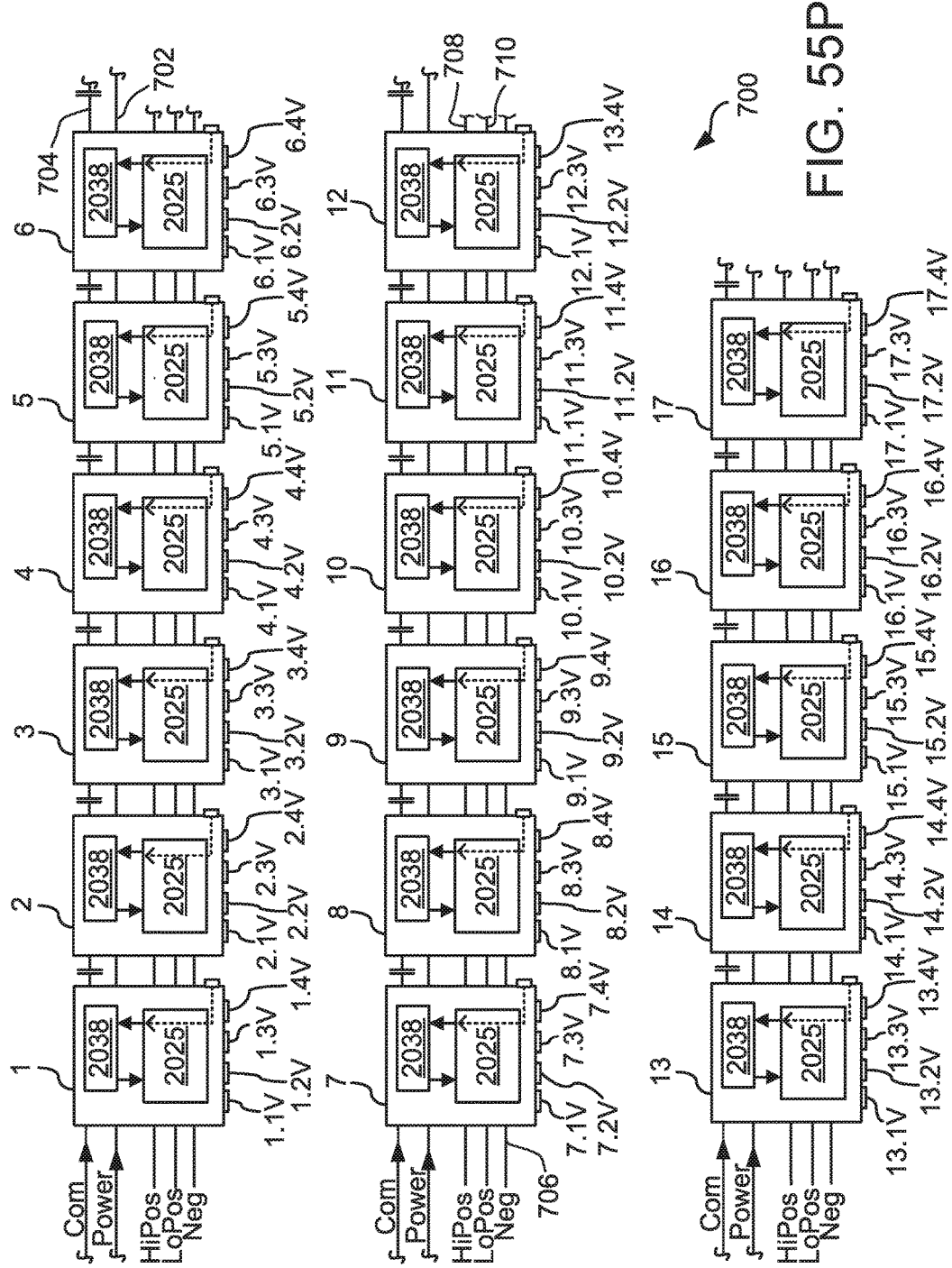
FIG. 55P is a schematic block diagram of a manifold of the present teachings.

Referring now to FIG. 55O, assemblage 2950 of modules 1-17 (FIG. 55P) may be stacked to allow input end blocks 2906 (FIG. 55K) to be interconnected to supply each bank of modules 1-17 (FIG. 55P) with one or more pressurized fluid lines. Connection ports 2907 (FIG. 55K) of end blocks 2906 (FIG. 55K) can be sealed closed or blocked. PCB 2035 can include connectors 2912 that can operably connect PCB 2035 with additional PCBs 2035 to interconnect, for example, but not limited to, valve modules 1-4 into manifold 2950 that can be of any size or complexity. Connectors 2912 can enable communications and/or electrical power buses to be assembled in a bank, such as, for example, modules 1-4. Connectors 2912 can enable electronic communication (power and/or data) between valve modules 1-4 in manifold assembly 2950 and, for example, but not limited to, an external (e.g. main or system) controller (not shown) included in a device in which manifold assembly 2950 can be installed. Banks of modules 1-4 can be placed on a number of individual module racks or frames 2970. In some configurations, each the banks can include four modules 1-4, though racks or frames 2970 may hold any number of modules 1-4. Each rack 2970 may include mating or coupling features (not shown) that can allow a first of racks 2970 to be stacked upon a second of racks 2970, forming a rack or frame assembly. For example, a first side of each rack 2970 may include a pin or projection (not shown). A second side of each rack 2970 opposite the first side may include a receiving structure (not shown) that can retain the projection from the first side of an adjacent rack 2970 connecting two of racks 2970 together. Cap 2972 can optionally top a terminal of racks 2970. Each rack 2970 may include tracks 2974 or a frame in which modules 1-4 may be retained. Tracks 2974 may enable modules 1-4 to be slid in and out of rack 2970. In some configurations, tracks 2974 can ensure that modules 1-4 are installed at a pre-determined orientation. Tracks 2974 may aid in alignment of connectors 2912. In some configurations, end blocks 2906 (FIG. 55K) can form at least part of the supporting structure of rack or frame 2970. Track 2974 can accommodate any number of manifold modules 1-4 in a bank, each module 1-4 having a slot in rack or frame 2970. Modules 1-4 can be concatenated in a bank by mating the pressure line inlet port (not shown) of one of modules 1-4 with pressure line outlet port (not shown) of another of modules 1-4 to form fluidic pressure bus. Modules 1-4 can be concatenated in a bank interconnecting PCBs 2035 with connectors 2912. Manifold assembly 2950 formed from a stack of modules 1-4 can be modified to accommodate any number or combination of manifold modules 1-4.

Continuing to refer to FIG. 55O, communications/power bus extension line 2913 may extend between modules 1-4 on one of racks 2970 to modules 1-4 on another of racks 2970. In some configurations, communications/power bus extension line 2913 may be integrated into each of racks 2970. Pneumatic (or in other systems, hydraulic) communication between modules 1-4 on different of racks 2970 may be established with pneumatic distribution lines housed or integrated within each of racks 2970. As racks 2970 are stacked, fluidic (e.g. pneumatic) communication from a first of racks 2970 to a second of racks 2970 may be automatically established. The connections may be made, for example, by press-fit plug/receptacle pairs (not shown) having leak-proof contact surfaces such as, for example, but not limited to, elastomeric gaskets or O-rings. In some configurations, pneumatic lines may run individually to each rack 2970.

Referring now to FIG. 55P, manifold 700 can include, but is not limited to including, a number of modules 1-17. Manifold 700 can be arranged to control operation of a fluid circuit including a number of cassettes 282A-C (FIGS. 55R-55T). Each of modules 1-17 (FIG. 55P) may be substantially identical. In some configurations, each module 1-17 (FIG. 55P) may include substantially the same electronic control board 2908 (FIG. 55K) for processor 2038 (FIG. 55P) associated with each of modules 1-17. Each of modules 1-17 (FIG. 55P) can include pneumatic block 2025 (FIG. 55P) described, for example, but not limited to, herein. In some configurations, each pneumatic block 2025 (FIG. 55P) can include four valve assemblies 2902 (FIG. 55K), that can be labeled, for example, valves 'n'0.1-'n'0.4 (FIG. 55S) and accompanying outlet ports 'n'0.1V-'n'0.4V (FIG. 55P), where 'n' follows the naming convention of valve modules 1-17. In some configurations, any number of valve assemblies 2902 (FIG. 55K) per pneumatic block 2025 (FIG. 55P), and any number of modules 1-17 (FIG. 55P), may be included. The portion of cassettes 282A-C (FIGS. 55R-55T) controlled by a particular port on manifold 700 is labeled correspondingly. For example, a fluid valve controlled by port "n"0.2V on module 1-17 can include the label "n"0.2 on cassette 282A-C (FIGS. 55R-55T).

Referring again to FIG. 55P, power bus 702 and communication bus 704 can extend from module 1 to module 17 throughout manifold 700. In some configurations, communications bus 704 can be, but is not limited to being, CAN-bus compatible. If communication is disrupted between one of modules 1-17 and others of modules 1-17, power bus 702 may remain intact so that all modules 1-17 have the opportunity to remain operational. Modules 1-17 may enter an autonomous mode of operation, for example, but not limited to, upon loss of communications. For example, certain modules 1-17 along manifold 700 may enter an autonomous mode of operation (e.g. for a designated period of time) upon loss of communications so that a pump, for example, may continue to operate when an upstream module 1-17 fails or is disconnected.

Continuing to refer primarily to FIG. 55P, negative 706, high positive 708, and low positive pressure 710 pneumatic buses can extend from module 1 to module 17 throughout manifold 700. In some configurations, there may be a negative pressure pneumatic bus and a positive pressure pneumatic bus. Each module 1-17 can include processor 2038 which can command pneumatic block 2025 of module 1-17 and may send signals to actuate the valves of the respective module 1-17. Additionally, each processor 2038 can receive pressure data from pressure sensors 2027 (FIG. 31) monitoring fluid flow paths in pneumatic block 2025, so that, for example, the pressure of the pumping chambers of each cassette 282A-C (FIGS. 55R-55T) can be monitored by processors 2038. Each module 1-17 may be assigned a role depending on the portion(s) of a fluid circuit in communication with its outlet ports 'n'0.1V-'n'0.4V. In some configurations, modules 1-17 can be assigned roles as, for example, but not limited to, fluid valve control modules and pump chamber modules. Fluid valve control modules may supply positive and negative pressure to sheeting over fluid valves of a cassette 282A-C (FIGS. 55R-55T). Positive pressure may be supplied to close the valves while negative pressure may be supplied to open the valves. The pump chamber modules may control the inlet and outlet fluid valves to pump chambers of a cassette 282A-C (FIGS. 55R-55T). The pump chamber modules may also control the application of pressure to sheeting over pump chambers to cause fluid to be pumped by cassette 282A-C (FIGS. 55R-55T). Other role assignments are possible. The role assignments for modules 1-17 and module ports can vary widely. In some configurations, if all of modules 1-17 are substantially identical, any module 1-17 may be assigned any role and may be installed in manifold 700 in any order. In some configurations, when modules 1-17 are connected to pneumatic lines, modules 1-17 may automatically control operation of, for example, but not limited to, fluid handling set 280 (FIG. 32). In some configurations, pump chambers may, for example, be paired with a corresponding pump chamber module. Any number of fluid valve control modules which are dedicated to specific cassettes 282A-C (FIGS. 55R-55T) may be present. Any number of support modules may be included.

Figure 55Q:
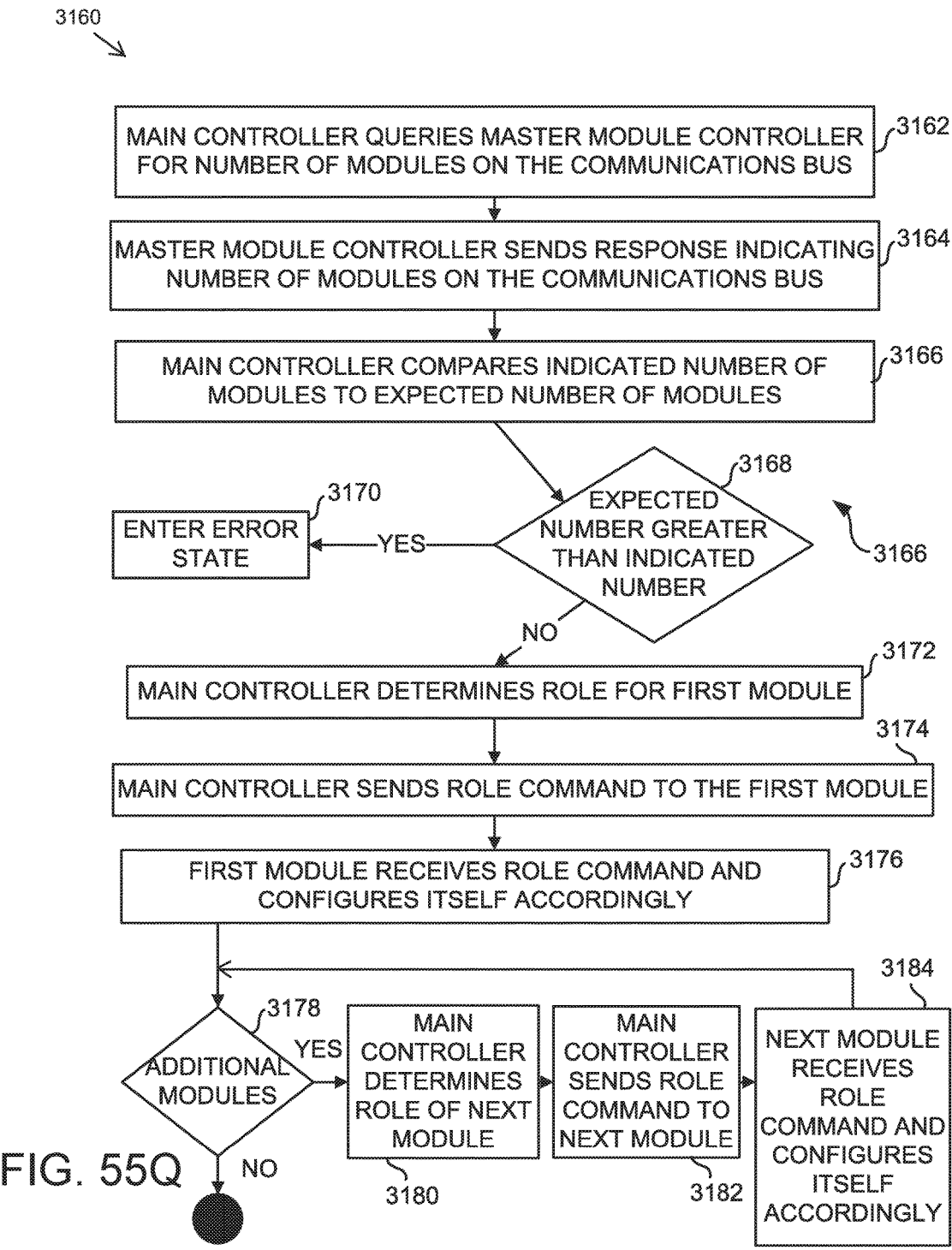
FIG. 55Q is a flowchart outlining a procedure which may be used to assign tasks to various modules in a manifold assembly.
Figure 55R:
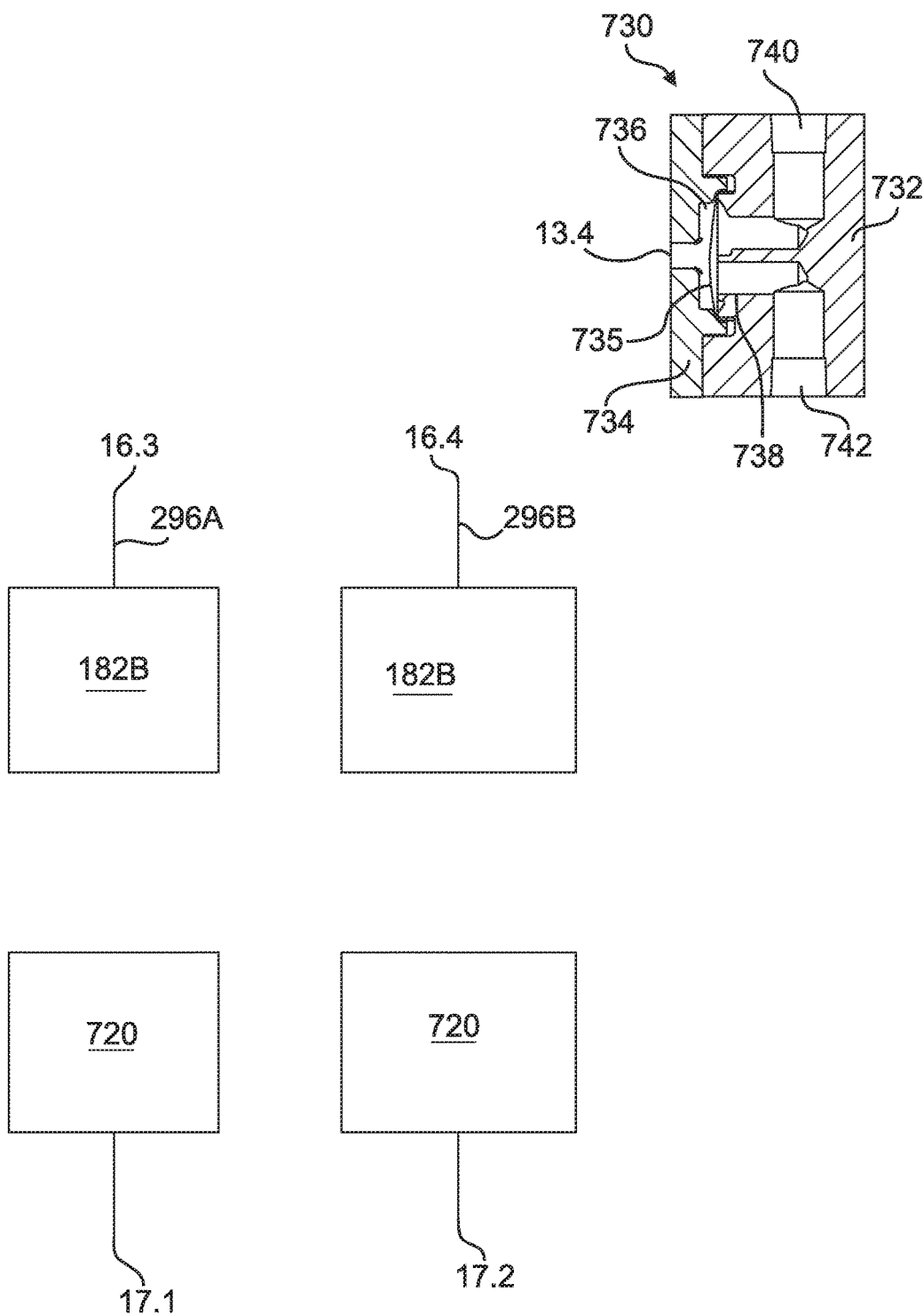
FIG. 55R is a schematic diagram of a valve block of the present teachings.
Figure 55S:
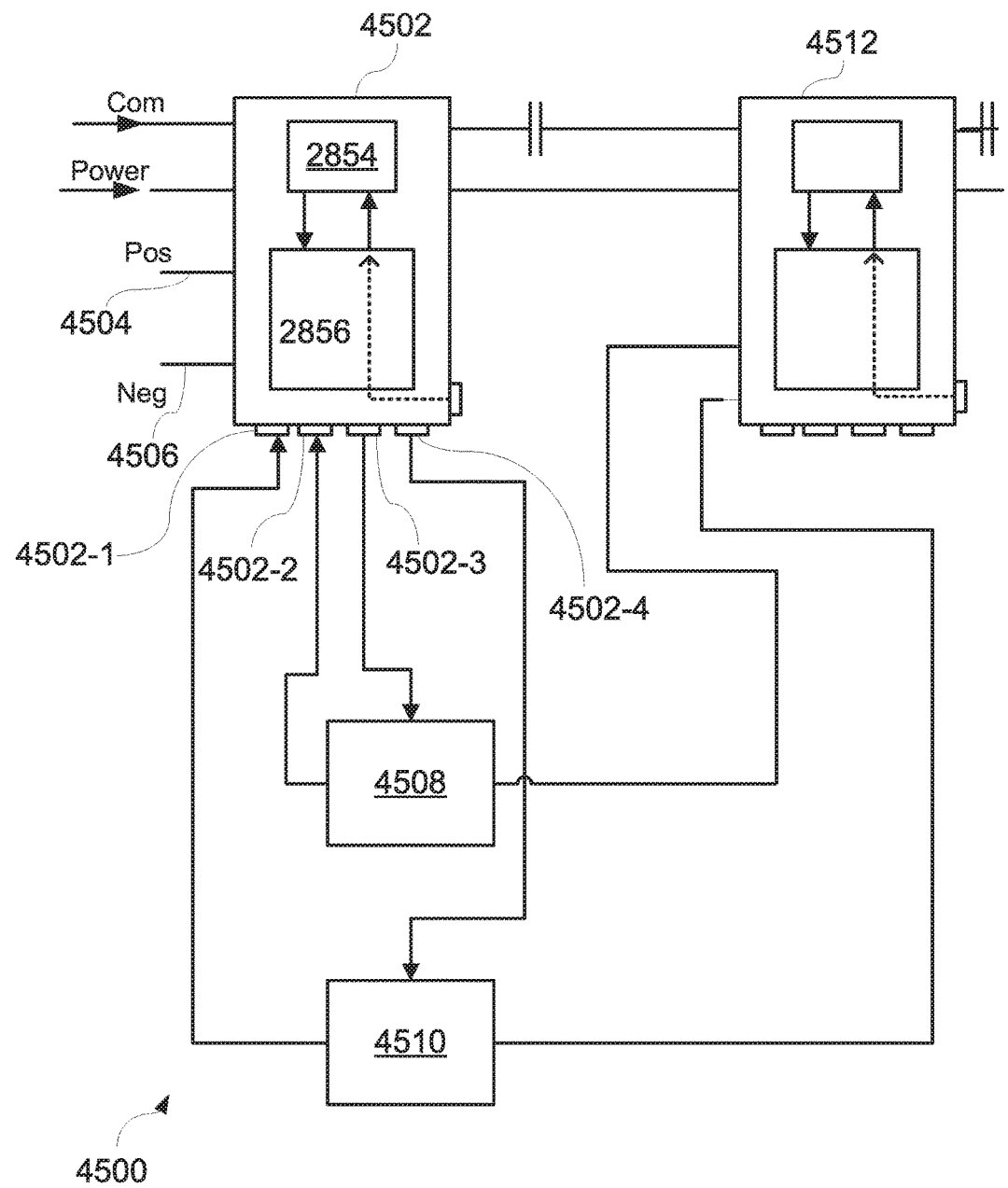
FIG. 55S is a schematic block diagram of a regulator of the present teachings.
Figure 55T:
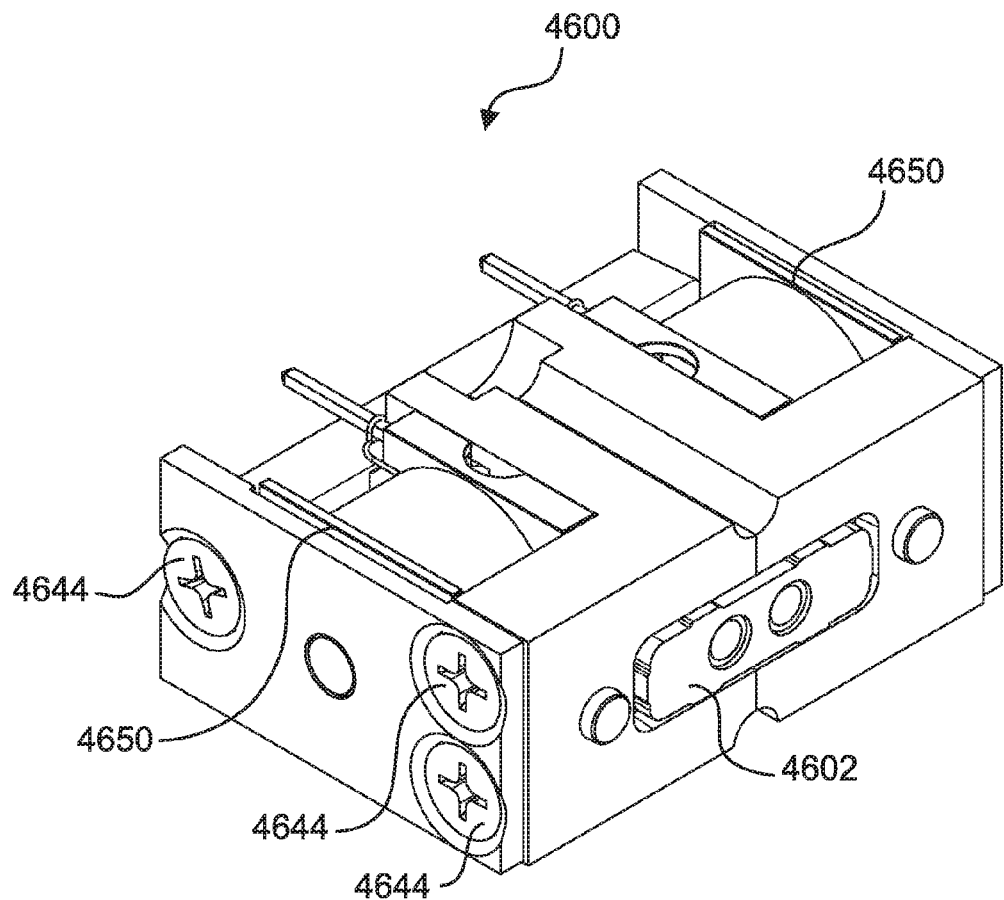
FIG. 55T is a perspective view of a pneumatic isolation assembly of the present teachings.

Referring now to FIG. 55Q, method 3160 can assign roles to modules 1-17 (FIG. 55P) in manifold assembly 700 (FIG. 55P). In some configurations, various modules 1-17 (FIG. 55P) can take on different roles from each other and perform tasks associated with those roles. In some configurations, the tasks may be pre-programmed onto a master module controller and can execute independent from a main controller. In some configurations, a main controller can take more of an active role in controlling modules 1-17 (FIG. 55P). Method 3160 can include sending 3162, by the main controller, a query to the master module controller requesting the number of modules operably connected, through, for example, but not limited to, the communications bus. Method 3160 can include sending 3164, by the master module controller, a response indicating the number of modules operably connected, through, for example, but not limited to, the communications bus. Method 3160 can include comparing 3166, by the main controller, the number of modules specified by the master controller to an expected number of modules. If 3168 the expected number of modules 1-17 (FIG. 55P) is greater than the number reported by the master module controller, method 3160 can include entering 3170, by the main controller, an error state. In the error state, a notification for display on a user interface can optionally be displayed. In some configurations, the main controller may enter an error state if the number of modules 1-17 (FIG. 55P) reported by the master module controller differs from the expected number. For example, an error state may be entered and a notification generated if the master module controller indicates that extra of modules 1-17 (FIG. 55P) are present.

Continuing to refer to FIG. 55Q, if 3168 the expected number of modules 1-17 (FIG. 55P) matches the number reported by the master module controller, method 3160 can include determining 3172, the main controller, at least one role for a first of modules 1-17 (FIG. 55P). Method 3160 can include sending 3174, by the main controller the at least one role to the first of modules 1-17 (FIG. 55P). Method 3160 can include configuring 3176, by the first of modules 1-17 (FIG. 55P), upon receipt of the at least one role, the first of modules 1-17 (FIG. 55P) according to the at least one role. If 3178 there are no further of modules 1-17 (FIG. 55P), method 3160 can terminate. If 3178 there are additional of modules 1-17 (FIG. 55P), method 3160 can include determining 3180, by the main controller, at least one role for another of modules 1-17 (FIG. 55P). Method 3160 can include sending 3182, by the main controller, the at least one role to another of modules 1-17 (FIG. 55P). Method 3160 can include configuring 3184, by module controller, upon receipt of the at least one task, another of modules 1-17 (FIG. 55P) according to the at least one role. If 3178 there are no further modules 1-17 (FIG. 55P), method 3160 can terminate. If 3178 there are additional of modules 1-17 (FIG. 55P), method 3160 can repeat steps 3180, 3182 and 3184 all of modules 1-17 (FIG. 55P) have been assigned at least one role.

Continuing to refer to FIG. 55Q, the at least one role generated by the main controller may, in some configurations, include the role of a pump chamber module or a fluid valve module, or a combination of the two. The configurations that could include, for example, pump chamber modules, can include configurations in which modules 1-17 (FIG. 55P) control pneumatic pathways leading to a pumping cassette. In some configurations, the module controller can automatically interpret the at least one role, and can set up valve configurations, sequencing and default states according the at least one role. In some configurations, the at least one role may include specifying valve configuration information to one of modules 1-17 (FIG. 55P). In some configurations, the at least one role can include specifying configuration settings for individual valves of one of modules 1-17 (FIG. 55P). In some configurations, the at least one role can include specifying a module number, a valve number (e.g. 1-4), and configuration setting. Each of modules 1-17 (FIG. 55P) may be configured to accept a plurality of valve assemblies 2902 (FIG. 55K). In some configurations, the number of valve assemblies 2902 (FIG. 55K) per module 1-17 (FIG. 55P) can be standardized to permit ready replacement or substitution of valve assembly 2902 (FIG. 55K) and gasket at an assigned location in one of modules 1-17 (FIG. 55P), or ready replacement of the entire of one of modules 1-17 (FIG. 55P) without necessitating re-programming of the module controller. In some configurations, the gasket mating valve assembly 2902 (FIG. 55K) to the fluidic bus (pneumatic or hydraulic) may have different communication holes or ports to the bus to permit or deny access of the valve to a particular pressure line in the bus. Possible configuration settings can include, but are not limited to including, the setting in TABLE X.

TABLE X

| Valve Configurations | Description |
|---|---|
| Fluid Valve | 3-way valve with an input connected to positive pressure and an input connected to negative pressure |
| Chamber Valve Pos | 2-way valve with an input connected to positive pressure |
| Chamber Valve Neg | 2-way valve with an input connected to negative pressure |
| Regulator | Valve which outputs to an accumulator and toggles to regulate a source pressure to an accumulator pressure |
| Vent | Valve which is connected to a vent reservoir or atmosphere |
| Measurement Valve | Valve arranged to make and break fluid communication between a reference volume and a control chamber |
| Blocked | Valve which is in a module but unused and has had its ports blocked off |

Continuing to refer to FIG. 55Q, in some configurations, each of modules 1-17 (FIG. 55P) may default to predetermined valve configuration settings. In some configurations, the main controller may not generate a role for a module if the default settings are provide the desired tasks. In some configurations, each of modules 1-17 (FIG. 55P) may default to a pump chamber control module configuration in which two valves of the module are configured as fluid valves, one is configured as a positive chamber valve, and another is configured as a negative chamber valve. In some configurations, roles may include primary or grouped tasks addressed to a master module controller. Any of the module controllers in a manifold assembly may be assigned to be a master module controller. The master module controller can receive a primary role assignment from a main or system controller via the communications bus. The primary or grouped role may include the task of assigning a role to a master module to coordinate the tasks of a specific secondary module or group of secondary modules. In some configurations, the primary or grouped role may include tasks that specify that the master module controller coordinates or synchronizes pumping performed by two or more pump chamber modules (e.g. pump chamber modules controlling two or more pump chambers of the same device or the same pump cassette). This may cause the specified secondary modules to effectively operate in tandem to provide the pumping device with greater potential throughput. In some configurations, the main controller can transmit a single role and/or at least one task with a group identifier. The master module controller of the primary module can receive the role and/or at least one task and transmit the role and/or at least one task to secondary modules associated with the group identifier. Although timing of inlet and outlet pump valve operations with an associated pump operation can be performed locally with the on-board controller of the individual pump control modules, synchronizing the operation of one pump/valve combination with another pump/valve combination may be a function of the group role and/or at least one task coordinated by the master module controller. The module controller can include software, firmware, and/or hardware installed on any of the on-board controllers of the valved manifold modules. In some configurations, a master module controller may be omitted. In some configurations, a controller external to the manifold assembly, such as a main or system controller, may perform the functions of the master module controller.

Continuing to still further refer to FIG. 55Q, a role can include tasks that specify that the master module controller coordinate operations of a pump chamber module with a volume measurement module, for example, but not limited to, a manifold module having a valved connection to a reference chamber and to vent for pressure/volume calculations. This may cause the master module controller to synchronize operations of the volume measurement module with the pump chamber module so that the volume measurement module performs a pressure measurement to determine the volume transferred in each pump stroke commanded by the pump chamber module.

Referring now primarily to FIG. 55R, in some configurations, modules 1-17 (FIG. 55P) may also be assigned roles which support or supplement the roles of other modules 1-17 (FIG. 55P). For example, some modules 1-17 (FIG. 55P) may act to vent components of a fluid circuit. The control chamber for a pump chamber, may, for example, be vented in various circumstances. Additionally, some support modules 1-17 (FIG. 55P) may be measurement modules which measure the volume of fluid which is transferred during pumping. Other support modules are also possible, for example some modules or module ports may play a support role in which pressures of various portions of a fluid circuit or pneumatic circuit are sensed by the module. In some configurations, module 15 (FIG. 55P) may optionally be a regulator module which regulates the pressure fed to modules 16, 17 (FIG. 55P) disposed downstream. Ports 16.3V and 16.4V (FIG. 55P) may be associated with pneumatic isolation assembly 4600 (FIG. 55W) instead of a valve such that the ports 16.3V, 16.4V (FIG. 55P) may be used for sensing pressure, for example. Pneumatic isolation assembly 4600 (FIG. 55W) may seal off a volume of the module in which a pressure sensor in communication with the associated port is located.

Continuing to refer to FIG. 55R, in some configurations, ports 16.3V, 16.4V (FIG. 55P) can be connected at 16.3 and 16.4 to level sensing lines 296A, 296B of storages reservoirs 182A, 182B. Pressure sensors associated with the ports 16.3V, 16.4V (FIG. 55P) can monitor the pressure in the level sensing lines 296A, 296B. The sensed pressure of the level sensing lines 296A, 296B may be used to determine the level or volume of a fluid contained within the storage reservoir 182A, 182B. Ports 17.1V and 17.2V (FIG. 55P) can be associated with pneumatic isolation assembly 4600 (FIG. 55W) and can be used for sensing pressure. In some configurations, ports 17.1V, 17.2V (FIG. 55P) may be connected at 17.1 and 17.2 to atmosphere or ambient pressure 720. The pressure sensors associated with ports 17.1V, 17.2V (FIG. 55P) may monitor ambient pressure 720 and generate a pressure offset value. The pressure offset value may be used when determining pressure from pressure data provided by other pressure sensors in a manifold 700 (FIG. 55P). The pressure offset value may be computed based on a predefined schedule as ambient pressure values may fluctuate throughout a day.

Continuing to refer to FIG. 55R, in some configurations, ports 17.1V and 17.2V (FIG. 55P) can be connected to ambient pressure 720 to provide redundancy. The pressure data or pressure offset values generated from the pressure sensors associated with each port 17.1V, 17.2V (FIG. 55P) may be compared against one another to ensure they are within a predefined range of each other. If the values are not within the predefined range of one another, an error state may be entered and a notification may be generated. In some configurations, only one port 17.1V, 17.2V (FIG. 55P) may be arranged to monitor atmospheric pressure and generate a pressure offset value. Port 13.4V (FIG. 55P) may be connected to fluid valve 13.4 which may be included in stand-alone valve block 730. Stand alone valve block 730 may include fluid flow body 732 separated by displaceable sheet or barrier 735 from pneumatic chamber body 734. Pneumatic chamber body 734 may include control volume 736 to which pressure from port 13.4V (FIG. 55P) may be supplied. The pressure may cause displacement of displaceable barrier 735 to open and close valve port 738 of stand-alone valve block 730. Fluid flow body 732 may include material that can include inlet flow path 740 and outlet flow path 742. Communication between inlet flow path 740 and outlet flow path 742 may be interrupted as displaceable barrier 735 is displaced against valve port 738 to outlet flow path 742. Positive pressure may be supplied to pneumatic control chamber 736 to displace barrier 735 against valve port 738 to close the valve. Negative pressure may be supplied to pneumatic control chamber 736 to displace barrier 735 away from valve port 738 to open the valve. Fluid lines may be coupled to inlet flow path 740 and outlet flow path 742 with any of a variety of fittings or connectors. Inlet flow path 740 and outlet flow path 742 may be associated with, for example, but not limited to, barbed connectors, luer-locks, and/or quick connects to facilitate connection to fluid lines.

Continuing to refer to FIG. 55R, fluid flow body 732 and pneumatic chamber body 734 may be coupled to one another in any suitable manner. For example, fluid flow body 732 and pneumatic chamber body 734 may be ultrasonically welded to one another with flexible barrier 735 captured in between. In some configurations, fluid flow body 732 and pneumatic chamber body 734 may be coupled together with fasteners. In some configurations, a gasket member may be included to provide a fluid tight seal. Flexible barrier 735 may be integral to the gasket member in some configurations. Stand-alone valve block 730 may be incorporated into any fluid line of a fluid circuit and may allow for flow through that line to be affectively occluded. In some configurations, at least one stand alone valve body 730 may be incorporated into fluid handling set 280 (FIG. 32). In some configurations, stand-alone valve body 730 may be attached to a fluid line such as fluid line 284 (FIG. 32) which can act as an inlet line to fluid handling set 280 (FIG. 32). Stand-alone valve block 730 may be replaced by a solenoid performing the same function.

Referring now to FIG. 55S, a portion of a manifold can include regulator module 4502 that can regulate the pressure of a pneumatic bus to a second or regulated pressure which is different from that of the pneumatic bus. Regulator module 4502 can include a valve (not shown) in pneumatic block 2856 of regulator module 4502 that can separate the pressure bus from a separate chamber or an accumulator 4508, 4510. The valve (not shown) can be toggled to regulate the pressure. The pressure of accumulator 4508, 4510 may be sensed by a pressure sensor (not shown) that can be monitored by controller 2854 of regulator module 4502. Controller 2854 may toggle the valve (not shown) using data from the pressure sensor (not shown). In some configurations, controller 2854 may command the valve (not shown) to toggle to place accumulator 4508, 4510 in communication with the pressure bus when the sensed pressure of accumulator 4508, 4510 falls below a first predetermined value. Controller 2854 may command that the valve close off communication between the pressure bus and accumulator 4508, 4510 when the sensed pressure of accumulator 4508, 4510 is above a second predetermined value. In some configurations, regulator module 4502 can operably communicate with positive pressure bus 4504 and negative pressure bus 4506. Regulator module 4502 may regulate the pressure of positive pressure bus 4504 to a lower positive pressure. Regulator module 4502 may regulate the pressure of negative pressure bus 4506 to a weaker negative pressure. In some configurations, ports 4502-1 and 4502-3 of regulator module 4502 can operably communicate with positive pressure accumulator 4508. Ports 4502-2 and 4502-4 of regulator module 4502 can operably communicate with negative pressure accumulator 4510.

Continuing to refer to FIG. 55S, accumulators 4508, 4510 may include any reservoir. In some configurations, accumulators 4508, 4510 may be identical. Accumulators 4508, 4510 may, for example, include plastic and/or metal tanks and may have an interior volume between 500 ml and 2 L. Port 4502-3 may be an outlet port for a valve of pneumatic block 2856 controlling fluid communication between positive pressure bus 4504 and positive pressure accumulator 4805. Port 4502-4 may be an outlet port for a valve of pneumatic block 2856 controlling fluid communication between negative pressure bus 4506 and negative pressure accumulator 4510. The valves associated with ports 4502-3 and 4502-4 may be toggled by controller 2854 based on the sensed pressure of their respective accumulators 4508, 4510. In some configurations, pneumatic block 2856 may include pneumatic isolation members or assemblies 4600 (FIG. 55W) that can be associated with ports 4502-1, 4502-2. Ports 4502-1, 4502-2 may be connected to a fluid volume such that the pressure sensors associated with ports 4502-1, 4502-2 may monitor the pressure of the fluid volume. In some configurations, port 4502-1 can be operably connected to negative pressure accumulator 4510 to periodically measure or monitor the pressure of negative pressure accumulator. Port 4502-2 can be operably connected to positive pressure accumulator 4508 to periodically measure or monitor the pressure of positive pressure accumulator 4508. Modules 4512 of manifold 4500 may draw from pressure accumulators 4508, 4510 and operate at the regulated pressure of accumulators 4508, 4510. In some configurations, if the fluid circuit includes at least one fluid handling cassette, the fluid valves of the cassette may be operated at greater pressures than the pump chambers of the cassette. Pump chambers of a cassette, or of a number of different cassettes in a fluid circuit, may be operated at different pressures. Modules 4512 controlling portions of the fluid circuit which operate at certain pressures may be disposed upstream of regulator module 4502 and modules 4512 which operate at other pressures may be disposed downstream of regulator module 4502. In some configurations, a plurality of regulator modules 4502 can enable a fluid circuit to be operated at more than two sets of pressures.

Referring now to FIG. 55T, pneumatic isolation assembly 4600 can be included in pneumatic block 2856 (FIG. 55V) of a module, for example, regulator module 4502 (FIG. 55V). Pneumatic isolation assembly 4600 may isolate a pressure bus or buses communicating with, for example, but not limited to, regulator module 4502 (FIG. 55V) from the port with which pneumatic isolation assembly 4600 is associated. Pneumatic isolation assembly 4600 may be associated with a port of, for example, but not limited to, regulator module 4502 (FIG. 55V) if the port is used, for example, for sensing purposes. In some configurations, pneumatic isolation assembly 4600 can include a modified fluid valve. Pneumatic isolation assembly 4600 can include gasket member 4602 that can block and/or isolate pressure buses feeding into pneumatic isolation assembly 4600 from the module port associated with pneumatic isolation assembly 4600. In some configurations, pneumatic isolation assembly 4600 can include any suitable means of isolating the pneumatic buses from a module port. In some configurations, a block of gasketing material may be attached to a module in place of, for example, a valve. Plugs or a similar structure may be coupled into the module or a fixative or glue may be used to seal off pneumatic ports. Pneumatic isolation assembly 4600 may be configured in many ways, including, but not limited to, omitting coil assemblies 4650. Pneumatic isolation assembly 4600 may be constructed from various materials, the choice of materials being unconstrained by magnetic flux paths which are not a concern in pneumatic isolation assembly 4600. In some configurations, fasteners 4644 may be omitted when, for example, pneumatic isolation assembly 4600 includes a single block of material or a number of pieces of material which may be, for example, but not limited to, snap fit, friction fit, and/or solvent bonded together.

Figure 56:
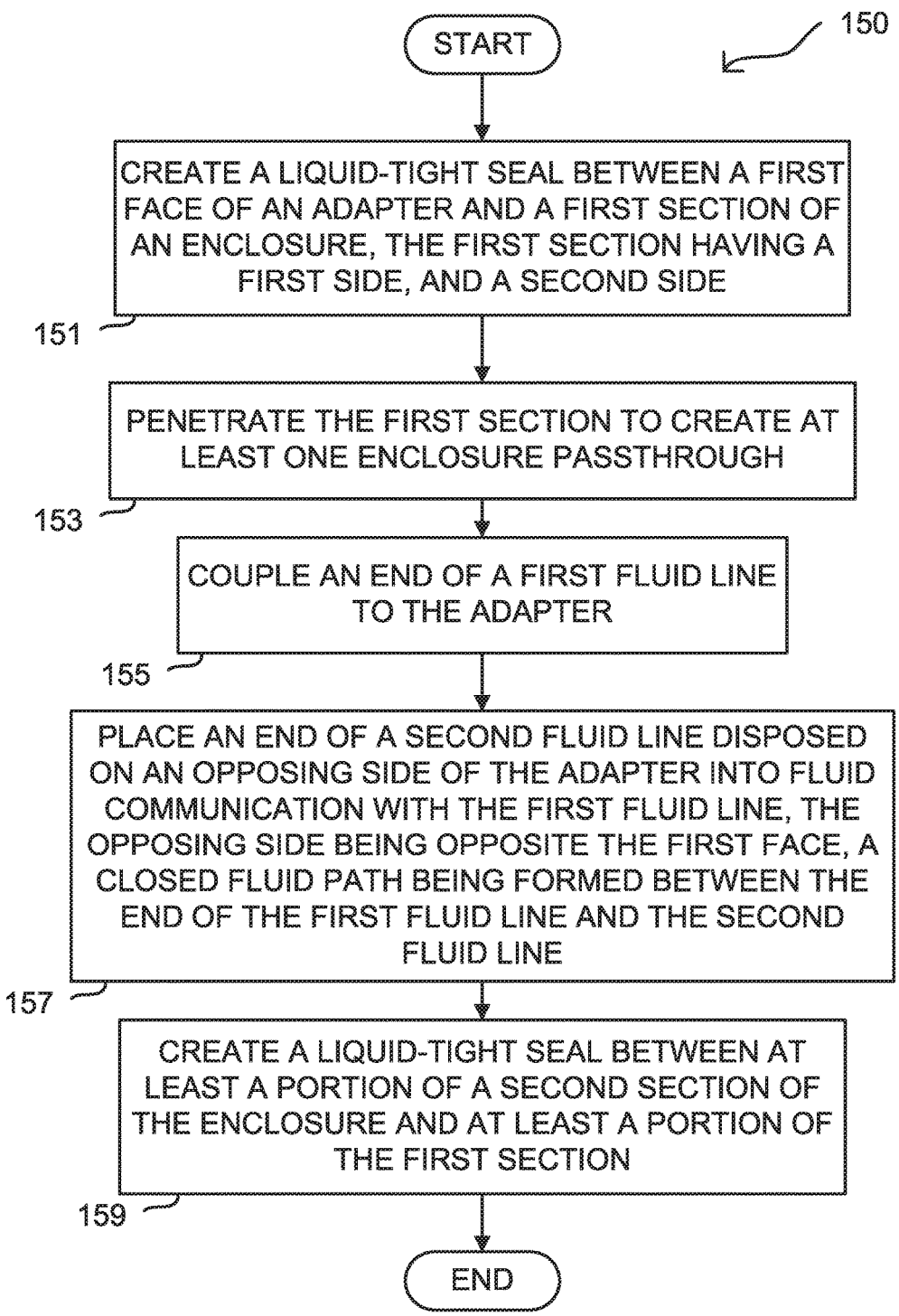
FIG. 56 is a flowchart of one example of a method of manufacture of an enclosure of the present teachings.

Referring now to FIG. 56, method 150 for manufacturing an enclosure can include, but is not limited to including, creating 151 a fluid/liquid-tight seal between a first face of an adapter and a first section of the enclosure, the first section having a first side, and a second side. The method 150 may include penetrating 153 the first section to create at least one enclosure pass-through. The method 150 may include coupling 155 an end of a first fluid line to the adapter. The method 150 may include placing 157 an end of a second fluid line disposed on an opposing side of the adapter into fluid communication with the first fluid line, the opposing side being opposite the first face, a closed fluid path being formed between the end of the first fluid line and the end of the second fluid line. The method 150 may also include creating 159 a fluid/liquid-tight seal between at least a portion of a second section of the enclosure and at least a portion of the first section.

Figure 57:
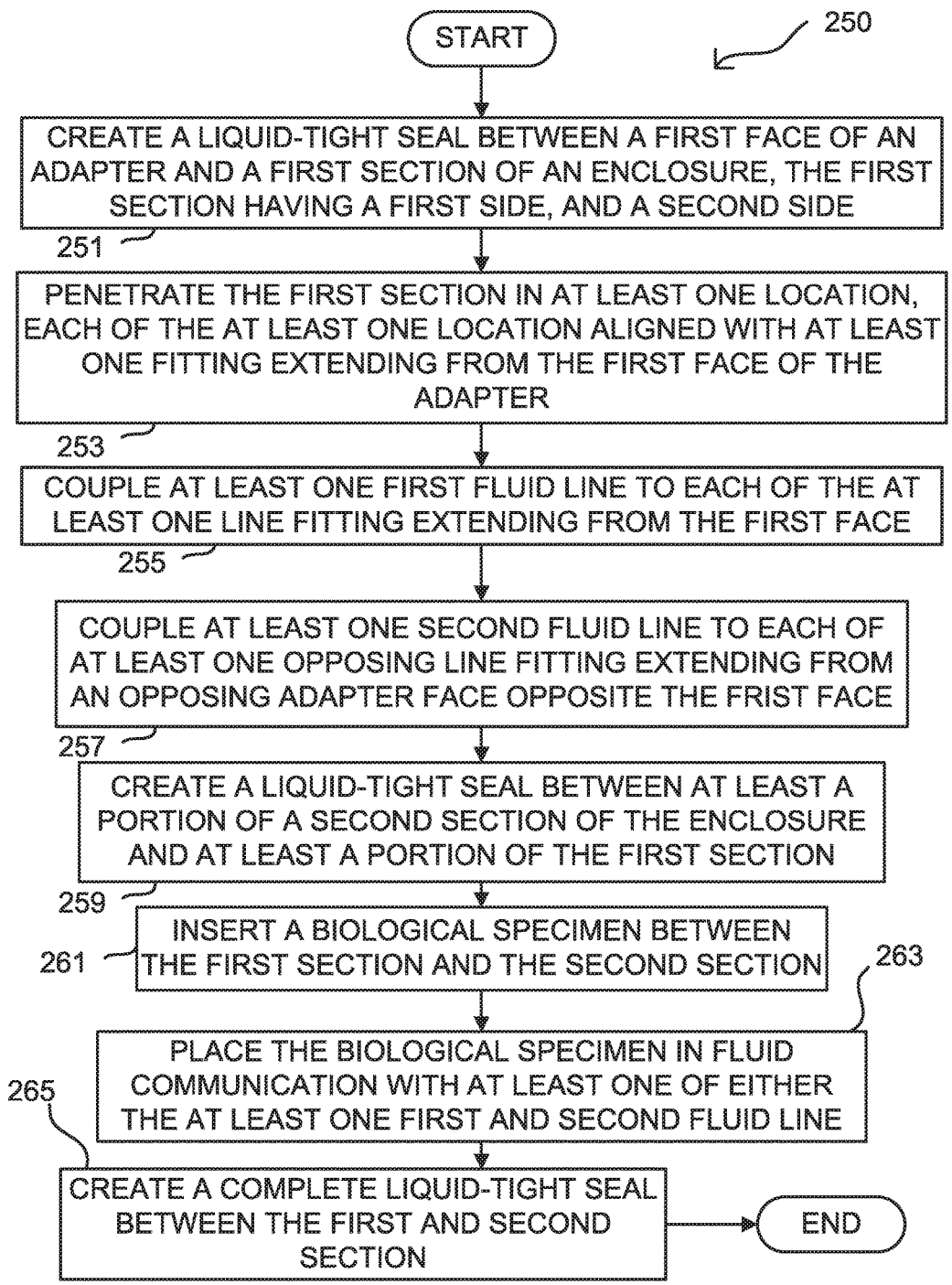
FIG. 57 is a flowchart of example of a method of using an enclosure of the present teachings.

Referring now to FIG. 57, method 250 for using an enclosure can include, but is not limited to including, creating 251 a fluid/liquid-tight seal between a first face of an adapter and a first section of the enclosure, the first section having a first side, and a second side. The method 250 may include penetrating 253 the first section in at least one location, each of the at least one location aligned with at least one line fitting extending from the first face of the adapter. The method 250 may include coupling 255 at least one first fluid line to each of the at least one line fitting extending from the first face. The method 250 may include coupling 257 at least one second fluid line to each of at least one opposing line fitting extending from an opposing adapter face opposite the first face. The method 250 may include creating 259 a fluid/liquid-tight seal between a portion of a second section of the enclosure and a portion of the first section. The method 250 may include inserting 261 a biological specimen between the first section and the second section. The method 250 may include placing 263 the biological specimen in fluid communication with at least one of either the at least one first and second fluid line. The method 250 may also include creating 265 a complete fluid/liquid-tight seal between the first section and the second section.

Figure 58:
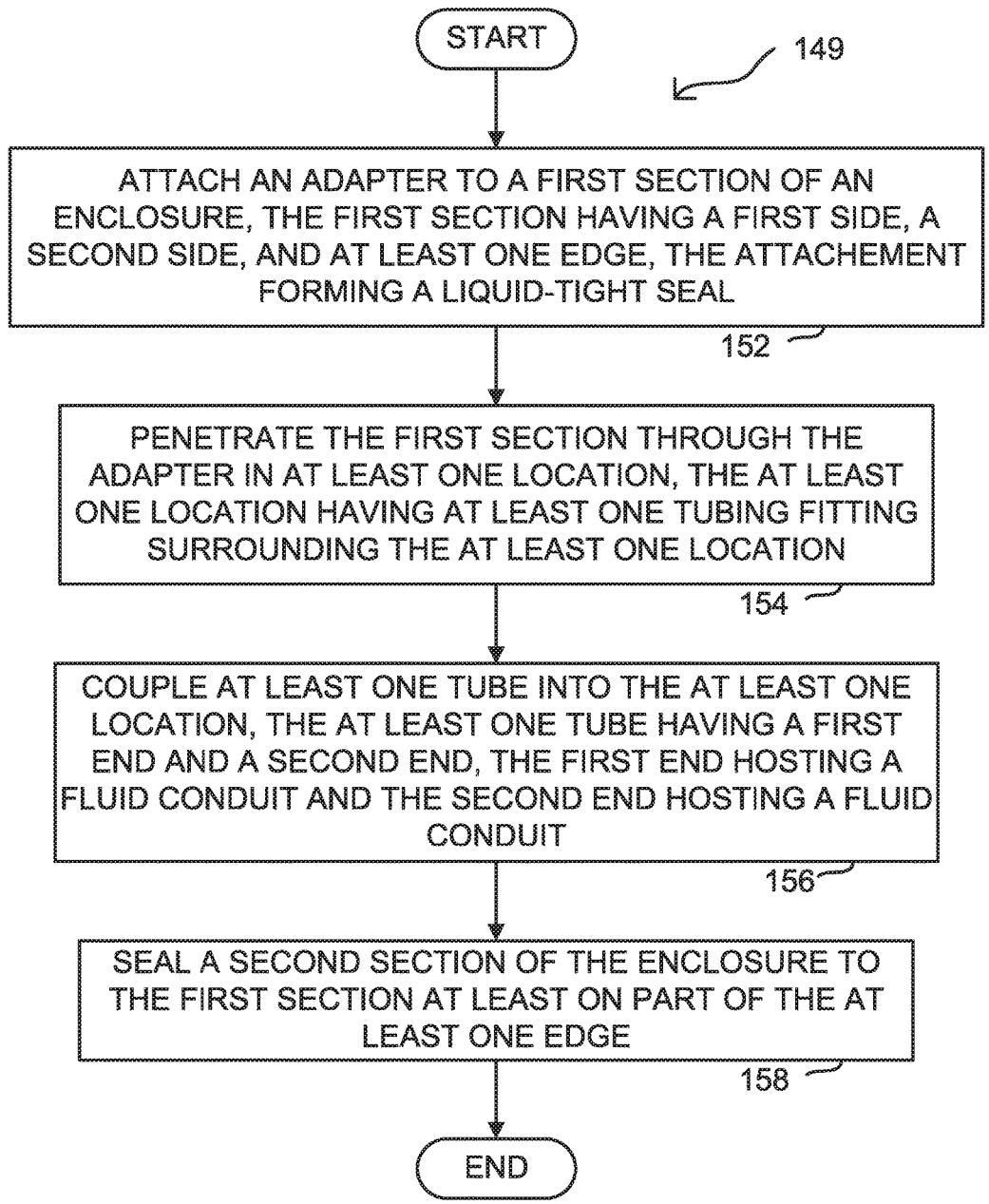
FIG. 58 is a flowchart of another example of a method of manufacture of an enclosure of the present teachings.

Referring now to FIG. 58, a method 149 for manufacturing an enclosure can include, but is not limited to including, attaching 152 an adapter to a first section of the enclosure. The first section may have a first side, a second side, and at least one edge. The attachment may create a fluid/liquid-tight seal. The method 149 may further include penetrating 154 the first section through the adapter in at least one location. The at least one location may have at least one tubing fitting surrounding the at least one location. The tubing fitting may be a barbed fitting or a locking interface such as a luer lock for non-limiting example. The method 149 may further include coupling 156 at least one tube to the at least one location. The at least one tube may have a first end and a second end. The first end may host a fluid conduit. The second end may host a fluid conduit. In some configurations, the fluid conduit in the first end may be continuous with the fluid conduit in the second end. Alternatively, the first end may host a cannula and the second end may host a cannula. The method 149 may further include sealing 158 a second section of the enclosure to the first section at least on part of the at least one edge.

Figure 59:
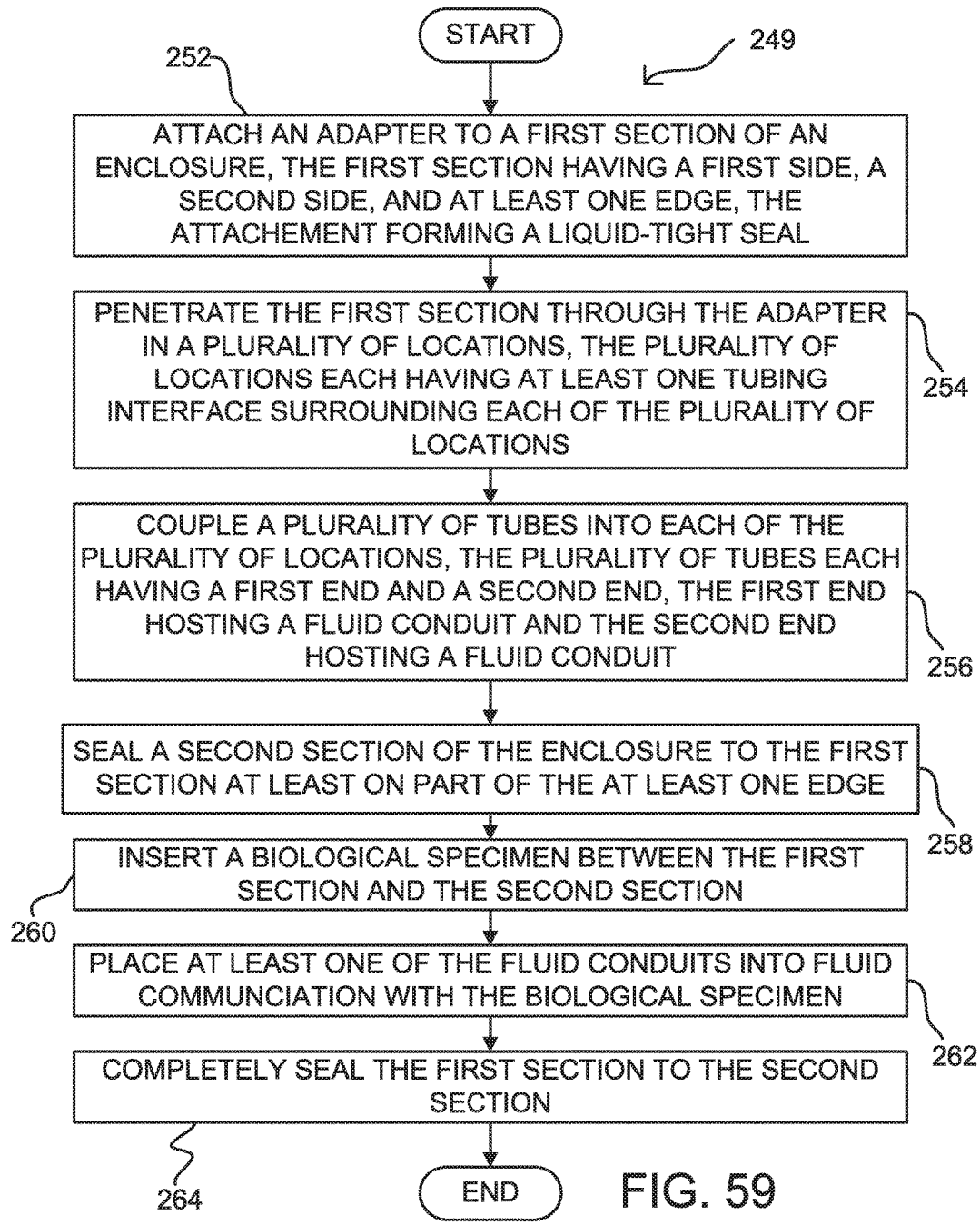
FIG. 59 is a flowchart of another example of a method of manufacture of an enclosure of the present teachings.

Referring now to FIG. 59, method 249 for manufacturing an enclosure can include, but is not limited to including, attaching 252 an adapter to a first section of an enclosure. The first section may have a first side, a second side, and at least one edge. The attachment may form a fluid/liquid-tight seal. The method 249 may further include penetrating 254 the first section through the adapter in a plurality of locations. The plurality of locations may each have at least one tubing interface surrounding each of the plurality of locations. The tubing interface may be a barbed fitting or a locking interface such as a luer lock for non-limiting example. The method 249 may further include coupling 256 a plurality of tubes to each of the plurality of locations. The plurality of tubes may each have a first end and a second end. The first end may host a fluid conduit and the second end may host a fluid conduit. The fluid conduit in the first end may be continuous with the fluid conduit in the second end. Alternatively, the first end may host a cannula and the second end may host a cannula. The method 249 may further include sealing 258 a second section of the enclosure to the first section at least on part of the at least one edge. The method 249 may further include inserting 260 a biological specimen between the first section and the second section. The method 249 may further include placing 262 at least one of the fluid conduits into fluid communication with the biological specimen. This may include introducing the fluid conduit into the biological specimen. Alternatively, the method 249 may include introducing at least one of the cannulae into the biological specimen. The method 249 may further include completely sealing 264 the first section to the second section.

Figure 60:
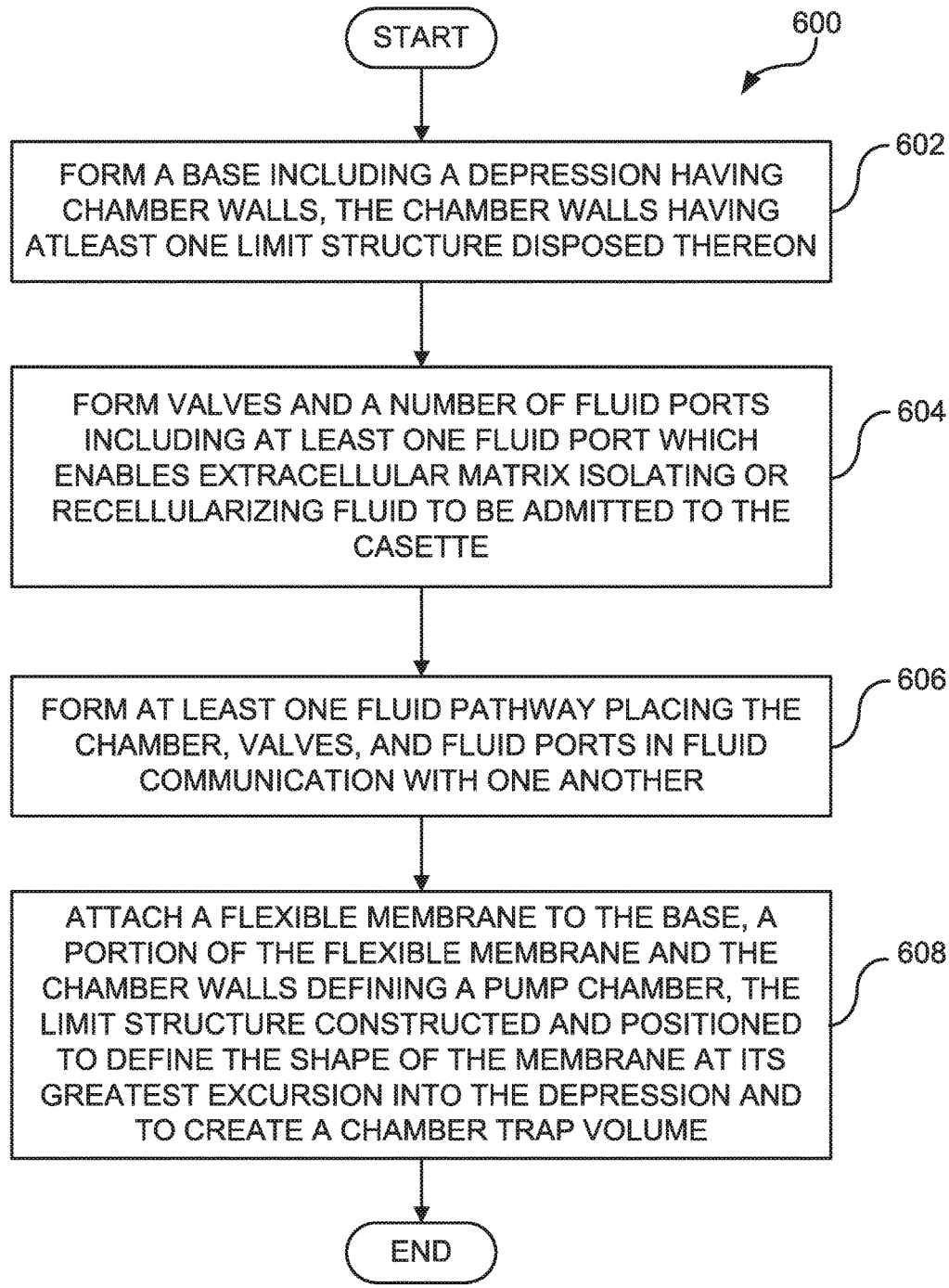
FIG. 60 is an example flowchart of a method for assembling a fluid pumping cassette for tissue engineering.

Referring now to FIG. 60, method 600 can be used to manufacture a fluid pumping cassette for tissue engineering. Method 600 may include forming 602 a base including a depression having chamber walls. Optionally, forming 602 a base may include forming a base with a depression having at least one limit structure or spacer disposed upon the chamber walls. The method 600 may include forming 604 valves, and a number of fluid ports. The fluid ports may include at least one fluid port which enables extracellular matrix isolating or recellularizing fluid to be admitted to the cassette, a reservoir fluid inlet, at least one waste port, and a number of fluid loop ports. The at least one fluid port which enables extracellular matrix isolating or recellularizing fluid to be admitted to the cassette may be a specimen fluid port. The method 600 may include forming 606 at least one fluid pathway which places the depression, valves, and fluid ports in fluid communication with one another. This fluid communication may be selective or interruptible fluid communication. For example, forming 606 the at least one fluid pathway may include forming the at least one fluid pathway such that valves allow various regions of the cassette to be fluidically isolated from one another if desired. The method 600 may include attaching 608 a flexible membrane to the base. The flexible membrane and chamber walls may define a pump chamber. The at least one limit structure may be constructed and positioned to defined the shape of the membrane at its greatest excursion into the depression and to create a chamber trap volume.

Still referring to FIG. 60, the method 600 may also include attaching fluid conduits to each of the fluid ports. The method 600 may include attaching a specimen fluid conduit to each of at least one specimen port. The specimen fluid conduit(s) may include a specimen fluid conduit end which is configured to interface with an enclosure or tissue engineering bioreactor or alternatively with a biological specimen.

Figure 61:
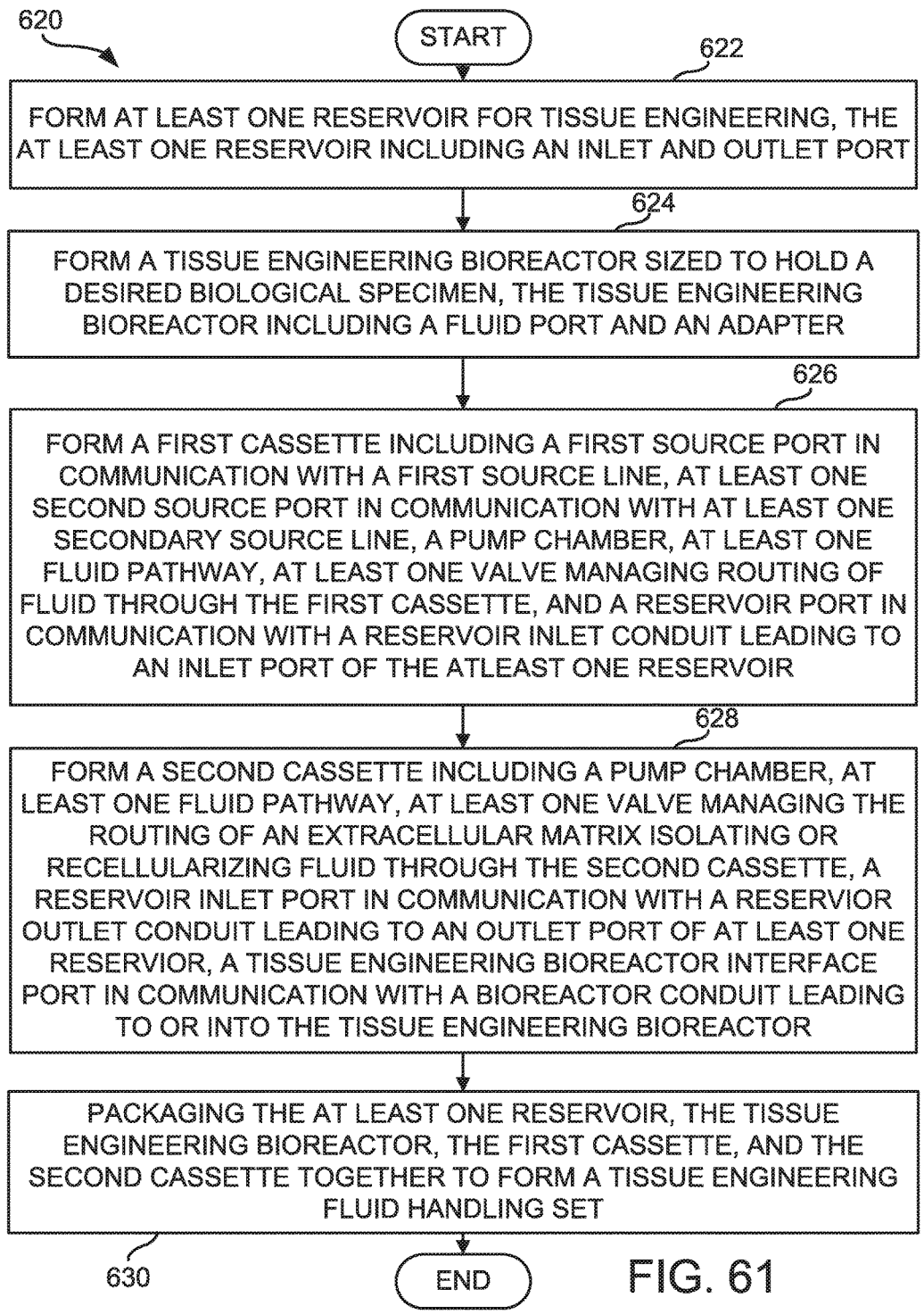
FIG. 61 is an example flowchart of a method which may be used for manufacturing a tissue engineering set.

Referring now to FIG. 61, an example method 620 which may be used for manufacturing a tissue engineering set is depicted. The method 620 may include, but is not limited to including, forming 622 at least one reservoir for tissue engineering. Forming 622 at least one reservoir may include forming the at least one reservoir with an inlet and an outlet port. The method 620 may include forming 624 a tissue engineering bioreactor sized to hold a desired biological specimen. Forming 624 the tissue engineering bioreactor may include forming the tissue engineering bioreactor with at least one fluid port and an adapter. The adapter may allow for fluid conduits to access an interior volume of the tissue engineering bioreactor in which the desired biological specimen is held. The method 620 may include forming 626 a first cassette including a first source port in communication with a first source line and at least one secondary source port in communication with at least one secondary source line. Forming 626 the first cassette may include forming the first cassette with a first pump chamber, at least one fluid pathway, and at least one valve managing the routing of fluid through the first cassette. Forming 626 the first cassette may include forming the first cassette with a reservoir port in communication with a reservoir inlet conduit coupled to an inlet port of the at least one reservoir. The method 620 may include forming 628 a second cassette including a pump chamber, at least one fluid pathway, and at least one valve managing routing of an extracellular matrix isolating or recellularizing fluid through the second cassette. Forming 628 the second cassette may include forming the second cassette with a reservoir inlet port in communication with a reservoir outlet conduit leading to an outlet port of the at least one reservoir. Forming 628 the second cassette may include forming the second cassette with a tissue engineering bioreactor interface port in communication with a bioreactor conduit leading to or into the tissue engineering bioreactor. In some configurations, method 620 may include forming a plurality of such second cassettes. The method 620 may include packaging 630 at least one reservoir, tissue engineering bioreactor, first cassette, and second cassette together to form a tissue engineering fluid handling set.

Various alternatives and modifications can be devised by those skilled in the art without departing from the disclosure. Accordingly, the present disclosure embraces all such alternatives, modifications and variances. Additionally, while several configurations of the present disclosure have been shown in the drawings and/or discussed herein, the disclosure is not limited thereto. Therefore, the above description should not be construed as limiting, but merely as exemplifications of particular configurations. And, those skilled in the art will envision other modifications within the scope and spirit of the claims appended hereto. The present teachings are also directed to a system and methods that can be executed in hardware, firmware, and/or software for accomplishing the methods discussed herein, and, possibly, computer readable media storing software for accomplishing these methods and system. The various modules described herein can be provided in conjunction with a single CPU, or on an arbitrary number of different CPUs. Other alternative computer platforms can be used. The operating system can be, for example, but is not limited to, WINDOWS®, LINUX®, and VMS. Communications links can be wired or wireless, for example, using cellular communication systems, military communications systems, and satellite communications systems. Any data and results can be stored for future retrieval and processing, printed, displayed, transferred to another computer, and/or transferred elsewhere. In compliance with the statute, the present teachings have been described in language more or less specific as to structural and methodical features. It is to be understood, however, that the present teachings are not limited to the specific features shown.

Referring again to FIGS. 46A-46D, 55Q, and 56-61, methods 1500 (FIG. 46A), 1550 (FIG. 46B), 1580 (FIG. 46C), 1530 (FIG. 46D), 3160 (FIG. 55Q), 150 (FIG. 56), 250 (FIG. 57), 149 (FIG. 58) 249 (FIG. 59), 600 (FIG. 60), 620 (FIG. 61), can be, in whole or in part, implemented electronically. Signals representing actions taken by elements of systems that implement the methods of the present configuration, and other disclosed configurations can travel over at least one live communications network. Control and data information can be electronically executed and stored on at least one computer-readable medium. The system can be implemented to execute on at least one computer node in at least one live communications network enabled by such protocols as TCP/IP and PCAN, for example. Common forms of at least one computer-readable medium can include, for example, but not be limited to, a floppy disk, a flexible disk, a hard disk, magnetic tape, or any other magnetic medium, a compact disk read only memory or any other optical medium, punched cards, paper tape, or any other physical medium with patterns of holes, a random access memory, a programmable read only memory, and erasable programmable read only memory (EPROM), a Flash EPROM, or any other memory chip or cartridge, or any other medium from which a computer can read. Further, the at least one computer readable medium can contain graphs in any form including, but not limited to, Graphic Interchange Format (GIF), Joint Photographic Experts Group (JPEG), Portable Network Graphics (PNG), Scalable Vector Graphics (SVG), and Tagged Image File Format (TIFF).

The configurations shown in drawings are presented only to demonstrate certain examples of the present teachings. The drawings described are illustrative and are non-limiting. In the drawings, for illustrative purposes, the size of some of the elements may not be drawn to a particular scale. Elements shown within the drawings that have the same numbers may be identical elements or may be similar elements, depending on the context.

The terms "first", "second", "third" and the like, whether used in the description or in the claims, are provided for distinguishing elements. It is to be understood that the terms so used are interchangeable under appropriate circumstances (unless clearly disclosed otherwise) and that the configurations of the disclosure described herein are capable of operation in other sequences and/or arrangements than are described or illustrated herein.

While the present teachings have been described above in terms of specific examples, it is to be understood that the present teachings are not limited to the disclosed examples. Many modifications and other examples are intended to be and are covered by this disclosure and the appended claims.

What is claimed is:

1. A set for decellularizing tissue comprising:
   at least one reservoir including a plurality of ports, the plurality of ports including at least one mix port and at least one pump port;
   at least one bioreactor including at least one bioreactor port, the at least one bioreactor surrounding the tissue;
   at least one pump cassette, the pump cassette including at least one pump, at least one reservoir port fluidically connecting the at least one pump cassette to the at least one reservoir at the at least one pump port, the at least one pump cassette including at least one bioreactor interface port fluidically connecting the at least one pump cassette to the at least one bioreactor at the at least one bioreactor port, the at least one pump cassette including at least one first fluid bus and at least one pump cassette valve, the at least one pump cassette valve managing the routing of a first fluid from the at least one reservoir through the at least one pump to the at least one bioreactor interface port;
   at least one mix cassette including at least one dilution port, the at least one dilution port fluidically coupling the at least one mix cassette with a medium, the at least one mix cassette include at least one reservoir port fluidically coupling the at least one mix cassette with the at least one reservoir, the at least one mix cassette including at least one solution port fluidically coupling the at least one mix cassette with at least one second fluid, the at least one mix cassette including at least one mix pump, the at least one mix cassette including at least one second fluid bus, the at least one mix cassette including at least one mix cassette valve managing the routing of the at least one second fluid from the at least one solution port through the at least one mix pump to the at least one reservoir port, the at least one mix pump mixing together a plurality of the at least one second fluid; and
   tubing enabling the fluidic connections at least among the at least one first fluid bus and the at least one second fluid bus.

2. The set as in claim 1 wherein the at least one reservoir further comprises:
   at least one vent port, at least one overflow port, and at least one level sensor sensing the amount of material in the at least one reservoir.

3. The set as in claim 1 wherein the at least one pump cassette further comprises:
   at least one waste port fluidically coupling the at least one pump cassette to at least one waste receptacle.

4. The set as in claim 1 wherein the at least one pump cassette further comprises:
   at least one loop line port enabling heating of a fluid circulating in the at least one pump cassette.

5. The set as in claim 4 wherein the at least one first fluid bus and the at least one pump cassette valve manage flow from the at least one reservoir through the at least one loop line port.

6. The set as in claim 1 wherein the at least one bioreactor comprises:
   an adapter including a first face and an second face opposing the first face;
   an enclosure including a first section and a second section, the first section including a first side and a second side, the enclosure including a liquid-tight seal between the first section and the first face, the enclosure including at least one enclosure pass-through, the enclosure including a liquid-tight seal between at least a portion of the second section and at least a portion of the first section;
   a first fluid line operably coupled to the adapter, the first fluid line coupling the at least one enclosure pass-through and the adapter; and
   a second fluid line disposed on the second face, the second fluid line fluidically coupled with the first fluid line, the first fluid line coupled with the second fluid line forming a closed fluid path.

7. The set as in claim 1 further comprising:
   a flexible sheet covering the at least one pump, the flexible sheet covering at least one mix cassette valve.

8. The set as in claim 7 further comprising:
   a controller generating at least one controller command; and
   at least one valve module, each of the at least one valve modules, having at least one pressure bus, each of the at least one valve modules having at least one valve operably communicating with the pressure bus, each of the at least one valve modules having an outlet port, the outlet port being associated with each of the at least one mix cassette valve, the outlet port operably communicating with the flexible sheet, the at least one valve module including a first module having a first module processor, the first module processor receiving the at least one controller command, the first module processor generating, based on the controller command, at least one second module command addressed to at least one second module, the at least one second module having a second module processor receiving the at least one second module command and generating, based on the at least second module command, at least one valve command governing fluid flow through the at least one mix cassette valve of the at least one second module, the at least one mix cassette valve controlling pressure applied to the flexible sheet via the outlet ports, the at least one controller command metering the fluid flow to the tissue and the bioreactor, the tissue being decellularized based on the fluid flow.

9. The set as in claim 7 further comprising:
   a controller generating at least one controller command; and
   at least one first valve module and at least one second valve module, each of the at least one first and second valve modules having at least one pressure bus and at least one mix cassette valve, the at least one mix cassette valve operably communicating with the pressure bus, each of the at least one mix cassette valves being associated with an outlet port, the outlet port operably communicating with the flexible sheeting, the first valve module having a first module processor, the first module processor receiving the at least one controller command, the first module processor generating, based on the controller command, at least one module command addressed to the at least second module, the at least one second valve module having a second module processor receiving the at least one second module command and generating, based on the at least one second module command, a plurality of valve commands, the plurality of valve commands governing fluid flow through the at least one mix cassette valve of the at least one second valve module, the at least one mix cassette valve controlling pressure applied to the flexible sheet via the outlet ports, the at least one controller command metering the fluid flow to the tissue, the tissue being recellularized based on the fluid flow.

10. The set as in claim 7 further comprising:
a recipe including recipe steps; and
a graphical user interface (GUI) receiving GUI input,
wherein the controller accesses the recipe steps, the GUI input, and at least one default value, the controller forming directions based on arbitrating the at least one default value, the recipe steps, and the GUI input, the controller executing the directions to engineer the tissue, the tissue including donor tissue.

11. The set as in claim 10 wherein the controller comprises updating the GUI and updating the recipe steps.

\* \* \* \* \*